(12) United States Patent
Schildkraut et al.

(10) Patent No.: US 11,479,766 B2
(45) Date of Patent: *Oct. 25, 2022

(54) METHODS FOR LABELING A POPULATION OF RNA MOLECULES

(71) Applicant: New England Biolabs, Inc., Ipswich, MA (US)

(72) Inventors: Ira Schildkraut, Ipswich, MA (US); Laurence Ettwiller, Ipswich, MA (US); Ivan R. Correa, Jr., Ipswich, MA (US); George Tzertzinis, Ipswich, MA (US); John Buswell, Ipswich, MA (US); Madalee G. Wulf, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 537 days.

This patent is subject to a terminal disclaimer.

(21) Appl. No.: 15/908,522

(22) Filed: Feb. 28, 2018

(65) Prior Publication Data
US 2018/0195061 A1 Jul. 12, 2018

Related U.S. Application Data

(63) Continuation-in-part of application No. 15/786,020, filed on Oct. 17, 2017, now Pat. No. 11,225,658, which is a continuation-in-part of application No. 15/137,394, filed on Apr. 25, 2016, now Pat. No. 10,428,368, application No. 15/908,522, which is a continuation-in-part of application No. 15/137,394, filed on Apr. 25, 2016, now Pat. No. 10,428,368, which is a continuation-in-part of application No. PCT/US2014/068737, filed on Dec. 5, 2014.

(60) Provisional application No. 62/409,151, filed on Oct. 17, 2016, provisional application No. 62/166,190, filed on May 26, 2015, provisional application No. 62/011,918, filed on Jun. 13, 2014, provisional application No. 62/002,564, filed on May 23, 2014, provisional application No. 61/920,380, filed on Dec. 23, 2013, provisional application No. 61/912,367, filed on Dec. 5, 2013.

(51) Int. Cl.
*C12N 15/10* (2006.01)
*C12Q 1/6806* (2018.01)
*C07H 21/02* (2006.01)

(52) U.S. Cl.
CPC ......... *C12N 15/1096* (2013.01); *C07H 21/02* (2013.01); *C12N 15/1065* (2013.01); *C12Q 1/6806* (2013.01)

(58) Field of Classification Search
CPC ......... C12P 19/34; C07H 19/04; C07H 21/02; C07H 1/02; C12N 15/11; C12N 15/1096; C12Q 1/6806
See application file for complete search history.

(56) References Cited

U.S. PATENT DOCUMENTS

| | | | | |
|---|---|---|---|---|
| 5,194,614 A | * | 3/1993 | Andrieux | C07C 217/60 544/400 |
| 5,795,782 A | | 8/1998 | Church et al. | |
| 6,015,714 A | | 1/2000 | Baldarelli et al. | |
| 6,022,715 A | * | 2/2000 | Merenkova | C12N 15/1096 435/6.16 |
| 6,627,067 B1 | | 9/2003 | Branton et al. | |
| 7,238,485 B2 | | 7/2007 | Akeson et al. | |
| 7,258,838 B2 | | 8/2007 | Li et al. | |
| 8,486,666 B2 | | 7/2013 | Schildkraut | |
| 2004/0044057 A1 | * | 3/2004 | Denny | C07D 233/64 514/396 |
| 2006/0003171 A1 | | 1/2006 | Igawa et al. | |
| 2009/0029477 A1 | | 1/2009 | Meller et al. | |

OTHER PUBLICATIONS

Warminski et al. mRNA cap modification through carbamate chemistry: Synthesis of amino- and carboxy-functionalized cap alanogues suitable for labelling and bioconjugation. European Journal of Organic Chemistry, pp. 6153-6169, Jul. 28, 2015. (Year: 2015).*
Paredes et al. Click chemistry for rapid labeling and ligation of RNA. Chembiochem, vol. 12, No. 1, pp. 125-131, Jan. 2011. (Year: 2011).*
Pourceau et al. Azide solid support for 3'-conjugation of oligonucleotides and their circularization by click chemistry. Journal of Organic Chemistry, vol. 74, pp. 6837-6842, Aug. 2009. (Year: 2009).*
Crooks, et al, Genome Res (2004) 14:1188-1190.
Baskin, et al., Proc. Natl. Acad. Sci. 2007 104: 16793-16797.
Sletten, et al., Accounts of Chemical Research, 44: 666-676, 2011.
Matz, et al Nucl. Acids Res., 27: 1558-1560, 1999.
Wu, et al., Nat Methods. 11: 41-6, 2014.
Soni, et al., Clin Chem 53: 1996-2001, 2007.
Adey, Genome Res., 24: 2041-9, 2014.
Amini, Nat Genet., 46: 1343-9, 2014.
Cabson, Nucleic Acids Res., 41:e112, 2013.
Dobin, et al, Bioinformatics, doi: 10.1093/bioinformatics/bts635, 2012, vol. 29, No. 1, pp. 15-21.
Hermanson, Bioconjugate Techniques, 2nd Ed; Academic Press: London, Bioconjugate Reagents, pp. 276-335, 2008.

(Continued)

*Primary Examiner* — Jennifer Dunston
(74) *Attorney, Agent, or Firm* — New England Biolabs, Inc

(57) ABSTRACT

A method of labeling, and optionally enriching, for a population of target RNA molecules in a mixture of RNAs is provided. In some embodiments, the method may comprise (a) adding a label to the 5' end of 5'-diphosphorylated or 5'-triphosphorylated target RNA molecules in a sample by incubating the sample with labeled GTP and a capping enzyme; and (b) optionally enriching for target RNA comprising the affinity tag-labeled GMP using an affinity matrix that binds to the affinity tag. The label may be an oligonucleotide, which may further comprise an affinity group attached either internally or at 5' or 3' end of the oligonucleotide where the oligonucleotide label may be added directly, or indirectly via a reaction with a reactive group to the target RNA.

40 Claims, 39 Drawing Sheets
(18 of 39 Drawing Sheet(s) Filed in Color)
Specification includes a Sequence Listing.

(56) References Cited

OTHER PUBLICATIONS

Kim, et al., ChemBioChem, 11:75-78, 2010.
Kim, et al., Bioorg. Med. Chem. Lett., 24:209-213, 2014.
Deleavey, et al., Chemistry & Biology, 19(8): 937-54, 2012.
Sletten, et al., Angew. Chem. Int. Ed., 48(38): 6974-98, 2009.
Evans, Australian Journal of Chemistry, 60: 384-395, 2007.
Tornoe, Journal of Organic Chemistry, 67: 3057-3064, 2002.
Li, Biotechnol. Appl. Biochem, 55:73-83, 2010.
Mao, et al., Journal of Biological Chemistry, 269:24472-24479, 1994.
Shuman, Journal of Biological Chemistry 265:11960-11966, 1990.
Sutton, et al., Nat Struct Mol Biol 14: 449-451, 2007.
Ramadevi, et al. Proc Natl Acad Sci. USA 95:13537-13542, 1998.
Gong, et al., Journal of Biological Chemistry 277:15317-15324, 2002.
Ho, et al., Journal of Virology, 70:6658-6664, 1996.
Ho, et al., Journal of Virology, 75:1744-1750, 2001.
Steiger, et al., RNA, 9:231-238, 2003.
Bougie, et al., Biochem J, 384:411-420, 2004.
Lima, et al., Cell, 99:533-543, 1999.
Spencer, et al., PNAS, 75:4793-1797, 1978.
Luo, et al., J. Virol., 64(9): 4321-1328, 1990.
Zhu, et al., Biotechniques, 30:892-897, 2001.
Efimov, et al., Nucl. Acids Res., 29(22):4751-1759, 2001.
Kim, et al., PLoS genetics, 8(8), e1002867, 2012.
Kore, et al, Nucleosides Nucleotides Nucleic Acids, 31:423-431, 2012.
Rostovtsev, et al, Angew. Chem. Int. Ed., 41:2596-2599, 2002.
Hong, et al., Angew. Chem. Int. Ed., 48:9879-9883, 2009.
Thomason, et al, J Bacteriol, 197:18-28, 2015.
Chan, et al, Nucleic Acids Res, 40:D646-52, 2012.
Siepel, et al, J Comput Biol, 11:413-428, 2004.
Bailey, et al., Proc Int Conf Intell Syst Mol Biol ISMB, 2:28-36, 1994.
Langmead, et al, Nat Methods, 9:357-359, 2012.
Romero, et al, Mol Microbiol, 94:963-987, 2014.
Salgado, et al, Nucleic Acids Res, 41:D203-13, 2013.
Bailey, et al, Nucleic Acids Res, 37:W202-8, 2009.
Thorvaldsdottir, et al, Brief Bioinform, 14:178-192, 2013.
Robinson, et al, Nat Biotech, 29:24-26, 2011.
Garalde, et al. Nature Methods doi: 10.1038/nmeth.4577, 15(3): 201-2016, Epub Jan. 15, 2018, printed as pp. 1-21.
Beharry, et al., Chemical Society Reviews, 40(8): 4422-37, 2011.
Parrish, et al., J. Virol., 81(23):12973-8, 2007.
Kolb, Angewandte Chemie International Edition, 40 (11): 2004-2021 (2001.
Kolb, et al., Drug Discov Today 2003 8: 1128-113.

* cited by examiner

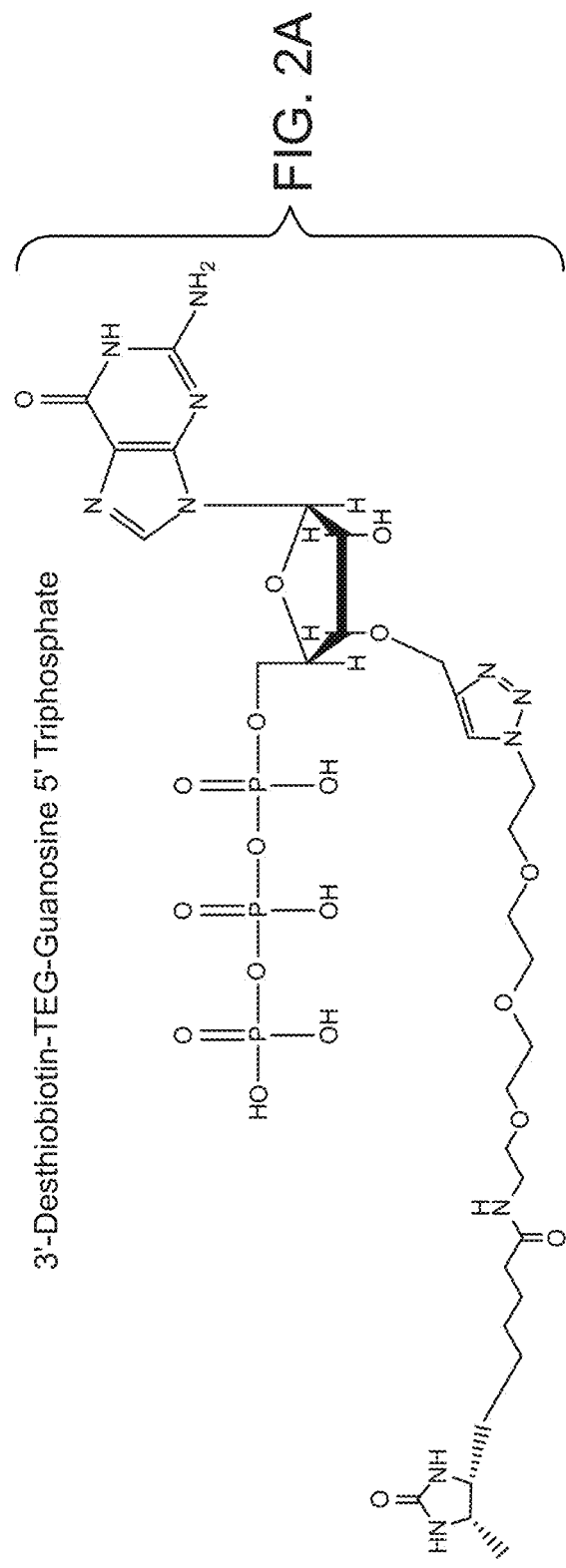
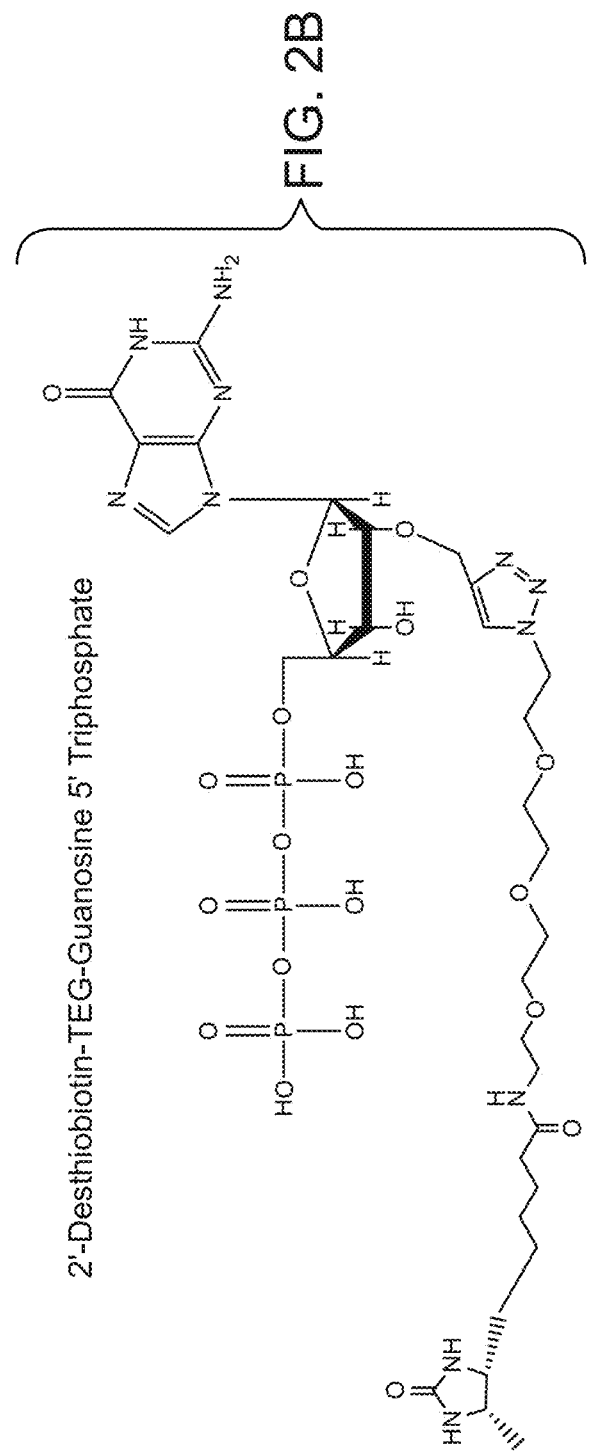
FIG. 2A
FIG. 2B

A. Example of TSS in *Akkermansia muciniphila*

B. Promoter structures.

C. Percentage of leaderless TSS

D. Ribosomal depletion

E. Correlation between biological replicates.

SEQUENCE LISTING

```
<160> NUMBER OF SEQ ID NOS: 21

<210> SEQ ID NO 1
<211> LENGTH: 844
<212> TYPE: PRT
<213> ORGANISM: Artificial Sequence
<220> FEATURE:
<223> OTHER INFORMATION: Synthetic construct

<400> SEQUENCE: 1

Met Asp Ala Asn Val Val Ser Ser Thr Ile Ala Thr Tyr Ile Asp
1               5                   10                  15

Ala Leu Ala Lys Asn Ala Ser Glu Leu Glu Gln Arg Ser Thr Ala Tyr
                20                  25                  30

Glu Ile Asn Asn Glu Leu Glu Leu Val Phe Ile Lys Pro Pro Leu Ile
            35                  40                  45

Thr Leu Thr Asn Val Val Asn Ile Ser Thr Ile Gln Glu Ser Phe Ile
        50                  55                  60

Arg Phe Thr Val Thr Asn Lys Glu Gly Val Lys Ile Arg Thr Lys Ile
65                  70                  75                  80

Pro Leu Ser Lys Val His Gly Leu Asp Val Lys Asn Val Gln Leu Val
                85                  90                  95

Asp Ala Ile Asp Asn Ile Val Trp Glu Lys Lys Ser Leu Val Thr Glu
            100                 105                 110

Asn Arg Leu His Lys Glu Cys Leu Leu Arg Leu Ser Thr Glu Glu Arg
        115                 120                 125

His Ile Phe Leu Asp Tyr Lys Lys Tyr Gly Ser Ser Ile Arg Leu Glu
    130                 135                 140
```

```
Leu Val Asn Leu Ile Gln Ala Lys Thr Lys Asn Phe Thr Ile Asp Phe
145                 150                 155                 160

Lys Leu Lys Tyr Phe Leu Gly Ser Gly Ala Gln Ser Lys Ser Ser Leu
            165                 170                 175

Leu His Ala Ile Asn His Pro Lys Ser Arg Pro Asn Thr Ser Leu Glu
            180                 185                 190

Ile Glu Phe Thr Pro Arg Asp Asn Glu Thr Val Pro Tyr Asp Glu Leu
            195                 200                 205

Ile Lys Glu Leu Thr Thr Leu Ser Arg His Ile Phe Met Ala Ser Pro
210                 215                 220

Glu Asn Val Ile Leu Ser Pro Pro Ile Asn Ala Pro Ile Lys Thr Phe
225                 230                 235                 240

Met Leu Pro Lys Gln Asp Ile Val Gly Leu Asp Leu Glu Asn Leu Tyr
            245                 250                 255

Ala Val Thr Lys Thr Asp Gly Ile Pro Ile Thr Ile Arg Val Thr Ser
            260                 265                 270

Asn Gly Leu Tyr Cys Tyr Phe Thr His Leu Gly Tyr Ile Ile Arg Tyr
            275                 280                 285

Pro Val Lys Arg Ile Ile Asp Ser Glu Val Val Phe Gly Glu Ala
            290                 295                 300

Val Lys Asp Lys Asn Trp Thr Val Tyr Leu Ile Lys Leu Ile Glu Pro
305                 310                 315                 320

Val Asn Ala Ile Asn Asp Arg Leu Glu Glu Ser Lys Tyr Val Glu Ser
                325                 330                 335

Lys Leu Val Asp Ile Cys Asp Arg Ile Val Phe Lys Ser Lys Lys Tyr
            340                 345                 350

Glu Gly Pro Phe Thr Thr Thr Ser Glu Val Val Asp Met Leu Ser Thr
            355                 360                 365

Tyr Leu Pro Lys Gln Pro Glu Gly Val Ile Leu Phe Tyr Ser Lys Gly
370                 375                 380

Pro Lys Ser Asn Ile Asp Phe Lys Ile Lys Lys Glu Asn Thr Ile Asp
385                 390                 395                 400

Gln Thr Ala Asn Val Val Phe Arg Tyr Met Ser Ser Glu Pro Ile Ile
                405                 410                 415

Phe Gly Glu Ser Ser Ile Phe Val Glu Tyr Lys Lys Phe Ser Asn Asp
            420                 425                 430

Lys Gly Phe Pro Lys Glu Tyr Gly Ser Gly Lys Ile Val Leu Tyr Asn
            435                 440                 445

Gly Val Asn Tyr Leu Asn Asn Ile Tyr Cys Leu Glu Tyr Ile Asn Thr
            450                 455                 460

His Asn Glu Val Gly Ile Lys Ser Val Val Pro Ile Lys Phe Ile
465                 470                 475                 480

Ala Glu Phe Leu Val Asn Gly Glu Ile Leu Lys Pro Arg Ile Asp Lys
            485                 490                 495

Thr Met Lys Tyr Ile Asn Ser Glu Asp Tyr Tyr Gly Asn Gln His Asn
            500                 505                 510

Ile Ile Val Glu His Leu Arg Asp Gln Ser Ile Lys Ile Gly Asp Ile
            515                 520                 525

Phe Asn Glu Asp Lys Leu Ser Asp Val Gly His Gln Tyr Ala Asn Asn
            530                 535                 540

Asp Lys Phe Arg Leu Asn Pro Glu Val Ser Tyr Phe Thr Asn Lys Arg
545                 550                 555                 560
```

```
Thr Arg Gly Pro Leu Gly Ile Leu Ser Asn Tyr Val Lys Thr Leu Leu
            565                 570                 575

Ile Ser Met Tyr Cys Ser Lys Thr Phe Leu Asp Asp Ser Asn Lys Arg
        580                 585                 590

Lys Val Leu Ala Ile Asp Phe Gly Asn Gly Ala Asp Leu Glu Lys Tyr
    595                 600                 605

Phe Tyr Gly Glu Ile Ala Leu Leu Val Ala Thr Asp Pro Asp Ala Asp
610                 615                 620

Ala Ile Ala Arg Gly Asn Glu Arg Tyr Asn Lys Leu Asn Ser Gly Ile
625                 630                 635                 640

Lys Thr Lys Tyr Tyr Lys Phe Asp Tyr Ile Gln Glu Thr Ile Arg Ser
                645                 650                 655

Asp Thr Phe Val Ser Ser Val Arg Glu Val Phe Tyr Phe Gly Lys Phe
            660                 665                 670

Asn Ile Ile Asp Trp Gln Phe Ala Ile His Tyr Ser Phe His Pro Arg
        675                 680                 685

His Tyr Ala Thr Val Met Asn Asn Leu Ser Glu Leu Thr Ala Ser Gly
    690                 695                 700

Gly Lys Val Leu Ile Thr Thr Met Asp Gly Asp Lys Leu Ser Lys Leu
705                 710                 715                 720

Thr Asp Lys Lys Thr Phe Ile Ile His Lys Asn Leu Pro Ser Ser Glu
                725                 730                 735

Asn Tyr Met Ser Val Glu Lys Ile Ala Asp Asp Arg Ile Val Val Tyr
            740                 745                 750

Asn Pro Ser Thr Met Ser Thr Pro Met Thr Glu Tyr Ile Ile Lys Lys
        755                 760                 765

Asn Asp Ile Val Arg Val Phe Asn Glu Tyr Gly Phe Val Leu Val Asp
    770                 775                 780

Asn Val Asp Phe Ala Thr Ile Ile Glu Arg Ser Lys Lys Phe Ile Asn
785                 790                 795                 800

Gly Ala Ser Thr Met Glu Asp Arg Pro Ser Thr Arg Asn Phe Phe Glu
                805                 810                 815

Leu Asn Arg Gly Ala Ile Lys Cys Glu Gly Leu Asp Val Glu Asp Leu
            820                 825                 830

Leu Ser Tyr Tyr Val Tyr Val Phe Ser Lys Arg
        835                 840

<210> SEQ ID NO 2
<211> LENGTH: 287
<212> TYPE: PRT
<213> ORGANISM: Artificial Sequence
<220> FEATURE:
<223> OTHER INFORMATION: Synthetic construct

<400> SEQUENCE: 2

Met Asp Glu Ile Val Lys Asn Ile Arg Glu Gly Thr His Val Leu Leu
1               5                   10                  15

Pro Phe Tyr Glu Thr Leu Pro Glu Leu Asn Leu Ser Leu Gly Lys Ser
            20                  25                  30

Pro Leu Pro Ser Leu Glu Tyr Gly Ala Asn Tyr Phe Leu Gln Ile Ser
        35                  40                  45

Arg Val Asn Asp Leu Asn Arg Met Pro Thr Asp Met Leu Lys Leu Phe
    50                  55                  60

Thr His Asp Ile Met Leu Pro Glu Ser Asp Leu Asp Lys Val Tyr Glu
65                  70                  75                  80
```

```
Ile Leu Lys Ile Asn Ser Val Lys Tyr Tyr Gly Arg Ser Thr Lys Ala
                85                  90                  95

Asp Ala Val Val Ala Asp Leu Ser Ala Arg Asn Lys Leu Phe Lys Arg
            100                 105                 110

Glu Arg Asp Ala Ile Lys Ser Asn Asn His Leu Thr Glu Asn Asn Leu
        115                 120                 125

Tyr Ile Ser Asp Tyr Lys Met Leu Thr Phe Asp Val Phe Arg Pro Leu
    130                 135                 140

Phe Asp Phe Val Asn Glu Lys Tyr Cys Ile Ile Lys Leu Pro Thr Leu
145                 150                 155                 160

Phe Gly Arg Gly Val Ile Asp Thr Met Arg Ile Tyr Cys Ser Leu Phe
                165                 170                 175

Lys Asn Val Arg Leu Leu Lys Cys Val Ser Asp Ser Trp Leu Lys Asp
            180                 185                 190

Ser Ala Ile Met Val Ala Ser Asp Val Cys Lys Lys Asn Leu Asp Leu
        195                 200                 205

Phe Met Ser His Val Lys Ser Val Thr Lys Ser Ser Trp Lys Asp
    210                 215                 220

Val Asn Ser Val Gln Phe Ser Ile Leu Asn Asn Pro Val Asp Thr Glu
225                 230                 235                 240

Phe Ile Asn Lys Phe Leu Glu Phe Ser Asn Arg Val Tyr Glu Ala Leu
                245                 250                 255

Tyr Tyr Val His Ser Leu Leu Tyr Ser Ser Met Thr Ser Asp Ser Lys
            260                 265                 270

Ser Ile Glu Asn Lys His Gln Arg Arg Leu Val Lys Leu Leu Leu
        275                 280                 285

<210> SEQ ID NO 3
<211> LENGTH: 58
<212> TYPE: PRT
<213> ORGANISM: Artificial Sequence
<220> FEATURE:
<223> OTHER INFORMATION: Synthetic construct

<400> SEQUENCE: 3

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 4
<211> LENGTH: 26
<212> TYPE: PRT
<213> ORGANISM: Artificial Sequence
<220> FEATURE:
<223> OTHER INFORMATION: Synthetic construct

<400> SEQUENCE: 4

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 5
```

```
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

His His His His His His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Asp Tyr Lys Asp Asp Asp Asp Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Tyr Pro Tyr Asp Val Pro Asp Tyr Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic construct

<400> SEQUENCE: 8

Glu Gln Lys Leu Ile Ser Glu Glu Asp Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic construct

<400> SEQUENCE: 9

Gly Lys Pro Ile Pro Asn Pro Leu Leu Gly Leu Asp Ser Thr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Trp Ser His Pro Gln Phe Glu Lys
1               5

<210> SEQ ID NO 11
<211> LENGTH: 38
```

```
<212> TYPE: PRT
<213> ORGANISM: Artificial Sequence
<220> FEATURE:
<223> OTHER INFORMATION: Synthetic construct

<400> SEQUENCE: 11

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 12
<211> LENGTH: 15
<212> TYPE: PRT
<213> ORGANISM: Artificial Sequence
<220> FEATURE:
<223> OTHER INFORMATION: Synthetic construct

<400> SEQUENCE: 12

Lys Glu Thr Ala Ala Ala Lys Phe Glu Arg Gln His Met Asp Ser
1               5                   10                  15

<210> SEQ ID NO 13
<211> LENGTH: 51
<212> TYPE: PRT
<213> ORGANISM: Artificial Sequence
<220> FEATURE:
<223> OTHER INFORMATION: Synthetic construct

<400> SEQUENCE: 13

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 14
<211> LENGTH: 34
<212> TYPE: DNA
<213> ORGANISM: Artificial Sequence
<220> FEATURE:
<223> OTHER INFORMATION: Synthetic construct

<400> SEQUENCE: 14
agatcggaag agcacacgtc tgaactccag tcac                          34

<210> SEQ ID NO 15
<211> LENGTH: 220
<212> TYPE: PRT
<213> ORGANISM: Artificial Sequence
<220> FEATURE:
<223> OTHER INFORMATION: Synthetic construct

<400> SEQUENCE: 15

Met Ser Val His Lys Thr Asn Asp Ala Phe Lys Val Leu Met Asn Ser
1               5                   10                  15

Ala Lys Glu Pro Ile Val Glu Asp Ile Pro Lys Lys Tyr Arg Lys Gln
            20                  25                  30
```

```
Ser Phe Arg Asp Asn Leu Lys Val Tyr Ile Glu Pro Glu Ser Tyr
        35                  40                  45

Lys Asn Val Ile Tyr Tyr Asp Asp Val Val Leu Val Arg Asp Met
 50                  55                  60

Phe Pro Lys Ser Lys Met His Leu Leu Leu Met Thr Arg Asp Pro His
 65                  70                  75                  80

Leu Thr His Val His Pro Leu Glu Ile Met Met Lys His Arg Ser Leu
                 85                  90                  95

Val Glu Lys Leu Val Ser Tyr Val Gln Gly Asp Leu Ser Gly Leu Ile
            100                 105                 110

Phe Asp Glu Ala Arg Asn Cys Leu Ser Gln Gln Leu Thr Asn Glu Ala
            115                 120                 125

Leu Cys Asn Tyr Ile Lys Val Gly Phe His Ala Gly Pro Ser Met Asn
130                 135                 140

Asn Leu His Leu His Ile Met Thr Leu Asp His Val Ser Pro Ser Leu
145                 150                 155                 160

Lys Asn Ser Ala His Tyr Ile Ser Phe Thr Ser Pro Phe Phe Val Lys
                165                 170                 175

Ile Asp Thr Pro Thr Ser Asn Leu Pro Thr Arg Gly Thr Leu Thr Ser
            180                 185                 190

Leu Phe Gln Glu Asp Leu Lys Cys Trp Arg Cys Gly Glu Thr Phe Gly
            195                 200                 205

Arg His Phe Thr Lys Leu Lys Ala His Leu Gln Glu
        210                 215                 220

<210> SEQ ID NO 16
<211> LENGTH: 36
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (34)..(36)
<223> OTHER INFORMATION: n is a, c, g, or u

<400> SEQUENCE: 16
acacucuuuc ccuacacgac gcucuuccga ucunnn                        36

<210> SEQ ID NO 17
<211> LENGTH: 67
<212> TYPE: DNA
<213> ORGANISM: Artificial Sequence
<220> FEATURE:
<223> OTHER INFORMATION: Synthetic construct

<400> SEQUENCE: 17
rurargrcra rcrcraruru rurgrarara rurcrargru rgrurutcgt atgccgtctt   60
ctgcttg                                                            67

<210> SEQ ID NO 18
<211> LENGTH: 25
<212> TYPE: RNA
<213> ORGANISM: Artificial Sequence
<220> FEATURE:
<223> OTHER INFORMATION: Synthetic construct

<400> SEQUENCE: 18
cuagaacuuc gucgaguacg cucaa                                        25
```

```
<210> SEQ ID NO 19
<211> LENGTH: 800
<212> TYPE: RNA
<213> ORGANISM: Artificial Sequence
<220> FEATURE:
<223> OTHER INFORMATION: Synthetic construct

<400> SEQUENCE: 19
gggagaccca agcuugguac cgagcucgga uccagccacc augggaguca aaguucuguu      60
ugcccugauc ugcaucgcug uggccgaggc caagcccacc gagaacaacg aagacuucaa     120
caucguggcc guggccagca acuucgcgac cacggaucuc gaugcugacc gcgggaaguu     180
gcccggcaag aagcugccgc uggaggugcu caaagagaug gaagccaaug cccggaaagc     240
uggcugcacc aggggcuguc ugaucugccu gucccacauc aagugcacgc caagaugaa     300 gaaguucauc ccaggacgcu gccacaccua cgaaggcgac aaagaguccg cacagggcgg     360
cauaggcgag gcgaucgucg acauuccuga gauuccuggg uucaaggacu uggagcccau     420
ggagcaguuc aucgcacagg ucgaucugu guggacugc acaacuggcu gcccucaaagg     480 gcuugccaac gugcagguguu cugaccugcu caagaagugg cugccgcaac gcugugcgac     540
cuuugccagc aagauccagg gccagguggaa caagaucaag ggggccggug ugacuaagc     600 ggccgcaaua aaauaucuuu auuuucauua caucuguug uugguuuuuu gugugucuag     660
aaauaauucu uacuguaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa                                                 800

<210> SEQ ID NO 20
<211> LENGTH: 16
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5' end having guanosine triphosphate cap
      (Gppp), 5' monophosphate, 5' diphosphate (pp), DTB-Gppp cap,
      5' -OH
<220> FEATURE:
<221> NAME/KEY: misc_feature
<222> LOCATION: (2)..(8)
<223> OTHER INFORMATION: n is a, c, g, or u

<400> SEQUENCE: 20
nnnnnnnnaa aaaaaa                                                      16

<210> SEQ ID NO 21
<211> LENGTH: 8
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5' end having 5' -OH, 5' monophosphate,
      5' triphosphate (ppp)
<220> FEATURE:
<221> NAME/KEY: misc_feature
```

```
<222> LOCATION: (2)..(8)
<223> OTHER INFORMATION: n is a, c, g, or u

<400> SEQUENCE: 21 nnnnnnnn                                                              8
```

METHODS FOR LABELING A POPULATION OF RNA MOLECULES

CROSS-REFERENCING

This application is a continuation-in-part of U.S. patent application Ser. No. 15/137,394 filed Apr. 25, 2016 and is a continuation-in-part of U.S. patent application Ser. No. 15/786,020, filed Oct. 17, 2017 which claims the benefit of U.S. provisional application Ser. No. 62/409,151, filed on Oct. 17, 2016. U.S. application Ser. No. 15/137,394 claims the benefit of U.S. provisional application Ser. No. 62/166,190, filed on May 26, 2015, and is a continuation-in-part of PCT/US2014/068737, filed on Dec. 5, 2014, which application claims the benefit of U.S. provisional application Ser. No. 61/912,367, filed on Dec. 5, 2013; 61/920,380, filed on Dec. 23, 2013; 62/002,564 filed on May 23, 2014; and 62/011,918 filed on Jun. 13, 2014, all of which applications are incorporated by reference herein in their entireties for all purposes.

SEQUENCE LISTING STATEMENT

This disclosure includes a Sequence Listing submitted electronically in ascii format under the file name "NEB-374-381-CIP-3-PUS_ST25.txt," which was created on May 20, 2022 and is 18,347 bytes in size. This Sequence Listing is incorporated herein in its entirety by this reference.

BACKGROUND

Prokaryotic and eukaryotic cells contain multiple types of RNA at least some of which can be characterized by different chemical constituents at their 5' ends. Within all cells, RNA polymerase initiates synthesis of RNA with a 5' terminal nucleotide having a 5' triphosphate. 5' monophosphate nucleotides are then successively added to the 3' end. However, for eukaryotes, RNA destined to become messenger RNA (mRNA) is rapidly capped with a $m^7G$ nucleotide linked to the 5' terminus via a 5' triphosphate linkage. This modification is a result of the capping enzyme. In contrast, the mRNA of bacteria and archaea maintain their 5' triphosphate. In all kingdoms of life, ribosomal RNA (rRNA) makes up the vast majority of the cell's RNA but its 5' end is generated by endonucleolytic cleavage to leave a 5' monophosphate terminus. Furthermore when RNA is degraded in the cell by RNases, the 5' ends are either 5' monophosphate or 5' hydroxyl groups.

When analyzing the sequence and quantity of specific RNAs, it is desirable to remove rRNA and degraded RNA from the complex mixture of RNAs. There are currently a number of procedures for rRNA depletion, but they all suffer some shortcomings. For example, depletion methods commonly require the hybridization of DNA oligonucleotides complementary to rRNA and removal of the hybrid molecules. This requires customizing the DNA sequence to match the rRNA. It also requires a priori knowledge of the ribosomal sequence. Another procedure that has been used has been the specific enzymatic degradation of 5' monophosphate RNA that would include rRNA, however this enzymatic reaction has proved inefficient and leaves substantial rRNA and degraded RNA in the mixture.

cDNA libraries are often made and sequenced in order to analyze gene expression, examine alternative splicing, identify transcription start sites and to identify operons. In many cases, the RNA sample used to make a cDNA library may be partially degraded. cDNA libraries made from partially degraded samples have cDNAs that are neither long nor full length, which can lead to problems with data analysis. Some of these problems may be addressed computationally. However, it would be much more desirable to have experimental methods so that the problems can be avoided, particularly for high throughput analysis. Bias may also be a problem where certain RNAs are favored in making a cDNA library and others are omitted or under represented in a library. Enrichment of targeted RNAs for assessing their representation in a population is desirable to determine transcriptional patterns and their biological meaning.

In some cases, the enriched targeted RNAs may be used for direct RNA sequencing without cDNA synthesis. Bypassing the need for cDNA synthesis is desirable so as to avoid amplification and thus eliminate PCR bias or reverse transcriptase bias. Additionally, typical direct RNA sequencing is compatible with very long reads, which are particularly useful, for instance, in the study of splice variants.

SUMMARY

Provided herein, among other things, is a method of labeling, and optionally enriching, for a population of RNA molecules in a mixture of RNAs. In some embodiments, this method may comprise: (a) adding a labeled GMP to the 5' end of 5'-diphosphorylated or 5'-triphosphorylated RNA molecules (target RNA) in a sample by incubating the sample with a capping enzyme and a labeled GTP linked to a label wherein the label is: (i) an oligonucleotide, or (ii) a reactive group and if the label is a reactive group, then covalently linking the oligonucleotide to the GMP through the reactive group, after step (a). In one aspect, the method may further include enriching for the labeled-GMP RNA comprising an affinity tag-labeled GMP using an affinity matrix that binds to the affinity tag. Examples of an affinity tag include a self-labeling protein tag (e.g. SNAP-TAG® or CLIP-TAG® (New England Biolabs, Ipswich, Mass.)). The affinity tag, GTP, GMP or oligonucleotide may be further modified or to carry a detectable dye (e.g. color or fluorescent dye).

In one embodiment, adding an oligonucleotide-labeled GMP to the 5' end of the target RNA can be performed in a one step or a two step reaction. The one-step reaction involves reacting a pre-assembled oligonucleotide-labeled GTP with the decapped target RNA and a capping enzyme, so as to form an oligonucleotide-labeled GMP targetRNA (see, e.g., FIG. 38). The two-step reaction involves reacting a reactive group-modified GTP with the decapped target RNA and a capping enzyme so as to form a reactive-target RNA; and then adding an oligonucleotide label for chemoselectively reacting with the reactive group on the GMP-RNA, to form an oligonucleotide-labeled targetRNA (see, e.g., FIG. 39).

In one embodiment, the labeled GTP is of Formula (ii), or a salt thereof, wherein Z is H, OH, SH, NH2, a lower alkyl, a lower acyloxy, a lower alkylamine, a lower acylamine, or a halogenyl; R is a linker; and L is (i) a reactive group that is capable of covalently linking to an oligonucleotide or (ii) an oligonucleotide that is optionally linked to an affinity tag.

Formula (II)

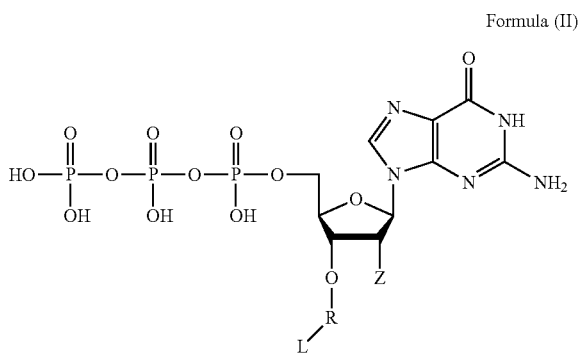

In one embodiment, L is an azide, an alkyne, an amine, an active ester, a thiol, or a maleimide. In another embodiment, step (b) is done via a click reaction (Kolb, Angewandte Chemie International Edition, 40 (11); 2004-2021 (2001)).

Where L is an oligonucleotide, the oligonucleotide may be selected from an oligoribonucleotide, a oligodeoxyribonucleotide, a peptide nucleic acid (PNA), a lock nucleic acid (LNA), an unlock nucleic acid (UNA), a triazole nucleic acid, or a combination thereof. The oligonucleotide may include one or more modified nucleotides. The oligonucleotide may be attached to the linker through an internal nucleotide or a branched spacer arm. The oligonucleotide may be attached to the linker by the 3' end or the 5' end. The oligonucleotide may include an affinity tag attached to the oligonucleotide through an internal nucleotide or a branched spacer arm. The affinity tag may be attached to the oligonucleotide at the 5' or 3' position. Examples of the affinity tag include biotin, desthiobiotin (DBT), avidin, streptavidin, protein A, maltose-binding protein, poly-histidine, HA-tag, c-myc tag, FLAG-tag, SNAP-TAG, S-tag and glutathione-S-transferase (GST). The affinity tag may be used to purify the oligonucleotide-labeled target RNA. This can be achieved by any of the following methods: size-selection, gel electrophoresis, ion exchange, size-exclusion, phenol-chloroform extraction, alcohol precipitation (e.g. ethanol or isopropanol precipitation), adsorption beads (e.g. AM PURE® beads (Beckman Coulter, Indianapolis, Ind.)), isopycnic gradient (e.g. CsCl gradient), affinity beads (e.g. streptavidin beads), liquid chromatography (e.g. HPLC), or hybridization (e.g. poly-dT beads or sequence-specific microarrays).

In one embodiment, step (b) of the method includes covalently linking the labeled GMP to the oligonucleotide by means of a reactive group selected from an azide, an alkyne, an amine, an active ester, a thiol, and a maleimide.

In one embodiment, the target RNA to which the oligonucleotide is attached via GMP is from a eukaryote that is naturally capped and the method comprises, prior to (a), enzymatically decapping the 5'-m7Gppp capped RNA in the sample to produce the 5'-terminal diphosphorylated or triphosphorylated uncapped RNA molecules of (a). Decapping may be done using a deadenylase having at least 90% identity to *Schizosaccharomyces pombe* HNT3 (SEQ ID NO:15), an apyrase, 5' RNA polyphosphatase (RppH), RNA phosphohydrolase or tobacco acid pyrophosphatase (TAP), a member of the histidine triad (HIT) superfamily of pyrophosphatases, DcpS, or an aprataxin (APTX).

In one embodiment, the oligonucleotide-labeled target RNA may be sequenced. In one example, the oligonucleotide comprises an affinity tag, and the oligonucleotide-labeled target RNA is enriched before sequencing.

In one embodiment, the method comprises: binding the oligonucleotide-labeled target RNA to an affinity matrix; eluting the enriched RNA from the affinity matrix for example by chemical cleavage; optionally removing the affinity tag from oligonucleotide-labeled target RNA; and obtaining a sequence for the target RNA. The affinity tag may alternatively be cleaved.

In one embodiment, a method is provided for making cDNA comprising: (a) treating a sample comprising a capped RNA with a decapping enzyme; (b) adding an oligonucleotide-labeled guanosine monophosphate (GMP) to the 5' end of the decapped RNA by incubating the decapped RNA with an oligonucleotide-labeled guanosine triphosphate (GTP) represented by Formula (ii), or a salt thereof, and a capping enzyme; (c) optionally including a purification step to purify the oligonucleotide-labeled RNA; (d) optionally adding a poly(A) tail or adaptor sequence in (a), (b), or (c); and (e) reverse transcribing the RNA to produce cDNA.

In one embodiment, a method is provided for making cDNA comprising: (a) treating a sample comprising a capped RNA with a decapping enzyme; (b) adding a reactive group-labeled GMP to the 5' end of the decapped RNA by incubating the decapped RNA with a reactive group-labeled GTP represented by Formula (I), or a salt thereof, and a capping enzyme; (c) covalently linking an oligonucleotide through a reaction with the reactive group-labeled RNA (d) optionally including a purification step to purify the oligonucleotide-labeled RNA; (e) optionally adding a poly(A) tail or adaptor sequence in (a), (b), (c) or (d); and (f) reverse transcribing the RNA to produce cDNA. In both the latter methods, the complementary sequence of the covalently linked oligonucleotide is incorporated in the cDNA sequence.

In one embodiment, a labeled GTP, is provided that includes an oligonucleotide; and GTP; wherein the GTP and the oligonucleotide are covalently linked via the 3' position of the sugar of the GTP and either the 3' end or 5' end of the oligonucleotide. In one embodiment, the labeled GTP has the Formula (ii):

Formula (II)

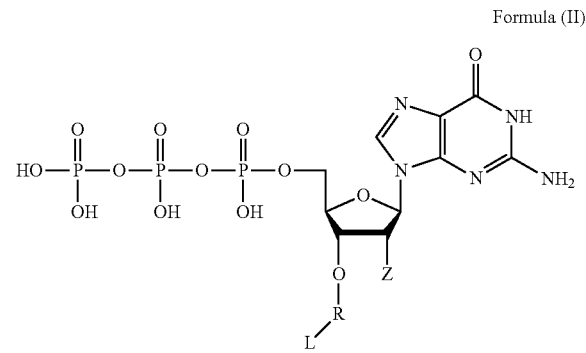

wherein: Z is H, OH, SH, $NH_2$, a lower alkyl, a lower acyloxy, a lower alkylamine, a lower acylamine, or a halogenyl; R is a linker; and L is an oligonucleotide. In one example, R contains a substituted or unsubstituted triazole. In another example, the oligonucleotide comprises an affinity tag.

In one embodiment, the RNA-oligonucleotide conjugate, comprising:

a target RNA comprising a 5' GTP cap; and an oligonucleotide that is joined by its 3' or 5' end to the 3' position of the sugar of the guanosine via a linker. The linker may include a substituted or unsubstituted triazole. The oligonucleotide may include an affinity tag.

The sample may contain any type of RNA, prokaryotic RNA, eukaryote RNA, a mixture of prokaryotic RNA and eukaryotic RNA. In some embodiments, the sample may comprise RNA from a microbiome.

In some embodiments, the sample may comprise RNA from a eukaryote. In these embodiments, the method may comprise, prior to step (a), enzymatically decapping the 5'-m$^7$Gppp capped RNA in the sample to produce the 5'-diphosphorylated RNA molecules of step (a). This step may be using any suitable deadenylase, e.g., a deadenylase having at least 90% identity to *Schizosaccharomyces pombe* HNT3 (SEQ ID NO: 15). This step may also use enzymes that belong to the HIT superfamily of nucleotidyltransferases and is referred to as APTX (RNA), also known as 5'deadenylase and Hnt3p. Two examples of such are the *Saccharomyces cerevisiae* APTX and the *Schizosaccharomyces pombe* APTX. These two enzymes demonstrate only 33% amino acid identity with each other. A further enzyme class belongs to the HIT superfamily of pyrophosphatases, the scavenger decapping enzymes (DcpS). Two examples of such are the *Saccharomyces cerevisiae* DcpS and the *Schizosaccharomyces pombe* DcpS (nhm1).

In some embodiments, the sample may comprise only eukaryotic RNA or a mixture of eukaryotic and prokaryotic RNA. In these embodiments, the method may comprise, prior to step (a): (i) dephosphorylating any 5' diphosphorylated or triphosphorylated RNA molecules in the sample to produce RNA molecules that contain a 5' hydroxyl or a 5' monophosphate; and, then, (ii) decapping any 5'-m$^7$Gppp capped mRNA molecules in the sample to produce the 5'-diphosphorylated RNA molecules of step (a). This embodiment should result in enrichment of a population of eukaryotic RNA molecules from the sample. This embodiment may be done using an RNA sample obtained from a microbiome, which may contain both eukaryotic and prokaryotic RNA.

In any embodiment, the method may further comprise enriching for poly(A) RNA using an affinity matrix that binds to poly(A). In these embodiments, the RNA population enriched by the method is full length eukaryotic mRNA, prokaryotic mRNA or any target RNA population to which a poly(A) tail has been selectively added to the 3' end. If implemented, the poly(A) enrichment is done at any step of the method, e.g., before step (a), in between steps (a) and (b) or after step (b).

The affinity tag added in step (a) of the method can be any suitable affinity tag. In some embodiments, the affinity tag may be biotin or DBT. The affinity tag may be placed directly on the reactive group as the label (L) or may be indirectly attached to the GMP via the label. For example, if an oligonucleotide is the label, then the affinity tag may be covalently linked to the free end of the oligonucleotide.

Some embodiments may comprise eluting the enriched target RNA from the affinity matrix. This can be done using biotin, if the RNA is captured on the affinity matrix via a DBT group or, alternatively, it can be done enzymatically (using an enzyme that cleaves the added affinity tag-labeled GMP from the RNA).

In certain embodiments, the affinity tag-labeled GMP has a cleavable linker. This cleavage reaction may be used to release enriched RNA from the affinity matrix. The release enriched RNA may be subsequently further enriched for full length mRNA or RNA to which a poly tail has been added by affinity binding of the released RNA to a poly d(T) containing matrix.

In some embodiments, enrichment of the target RNA may include an additional purification step for example, size-selection, gel electrophoresis, ion exchange, size-exclusion, phenol-chloroform extraction, alcohol precipitation (e.g. ethanol or isopropanol precipitation), adsorption beads (e.g. AMPURE beads), isopycnic gradient (e.g. CsCl gradient), affinity beads (e.g. streptavidin beads), liquid chromatography (e.g. HPLC), or hybridization (e.g. poly-dT beads or sequence-specific microarrays).

Some embodiments may comprise removing the modified GMP (e.g. an affinity tag labeled GMP) from the enriched RNA, to leave a 5'-monophosphate or a 5'-diphosphate terminus on the enriched RNA. Once the modified GMP is removed from the enriched RNA, the method may comprise ligating an adaptor onto at least the 5' end (i.e., the 5' end or the 5' and the 3' end) of the enriched RNA. Alternatively, a 5'adapter can be introduced by template switching which does not require removal of the modified GMP (e.g. an affinity tag labeled GMP). These adaptors containing priming sites can be used to amplify the RNA, e.g., by PCR. In an embodiment, a terminal transferase (New England Biolabs, Ipswich, Mass.) may be used to add for example, a string of G's at the 3' end of the cDNA which can then be used as a PCR priming site.

Some embodiments may comprise sequencing the enriched RNA. The method may be implemented in a variety of different ways so that a particular population of RNA molecules is enriched and sequenced.

For example, in some embodiments, the sequencing may be done by: (i) optionally eluting the enriched RNA from the affinity matrix; (ii) removing the affinity tag-labeled GMP from the 5' end of the enriched RNA; (iii) ligating an adaptor to at least the 5' end of the enriched RNA; (iv) making cDNA from the enriched RNA; and (v) sequencing the cDNA. In these embodiments, cDNA synthesis may be done using an oligo(dT) primer. If cDNA synthesis is done using an oligo(dT) primer, the method may optionally comprise: adding a 3' poly(A) tail to the RNA if the enriched RNA comprises RNA molecules that do not have a poly(A) tail (as is the case for most prokaryotic RNA, but some eukaryotic RNA molecules do not contain a poly(A) tail and can be isolated using this method); and/or enriching for poly(A) RNA using an affinity matrix that binds to poly(A). In these embodiments, the method may further comprise, after step (iv) and before step (v), amplifying the cDNA using primers that hybridize with the 3' end and the 5' end of the cDNA.

Present embodiments describe methods for adding an additional oligonucleotide to the 5' end of an RNA. This creates a number of novel possibilities for transcriptome analysis. For example, if an enzyme can either copy, read or translocate an RNA sequences from the 3' end to the 5' oligonucleotide without interruptions, the possibility exists to remove any inherent bias that arises through template switching, cap jumping or direct sequencing methods. Moreover, some enzymes in in vitro assays when reading or translocating an RNA from 3'-5', may skip the last few nucleotides at the 5' end of the RNA. The addition of the oligonucleotide can provide a means for the enzyme to read the target RNA to its last base on the 5' end even if it continues into the oligonucleotide. The enzyme might be, for example, a reverse transcriptase for cDNA synthesis, a helicase for nanopore sequencing, an RNA polymerase for RNA replication, or a modifying enzyme for stabilizing the transcript (see for example, (Garalde, D. R. et al. Nature Methods doi: 10.1038/nmeth.4577). In some embodiments, an enriched oligonucleotide 5' labeled RNA can facilitate sequencing in a nanopore device. In some embodiments, oligonucleotide attached at the 5' of the target RNA further comprises an affinity tag for enrichment prior to RNA sequencing.

In another example, the enriched RNA may comprise a poly(A) tail. In these embodiments, the method may comprise: (i) optionally eluting the enriched RNA from the affinity matrix; (ii) making cDNA from the enriched RNA in the presence of a template switching oligonucleotide, using an oligo(dT) primer that hybridizes to the poly(A) tail, wherein the reverse transcriptase used to make the cDNA switches templates from an RNA molecule to the template switching oligonucleotide during cDNA synthesis to produce cDNAs that contains a 5' end having the sequence of oligo(dT) primer and a 3' end containing the reverse complement of the template switching oligonucleotide; and (iii) sequencing the cDNA.

In these embodiments, the method may further comprise: adding a 3' poly(A) tail to the RNA where the RNA molecules do not otherwise have a poly(A) tail (e.g., as is the case for most prokaryotic RNA, and some eukaryotic RNA molecules including fragmented eukaryotic mRNA that can be enriched using this method); and/or enriching for poly(A) RNA using an affinity matrix that binds to poly(A). In these embodiments, the method may further comprise after (ii) and before (iii) amplifying the cDNA using primers that hybridize with the 3' end and the 5' end of the cDNA.

The sequence obtained by this method can be used for a variety of applications. For example, in some embodiments, the method may further comprise identifying transcriptional start sites (TSS) using the sequences of the enriched RNA. In some embodiments, the method may further comprise identifying splice variants in the sequenced RNA. In some embodiments, the method may further comprise analyzing operons using the sequences of enriched RNA.

In certain embodiments, the method may further comprise enzymatically adding a poly(A) tail to total RNA (prokaryotic and eukaryotic) prior to enrichment or to the enriched RNA so as to provide a site for oligo(dT) primer for cDNA synthesis. In some embodiments, a poly(dA) tail can be added to fragments of eukaryotic mRNA or other eukaryotic RNAs.

In certain embodiments, the method may further comprise enzymatically ligating an oligonucleotide adaptor to the 3' end prokaryotic RNA, wherein the method comprises: (i) eluting the enriched RNA from the affinity matrix; (ii) making cDNA from the enriched RNA using a primer that hybridizes to the oligonucleotide adaptor, wherein the reverse transcriptase used to make the cDNA switches templates from an RNA molecule to a template switching oligonucleotide during cDNA synthesis to produce cDNAs that contains a 5' end having the sequence of the primer and a 3' end containing the reverse complement of the template switching oligonucleotide; and (iii) sequencing the cDNA.

In certain embodiments, cDNA synthesis may be done using an oligo(dT) primer and the method optionally comprises: adding a 3' poly(A) tail to the RNA if no poly(A) is naturally present; and/or enriching for poly(A) RNA using an affinity matrix that binds to poly(A).

In general, in one aspect, a method is provided for forming a 5' capped labeled RNA. The method includes combining a preparation comprising uncapped RNA having a 5' diphosphate or 5' triphosphate with a capping enzyme and a labeled modified nucleotide, for example, a compound as described above, so as to convert the uncapped RNA into 5' capped labeled RNA. An additional step may include enriching labeled, capped RNA by immobilizing the labeled capped RNA on an affinity substrate and washing away the unlabeled RNA or where the label is an oligonucleotide, selectively amplifying the oligonucleotide labeled capped RNA. In one aspect, immobilized labeled capped RNA may be eluted from the affinity substrate prior to sequencing where the elution step is optional.

Also provided in one embodiment, is a method that includes adding an affinity tag-labeled GMP to the 5' end of 5'-diphosphorylated or 5'-triphosphorylated RNA molecules in a sample by incubating the sample with the labeled mononucleotide (Formula I);

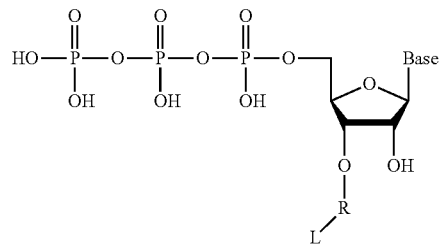

and a capping enzyme. In one embodiment, Formula I may be further modified by a small additional group (Z) at the 2' position in place of the OH group at that position wherein Z may be an H, SH, NH2, a lower alkyl, e.g. methyl, lower alkoxy, e.g. methoxy, lower acyloxy, e.g. acetoxy, lower alkylamine, e.g. methylamine, lower, acylamine, e.g. acetamide, or halogenyl, e.g. chloro.

In any embodiment, this method may further comprise (ii) enriching for RNA comprising the affinity tag-labeled GMP using an affinity matrix that binds to the affinity tag. In any embodiment, this method may further comprise chemically cleaving the cleavable linker, thereby releasing the enriched RNA from the affinity matrix. The chemically cleaving may be done by a palladium catalyst under aqueous conditions, for example. In any of these embodiments, the method may comprise ligating an adaptor to the free 3' OH generated by the chemical cleavage reaction.

Also provided is a method comprising: (i) adding an affinity tag-labeled GMP to the 5' end of 5'-diphosphorylated or 5'-triphosphorylated RNA molecules in a sample by incubating the sample with the chemically cleavable labeled mononucleotide shown above and a capping enzyme. In any embodiment, this method may further comprise (ii) enriching for RNA comprising the affinity tag-labeled GMP using an affinity matrix that binds to the affinity tag. In any embodiment, this method may further comprise chemically cleaving the cleavable linker, thereby releasing the enriched RNA from the affinity matrix. The chemically cleaving may be done by a palladium catalyst under aqueous conditions, for example. In any of these embodiments, the method may comprise ligating an adaptor to the free 3' OH generated by the chemical cleavage reaction.

In one aspect, the RNA in the preparation comprises a naturally capped RNA and prior to performing the method above, the naturally capped RNA is combined with a decapping enzyme for removing the cap wherein the uncapped RNA has a 5' terminal diphosphate or triphosphate.

Examples of capping enzymes include Vaccinia Capping Enzyme (VCE) (New England Biolabs, Ipswich, Mass.), a Bluetongue Virus capping enzyme, a Chlorella Virus capping enzyme, and a *Saccharomyces cerevisiae* capping enzyme. In one aspect, the label such as a receptor binding small molecule on the 5' labeled capped RNA is capable of targeting the 5' labeled capped RNA to cells in vivo. In another aspect, the 5' capped labeled RNA is capable of being detected in a complex environment by means of the label such as a fluorescent label in vivo or in vitro.

In general, in one aspect, a preparation is provided that includes a capping enzyme and a compound of the type described above. In another aspect, a kit is provided that includes the capping enzyme, a compound and instructions for selective labeling of RNA having 5' diphosphate or triphosphate with a labeled modified nucleotide as described above and optionally enriching for the same. The kit may further include an affinity matrix suitable for binding the labeled RNA.

In general in one aspect, a method is provided for enriching for prokaryotic non-rRNA in a mixture comprising eukaryotic and prokaryotic RNA. The method includes combining a mixture of RNA comprising eukaryotic and prokaryotic RNA with a compound described above, in the presence of a capping enzyme, so as to form 5' capped labeled prokaryotic non-rRNA; immobilizing the 5' capped labeled RNA; and removing unreacted RNA. In one aspect, the method further includes sequencing the 5' capped labeled RNA. In another aspect, the sequences are compiled into a transcriptome for a single organism or cell or a metatranscriptome for a plurality of different organisms or cells.

In general in one aspect, a method is provided for determining TSS of RNA, that includes: obtaining total RNA from prokaryotic cells or eukaryotic cells or a mixture of eukaryotic and prokaryotic cells; capping uncapped or decapped RNA with modified labeled nucleotide such as a compound described above, in the presence of a capping enzyme, thereby forming 5' capped labeled RNA; and sequencing the 5' capped labeled RNA so as to determine the TSS of RNA. An example of uncapped eukaryotic RNA with a 5' diphosphate or 5' triphosphate is nascent eukaryotic RNA. An example of uncapped prokaryotic RNA with a 5' diphosphate or triphosphate is mRNA and small RNAs.

In one aspect, 5' capped labeled RNA is fragmented prior to sequencing. In another aspect, the immobilized 5' capped labeled RNA is eluted and may be sequenced or hybridized to a probe for identifying the immobilized 5' capped labeled RNA wherein the step of hybridizing occurs when the RNA is immobilized or after the RNA is eluted from a matrix. In another aspect, the RNA sequences or the identified RNAs are compiled into a transcriptome or metatranscriptome. In another aspect, the RNA sequences or the identified RNAs are sequence specific markers (SSM) and/or TSS and may be available at single base resolution. The SSM may constitute a signature profile.

In general, in one aspect, a method is provided for selectively binding a target RNA in a RNA population to a matrix, wherein the target RNA is characterized by a 5' triphosphate or 5' diphosphate that has been capped with a labeled modified nucleotide such as a compound as described above, the capped target RNA having a binding affinity to a matrix; and eluting the target RNA from the matrix to form an at least twofold or threefold or fourfold or fivefold enriched preparation of the target RNA when the representation of the eluted target RNA is compared to the representation of the target RNA in the RNA population. In one aspect, the eluted oligonucleotides comprise TSS. The TSS may be identified with single base resolution. In another aspect, the eluted oligonucleotides are sequenced to obtain a 5' SSM. In another aspect, the oligonucleotides which may be immobilized on the matrix or eluted into solution may be hybridized to probes, for example, in an array.

In one aspect, the RNA population includes capped RNA and/or uncapped RNA with or without a 5' triphosphate or 5' diphosphate. In another aspect, the method comprises fragmenting the population of RNA or the target RNA into oligonucleotides prior to capping or after capping with a labeled modified nucleotide for binding labeled capped fragmented RNA selectively to the matrix. For example, the fragmented RNA may have a length in the range of 8-800 nucleotides. In another aspect, the 3' phosphate on the fragmented capped labeled RNA is removed with a kinase.

In one aspect, the target RNA may be a prokaryotic transcriptome, a metatranscriptome for example from a microbiome or from a eukaryotic tissue sample, a nascent eukaryotic RNA and/or eukaryotic mRNA.

In one aspect, the eluted enriched target RNA is sequenced and the sequencing reads are quantified. In another aspect, the 5' TSS in the target RNA are quantified to obtain SSM for the RNA population. In one aspect, the SSM may be correlated with a phenotype of a eukaryotic host or a complex mixed population of microbes. In one aspect, target RNA with a 5' triphosphate or 5' diphosphate is labeled with (i) DBT or a derivative thereof to form a cap for binding reversibly to the matrix; or (ii) an oligonucleotide to form a cap for cap jumping and selective adapter dependent amplification. In a further aspect, biotin may be added for eluting the target RNA from the matrix.

Another aspect of the method includes decapping any capped RNA in the RNA population for recapping with a labeled modified nucleotide. Adapters may be added to the decapped ends of the eluted RNA for reverse transcribing to DNA and amplifying the DNA prior to sequencing. After sequencing, TSS may be obtained at single base resolution In general in one aspect, a method is provided that includes selectively labeling oligonucleotides with a 5' triphosphate or 5' di-phosphate with a labeled modified nucleotide such as described above. In one aspect, the fragmented RNA have a length in the range of 5-1000 nucleotides preferably 8-800 nucleotides or 10-500 nucleotides. In another aspect, the labeled target oligonucleotides include TSS. In another aspect, the labeled target oligonucleotides are sequences to obtain 5' SSM. Sequencing of the target oligonucleotides can provide single base resolution. SSM can be assembled into a signature profile for a transcriptome or metatranscriptome and can then be correlated with a phenotype of a eukaryotic or prokaryotic cell or cells.

In another aspect, the eluted target oligonucleotides are quantified by obtaining sequencing reads for each target oligonucleotide. The label associated with the modified nucleotide may be DBT-GTP or a derivative thereof.

Target RNA having a labeled modified nucleotide at the 5' end can be distinguished in a mixture of molecules by means of the label on the modified nucleotide. A suitable label can be selected so as to achieve one or more of the following: enrichment of a target RNA, for example using DBT; selective amplification of a target RNA, for example using an oligonucleotide; labeling of a target RNA for example using a fluorescent label; sequencing of a target RNA after enrichment; stabilization of a target RNA for example by protection against enzyme digestion; or during in vivo administration of a target RNA; and targeted delivery of an RNA in vivo.

This disclosure also provides, among other things, a compound represented by Formula (I):

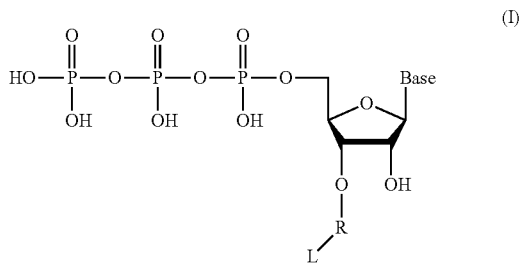

or a salt thereof is provided where the Base is a purine or a pyrimidine, R is a linker; and L is a label. In one aspect, the label is selected from the group consisting of an affinity label, a detection label, a reactive group, an oligonucleotide, and a combination thereof. For example, the label can be an affinity label selected from the group consisting of a biotin moiety, DBT, avidin, streptavidin, protein A, maltose-binding protein, poly-histidine, HA-tag, c-myc tag, FLAG-tag, SNAP-TAG, S-tag, and GST. In one example of a detection label, the label may be a fluorescent label. In one aspect, the base is a purine where the purine is guanosine, inosine or an analog thereof. In one example, the compound may be 3'-O-(2-aminoethylcarbamoyl) (EDA)-biotin GTP or 3'-DBT-tetraethylene glycol (TEG)-GTP.

BRIEF DESCRIPTION OF THE FIGURES

The patent or application file contains at least one drawing executed in color. Copies of this patent or patent application publication with color drawings will be provided by the Office upon request and payment of the necessary fee.

The figures and drawings are intended to illustrate one or more versions of the compositions and/or methods described herein. Unless stated otherwise, these are not intended to be limiting for the purpose of interpreting the scope of any claims.

FIGS. 2A-2B shows the chemical structures of two different labeled mononucleotides. FIG. 2A is the chemical structure of purified 3'-DBT-TEG-guanosine 5' triphosphate (DTB-GTP) with a linker attached to the oxygen at the 3' position of the ribose.

FIG. 2B is the chemical structure of 2'-DBT-TEG-guanosine 5' triphosphate with a linker attached to the oxygen at the 2' position of the ribose.

FIG. 2C shows labeled modified nucleotide and target transcript RNA where the label is an oligonucleotide.

FIG. 2D shows the reaction product of labeled modified nucleotide and target transcript RNA where the label is an oligonucleotide.

FIG. 13 depicts a gel stained with SYBR® gold (Molecular Probes, Eugene, Oreg.). A 25mer T7 triphosphorylated transcript was incubated with VCE in the absence (none) or the presence of 0.5 mM GTP or 0.5 mM 3'DTB-GTP. The reactions were electrophoresed on a 15% TBE (Tris Borate EDTA) Urea polyacrylamide gel.

FIG. 14 depicts a 25mer T7 5' diphosphorylated transcript incubated with VCE in the absence (none) or the presence of 0.5 mM GTP or 0.5 mM 2' DTB-GTP or 0.5 mM 3' DTB-GTP. The reactions were electrophoresed on a 15% TBE Urea polyacrylamide gel and stained with SYBR gold. The diphosphorylated transcript had been prepared from the 25mer triphosphate transcript by incubation with *S. cerevisiae* Cet1p. As a demonstration of the conversion by CetP1 to the diphosphate the transcript was capped with *S. cerevisiae* CEG, whereas the 25mer triphosphate was not a substrate for *S. cerevisiae* CEG (data not shown).

FIG. 15 depicts 32P uniformly labeled 300-mer T7 transcript incubated with VCE and either GTP or 3'DTB-GTP or 2'DTB-GTP (See Methods). The transcripts were adsorbed to streptavidin beads washed and eluted with biotin. The percent of the transcript recovered by elution was determined by scintillation counting.

FIG. 16 depicts a 21-mer synthetic 5' monophosphate RNA (Integrated DNA Technologies, Coralville, Iowa) lanes 1 and 2 or 25mer T7 triphosphorylated transcript lanes 3 and 4 incubated with 0.5 mM 3'DTB-GTP. Lanes 1 and 3 contained no VCE; lanes 2 and 4 contained VCE. The reactions were electrophoresed on a 15% TBE Urea polyacrylamide gel and stained with SYBR gold.

FIG. 17 depicts a 3' DTB-GTP capped 25mer T7 transcript incubated with 0, 0.1, 0.3 and 1.0 μl of RppH for 30 minutes at 37° C. in 1× Thermopol® Buffer (New England Biolabs, Ipswich, Mass.). The reactions were electrophoresed on a 15% TBE Urea polyacrylamide gel and stained with SYBR gold.

FIG. 18 depicts a mixture of the 25-mer transcript capped with either 3' DTB-GTP or GTP incubated with 0, 0.005, 0.05, and 0.5 ul of RppH for 30 minutes at 37° C. in 1× Thermopol Buffer. The reactions were electrophoresed on a 15% TBE Urea polyacrylamide gel and stained with SYBR gold.

FIG. 19 depicts: Panel A, Schema of Cappable-seq protocol and the associated control library. Panel B, Replicate analysis. The correlation coefficient between replicate 1 and replicate 2 relative read score (RRS) is 0.983. Panel C, Enrichment score as a function of the mean of RRS for the 36078 putative TSSs found in *E. coli* grown on minimal media. In blue are TSS that are enriched in Cappable-seq library. Grey are positions that are depleted in Cappable-seq. The removal of depleted positions eliminates 1354 spurious TSS primarily located in ribosomal loci.

FIG. 20 depicts: Panel A, Histograms showing the distribution of reads (in % of total mapped reads) mapping to intergenic regions (light blue), protein coding regions (purple), transfer RNA (tRNA) (red) and rRNA (dark red) for the unenriched control library, Cappable-seq library, Xrn1 treated library and Xrn1 minus library. Cappable-seq library show a strong depletion of reads mapping to rRNA compare to control while dRNA-seq show an enrichment of reads mapping to rRNA and tRNA in the Xrn1 treated library. Panel B, Enrichment/depletion of known processed sites in Cappable-seq and dRNA-seq compare to controls, function of the mean of normalized trimmed read counts at these sites. Most of the processed sites are depleted in Cappable-seq while most of the processed sites from tRNA (blue) and some rRNA (orange) are enriched in dRNA-seq. The rRNA processed sites enriched in dRNA-seq correspond to the processed site of the mature 5S RNA. Panel C, Enrichment score for all positions in the genome passing read threshold (RRS>1.5) in either the assay or control library for both Cappable-seq and dRNA-seq experiments. Negative scores are depleted regions and positive scores are enriched regions in Cappable-seq or dRNA-seq compared to control. Red points are annotated TSS from Regulon DB.

FIG. 22 depicts: Panel A, Plot of the total number of clusters function of the distance cutoff (in bp) for the real data (black) and randomly generated positions across the *E. coli* genome (blue). At a distance cutoff of 5, the estimated percentage of dependent and independent events are 80% and 3% respectively. Panel B, Sequence logo at promoters of precise and imprecise TSS. The information content at each position is measured in bits. Positions varies from −15 base to +2 up and downstream the TSS (+1). Position weight matrices logo generated using WebLogo (Crooks, et al, *Genome Res* (2004) 14:1188-1190).

FIG. 23 depicts: Panel A, Distribution of enrichment scores for TSS that are overlapping with the composite dataset of known TSS (red) and Cappable-seq specific TSS (green). Panel B, Distribution of RRS for TSS common to the composite dataset of known TSS (red) and Cappable-seq specific TSS (green).

FIG. 24 depicts characteristics of the promoter region found using Cappable-seq. Panel A, The average phastcon score is plotted for each position from −100 bases upstream to +30 bases downstream of the Cappable-seq TSS (position 0) and the Cappable-seq specific TSS. Panel B, Sequence logo upstream of all Cappable-seq TSS and Cappable-seq specific TSS. Panel C, Over-represented motifs found in the promoter regions of Cappable-seq and Cappable-seq specific datasets. Panel D, Fraction of promoters having the sigma 70-10 motifs in the composite dataset of known TSS, Cappable-seq TSS, TSS common to Cappable-seq and the composite dataset of known TSS, and Cappable-seq specific TSS.

FIG. 25 depicts: Panel A, Sequence logo of the nucleotide bias from −2 to +2 position of TSS. Panel B, Distribution of the strength of the TSS (in RRS in Cappable seq) as classified according to their −1+1 configuration with R being purine (A or G) and Y being pyrimidine (C or T). Panel C, Relative abundance of reads for each of the 16 possible TSS −1+1 dinucleotides. Blue boxes are YR motifs, green boxes are YY or RR motifs and pink boxes are RY motifs. Percentages corresponds to the percentage of TSS having the aforementioned −1+1 configuration. Panel D, Over-represented motifs at −35 and −10 bp upstream of TSS with the −1C+1C dinucleotide configuration.

FIG. 26 depicts: Panel A, Distribution of the number of sense and antisense intragenic TSS as a function of the position within genes. Panel B, Box plot representing the distribution of the TSS strength (RRS score) for intergenic (red), sense intragenic (blue) and antisense intragenic (grey) TSS. Panel C, Distribution of intragenic sense (blue) and antisense (grey) TSS strength as a function of their position within genes.

FIG. 27 depicts the frequency of intragenic TSS relative to the first, second and third position of the codon for (panel A) the sense TSS and (panel B) the antisense TSS. Graphics on the left represent the overall frequency of TSS at each codon position across the entire gene length while the graphic on the right represent the frequency of TSS at each codon position as a function of the relative position within the coding gene (in 10% increments of the total gene length).

FIG. 28 depicts the analysis of TSS for four representative species across four phyla of bacteria. Panel A, IGV display of read distribution in Akkermansia muciniphila in both biological replicates. Panel B, Promoter structures in all four species generated with Weblogo (for Biological replicate 1). The X axis represent the distance away from the TSS found by Cappable-seq. Y axis represent the amount of information present at every position in the sequence, measured in bits. Panel C, Percentage of leaderless TSS in replicate 1. Panel D, Read genomic distribution for replicate 1. Panel E, The correlation coefficient of RRS of TSS in the four representative species between the two biological replicate (two mouse gut microbiome) is 0.81.

TERMS

Figure 1:
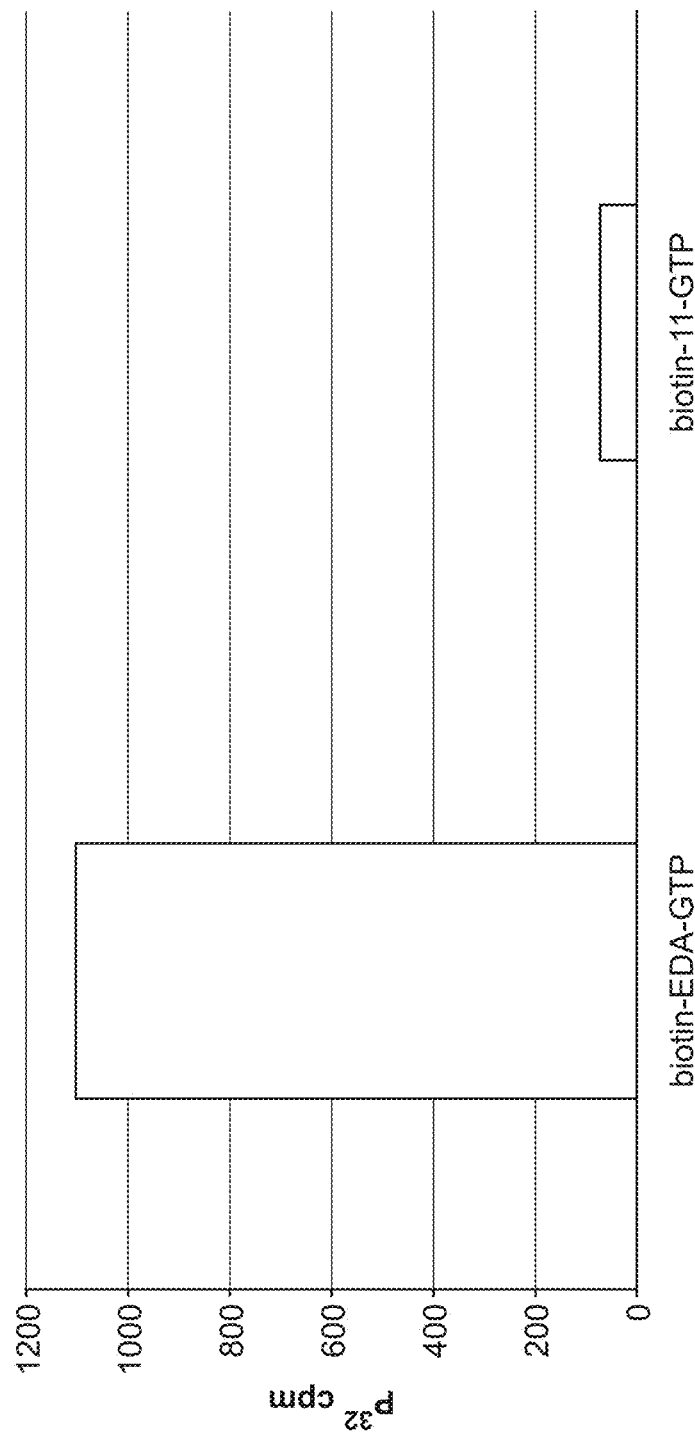
FIG. 1 is a histogram that contrasts the label position in the ribose moiety versus the purine base of a labeled compound for RNA capping. Biotin-EDA-GTP (Jena Biosciences, Germany) has biotin attached as a mixture of the 2' and 3' OH positions on the ribose ring. Biotin-11-GTP (Perkin Elmer, Waltham, Mass.) has biotin covalently linked to the guanine base. As described in Example 1, the RNA that was reacted with 2'/3' biotin EDA GTP was selectively bound to streptavidin as compared to transcript reacted with biotin-11-GTP. For these purposes labeling a position on the nucleotide base is much less effective than labeling a position on the ribose.

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise.

As used herein, the articles "a", "an", and "the" relate equivalently to a meaning as singular or plural unless the context dictates otherwise.

As used herein and as conventionally understood by those in the relevant art, a "nucleotide" comprises a base, a sugar and one or more phosphate groups. The base (also referred to as a "nitrogenous base" or a "nucleobase") is typically a purine or pyrimidine. The sugar is typically a five-carbon ribose (as in ribonucleotides) or a 2-deoxyribose (as in deoxyribonucleotides), which is bound via a glycosidic linkage to the base. Nucleotides typically have one, two or three phosphate groups (mono-, di- or tri-phosphates). Generally, the phosphate groups form a chemical bond at the 5-carbon position of the sugar, although they can also bond at the 2 or 3-carbon positions of the sugar group. Cyclic nucleotides form when a phosphate group is bound to two hydroxyl groups on the sugar. A "nucleoside" comprises a nucleobase and sugar. A nucleotide can thus also be called a nucleoside mono-, di- or tri-phosphate.

"Signature" refers to a collection of sequence specific markers (SSM).

"Sequence specific markers" (SSM) refers to the 5' terminal nucleic acid sequence of RNA molecules.

"Biological sample" refers to a sample from an environment within or external to a biological organism that is composed eukaryotic and/or prokaryotic cells. Examples of biological samples include feces, skin, saliva, lesion, soil, and water, a sample of organisms from a fermentation vessel or other organisms evolved from an environmental constraint that results in adaptive evolution.

"Chemoselective group", refers to one of a pair of groups that selectively react with one another to form a covalent bond. Chemoselective functional groups of interest include, but are not limited to, thiols and maleimide or iodoacetamide, as well as groups that can react with one another via a click reaction, e.g., azide and alkyne groups (e.g., cyclooctyne groups).

The term "click reaction" refers to a 1,3-cycloaddition between an azide and alkyne to form a five membered heterocycle. In some embodiments, the alkyne may be strained (e.g., in a ring such as cyclooctyne) and the cycloaddition reaction may done in copper free conditions. Dibenzocyclooctyne (DBCO) and difluorooctyne (DIFO) are examples of alkynes that can participate in a copper-free cycloaddition reaction, although other groups are known (see, e.g., Kolb, et al (Drug Discov Today 2003 8: 1128-113), Baskin et al (Proc. Natl. Acad. Sci. 2007 104: 16793-16797) and Sletten, et al (Accounts of Chemical Research 2011 44: 666-676) for a review of this chemistry).

"Target RNA" refers to an RNA that has a 5' diphosphate or triphosphate or can be converted to an RNA with 5' diphosphate or triphosphate by decapping or by kinase.

"Distinguishing an RNA" refers to any of: enrichment, selective amplification, selective labeling, sequencing and selective protection from enzyme digestion.

As used herein, the term "affinity matrix that binds to biotin" refers to a support (e.g., beads, which may be magnetic) that is linked to streptavidin or avidin, or a functional equivalent thereof.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

As used herein, the term "oligonucleotide" refers to a multimer of at least 2, e.g., at least 5, at least 10, at least 15 or at least 30 nucleotides. In some embodiments, an oligonucleotide may be in the range of 2-100 nucleotides in length, e.g., 5-50 nucleotides. Any oligonucleotide used herein may be composed of G, A, T and C, or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although many others are known. As noted above, an oligonucleotide may be an LNA, a PNA, a UNA, or a morpholino oligomer, for example. The oligonucleotides used herein may contain natural or non-natural nucleotides or linkages. (e.g., a phosphothioester linkage).

DETAILED DESCRIPTION OF EXEMPLARY EMBODIMENTS

Figure 31:
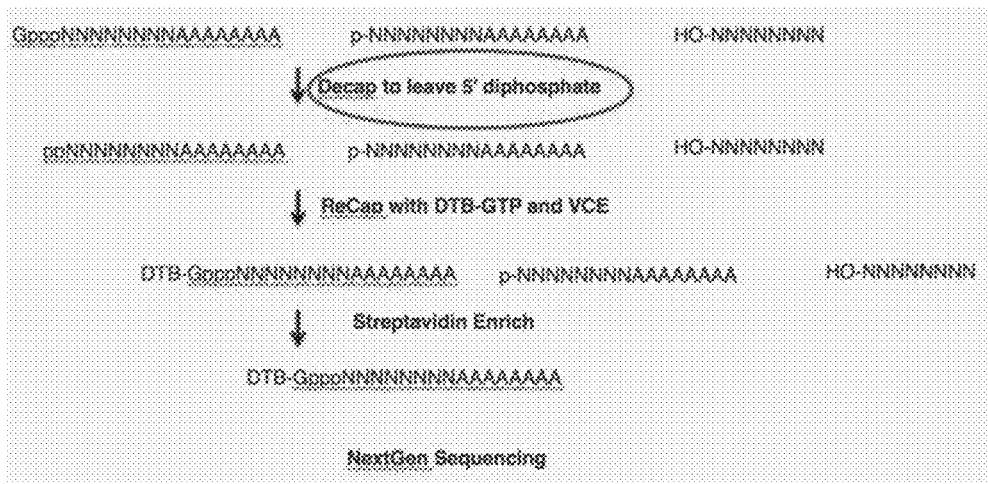
FIG. 31 illustrates a way for enriching for capped mRNA, by decapping the RNA and then recapping the RNA with a desthiobiotinylated or biotinylated nucleotide. As shown, RNA molecules that have been produced by mechanical or enzymatic breakage should have a 5'monophosphate terminus or a 5'-OH-terminus, and, as such, are not recapped using VCE and DTB-GTP or biotin-GTP (B-GTP). If the RNA is re-capped with DBT, it can be released from the support. If the RNA is re-capped with biotin, it can be processed while it is immobilized to the support. Example RNAs (SEQ ID NO: 20 and SEQ ID NO: 21) are shown with the indicated 5' features.

Provided herein, among other things, is a method of labeling, and optionally enriching, for a population of RNA molecules in a mixture of RNAs (e.g., a mixture of RNA molecules that may contain any combination of RNA molecules that have a 5' $m^7$Gppp cap, RNA molecules that have a 5' triphosphate, RNA molecules that have a 5' diphosphate, RNA molecules that have a 5' monophosphates and/or or molecules that have a 5' hydroxyl). In some embodiments, this method may comprise: (a) adding an affinity tag-labeled GMP to the 5' end of 5'-diphosphorylated or 5'-triphosphorylated RNA molecules in a sample by incubating the sample with an affinity tag-labeled GTP and a capping enzyme; and (b) enriching for RNA comprising the affinity tag-labeled GMP using an affinity matrix that binds to the affinity tag. In some embodiments, the 5'-diphosphorylated or 5'-triphosphorylated molecules in the sample may be the 5' ends that naturally occur in a population of RNA molecules, e.g., bacterial RNA. In other embodiments, the 5'-diphosphorylated or 5'-triphosphorylated molecules in the sample may be produced enzymatically by decapping eukaryotic RNA molecules that contain a 5' m$^7$Gppp cap using a decapping enzyme, as illustrated in FIG. 31.

Figure 32:
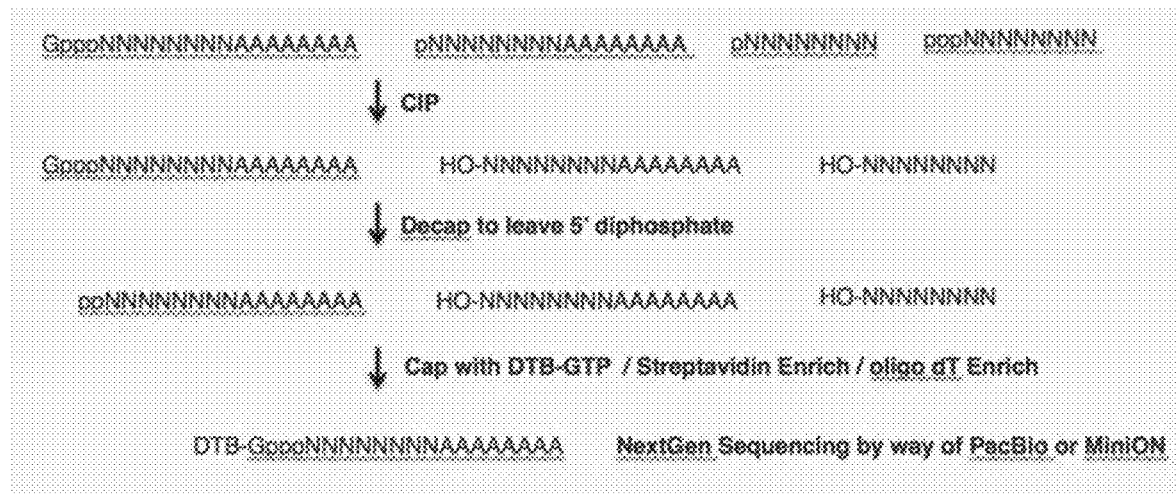
FIG. 32 illustrates a way that for excluding RNA with a triphosphate terminus from a capping reaction by first treating the RNA with CIP. Example RNAs (SEQ ID NO: 20 and SEQ ID NO: 21) are shown with the indicated 5' features.
Figure 33:
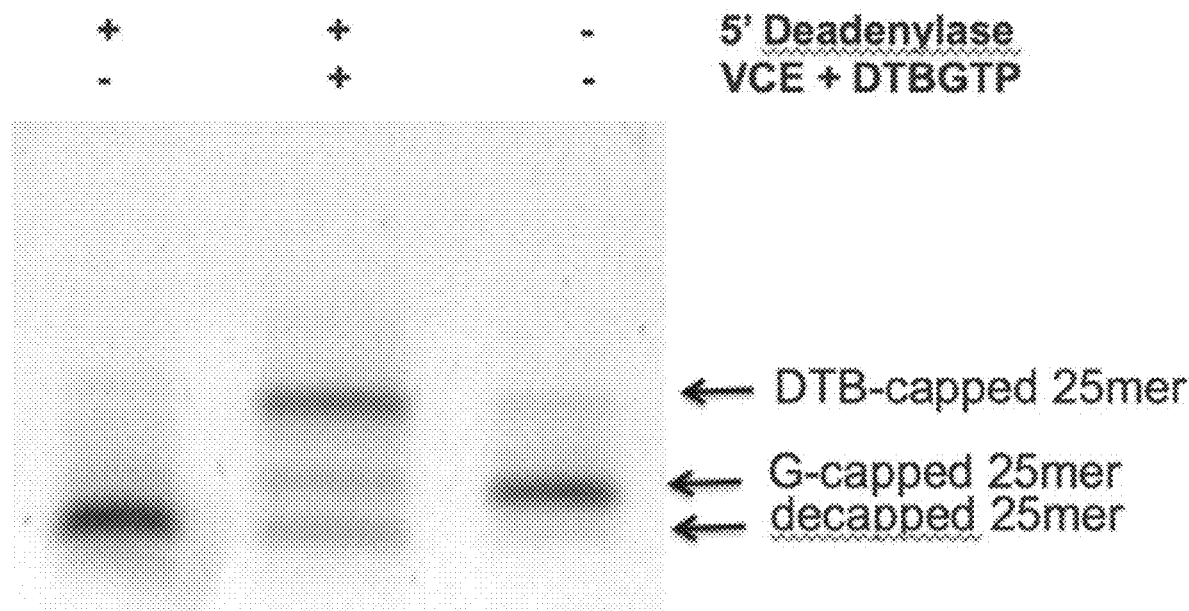
FIG. 33 shows that a $^7$mG capped transcript can be decapped by a 5' deadenlase and then recapped with a desthiobiotinylated nucleotide.
Figure 34:
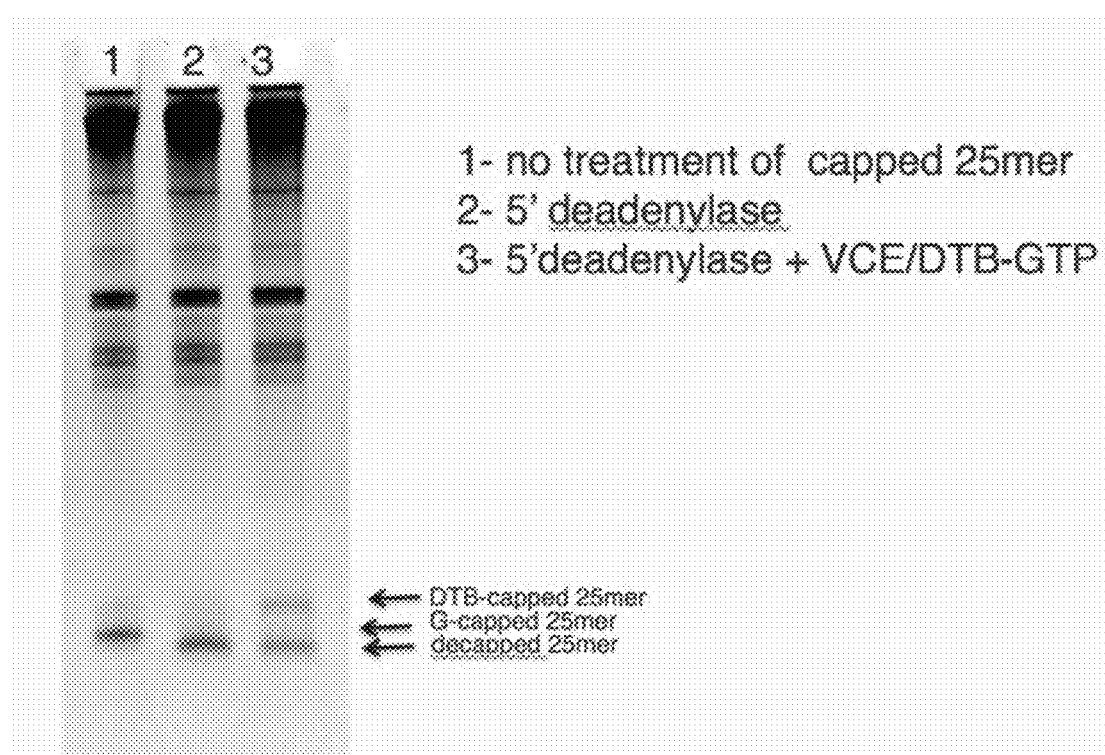
FIG. 34 shows that a $^7$mG capped transcript can be decapped by a 5' deadenlase and then recapped with a desthiobiotinylated nucleotide in the presence of *E. coli* RNA.
Figure 35:
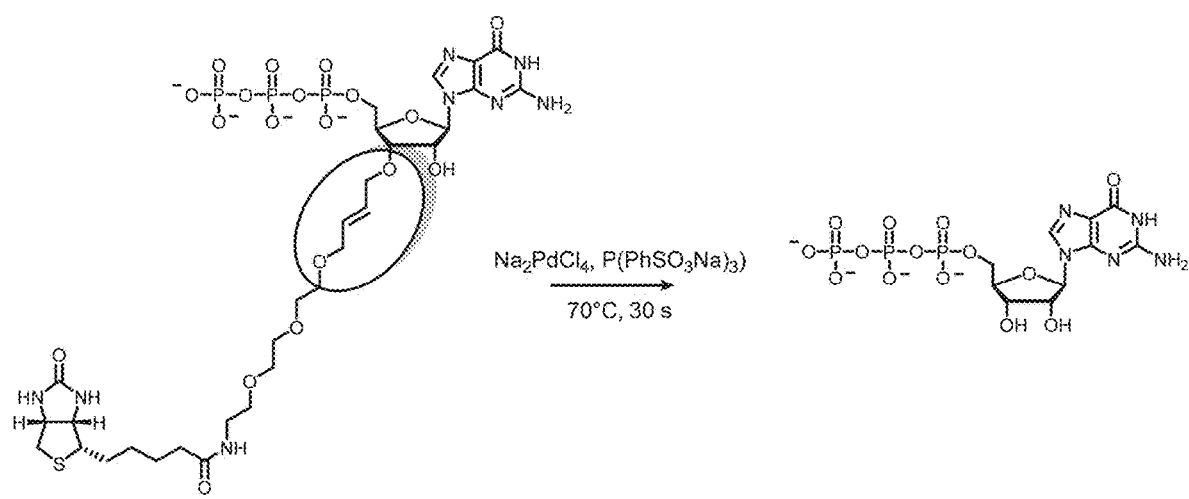
FIG. 35 shows the chemical structure of a cleavable 3'-biotin labeled guanosine 5'-triphosphate, wherein the cleavable linker comprises a 3'-O-allyl linkage. The palladium catalyzed reaction cleaves the 3'-O-allyl linker and regenerates a free 3'-OH guanosine 5'-triphosphate.

Depending on how the method is implemented, method can be used to enrich for: eukaryotic RNAs that have a 5' m$^7$Gppp cap; eukaryotic RNAs that have a 5'm$^7$Gppp cap and a poly(A) tail (e.g., full length mRNAs); or prokaryotic RNAs that have a triphosphate cap (which RNAs may or may not be full length), as well as other types of RNA, from a sample that comprises eukaryotic RNA, prokaryotic RNA or a mixture of both eukaryotic and prokaryotic RNA. For example, prokaryotic RNA can be enriched from such a sample by (a) adding an affinity tag-labeled GMP to the 5' end of 5'-diphosphorylated or 5'-triphosphorylated RNA molecules in a sample by incubating the sample with an affinity tag-labeled GTP and a capping enzyme; and (b) enriching for RNA comprising the affinity tag-labeled GMP using an affinity matrix that binds to the affinity tag, as discussed above. Alternatively, if enrichment of a eukaryotic RNA is desired, then the sample may be first treated with a phosphatase or the like (e.g., an alkaline phosphatase, a 5' RppH or an apyrase), thereby converting all tri- and di-phosphate termini (which are naturally present in bacterial RNA) to non-tri or di-phosphate termini, followed by a decapping reaction using a 5'deadenylase (see for example, U.S. Pat. No. 8,486,666 or S. pombe HNT3 (SEQ ID NO: 15) or variant thereof) and then capping the decapped molecules with a capping enzyme (e.g., VCE) using as a substrate, an affinity tag-labeled GMP, such as shown in FIG. 32 or for example, biotin labeled GMP.

A population of RNA molecules that have at each 5' terminus a modified GTP and at each 3' end a poly adenylated terminus represent the full length population of eukaryotic mRNA and may contain all the possible splice variant RNA molecules. The above embodiments may be coupled with a step that recognizes poly(A) either as a natural adapter for amplification or as a tag for binding to a poly d(T) affinity substrate (e.g., oligod(T) beads, which may be magnetic), to isolate and concentrate full length RNAs (particularly full length eukaryotic RNAs).

Accordingly, the full length G-capped RNAs can be isolated by imposing the additional selective procedure of capturing the 3' poly adenylated terminus of G-capped RNA from a collection of RNAs.

After the population of RNA molecules has been enriched, the RNAs may be converted to cDNA, optionally amplified, and sequenced by a variety of methods. For example, in some embodiments, cDNA synthesis may be primed by an oligod(T) primer. If the target population of RNA does not already have a poly(A) tail, then in some embodiments, a "synthetic" poly(A) tail may be added to the RNA, e.g., using a polyA polymerase or by ligating an oligonucleotide onto those molecules. Alternatively, an adaptor can be ligated onto the 3' end of the enriched RNAs, and cDNA synthesis may be primed by a primer that hybridizes to the added adaptor.

In some embodiments, cDNA may be made by enzymatically removing the affinity tag-labeled GMP (for examples using apyrase (New England Biolabs, Ipswich, Mass.), RppH (New England Biolabs, Ipswich, Mass.), RNA polyphophatase (Epicentre, Madison, Wis.) or TAP (New England Biolabs, Ipswich, Mass.) and then ligating adaptors onto at least the 5' ends of the RNA molecules. Alternatively, an adaptor sequence may be added onto the 5' end of a cDNA by template switching (see, generally Matz, et al Nucl. Acids Res. 1999 27: 1558-1560 and Wu, et al., Nat Methods. 2014 11: 41-6). In such template switching methods, the reverse transcriptase switches template from an RNA molecule to a synthetic oligonucleotide, thereby copying the sequence of the synthetic oligonucleotide onto the end of the cDNA. In embodiments that rely on template switching, the affinity tag-labeled GMP does not need to be removed beforehand.

Reverse transcriptases of the Maloney Murine Leukemia Virus (MMLV) family are known to add several non-templated nucleotides during cDNA synthesis. These added nucleotides can be advantageous to cDNA library preparation when an oligonucleotide containing complimentary nucleotides to these non-templated additions is added to the reverse transcription reaction. In this case, the reverse transcriptase is able to switch from the original RNA template molecule to this new "template switching oligonucleotide" and continue the cDNA synthesis. Consequently, adapter sequences can be incorporated into the cDNA molecule without the use of 5'-ligation technology or additional PCR steps currently used for RNAseq, thus eliminating the known biases currently observed with these techniques. Furthermore, template switching with 5'-capped RNA is more efficient and less biased than with uncapped RNA and thus reflects an important benefit to capping RNA samples prior to library preparation with template switching.

To further reduce any bias associated with cDNA library preparation of a sample of RNAs containing different sequences, the template switching oligonucleotide can be incorporated directly into a labeled 5'-cap structure on the target RNA using appropriate chemistry (i.e. copper-catalyzed azide-alkyne cycloaddition). With this modification, template switching will be even more efficient as the reverse transcriptase can read through directly to the adapter sequence, further reducing sequence-specific biases. In some embodiments, the method of making a cDNA comprises reverse transcribing an oligonucleotide-labeled target RNA to make a cDNA, wherein the cDNA having the sequence at the 3'end corresponding to a complement of the oligonucleotide label linked via the cap at the 5'end of the target RNA, and optionally, a polyT sequence at the 5' end of the cDNA. In some embodiments, oligonucleotide attached at the 5' of the target RNA further comprises an affinity tag for enrichment prior sequencing.

After the cDNA has been made, the cDNA be amplified and/or cloned, and then sequenced using suitable phased sequencing method. Sequencing may be done in a variety of different ways, e.g., using Illumina's reversible terminator method, Roche's pyrosequencing method (454), Life Technologies' sequencing by ligation (the SOLiD™ platform), Life Technologies' Ion Torrent platform, Pacific Biosciences' fluorescent base-cleavage method. In some embodiments, however, the products may be sequenced using a long read sequencing approach such as nanopore sequencing (e.g. as described in Soni, et al., Clin Chem 53: 1996-2001 2007, and developed by Oxford Nanopore Technologies) or Pacific Biosciences' fluorescent base-cleavage method (which currently have an average read length of over 10 kb, with some reads over 60 kb). Alternatively, the products may be sequenced using, the methods of Moleculo (Illumina, San Diego, Calif.), 10× Genomics (Pleasanton, Calif.), or NanoString Technologies (Seattle, Wash.). In these methods, the sample is optionally diluted and then partitioned into a number of partitions (wells of a microtitre plate or droplets in an emulsion, etc.) in an amount that limits the probability that each partition does not contain two molecules of the same locus (e.g., two molecules containing the same gene). Next, these methods involve producing indexed amplicons of a size that is compatible with the sequencing platform being used (e.g., amplicons in the range of 200 bp to 1 kb in length) where amplicons derived from the same partitions are barcoded with the same index unique to the partition. Finally, the indexed amplicons are sequenced, and the sequence of the original, long, molecules can be reconstituted using the index sequences. Can also be done using barcoded transposons (see, e.g., Adey Genome Res. 2014 24: 2041-9 and Amini Nat Genet. 2014 46: 1343-9), and by using the "reflex" system of Population Genetics Technologies (Casbon, Nucleic Acids Res. 2013 41:e112). Additional alternatives include 10× Genomics (Pleasanton, Calif.) or other developed sequencing platforms.

Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and US patent application publications US 2006/0003171 and US 2009/0029477.

A population of full length RNAs enriched by this method should contain all possible splice variants. Examination of the sequence of the enriched molecules can provide insight into RNA splicing, TSS and operon analysis.

As noted above, some embodiments of the method may make use of a deadenylase for providing a capable 5' end. In some embodiments, the deadenylase may have an amino acid sequence that is at least 90% identical, e.g., at least 95% identical at least 98% identical, or at least 99% identical to a wild type amino acid sequence (e.g., SEQ ID NO:15).

The problem of sequencing target RNA species in prokaryotes has been made more difficult by the presence of a large amount of rRNA which varies in sequence between strains and other contaminating polynucleotides. Existing depletion techniques have a disadvantage in that some sequence specific to rRNA must be known to prepare suitable labeled oligonucleotides (RiboMinus™, Life Technologies, Grand Island, N.Y.).

Embodiments described herein are directed to enrichment of target RNAs and not depletion of specific contaminants. In this approach, the target RNA becomes immobilized and the unwanted RNA is removed by washing. An advantage of enrichment over depletion is that for enrichment, the removal of unwanted molecules is more effective and comprehensive than occurs through depletion which actually targets specific contaminants but may not remove all contaminants of a single species and none of the species of contaminant that is not targeted. When the target RNA is in low abundance, enrichment of the target RNA has the advantage of obtaining much larger amount of material that can be used for further analysis. Although not required, enrichment methods and depletion methods may be used sequentially.

In order for enrichment to be successfully accomplished, the target RNA should be efficiently recognized. Here this is achieved by labeling only those RNA molecules with a 5' tri-phosphate or di-phosphate regardless of its sequence or size. This is accomplished by using a modified labeled nucleotide and a capping enzyme. It has been shown here that capping enzymes such as VCE is capable of using a labeled modified nucleotide as a substrate when the modified nucleotide has a linker and a label.

To form the modified nucleotide, the specific location on the ribose for attaching the linker and label enables efficient capping. A modified nucleotide carrying a biotin label where the linker and label substitute for the hydrogen on the oxygen at carbon 3 of the ribose of the nucleotide is recognized by the capping enzyme and attached as a cap to the RNA. Whereas if the same linker and label replaces the hydrogen on the oxygen at carbon 2 of the ribose of the nucleotide, the capping enzyme does not efficiently attach the labeled modified nucleotide to the RNA (see FIG. 2A-2B, FIG. 3).

The capping enzyme is observed to be tolerant of the type of linker and label providing the position on the ribose is maintained. For example, no significant effect on capping efficiency is seen (see for example an EDA linker or a TEG linker). Similarly no significant effect on capping efficiency was observed when the label was varied (see for example, biotin and DBT) (see for example FIG. 1 and FIG. 4).

Embodiments provide uses for the enrichment methods. These include:

(a) Expression profiling of organisms in varying conditions by obtaining sequences of RNA populations excluding rRNAs. In prokaryotes, mRNA has a 5' triphosphate where eukaryotic mRNA is capped. However, eukaryotic mRNA can be decapped with a 5' deadenylase as described below and then recapped with labeled modified nucleotides for enrichment from eukaryotic rRNA. RRNA has a 5' monophosphate and is therefore not amenable to decapping and recapping whereas eukaryotic mRNA is amenable to decapping and recapping. This method is particularly useful where the sequence of mRNAs may be unknown prior to analysis. This approach can reveal the presence, absence and biome characteristics of endosymbionts and/or parasites in a host.

(b) Transcriptomics of individual organisms involves analyzing all or a specific subset of non-rRNA species after enrichment as described herein. Meta-transcriptomics of mixed populations of cells such as may be found in a tissue or in a microbiome or environmental samples can also be determined after enrichment and removal of rRNA. Optionally a molecular signature of the meta-transcriptome can be obtained by digital gene expression profiling. In one example, where a microbial population in the context of a eukaryotic organism is analyzed, a small amount of prokaryotic mRNA of interest can be enriched while the large population of non-target RNAs include rRNAs, tRNA and other so-called "house-keeping RNA" in addition to eukaryotic mRNA, rRNA and tRNAs can be removed.

By way of illustration, example 4 describes enrichment of mRNA from *E. coli* from a mixture of total human RNA and total *E. coli* RNA. Universal Human Reference (UHR) RNA (Agilent) was mixed with total *E. coli* RNA and incubated with 3' DBT-TEG-GTP and VCE. An aliquot of total RNA was saved while the remainder was adsorbed to streptavidin beads. The beads were washed and the captured RNA was eluted using biotin. Barcoded Libraries were made using the NEBNEXT Ultra Directional RNA Library Prep Kit for Illumina® as described by the manufacturer for both the total and enriched RNA fractions and sequenced on the Illumina MISEQ. Reads were mapped to a composite *E. coli*/human genome using STAR: ultrafast universal RNA-seq aligner (Dobin et al, Bioinformatics, doi: 10.1093/bioinformatics/bts635 (2012)).

(c) Viral RNA analysis. Virus RNA enrichment can be used for detection of virus and virus load and intracellular variants in eukaryotes for determining drug resistance, antigenic determinants, etc.

(d) Identification of TSS can be ascertained by fragmenting RNA before or after capping with modified labeled nucleotides. Only the 5' end fragment becomes immobilized and the remainder of the RNA including rRNA, non-5' terminal fragments and other 5' non triphosphorylated will be washed away. The sequencing burden is then much reduced allowing for simultaneous sequencing of mixed populations of prokaryotes (meta-transcriptome analysis) or obtaining reads of a greater number of samples from a single population (transcriptome analysis). Novel TSS in prokaryote transcriptomes were identified which had not been previously detected using alternative less sensitive methods.

Figure 9:
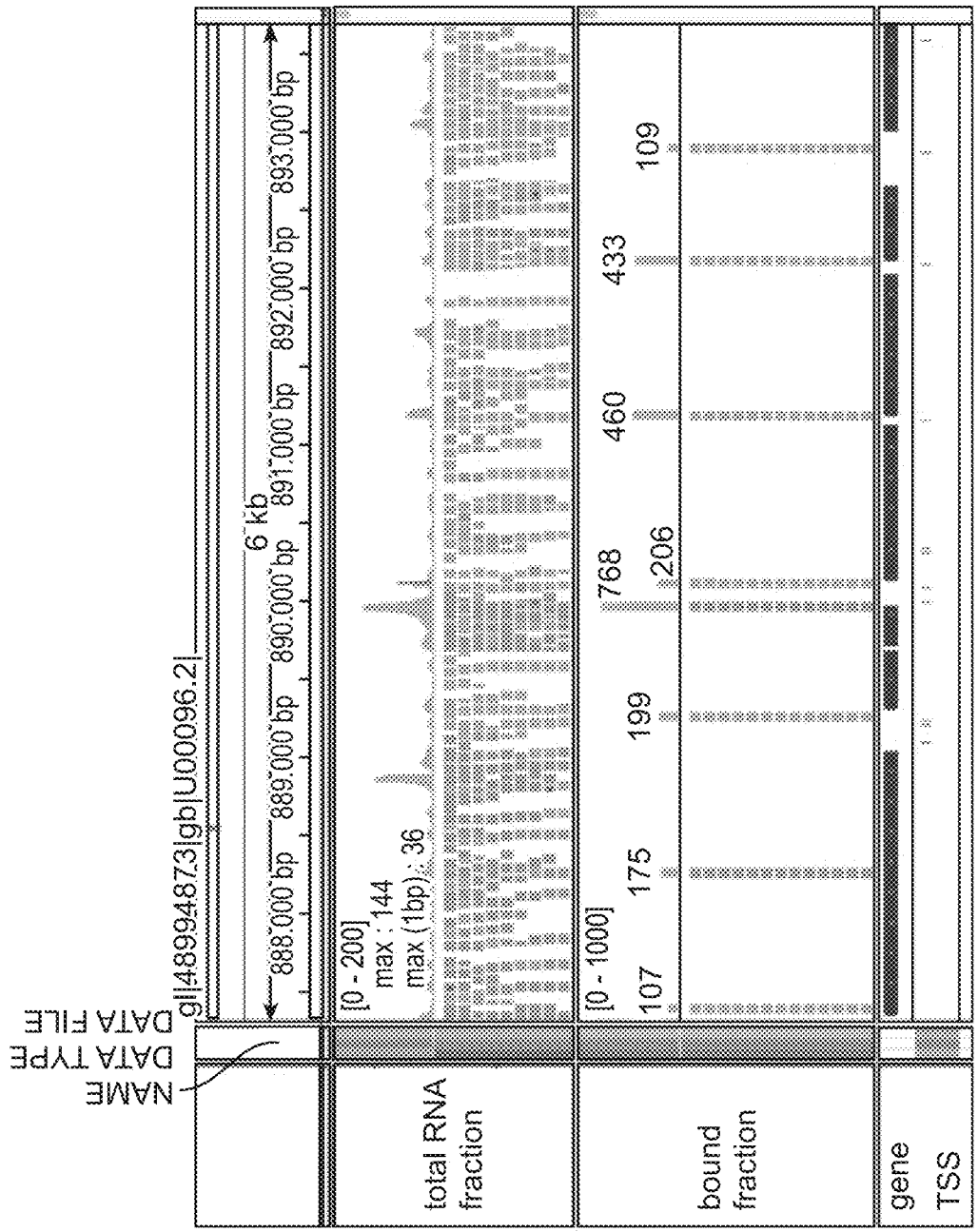
FIG. 9 shows that enrichment of non-rRNA and use of a small RNA library preparation for the samples results in sequencing reads positioned at TSS with single base pair resolution. Panel "total RNA fraction" shows individual read positions corresponding to positions distributed along the entire stretch of the genome fragment by forming an RNA library of total RNA. Panel "bound fraction", shows sequencing reads in the enriched fraction corresponding to TSS with single base resolution. Panel "gene" shows the position of genes in the genome fragment.

RNA SEQ methods that utilize RNA fragmentation and random priming followed by first and second strand cDNA synthesis prior to adapter ligation and PCR amplification resulted in peaks corresponding to TSS (see for example FIG. 7) although the precise start site varied within a limited nucleotide range. Surprisingly, substitution of RNA seq methods (NEB Next Ultra Directional RNA library Prep kit) with small fragment libraries utilizing adapter ligation to 3' and 5' ends of the RNA followed by first strand cDNA synthesis only and then PCR enrichment (NEBNEXT Small Library Prep Kit) provided single base resolution at the TSS (FIG. 9).

Embodiments of the enrichment method enables the characterization of populations of prokaryotes such as occur in the microbiome using TSS signatures. This is an alternative to whole metatranscriptome sequencing and species identification. TSS signatures contain a much reduced complexity of the data per individual transcriptome, providing important data on which and how much primary transcript RNA is produced in a prokaryotic or eukaryotic cell or cells in a selected environment. The TSS signatures in eukaryotes may be correlated to the transcriptome of an individual cell or tissue to provide markers of health and disease including cancer.

In a diagnostic procedure to which this analysis may be applied, a biological fluid may be obtained from a subject that potentially contains unknown prokaryotic and host eukaryotic cells. In one embodiment, the total RNA is isolated from this sample is fragmented for example, to about 20-200 nucleotides although the fragments may be longer or shorter than this depending on the amount of discriminatory power desired.

For analysis of the prokaryotic population, the 5' end of prokaryotic RNA is uncapped and 5'-triphosphorylated or 5'-diphosphorylated. These characteristics distinguish the 5' end of prokaryotic RNA from the 5' end of eukaryotic RNA and also ribosomal and transfer RNAs. By attaching a tag on the 5' end by for example DBT, only those fragments of RNA at the 5' end of the prokaryotic RNA are bound to a suitable solid surface through the tag. Unbound material is washed away and the bound material can be eluted in the case of DBT, in the presence of free biotin.

The released RNA can then be decapped, ligated to adaptors, reverse transcribed, amplified and sequenced using methods known in the art or can be sequenced using high-throughput sequencing methods.

The transcriptome or meta-transcriptome can be analyzed by means of quantitatively determining SSM of the RNAs obtained from the entire population of RNAs. Quantification can be obtained by counting the number of identical SSM in the RNA enriched sample. The length of the signature may be determined by the diversity of the population to be analyzed and the discriminatory power that is desired. A particular organism may be recognized by a few or hundreds or thousands of SSM. The panel of SSM represents a simplified representation of a functional state of a transcriptome or meta-transcriptome for correlation with a phenotype. Correlations and associations can be achieved by analyzing signatures of both a population from healthy hosts and those with an altered phenotype to determine qualitative and quantitative variations in the amounts and types of RNA produced by prokaryotes in the host samples. This approach of RNA analysis obviates the need to identify, classify and optionally diagnose individual bacterial species or eukaryotic genomes.

(e) Identification of lagging strand oligonucleotide primer sequences which are generated by primase during DNA replication. For example to determine leading and lagging strands and to locate the origin of replication and whether this might change in response to varying factors.

(f) Identifying labeled RNAs in vivo or in vitro by imaging. Labels on the modified nucleotide may include fluorescent labels.

(g) Identifying the properties of selected stabilized RNAs. Labels on the modified nucleotide may include a stabilizing label.

(h) Identifying different types of RNA by sequential analysis. For example, a first enrichment of eukaryotic total RNA would separate nascent RNA from the remainder of the RNA which could be recovered in the eluent for a second enrichment procedure. The second enrichment step might be achieved after decapping with a cap specific enzyme such as Vaccinia D9 or D10. A subset of total mRNA, the decapped RNA, could then be capped using a modified nucleotide such as described herein. Alternatively, one or more enrichment steps might be accompanied by a prior art depletion step.

Labeled Modified Nucleotide Compounds

The labeled mononucleotide compounds may be a ribonucleotide or a nucleoside triphosphate. As discussed in Example 3, the label may be positioned at the 3' hydroxyl (OH) position of the sugar ring in the nucleotide. In contrast, labeling of the ribose 2' hydroxyl group is not suitable for the methods as described herein. In an embodiment, the labeled mononucleotide is not methylated.

An example of a labeled mononucleotide is shown in Formula (I):

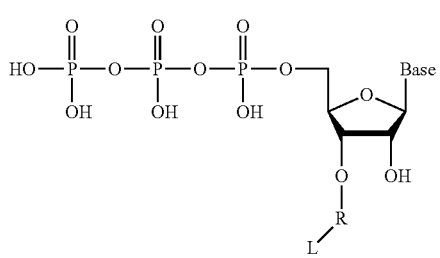

wherein the base is any nucleobase, R is a linker and L is a label. In one embodiment, R is a cleavable linker that, when cleaved, re-generates a free 3' OH and L is an affinity tag. In any embodiment, R may be contain an allyl group, e.g., an allyl ether, allyl ester or allyl carbonate linker, wherein the allyl group may be optionally substituted with one or more alkylene or modified alkylene groups as defined under (a) to (f) below. For example, in any embodiment, R may be an allyl ether.

In one embodiment, the base is a purine, pyrimidine, or analogs thereof, natural or synthetic. In an embodiment, the base is guanine or analog while in another embodiment, the base is inosine or analog thereof.

A linker R may be a covalent or electrovalent bond between the oxygen and a label. The linker R may be a flexible linker connecting a label L or a plurality of same or different labels to the oxygen in the 3' hydroxyl (OH) position of the ribose ring.

Linker molecules separating the label from the ribose may serve as steric spacers and do not necessarily have to be of defined length. Examples of suitable linkers may be selected from any of the hetero-bifunctional cross linking molecules described by Hermanson, Bioconjugate Techniques, 2nd Ed; Academic Press: London, Bioconjugate Reagents, pp 276-335 (2008), incorporated by reference.

The linker R can also increase the solubility of the compound in the appropriate solvent. The linkers used are chemically stable under the conditions of the actual application. The linker does not interfere with the mRNA capping reaction nor with the detection of the label L, but may be constructed such as to be cleaved at some point in time after the reaction of the compound of Structural Formula (I) with the capping enzyme.

The linker R may be a straight or branched chain alkylene group with 1 to 300 carbon atoms, wherein optionally:
(a) one or more carbon atoms are replaced by oxygen, in particular wherein every third carbon atom is replaced by oxygen, e.g. a polyethyleneoxy group with 1 to 100 ethyleneoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH═CH— or —C≡C—;
(e) one or more carbon atoms are replaced by a phenylene, a saturated or unsaturated cycloalkylene, a saturated or unsaturated bicycloalkylene, a divalent heteroaromatic or a divalent saturated or unsaturated heterocyclyl group;
(f) two adjacent carbon atoms are replaced by a disulfide linkage —S—S—;
or a combination of two or more, especially two or three, alkylene and/or modified alkylene groups as defined under (a) to (f) hereinbefore, optionally containing substituents.

A linker R may be a straight chain alkylene group with 1 to 25 carbon atoms or a straight chain polyethylene glycol group with 4 to 100 ethyleneoxy units, optionally attached to a —CH═CH— or —C≡C— group. Further preferred is a straight chain alkylene group with 1 to 25 carbon atoms wherein carbon atoms are optionally replaced by an amide function —NH—CO—, and optionally carrying a photo-cleavable subunit, e.g. o-nitrophenyl. Further preferred are branched linkers comprising a polyethylene glycol group of 3 to 6 ethylene glycol units and alkylene groups wherein carbon atoms are replaced by amide bonds, and further carrying substituted amino and hydroxy functions. Other preferred branched linkers have dendritic (tree-like) structures wherein amine, carboxamide and/or ether functions replace carbon atoms of an alkylene group.

In one embodiment, any functionalized polyethylene glycol derivative may be used as a linker such as any of the pegylation products described in catalogs of Nanocs, Inc., Fisher Scientific, or VWR, Sigma-Aldrich Chemical, all of which are incorporated herein by reference.

A linker R may be a straight chain alkylene group of 2 to 40 carbon atoms optionally substituted by oxo wherein one or two carbon atoms are replaced by nitrogen and 0 to 12 carbon atoms are replaced by oxygen. For example, the linker R is a straight chain alkylene group of 2 to 10 carbon atoms wherein one or two carbon atoms are replaced by nitrogen and one or two adjacent carbon atom are substituted by oxo, for example a linker —CH2-NH(C═O)— or —CH2-NH(C═O)—(CH2)5-NH—.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid, in particular a naturally occurring α-amino acid, is incorporated in the linker wherein carbon atoms are replaced by amide functions —NH—CO— as defined in (b) above. In such a linker, part of the carbon chain of the alkylene group is replaced by a group —(NH—CHX—CO)n- wherein n is between 1 and 100 and X represents a varying residue of an α-amino acid.

A further substituent is one which leads to a photocleavable linker R2, e.g. an o-nitrophenyl group. In particular this substituent o-nitrophenyl is located at a carbon atom adjacent to an amide bond, e.g. in a group —NH—CO—CH2-CH(o-nitrophenyl)-NH—CO—, or as a substituent in a polyethylene glycol chain, e.g. in a group —O—CH2-CH(o-nitro-phenyl)-O—. Other photocleavable linkers considered are e.g. diazobenzene, phenacyl, alkoxybenzoin, benzylthioether and pivaloyl glycol derivatives.

A further example of a cleavable linker R is one which the linker is chemically cleaved. Chemically cleavable linkers include disulfide bridges and azo compounds (cleaved by reducing agents such as dithiothreitol (DTT), β-mercaptoethanol or tris(2-carboxyethyl)phosphine (TCEP)); hydrazones and acylhydrazones (cleaved by transimination in a mildly acidic medium); levulinoyl esters (cleaved by aminolysis, e.g. by hydroxylamine or hydrazine); thioesters, thiophenylesters and vinyl sulfides (cleaved by thiol nucleophiles such as cysteine); orthoesters, ketals, acetals, vinyl ethers, phosphoramidates and β-thiopropionates (cleaved by acidic conditions); vicinal diols (cleaved by oxidizing agents such as sodium periodate); and allyl esters, 8-hydroxyquinoline esters, and picolinate esters (cleaved by organometallic and metal catalysts).

A cleavable linker of particular interest is an allyl linker. Allyl linkers, e.g. allyl ethers, allyl esters or allyl carbonates, are chemically cleavable by a Pd catalyst under aqueous conditions. Examples of Pd catalysts include palladium(0), e.g. in tetrakis(triphenylphosphine)palladium, and palladium(II), e.g. in sodium tetrachloropalladate (Na2PdCl4). The cleavage of a 3'-O-allyl linker regenerates a free 3'-OH in a so-called traceless or scarless cleavage process, i.e. the linker portion is completely removed from the ribose ring of a nucleotide without leaving any molecular scar. Allyl linkers have been successfully used in DNA sequencing-by-synthesis technologies based on cyclic reversible termination (see for example Kim T.-S. et al., ChemBioChem 2010, 11:75-78; Kim, D.-R. et al., Bioorg. Med. Chem. Lett. 2014, 24:209-213).

A phenylene group replacing carbon atoms as defined under (e) above is e.g., 1,2-, 1,3-, or preferably 1,4-phenylene. In a particular embodiment, the phenylene group is further substituted by a nitro group, and, combined with other replacements as mentioned above under (a), (b), (c), (d), and (f), represents a photocleavable group, and is e.g. 4-nitro-1,3-phenylene, such as in —CO—NH—CH2-(4-nitro-)1,3-phenylene-CH(CH3)-O—CO—, or 2-methoxy-5-nitro-1,4-phenylene, such as in —CH2-O-(2-methoxy-5-nitro-)1,4-phenylene-CH(CH3)-O—, or 2-nitro-1,4-phenylene, such as in —CO—O—CH2-(2-nitro-)1,4-phenylene-CO—NH—. Other particular embodiments representing photocleavable linkers are e.g. -1,4-phenylene-CO—CH2-O—CO—CH2-(a phenacyl group), -1,4-phenylene-CH(OR)—CO-1,4-phenylene-(an alkoxybenzoin), or −3,5-dimethoxy-1,4-phenylene-CH2-O-(a dimethoxybenzyl moiety).

A saturated or unsaturated cycloalkylene group replacing carbon atoms as defined under (e) hereinbefore may be derived from cycloalkyl with 3 to 7 carbon atoms, preferably from cyclopentyl or cyclohexyl, and is e.g. 1,2- or 1,3-cyclopentylene, 1,2-, 1,3-, or preferably 1,4-cyclohexylene, or also 1,4-cyclohexylene being unsaturated e.g. in 1- or in 2-position.

A saturated or unsaturated bicycloalkylene group replacing carbon atoms as defined under (e) hereinbefore is derived from bicycloalkyl with 7 or 8 carbon atoms, and is e.g. bicycle [2.2.1] heptylene or bicyclo[2.2.2]octylene, preferably 1,4-bicyclo[2.2.1]-heptylene optionally unsaturated in 2-position or doubly unsaturated in 2- and 5-position, and 1,4-bicyclo[2.2.2]octylene optionally unsaturated in 2-position or doubly unsaturated in 2- and 5-position.

A divalent heteroaromatic group replacing carbon atoms as defined under (e) hereinbefore may, for example, include 1,2,3-triazole moiety, preferably 1,4-divalent 1,2,3-triazole. A divalent heteroaromatic group replacing carbon atoms as defined under (e) hereinbefore is e.g. triazolidene, preferably 1,4-triazolidene, or isoxazolidene, preferably 3,5-isoxazolidene. A divalent saturated or unsaturated heterocyclyl group replacing carbon atoms as defined under (e) hereinbefore is e.g. derived from an unsaturated heterocyclyl group, e.g. isoxazolidinene, preferably 3,5-isoxazolidinene, or a fully saturated heterocyclyl group with 3 to 12 atoms, 1 to 3 of which are heteroatoms selected from nitrogen, oxygen and sulfur, e.g. pyrrolidinediyl, piperidinediyl, tetrahydrofuranediyl, dioxanediyl, morpholinediyl or tetrahydrothiophenediyl, preferably 2,5-tetrahydrofuranediyl or 2,5-dioxanediyl. A particular heterocyclyl group considered is a saccharide moiety, e.g. an α- or β-furanosyl or α- or β-pyranosyl moiety.

The extension "-ylene" as opposed to "-yl" in for example "alkylene" as opposed to "alkyl" indicates that said for example "alkylene" is a divalent moiety connecting two moieties via two covalent bonds as opposed to being a monovalent group connected to one moiety via one covalent single bond in said for example "alkyl". The term "alkylene" therefore refers to a straight chain or branched, saturated or unsaturated hydrocarbon moiety; the term "heteroalkylene" as used herein refers to a straight chain or branched, saturated or unsaturated hydrocarbon moiety in which at least one carbon is replaced by a heteroatom; the term "arylene" as used herein refers to a carbocyclic aromatic moiety, which may consist of 1 or more rings fused together; the term "heteroarylene" as used herein refers to a carbocyclic aromatic moiety, which may consist of 1 or more rings fused together and wherein at least one carbon in one of the rings is replaced by a heteroatom; the term "cycloalkylene" as used herein refers to a saturated or unsaturated non-aromatic carbocycle moiety, which may consist of 1 or more rings fused together; the term "heterocycloalkylene" as used herein refers to a non-aromatic cyclic hydrocarbon moiety which may consist of 1 or more rings fused together and wherein at least one carbon in one of the rings is replaced by a heteroatom. Exemplary multivalent moieties include those examples given for the monovalent groups hereinabove in which one or more hydrogen atoms are removed.

Cyclic substructures in a linker R reduce the molecular flexibility as measured by the number of rotatable bonds within R, which leads to a better membrane permeation rate, important for all in vivo cell culture labeling applications.

A linker R may carry one or more same or different labels, e.g. 1 to 100 same or different labels, in particular 1 to 5, preferably one, two or three, in particular one or two same or different labels.

The label L may be selected from one or more of: an affinity label, a detection label, a reactive group and combinations thereof. In certain cases, the label may contain both an affinity label and a detection label.

Affinity labels are moieties that can be used to separate a molecule to which the affinity label is attached from other molecules that do not contain the affinity label. In many cases, an affinity label is a member of a specific binding pair, i.e. two molecules where one of the molecules through chemical or physical means specifically binds to the other molecule. The complementary member of the specific binding pair, which can be referred to herein as a "capture agent" may be immobilized (e.g., to a chromatography support, a bead or a planar surface) to produce an affinity chromatography support that specifically binds the affinity tag. In other words, an "affinity label" may bind to a "capture agent", where the affinity label specifically binds to the capture agent, thereby facilitating the separation of the molecule to which the affinity tag is attached from other molecules that do not contain the affinity label. Exemplary affinity tags include, but are not limited to, a biotin moiety (where the term "biotin moiety" is intended to refer to biotin and biotin analogs such as DBT, oxybiotin, 2'-iminobiotin, diaminobiotin, biotin sulfoxide, biocytin, etc., that are able to bind to streptavidin with an affinity of at least 10-8M), avidin, streptavidin, protein A, maltose-binding protein, chitin binding domain, SNAP-TAG poly-histidine, HA-tag, c-myc tag, FLAG-tag, GST, an epitope binding molecule such as an antibody, and polynucleotides that are capable of hybridizing to a substrate but excludes an alkyl group.

Exemplary detectable labels include, but are not limited to, optically detectable labels (e.g., fluorescent, chemiluminescent or colorimetric labels), radioactive labels, and spectroscopic labels such as a mass tag. Exemplary optically detectable labels include fluorescent labels such as xanthene dyes, e.g. fluorescein and rhodamine dyes, such as fluorescein isothiocyanate (FITC), 6 carboxyfluorescein (commonly known by the abbreviations FAM and F), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, Cy5, and FRET labels, etc.

In some embodiments the label may be an oligoribonucleotide or an oligodeoxyribonucleotide, attached to the linker in either a 5' to 3' or a 3' to 5' orientation, a PNA, a LNA, an UNA, a triazole nucleic acid, or a combination thereof. The oligonucleotide may include one or more modified nucleotides including unnatural nucleotides.

Chemical modification of oligonucleotides is a widely used strategy for optimization of their biological activity and potency, such as target binding affinity, duplex conformation, hydrophobicity, stability, nuclease resistance, and immunostimulatory properties. Chemical modification can confer unique properties to oligonucleotides or oligonucleotide conjugates. Some chemically modified nucleotides can be incorporated into oligonucleotides to crosslink them to DNA, RNA or proteins upon exposure to UV light (e.g., 5-bromo-dU). Some chemically modified nucleotides are duplex-stabilizing modifications and can be incorporated into oligonucleotides to increase the oligonucleotide Tm (e.g., Super T). Some nucleobase modifications confer additional fluorescent properties oligonucleotides. (e.g., 2-aminopurine) Some modified nucleobases, also known as universal bases, do not favor any particular base-pairing and enable random incorporation of any specific base during amplification (e.g. 5-nitroindole). Modifications of the 2'-sugar position (e.g., 2'-methyl and 2'-methoxyethyl) promote the A-form or RNA-like conformation in oligonucleotides, considerably increasing their binding affinity to RNA, and having enhanced nuclease resistance. The 2'-modification can reduce oligonucleotide immunostimulatory and off-target effects. Some modified nucleotides can trigger RNAse H activity (e.g., oxepane nucleic acids, ONA). Oligonucleotides comprising bridged rings (also known as bridged nucleic acids, e.g. Locked nucleic acids, LNAs) lock the base in the C3'-endo position, favoring RNA A-type helix duplex geometry, increasing Tm and nuclease resistance. Modifications of the oligonucleotide backbone (e.g., a phosphororothioate linkage) have been used to increase the resistant oligonucleotides to exo- and endonucleases. Oligonucleotides comprising backbone modifications have been widely used as antisense reagents or in synthetic siRNA for the control of gene expression. Examples and uses of oligonucleotide chemical modifications are reviewed in a variety of publications, such as in Deleavey, G. F. and Damha, G. M. "Designing Chemically Modified Oligonucleotides for Targeted Gene Silencing" Chemistry & Biology 2012, 19(8): 937-54.

Examples of naturally occurring or synthetic modified nucleobases in oligonucleotides include but are not limited to 2-aminopurine, 2,6-diaminopurine, 5-iodouracil, 5-bromouracil, 5-fluorouracil, 5-hydroxyuracil, 5-hydroxymethyluracil, 5-formyluracil, 5-proprynyluracil, 5-methylcytosine, 5-hydromethylcytosine, 5-formylcytosine, 5-carboxycytosine, 5-iodocytosine, 5-bromocytosine, 5-fluorocytosine, 5-proprynylcytosine, 4-ethylcytosine, 5-methylisocytosine, 5-hydroxycytosine, 4-methylthymine, thymine glycol, ferrocene thymine, pyrrolo cytosine, inosine, 1-methyl-inosine, 2-methylinosine, 5-hydroxybutynl-2'-deoxyuracil (Super T), 8-aza-7-deazaguanine (Super G), 5-nitroindole, formylindole, isothymine, isoguanine, isocytosine, pseudouracil, 1-methyl-pseudouracil, 5,6-dihydrouracil, 5,6-dihydrothymine, 7-methylguanine, 2-methylguanine, 2,2-dimethylguanine, 2,2,7-trimethylguanine, 1-methylguanine, hypoxanthine, xanthine, 2-amino-6-(2-thienyl)purine, pyrrole-2-carbaldehyde, 4-thiouracil, 4-thiothymine, 2-thiothymine, 5-(3-aminoallyl)-uracil, 5-(carboxy)vinyl-uracil, 5-(1-pyrenylethynyl)-uracil, 5-fluoro-4-O-TMP-uracil, 5-(C2-EDTA)-uracil, C4-(1,2,4-triazol-1-yl)-uracil, 1-methyladenine, 6-methyladenine, 6-thioguanine, thienoguanine, thienouracil, thienocytosine, 7-deaza-guanine or adenine, 8-amino-guanine or adenine, 8-oxo-guanine or adenine, 8-bromo-guanine or adenine, ethenoadenine, 6-methylguanine, 6-phenylguanine, nebularine, pyrrolidine, and puromycin.

Other examples of modifications in oligonucleotides are ribose modifications including but not limited to dideoxynucleotides (e.g., ddGTP, ddATP, ddTTP, and ddCTP), 2'-O-alkyl-nucleotides (e.g., 2'-O-methyl-nucleotides), 2'-O-methoxyethyl-nucleotides (MOE), 2'-fluoro-nucleotides, 2'-O-allyl-nucleotides, 2'-O-alkylamine-nucleotides (e.g., 2'-O-ethylamine-nucleotides), 2'-O-cyanoethyl-nucleotides, 2'-O-acetalester-nucleotides, 4'-C-aminomethyl-2'-O-methyl-nucleotides, and 2'-azido-nucleotides. Further examples of ribose modifications in oligonucleotides include bridged oligonucleotides such as 2'-O,4'-C-methylene-β-D-ribonucleic acids or locked nucleic acids (LNAs), methylene-cLNA, 2',4'-(N-methoxy)aminomethylene bridged nucleic acids (N-MeO-amino BNA), 2',4'-aminooxymethylene bridged nucleic acids (N-Me-aminooxy BNA), 2'-O,4'-C-aminomethylene bridged nucleic acids (2', 4'-BNA(NC)), and 2'4'-C—(N-methylaminomethylene) bridged nucleic acids (2',4'-BNA(NC)[NMe]).

Further examples of ribose modifications include but are not limited to oligonucleotides in which the ribofuranose ring of DNA and RNA is replaced with five- or six-membered modified ribose molecules, such as 1,5 anhydrohexitol (HNA), cyclohexenyl (CeNA), arabinose (ANA), 2'-fluoro-arabinose (FANA), α-L-threofuranosyl (TNA), 4'-thioribose (4'S-RNA), 2'-fluoro-4'-thioarabinose (4'S-FANA), 4'-selenoribose (4'Se-RNA), oxepane (ONA), and methanocarba (MC). Further examples of ribose modifications include but are not limited to oligonucleotides in which the ribofuranose ring of DNA and RNA is replaced with bicyclic, tricyclic, or expanded ring systems, such as tricyclo (tc)-DNA. Other examples of ribose modifications include but are not limited to oligonucleotides in which the ribofuranose ring of DNA and RNA is replaced with acyclic systems, such as the highly flexible unlocked nucleic acid (UNA or seconucleoside), wherein the covalent C2'-C3' bond of a ribose sugar is missing, and as a result is not conformationally restrained, and can be used to influence oligonucleotide flexibility.

Other examples of modifications in oligonucleotides are backbone modifications including but not limited to phosphorothioate (replacement of one non-bridging oxygen atom of the phosphate group with a sulfur atom), phosphorodithioate (both non-bridging oxygen atoms of the phosphate group are replaced with sulfur), alkyphosphonate (a non-bridging oxygen atom of the phosphate group has been replaced with alkyl group, e.g. methyl), arylphosphonate (a non-bridging oxygen atom of the phosphate group has been replaced with aryl group, e.g. phenyl), N-phosphoramidate (an oxygen atom is replaced with an amino group either at the 3'- or 5'-oxygen), boranophosphate (one non-bridging oxygen atom of the phosphate group is replaced with BH3), phosphonoacetate (PACE, one non-bridging oxygen atom of the phosphate group is replaced with an acetate group), and 2',5'-phosphodiester linkages. Further examples of backbone modifications in oligonucleotides include neutral backbone modifications such as a morpholine nucleic acid, an amide-linked nucleic acid, a triazole nucleic acid, and a PNA. Further examples of backbone modifications include the use of inverted bases. Inverted bases enable the formation of 3'-3' and 5'-5' linkages, impart nuclease resistance and allow the study of strand orientation effects on molecular biological function.

Other examples of modifications in oligonucleotides are modifications that are incorporated through conjugation with compounds that confer unique properties to the modified oligonucleotide. Examples include oligonucleotides conjugated to cationic units (e.g., Zip Nucleic Acids, ZNA). ZNA show increased affinity for their targets by reducing the electrostatic repulsion between nucleic acid strands. Other examples include oligonucleotides conjugated to azobenzene. Azobenzene switches between cis and trans conformations upon irradiation with UV or visible light and this property can be used to photocontrol a number of biological processes, including the rate of duplex formation, the rate of DNA transcription by RNA polymerases, and the rate of RNA cleavage with RNAse H. The properties of azobenzene and uses in biological systems are reviewed in a variety of publications, such as in Beharry, A. A. et al. "Azobenzene photoswitches for biomolecules" Chemical Society Reviews 2011, 40(8): 4422-37. Other examples include oligonucleotides conjugated to psolaren. Psolaren intercalates into the DNA double helix and can crosslink to thymine or uracil when irradiated with ultraviolet (UV). Further examples of intercalators, include Twisted Intercalating nucleic acids (TINA). TINA show enhancement in Tm and can be used to improve triplex formation as well as to improve PCR performance using lower primer concentrations and higher annealing temperatures, therefore reducing the amount of undesired mismatch product formed. TINA oligos can differentiate single base mutations with much faster PCR cycle times. Other examples of modifications that confer unique properties to oligonucleotides include cholesteryl moieties, acridine, dinitrophenol, and 1,4,7,10-tetraazacyclododecane-1,4,7,10-tetraacetic acid (DOTA).

Further examples are oligonucleotides conjugated to fluorescent or quencher groups. A variety of different fluorescent groups may be used, including but not limited to Alexa Fluor dyes, including Alexa Fluor 350, 405, 430, 488, 514, 532, 546, 555, 568,594, 610, 633, 647, 660, 680, 700, 750, and 790 (Molecular Probes, Thermo Fisher Scientific, Waltham, Mass., USA); coumarin dyes, including 3-cyano-7-hydroxycoumarin, 6,8-difluoro-7-hydroxy-4-methylcoumarin, 7-amino-4-methylcoumarin, 7-ethoxy-4-trifluormethylcoumarin, 7-hydroxy-4-methylcoumarin, 7-hydroxycoumarin-3-carboxylic acid, 7-dimethylamino-coumarin-4-acetic acid, 7-amino-4-methyl-coumarin-3-acetic acid, and 7-diethylamino-coumarin-3-carboxylic acid (Thermo Fisher Scientific, Waltham, Mass., USA); BODIPY dyes, including BODIPY 493/503, FL, R6G, 530/550, TMR, 558/568, 564/570, 576/589, 581/591, TR, 630/650, and 650/655 (Thermo Fisher Scientific, Waltham, Mass., USA); Quantum Dots, including Qdot® 545 ITK™, Qdot® 565 ITK™, Qdot® 585 ITK™, Qdot® 605 ITK™, Qdot® 655 ITK™, Qdot® 705 ITK™, and Qdot® 800 ITK™ (Thermo Fisher Scientific, Waltham, Mass., USA); Oregon Green dyes, including Oregon Green 488, 488, and 514 (Thermo Fisher Scientific, Waltham, Mass., USA); LanthaScreen™ Tb Chelates (Thermo Fisher Scientific, Waltham, Mass., USA); Rhodamine 110, Rhodamine Green, Rhodamine Red, Texas Red-X, Cascade Blue, Pacific Blue, Marina Blue, Pacific Orange, Dapoxyl Sulfonyl Chloride, Dapoxyl Carboxylic Acid, 1-Pyrenebutanoic Acid, 1-Pyrenesulfonyl Chloride, 2-(2,3-Naphthalimino)ethyl Trifluoromethanesulfonate, 2-Dimethylaminonaphthalene-5-Sulfonyl Chloride, 2-Dimethylaminonaphthalene-6-Sulfonyl Chloride, 3-Amino-3-Deoxydigoxigenin Hemisuccinamide, 4-Sulfo-2,3,5,6-Tetrafluorophenol, 5-(and-6)-Carboxyfluorescein, 5-(and-6)-Carboxynaphthofluorescein, 5-(and-6)-Carboxyrhodamine 6G, 5-(and-6)-Carboxytetramethylrhodamine, 5-(and-6)-Carboxy-X-Rhodamine, 5-Dimethylaminonaphthalene-1-Sulfonyl Chloride (Dansyl Chloride), 6-((5-Dimethylaminonaphthalene-1-Sulfonyl)amino)Hexanoic Acid, Succinimidyl Ester (Dansyl-X, SE), Lissamine Rhodamine B Sulfonyl Chloride, Malachite Green isothiocyanate, NBD Chloride, 4-Chloro-7-Nitrobenz-2-Oxa-1,3-Diazole (4-Chloro-7-Nitrobenzofurazan), NBD Fluoride; 4-Fluoro-7-Nitrobenzofurazan, 4-Fluoro-7-Nitrobenz-2-Oxa-1,3-Diazole, NBD-X, and PyMPO (Thermo Fisher Scientific, Waltham, Mass., USA); CyDyes, including Cy 3, Cy 3B, Cy 3.5, Cy 5, Cy 5.5, Cy 7 (GE Healthcare, Little Chalfont, United Kingdom); ATTO dyes, including ATTO 390, 425, 465, 488, 495, 520, 532, 550, 565, 590, 594, 610, 611X, 620, 633, 635, 637, 647, 647N, 655, 680, 700, 729, and 740 (ATTO-TEC GmbH, Siegen, Germany); DY dyes, including DY 350, 405, 415, 490, 495, 505, 530, 547, 548, 549, 550, 554, 555, 556, 560, 590, 591, 594, 605, 610, 615, 630, 631, 632, 633, 634, 635, 636, 647, 648, 649, 650, 651, 652, 654, 675, 676, 677, 678, 679, 680, 681, 682, 700, 701, 703, 704, 730, 731, 732, 734, 749, 750, 751, 752, 754, 776, 777, 778, 780, 781, 782, 800, 831, 480XL, 481XL, 485XL, 510XL, 520XL, and 521XL (Dyomics, Jena, Germany); CF dyes, including CF 350, 405, 485, 488, 532, 543, 555, 568, 594, 620R, 633, 640R, 647, 660C, 660R, 680, 680R, 750, 770, and 790 (Biotium, Inc. Hayward, Calif., USA); CAL Fluor® dyes, including CAL Fluor Gold 540, Orange 560, Red 590, Red 610, Red 635 (Biosearch Technologies, Novato, Calif., USA); Quasar® dyes, including Quasar 570, 670, 705 (Biosearch Technologies, Novato, Calif., USA); Biosearch Blue and Pulsar 650 (Biosearch Technologies, Novato, Calif., USA); DyLight Fluor dyes, including DYLight 350, 405, 488, 550, 594, 633, 650, 680, 755, 800 (Thermo Fisher Scientific, Waltham, Mass., USA); FluoProbes dyes, including FluoProbes 390, 488, 532, 547H, 594, 647H, 682, 752, 782 (Interchim, Inc., Montluçon Cedex, France); SeTau dyes, including SeTau 380, 425, 405, 404,655, 665, and 647 (SETA BioMedicals, Urbana, Ill., USA); Square dyes, including Square 635, 660, and 685 (SETA BioMedicals, Urbana, Ill., USA); Seta dyes, including, Seta 470, 555, 632, 633, 646, 650, 660, 670, 680, and 750 (SETA BioMedicals, Urbana, Ill., USA); SQ-565 and SQ-780 (SETA BioMedicals, Urbana, Ill., USA); Chromeo™ dyes, including Chromeo 488, 494, 505, 546, and 642 (Active Motif, Carlsbad, Calif., USA); Abberior STAR dyes, including STAR 440SX, 470SX, 488, 512, 580, 635, and 635P (Abberior GmbH, Gottingen, Germany); Abberior CAGE dyes, including CAGE 500, 532, 552, and 590 (Abberior GmbH, Gottingen, Germany); Abberior FLIP 565 (Abberior GmbH, Gottingen, Germany); IRDye Infrared Dye, including IRDye® 650, 680LT, 680RD, 700DX, 750, 800CW, and 800R5 (LI-COR Biosciences, Lincoln, Nebr., USA); Tide Fluor™ dyes, including TF1, TF2, TF3, TF4, TF5, TF6, TF7, and TF8 (AAT Bioquest, Inc., Sunnyvale, Calif., USA); iFluor™ dyes, including iFluor™ 350, 405, 488, 514, 532, 555, 594, 610, 633, 647, 680, 700, 750, and 790 (AAT Bioquest, Inc., Sunnyvale, Calif., USA); mFluor™ dyes, including mFluor™ Blue 570, Green 620, Red 700, Red 780, Violet 450, Violet 510, Violet 540, and Yellow 630 (AAT Bioquest, Inc., Sunnyvale, Calif., USA); trFluor™ Eu and trFluor™ Tb (AAT Bioquest, Inc., Sunnyvale, Calif., USA); HiLyte Fluor™ dyes, including HiLyte Fluor™ 405, 488, 555, 594, 647, 680, and 750 (AnaSpec, Inc., Fremont, Calif., USA); Terbium Cryptate and Europium Cryptate (Cisbio Bioassays, Codolet, France); and other nucleotide classical dyes, including FAM, TET, JOE, VIC, HEX, NED, TAMRA, ROX, Texas Red (Biosearch Technologies, Novato, Calif., USA). A variety of different quencher groups may be used, including but not limited to QSY 35, QSY 9, QSY 7, and QSY 21 (Thermo Fisher Scientific, Waltham, Mass., USA); Black Hole Quencher™, including BHQ-0, BHQ-1, BHQ-2, and BHQ-3 (Biosearch Technologies, Inc., Novato, Calif., USA); ATTO 540Q, ATTO 580Q, and ATTO 612Q (ATTO-TEC GmbH, Siegen, Germany); 4-dimethylamino-azobenzene-4'-sulfonyl derivatives (Dabsyl), 4-dimethylaminoazobenzene-4'-carbonyl derivatives (Dabcyl), DNP and DNP-X [6-(2,4-Dinitrophenyl)aminohexanoic acid] (AAT Bioquest, Inc., Sunnyvale, Calif., USA); DYQ quenchers, including DYQ 425, 505, 1, 2, 660, 661, 3, 700, 4 (Dyomics, Jena, Germany); IRDye® QC-1 (LI-COR Biosciences, Lincoln, Nebr., USA); Tide Quencher™, including TQ1, TQ2, TQ3, TQ4, TQ5, TQ6, and TQ7 (AAT Bioquest, Inc., Sunnyvale, Calif., USA); QXL™ quenchers, including QXL™ 490, 570, 610, 670, and 680 (AnaSpec, Inc., Fremont, Calif., USA); BlackBerry® Quenchers, including BBQ-650 (Berry & Associates, Inc., Dexter, Mich., USA).

Other examples of modifications in oligonucleotides are oligonucleotides conjugated to affinity groups. A variety of different affinity groups may be used, including but not limited to biotin, DBT, digoxigenin, glutathione, heparin, maltose, coenzyme A, protein A, Brilliant Blue FCF (BB FCF), azorubine, phytoestrogen, nickel, cobalt, zinc, polyhistidine, HA-tag, c-myc tag, FLAG-tag, S-tag, a hapten to an antibody, a mono- or oligosaccharide ligand to a lectin, hormones, cytokines, toxins, dyes, and vitamins. Examples of specific binding partners to the aforementioned affinity groups, in no particular order, include but are not limited to avidin, streptavidin, neutravidin, maltose-binding protein, GST, antibodies, lectins, nickel, cobalt, zinc, and polyhistidine. Further examples include groups that form an irreversible bond with a protein tag, including benzylguanine or benzylchoropyrimidine (SNAP-TAG); benzylcytosine (CLIP-TAG); haloalkane (HaloTag); CoA analogues (MCP-tag and ACP-tag); trimpethoprim or methotrexate (TMP-tag); FlAsH or ReAsH (Tetracysteine tag); a substrate of biotin ligase; a substrate of phosphopantetheline transferase; and a substrate of lipoic acid ligase. An affinity group is used for selectively enriching samples by means of affinity purification methods, wherein the affinity binding partner is immobilized in a column, bead, microtiter plate, membrane or other solid support.

In some embodiments, the oligonucleotide is selected from an oligoribonucleotide, a oligodeoxyribonucleotide, or a combination thereof. In some embodiments, the oligonucleotide further comprises one or more modified nucleotides, including modified nucleobases, ribose modifications, backbone modifications, or a combination thereof. In some embodiments, the oligonucleotide may be a PNA, a LNA, an UNA, a bridge nucleic acid (BNA), a triazole nucleic acid, a morpholine nucleic acid, an amide-linked nucleic acid, or a combination thereof. In some embodiments, the oligonucleotide may be 1,5 anhydrohexitol nucleic acid (HNA), cyclohexenyl nucleic acid (CeNA), arabinose nucleic acid (ANA), 2'-fluoro-arabinose nucleic acid (FANA), α-L-threofuranosyl nucleic acid (TNA), 4'-thioribose nucleic acid (4'S-RNA), 2'-fluoro-4'-thioarabinose nucleic acid (4'S-FANA), 4'-selenoribose nucleic acid (4'Se-RNA), oxepane nucleic acid (ONA), methanocarba nucleic acid (MC), or a combination thereof. In some embodiments, the oligonucleotide may comprise one or more phosphororothioate, phosphorodithioate, alkyphosphonate, arylphosphonate, N-phosphoramidate, boranophosphate, phosphonoacetate, 2',5'-phosphodiester linkages, or a combination thereof. In some embodiments, the oligonucleotide may comprise one or more 2'-O-ribose modifications, including 2'-O-alkyl-nucleotides (e.g., 2'-O-methyl-nucleotides), 2'-O-methoxyethyl-nucleotides (MOE), 2'-fluoro-nucleotides, 2'-O-allyl-nucleotides, 2'-O-alkylamine-nucleotides (e.g., 2'-O-ethylamine-nucleotides), 2'-O-cyanoethyl-nucleotides, 2'-O-acetalester-nucleotides, 4'-C-aminomethyl-2'-O-methyl-nucleotides, and 2'-azido-nucleotides.

In some embodiments, the oligonucleotide is attached to the linker through an internal nucleotide. Examples of internal nucleotides that enable attachment chemistry include but are not limited to "Int Amino Modifier C6 dT" (a dT base modified base with a spacer arm terminating in an amine group), "Int 5-Octadiynyl dU" (a dT base modified base with an eight-carbon spacer arm terminating in an alkyne group), and "Int Azide" (a dT base modified base with a spacer arm terminating in an azide group). In some embodiments, the oligonucleotide is attached to the linker through a branched spacer with an appropriate reactive group. Examples of internal branched spacers that enable attachment chemistry include but are not limited to "Int Uni-Link' Amino Modifier" (an amino-modifier phosphoramidite from Clontech (Mountain View, Calif.) that provides a free primary amine via a branched six-carbon aliphatic spacer arm that is attached an oligonucleotide phosphate backbone) and "Int Dithiol" (an dithiol-modifier phosphoramidite that provides a reactive thiol groups via a branched aliphatic carbon spacer arm that is attached an oligonucleotide phosphate backbone). Oligonucleotides containing internal nucleotides or internal spacers with appropriate attachment chemistry can be obtained from a variety of suppliers, such as Integrated DNA Technologies (IDT, Coralville, Iowa). A wide range of phosphoramidites with internal modifications for the chemical synthesis of DNA and RNA oligonucleotides can be obtained from a variety of suppliers such as Glen Research (Sterling, Va.).

In some embodiments, the oligonucleotide is attached to the linker through an internal nucleotide (ribonucleotide or deoxyribonucleotide). Examples of internal nucleotides that enable attachment chemistry include but are not limited to a dT, dG, dA, dC or U modified bases with a spacer arm terminating in an amine group (e.g., "Int Amino Modifier C6 dT" from IDT; "Thymidine-5-C2 and C6 Amino Linker", "2'-Deoxyguanosine-N2-C6 Amino Linker", "2'-Deoxyadenosine-8-C6 Amino Linker", "2'-Deoxycytidine-5-C6 Amino Linker", and "Uridine-C6-Amino Linker" from Tri-Link), a dT base modified base with an eight-carbon spacer arm terminating in an alkyne group (e.g., an "Int 5-Octadiynyl dU" from IDT), and a dT base modified base with a spacer arm terminating in an azide group (e.g., an "Int Azide" from IDT). In some embodiments, the oligonucleotide is attached to the linker through a branched spacer with an appropriate reactive group. Examples of internal branched spacers that enable attachment chemistry include but are not limited to branched aliphatic carbon spacers wherein the non-bridging arm (i.e., the one not internally attached to the oligonucleotide phosphate backbone) terminates in an amine group (e.g., an "Int Uni-Link™ Amino Modifier" from IDT, Coralville, Iowa) or in a dithiol group (e.g., an "Int Dithiol" from IDT, Coralville, Iowa). Oligonucleotides containing internal nucleotides or internal spacer arms with appropriate attachment chemistry can be obtained from a variety of suppliers, such as Integrated DNA Technologies (IDT, Coralville, Iowa) and TriLink Biotechnologies (San Diego, Calif.). A wide range of phosphoramidites with internal modifications for the chemical synthesis of DNA and RNA oligonucleotides can be obtained from a variety of suppliers, such as Glen Research (Sterling, Va.).

In some embodiments, the oligonucleotide is attached to the linker either in a 5' to 3' or a 3' to 5' orientation. Examples of 5'-modifiers that enable attachment chemistry at the 5' end of oligonucleotides include but are not limited to 5' Amino Modifier CU, 5' Amino Modifier C6, 5' Uni-Link™ Amino Modifier, 5' Thiol Modifier C6 S-S, 5' Amino Modifier C6 dT, 5' Dithiol, 5' Azide, 5' Hexynyl, 5' 5-Octadiynyl dU, and 5' Acrydite. Examples of 3'-modifiers that enable attachment chemistry at the 3' end of oligonucleotides include but are not limited to 3' Thiol Modifier C3 S-S, 3' Amino Modifier, 3' Amino Modifier C6 dT, 3' Dithiol, 3' Azide, and 3' 5-Octadiynyl dU. Oligonucleotides containing 5'-modifiers or 3'-modifiers with appropriate attachment chemistry can be obtained from a variety of suppliers, such as Integrated DNA Technologies (Coralville, Iowa). A wide range of phosphoramidites and solid supports for the chemical synthesis DNA and RNA oligonucleotides with 5' or 3' modifications can be obtained from a variety of suppliers, such as Glen Research (Sterling, Va.).

A variety of different chemoselective groups may be used to attach an oligonucleotide to a linker; an amino acid; a peptide; a protein; a monosaccharide; a disaccharide; a polysaccharide; an ion-complexing group; an ethylenediamine tetraacetic acid; a nitrilotriacetic acid; a nucleotide; an oligonucleotide; a nucleic acid polymer; a substrate of an enzyme; an inhibitor of an enzyme; an agonist of a receptor; an affinity group; a cofactor of an enzyme; a hormone; a toxin; a fluorophore; a hapten; an antigen; a drug; a lipid; a lipid assembly; a non-biological organic polymer; a polymeric microparticle; an animal cell; a plant cell; a bacterium, a yeast; a virus; a protist. The chemoselective group on the oligonucleotide may react with a suitable reactive site on the selected target forming a covalent or noncovalent bond with the target. The suitable reactive site on the selected target compound or biomolecule may be naturally occurring or installed synthetically.

In some embodiments, the oligonucleotide comprises one or more reactive groups. In some embodiments, the oligonucleotide comprises a reactive group selected from the group consisting of a carbonyl; a carboxyl; an active ester, e.g. a succinimidyl ester; a maleimide; an amine; a thiol; an alkyne, an azide; an alkyl halide; an isocyanate; an isothiocyanate; an iodoacetamide; a 2-thiopyridine; a 3-arylproprionitrile; a diazonium salt; an alkoxyamine; a hydrazine; a hydrazide; a phosphine; an alkene; a semicarbazone; an epoxy; a phosphonate; and a tetrazine. Examples of chemoselective reactions are: between an amine reactive group and an electrophile such an alkyl halide or an N-hydroxysuccinimide ester (NHS ester); between a thiol reactive group and an iodoacetamide or a maleimide; between an azide and an alkyne (azide-alkyne cycloaddition or "Click Chemistry"). Examples and uses of chemoselective reactions in biological systems are reviewed in a variety of publications, such as in Sletten, E. M. and Bertozzi C. R. "Bioorthogonal Chemistry: Fishing for Selectivity in a Sea of Functionality" Angewandte Chemie International Edition English 2009, 48(38): 6974-98.

In some embodiments, the oligonucleotide comprises a reactive group either internally or attached in the 5' or 3' position. In some preferred embodiments, the reactive group comprises an azide, an alkyne, an amine, an aminooxy, a hydrazine, a hydrazide, or a thiol. In some embodiments, the oligonucleotide comprises a reactive group and an affinity group. In some preferred embodiments, the oligonucleotide comprises an affinity tag at the 5' end and azide group at the 3' end. In some preferred embodiments, the oligonucleotide comprises an affinity tag at the 3' end and azide group at the 5' end. In some preferred embodiments, the oligonucleotide comprises an affinity tag at the 5' end and alkyne group at the 3' end. In some preferred embodiments, the oligonucleotide comprises an affinity tag at the 3' end and alkyne group at the 5' end. In some preferred embodiments, the oligonucleotide comprises an affinity tag at the 5' end and aminooxy group at the 3' end. In some preferred embodiments, the oligonucleotide comprises an affinity tag at the 3' end and aminooxy group at the 5' end. In some preferred embodiments, the oligonucleotide comprises an affinity tag at the 5' end and amine group at the 3' end. In some preferred embodiments, the oligonucleotide comprises an affinity tag at the 3' end and amine group at the 5' end. In some preferred embodiments, the oligonucleotide comprises an affinity tag at the 5' end and thiol group at the 3' end. In some preferred embodiments, the oligonucleotide comprises an affinity tag at the 3' end and thiol group at the 5' end. In some preferred embodiments, the affinity group is biotin or DBT. In some preferred embodiments, the alkyne comprises a propargyl moiety.

In some embodiments, the oligonucleotide is attached a GTP through a linker (see definition of linker). In some embodiments, the oligonucleotide is attached to the linker either in a 5' to 3' or a 3' to 5' orientation. In some embodiments, the oligonucleotide is attached to the linker through an internal nucleotide. In some embodiments, the oligonucleotide is attached to the linker through a branched spacer arm. In some preferred embodiments, the linker is attached to a GTP at the GTP 3'-position. In some embodiments, the 2'-position of GTP is H, SH, NH2, a lower alkyl, e.g. methyl, lower alkoxy, e.g. methoxy, lower acyloxy, e.g. acetoxy, lower alkylamine, e.g. methylamine, lower, acylamine, e.g. acetamide, or halogenyl, e.g. chloro. In some preferred embodiments, 2'-position of GTP is OH. In some embodiments, the oligonucleotide attached to GTP further comprises an affinity group either internally or attached in the 5' or 3' position.

In some embodiments, the oligonucleotide comprises a cleavable linker between the affinity group and the site of attachment to the target compound or biomolecule. This strategy allows specific elution of target of interest. The cleavable linker can be cleavable, for example, by chemical, thermal or photochemical reaction. Chemically cleavable linkers include disulfide bridges and azo compounds (cleaved by reducing agents such as DTT, β-mercaptoethanol or TCEP); hydrazones and acylhydrazones (cleaved by transimination in a mildly acidic medium); levulinoyl esters (cleaved by aminolysis, e.g. by hydroxylamine or hydrazine); thioesters, thiophenylesters and vinyl sulfides (cleaved by thiol nucleophiles such as cysteine); orthoesters, ketals, acetals, vinyl ethers, phosphoramidates and β-thiopropionates (cleaved by acidic conditions); vicinal diols (cleaved by oxidizing agents such as sodium periodate); and allyl esters, 8-hydroxyquinoline esters, and picolinate esters (cleaved by organometallic and metal catalysts). Further examples include, acid or base labile groups, including among others, diarylmethyl or trimethylarylmethyl groups, silyl ethers, carbamates, oxyesters, thiesters, thionoesters, and α-fluorinated amides and esters. Examples of photocleavable cleavable linkers include o-nitrophenyl group, diazobenzene, phenacyl, alkoxybenzoin, benzylthioether and pivaloyl glycol derivatives.

In some embodiments, the label is a chemoselective group that can be indirectly detected by reacting with a suitable reagent or substrate that contains one or more sites that covalently react with the reactive group.

A variety of different chemoselective groups may be used. For example, bis-NHS esters and maleimides (which react with amines and thiols, respectively), may be used. In other cases, the chemoselective group on the nucleoside may react with a reactive site on suitable reagent or substrate via click chemistry. In these embodiments, the nucleoside may contain an alkyne or azide group. Click chemistry, including azide-alkyne cycloaddition, is reviewed in a variety of publications including Kolb, et al., *Angewandte Chemie International Edition* 40: 2004-2021 (2001), Evans, *Australian Journal of Chemistry*, 60: 384-395 (2007) and Tornoe, *Journal of Organic Chemistry*, 67: 3057-3064 (2002).

The label can be detected directly or indirectly. Indirect detection means that the label is detected after interaction or reaction with another substrate or reagent. For example, through chemical conjugation, affinity partner binding, epitope binding with an antibody, substrate cleavage by an enzyme, donor-acceptor energy transmission (e.g., FRET), etc.

Label combinations for tandem affinity purification found in the literature was summarized in Li, Biotechnol. *Appl. Biochem*, 55:73-83 (2010). The table on page 74 of Li included the following where affinity tag/sequence or size (KDa)/Affinity matrix/Elution strategy is presented:

TABLE 1

| Affinity tag | Sequence or size (KDa) | Affinity matrix | Elution strategy |
|---|---|---|---|
| Z domain* | VDNKFNKEQQNAFYEILHLPNL NEEQRNAFIQSLKDDPSQSANL LAEAKKLNDAQAPK (SEQ ID NO: 3) | IgG | IgG or low pH |
| CBP | KRRWKKNFIAVSAANRFKKISS SGAL (SEQ ID NO: 4) | Calmodulin | 2 mM EGTA |
| His tag | HHHHHH (SEQ ID NO: 5) | Ni2+, Co2+ | 150-500 mM imidazole |
| FLAG | DYKDDDDK (SEQ ID NO: 6) | Antibody | FLAG peptide or low pH |
| HA | YPYDVPDYA (SEQ ID NO: 7) | Antibody | HA peptide or low pH |
| Myc | EQKLISEEDL (SEQ ID NO: 8) | Antibody | Low pH |
| V5 | GKPIPNPLLGLDST (SEQ ID NO: 9) | Antibody | V5 peptide or low pH |
| Strep II | WSHPQFEK (SEQ ID NO: 10) | StrepTactin | 2.5-5 mM DBT |
| SBP | MDEKTTGWRGGHVVEGLAGELE QLRARLEHHPQGQREP (SEQ ID NO: 11) | Streptavidin | 2 mM biotin |
| S-peptide | KETAAAKFERQHMDS (SEQ ID NO: 12) | S-protein | Denaturant or low pH |
| CBD | TNPGVSAWQVNTAYTAGQLVTY NGKTYKCLQPHTSLAGWEPSNV PALWQLQ (SEQ ID NO: 13) | Chitin | Thiol reagents or pH and temperature shift (when fused with intein) |
| GST | 26 | Glutathione | 10 mM reduced glutathione |
| MBP | 40 | Maltose | 10 mM maltose |

*Z domain is a synthetic Fc-region-binding domain derived from the B domain of ProtA.

In some embodiments, the labeled modified nucleotide is 3'-O-(2-aminoethylcarbamoyl) (EDA)-biotin GTP. In some embodiments, the labeled nucleotide is 3'-DBT-triethylene glycol (TEG)-GTP. Example 2 describes the synthesis of 3' DBT-TEG-GTP. An advantageous feature of a DBT label is that it binds streptavidin less tightly than biotin and can be displaced by biotin ensuring that elution of enrich RNA is readily achieved. Where elution of the enriched RNA is not required, biotin labeled GTP may be used for its tighter binding properties compared to DBT.

In some embodiments the labels permit any variety of subsequent analysis of the labeled capped RNAs, including and without limitation isolation, purification, immobilization, identification, localization, amplification, and other such procedures known in the art.

The labeled modified nucleotide is described herein for use adding a label to targeted RNA molecules at the 5' end where the 5' end is characterized by a terminal di-phosphate or tri-phosphate. RNA with a 5' monophosphate or a cap (5' $m^7Gppp$) are not amenable directly to labeling. However, if the 5' $m^7G$ or 5' $m^7Gpp$ can be removed from a 5' capped RNA or one phosphate or two phosphates can be added to the 5' monophosphate, then these RNAs become substrates for labeled modified nucleotides.

The RNA from a biological sample generally include a diverse mixture of different species of capped and uncapped RNA; and may include non-RNA biological molecules such as any of those found in a cell lysate; and may additionally or alternatively include various natural or synthetic chemical formulations. In one embodiment, the RNA preparation does not include RNA polymerase.

The enrichment of selected species of RNAs for analysis (such as prokaryotic non-rRNA) minimizes problems of analysis associated with an overwhelming fraction of uninformative RNA (such as rRNA) that can mask a small minority of informative RNA.

The enrichment methods described herein are not dependent upon in vitro transcription, in vitro synthesis or cDNA intermediate synthesis methods from a genomic, cDNA, or other nucleotide sequence template.

The RNA may be obtained from one or more sources, including viruses, prokaryotic cells, eukaryotic or archaea cells or a mixture derived from tissue culture, biopsies, swabs, archived (such as paraffin embedded samples), the environment (air, water or land), or waste products.

The RNA preparations may include total cell RNA, size selected RNA, labeled RNA, and/or purified RNA. The RNA may be degraded or fragmented naturally or by means of standard techniques, such as mechanical shearing, enzymatic digestion, chemical cleavage, or sonication.

The RNA may include one or more of in vitro transcribed RNA, artificially synthesized RNA or obtained from RNA libraries. RNA may be obtained as RNA pol I transcripts, RNA pol II transcripts, RNA pol III transcripts, nascent RNA, primase, or prokaryotic RNA polymerase or any combination thereof.

The RNA may be a mixture of RNA species that include one or more of single stranded or double stranded RNAs. Single stranded RNAs include mRNA, rRNA, tRNAs, microRNAs (miRNAs), long non-coding RNAs (LNC-RNAs) that can be distinguished by the 5' ends. For example, prokaryotic and eukaryotic mature rRNA and tRNA have a 5'-monophosphate (5'P). Eukaryotic mRNA, with the exception of nascent transcripts and mature uncapped RNA, has a 5'-Gppp. Archaea, bacterial mRNA and small RNAs typically are uncapped and have a terminal 5' tri-phosphate (5'PPP). Naturally degraded RNA has a 5'-OH or 5'-P. A naturally occurring capped RNA has a 5'-$m^7Gppp$.

An RNA preparation can be suitably prepared using any one or more of the methods described below to suitably optimize the RNA for enrichment. This may involve a capping reaction using a labeled compound described herein, and/or used to remove or deplete from the preparation, a population of RNA not intended for capping using a labeled compound as described herein. For example, a population of RNAs having a 5' tri- or di-phosphate, that is present in a complex mixture, can be enriched using various modifications to the enrichment protocol. For example fragmenting the RNA before enrichment will result in a library where only the 5' end of the RNA is analyzed which is useful for determining TSS. When the RNA is not fragmented before enrichment the resulting library will contain full length transcripts which are useful for transcriptome analysis. Furthermore after enrichment, the enriched RNAs can be prepared for RNA sequence analysis by different methods. When the RNA protocol for enrichment includes fragmentation and the preparation for sequencing includes decapping, followed by small RNA library preparation which includes 5' end ligation (NEBNEXT Small Library Prep), TSS to single base resolution emerge from the analysis. In another case, where the RNA protocol for enrichment includes fragmentation and the preparation for sequencing does not include decapping, standard RNASEQ libraries can be generated (NEBNEXT Ultra Directional RNA Library Prep Kit) which can be analyzed for approximate positional TSS. In another case where the RNA was not fragmented, the RNA after enrichment can be left capped and standard RNASEQ libraries can be generated (NEBNEXT Ultra Directional RNA Library Prep Kit) which can be analyzed to determine full length transcripts.

In some embodiments, an uncapped RNA that has 5'-PPP or 5'-PP can be converted into a capped RNA by means of a capping enzyme. Capping reactions may involve more than one enzyme. Examples of different RNAs having 5'-PPP or 5'-PP include prokaryotic non-rRNA, uncapped eukaryotic nascent RNA, eukaryotic RNA polymerase III transcripts, eukaryotic RNA polymerase I transcripts, virus RNA, piwi RNA and primase RNA. The 5' end of RNA generated by degradation either has a monophosphate at the 5' end or a 5'OH. Prokaryotic rRNA has a 5' monophosphate whereas eukaryotic rRNA has a 5' monophosphate.

Examples of suitable capping enzymes include viral capping enzymes and their homologs such as VCE (see for example, Mao, et al., *Journal of Biological Chemistry*, 269:24472-24479 (1994), and Shuman, *Journal of Biological Chemistry* 265:11960-11966 (1990)) The VCE is composed of two proteins. The larger protein contains the active sites for all three activities (triphosphatase, guanylyltransferase and methylase) the smaller protein is bound to the larger one and is required in order for the methylase to be active. Other examples of capping enzymes include Bluetongue Virus capping enzyme (see for example Sutton, et al., *Nat Struct Mol Biol* 14: 449-451 (2007) and Ramadevi, et al. *Proc Natl Acad Sci. USA* 95:13537-13542 (1998)) and Chlorella Virus capping enzyme (see for example, Gong, et al., *Journal of Biological Chemistry* 277:15317-15324 (2002), Ho, et al., *Journal of Virology*, 70:6658-6664 (1996) and Ho, et al., *Journal of Virology*, 75:1744-1750 (2001) and yeast capping enzymes such as from *S. cerevisiae*, and related homologs (see for example, Steiger, et al., *RNA*, 9:231-238 (2003), Bougie, et al., *Biochem J*, 384:411-420 (2004) and Lima, et al., *Cell*, 99:533-543 (1999). The capping enzyme used herein includes a wild type amino acid sequence or variants or thereof having a sequence that is at least 90% identical, e.g., at least 95% identical at least 98% identical, or at least 99% identical to a wild type amino acid sequence (e.g., SEQ ID NO:1 and SEQ ID NO:2).

Conditions suitable for capping enzyme activity include those recommended by manufacturers of commercially available enzymes (see for example, New England Biolabs, Ipswich, Mass.) that are routine for those in the relevant art. For example, the enzymes are active in suitable buffers at temperature ranges of about 15° C. to about 42° C., for example, about 37° C.

A capped RNA can be decapped to form an uncapped RNA having a 5' terminal monophosphate using enzymes for example Vaccinia decapping enzyme D9, Vaccinia decapping enzyme D10, human Dcp2, TAP, and Nudt 16; RppH (see for example, U.S. Pat. No. 8,486,666).

Uncapped substrate can be recapped with a labeled compound such as described herein. Any methods for removing the cap and leaving a 5' diphosphate or 5' triphosphate on the RNA will be suitable for subsequent capping reactions with a labeled mononucleotide using the methods described herein. For example, decapping can be achieved using an enzyme such as 5' deadenylase (e.g., S. cerevisiae 5' deadenylase (see U.S. Pat. No. 8,486,666)), DcpS (e.g., human DcpS or S. cerevisiae DcpS) and the like.

RNA with a 5' monophosphate is not a substrate for a capping enzyme, unless the 5' monophosphate is converted to a 5' diphosphate or 5' triphosphate by adding phosphates with a kinase. An example of a suitable kinase is 5'-phosphate-polyribonucleotide kinase (Spencer, et al., *PNAS*, 75:4793-4797 (1978)). The kinase phosphorylates the 5' monophosphate RNA into 5' di- and/or 5' tri-phosphate RNA, which is then a suitable substrate for a capping enzyme to cap the RNA with a labeled mononucleotide as described herein.

However, if the phosphate groups are removed from the 5' terminus by for example, cleaving with an enzyme such as a phosphatase then uncapped RNA can no longer be capped. Phosphatases include enzymes that remove all phosphate groups leaving behind a 5' hydroxyl group on the RNA. Examples of such enzymes include calf intestine alkaline phosphatase (CIP), bacterial antarctic phosphatase, and shrimp alkaline phosphatase. Other phosphatases can cleave just the terminal phosphate groups to leave a monophosphate at the 5' terminus of RNA. Examples of such enzymes include RppH, apyrase and analogs, derivatives and related enzymes.

A composition is also provided. In certain embodiments, the composition may comprise: a) a compound, as described above, b) a capping enzyme, as described above, and c) uncapped RNA. In some embodiments, the composition may additionally comprise a substrate (e.g., beads or the like) comprising a group that binds to or reacts with the capture moiety of the compound. As would be recognized, the composition may be buffered and may contain other components, e.g., salt, divalent cations, etc., that are required by the enzyme.

Kits

Also provided by this disclosure is a kit for practicing the subject method, as described above. A subject kit may contain at least: a) a compound, as described above and b) a capping enzyme, as described above. In some embodiments, the kit may additionally comprise a substrate (e.g., beads or the like) comprising a group that binds to or reacts with the capture moiety of the compound. Examples of compounds described above further include one or more decapping enzymes, a modified oligonucleotide comprising DBT or biotin, deadenylases, decapping enzymes such as alkaline phosphatase, apyrase or 5' RppH, any reagents requires for an azide-alkyne cycloaddition. In certain embodiments, the kit may comprise a composition comprising a fusion protein, as described above, and a reaction buffer. The fusion protein itself may be in a storage buffer that contains a stabilizing agent, e.g., glycerol. In addition, the kit may also comprise reagents for performing the reaction, e.g., one or more buffers. A reaction buffer may be formulated to provide optimal conditions for decapping and/or capping and for the reverse polymerase and/or polymerase activity of an enzyme, or a concentrated form thereof (e.g., at a 5× or 10× concentrate). In certain embodiments, the buffer may contain a buffering agent (e.g., Tris or the like), salt (e.g., NaCl$_2$ or the like), the salt of a divalent cation (MgCl or the like) and other necessary components.

The components of the kit may be combined in one container, or each component may be in its own container. For example, the components of the kit may be combined in a single reaction tube or in one or more different reaction tubes. Further details of the components of this kit are described above. The kit may also contain other reagents described above and below that are not essential to the method but nevertheless may be employed in the method, depending on how the method is going to be implemented.

In addition to above-mentioned components, the subject kits may further include instructions for using the components of the kit to practice the subject methods, i.e., to provide instructions for sample analysis. The instructions for practicing the present method may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

RNA may be added to the reaction vessel containing these components and reacted accordingly. After enrichment, RNA can be subsequently manipulated as described below.

In some embodiments, the RNAs capped with a labeled oligonucleotide or a reactive group using a capping enzyme can be subsequently manipulated. For example, the labeled capped RNAs can be isolated (captured, purified, enriched) by, for example affinity binding to a suitable matrix. Any suitable matrix can be used, such as and without limitation, a solid, semi-solid, or porous matrix. The matrix can be in any suitable form such as beads including magnetic beads, column, plate, or microfluidic device. Such matrices can be treated, adsorbed, affinity coated, with a binding reagent, ligand or labeling partner specific for binding the label on the mononucleotide. The matrix may be made of any suitable materials, including metal, polystyrene, glass, paper, protein or other biological or chemical reagent such as a polymer. Once bound to the matrix, the bound capped RNAs can be washed, eluted or otherwise isolated and optionally purified from the mixture for subsequent analysis as desired.

Enrichment by immobilization on a matrix can be achieved at temperatures in the range of 25° C. to 80° C., for example, 25° C. to 75° C. or 30° C. to 60° C.

In some embodiments, the RNAs capped according to the methods described herein may be fragmented before or after capping. Such fragmenting reduces the sizes of the RNA to any desired length. For example, the RNA fragments can be around 10-10000 nucleotides in length, or ranges in between, e.g., 100-1000 nucleotides, 10-500 nucleotides, 3000-5000 nucleotides, or about 50, 100, 200, 250 nucleotides. Fragmenting can be achieved using standard techniques, including mechanical shearing, chemical, enzymatic digestion and sonication.

In some embodiments, the 3' ends of RNA can be reacted with T4 Polynucleotide Kinase (New England Biolabs, Ipswich, Mass.) in the absence of ATP, to remove 2'-3' cyclic phosphate or 3' phosphate.

In some embodiments, the capped RNAs can be sequenced. Sequencing will not only identify the nucleotide sequence of the RNA and characterize it along with the population of other labeled capped RNAs if desired such as in microbiome analysis and expression profiling but sequencing can also pinpoint and identify the TSS sequence of RNAs. Sequencing can also identify nascent RNAs that is newly transcribed. cDNA library preparation for Next-Generation sequencing can be done on the labeled capped RNAs using the NEBNEXT Ultra Directional RNA Library Prep Kit for Illumina or equivalent protocols.

The labeled capped RNAs can be directly ligated to adapters for preparing small RNA libraries (using the NEBNEXT Small RNA Library Prep Set for Illumina or equivalent protocol). In this case, the labeled capped RNAs may be decapped prior to ligation with an adapter or vector where necessary. Such a library will represent the specific population of RNAs capped with the labeled nucleotide as described herein (e.g., enriched capped mRNAs, uncapped RNAs, etc.). Alternatively the labeled capped RNAs can be reverse transcribed using a template switching oligonucleotide (Luo, et. al., *J. Virol.*, 64(9): 4321-4328 (1990); Zhu, et al., *Biotechniques* 30:892-897 (2001)) that enables introduction of a necessary priming sequence for the generation of DNA libraries for NextGen sequencing.

When the label of the capping nucleotide is composed of an oligonucleotide, cap jumping (Efimov, et al., *Nucl. Acids Res.*, 29(22):4751-4759 (2001)) can be used to introduce the necessary priming sequence for the generation of DNA libraries for NextGen sequencing.

In some embodiments, the labeled modified nucleotide is a cleavable 3'-biotin labeled guanosine 5'-triphosphate, wherein the cleavable linker comprises a 3'-O-allyl linkage. The cleavable labeled modified nucleotide is described for use adding a label to target RNA molecules at the 5' end where the 5' end is characterized by a terminal di-phosphate or tri-phosphate. Example 22 describes the synthesis of a cleavable 3'-biotin labeled guanosine 5'-triphosphate. An advantageous feature of a biotin label is that it binds streptavidin very tightly. Once formed, the biotin-streptavidin complex tolerates changes in pH, presence of detergents or high salt concentration, remaining stable even under very stringent washing conditions such as 4% SDS, 8 M urea, organic solvents (e.g. 20% isopropanol/ethanol), and thus allows efficient removal of non-specifically binding molecules. Elution of enriched RNA is readily achieved after cleavage of the allylic linker using Pd catalysts such as palladium(0), e.g. in tetrakis(triphenylphosphine)palladium, and palladium(II), e.g. in sodium tetrachloropalladate (Na2PdCl4).

Also provided is a method comprising: (i) adding an affinity tag-labeled GMP to the 5' end of 5'-diphosphorylated or 5'-triphosphorylated RNA molecules in a sample by incubating the sample with the chemically cleavable labeled mononucleotide shown above and a capping enzyme. In any embodiment, this method may further comprise (ii) enriching for RNA comprising the affinity tag-labeled GMP using an affinity matrix that binds to the affinity tag. In any embodiment, this method may further comprise chemically cleaving the cleavable linker, thereby releasing the enriched RNA from the affinity matrix. The chemically cleaving may be done by a palladium catalyst under aqueous conditions, for example. In any of these embodiments, the method may comprise ligating an adaptor to the free 3' OH generated by the chemical cleavage reaction.

An advantageous feature of a cleavable biotin labeled guanosine 5'-triphosphate is that it permits the enrichment of target RNA molecules using a suitable streptavidin matrix and after chemical cleavage of the linker it regenerates a free 3'-OH in a so-called traceless or scarless cleavage process. Because the linker portion is entirely removed, the enriched capped RNA is released in its naturally occurring form, i.e. without a linker R and a label L or fragments thereof. Thus, sequence specific bias attributed to enzymes in the presence of a labeled modified nucleotide during reverse transcription of labeled capped RNA and/or template switching in the presence of a template switching oligonucleotide can be eliminated. The elimination of bias is useful for improved accuracy of analyzing RNA sequences in steps involving down-stream amplification and sequencing.

All reference cited herein including U.S. application Ser. No. 15/786,020, filed Oct. 17, 2017; U.S. application Ser. No. 15/137,394 filed Apr. 25, 2016; PCT/US2014/068737, filed on Dec. 5, 2014; U.S. provisional Ser. No. 61/912,367, filed Dec. 5, 2013; U.S. provisional application Ser. No. 61/920,380, filed Dec. 23, 2013; U.S. provisional application Ser. No. 62/002,564 filed May 23, 2014; U.S. provisional application Ser. No. 62/001,918 filed Jun. 13, 2014; U.S. provisional application Ser. No. 62/409,151, filed Oct. 17, 2016; and U.S. provisional application Ser. No. 62/166, 190 filed May 26, 2016, are incorporated by reference.

EXAMPLES

Example 1: RNA Capping Using Biotin-11-GTP or 2'/3' EDA-Biotin-GTP: Comparison of the Label Position on the Nucleotide Base Versus the Sugar Ring A 300mer uniformly $P^{32}$ labeled in vitro RNA transcript was incubated with VCE and VCE buffer and either biotin-11-GTP (label on the guanosine ring) or 2'/3' Biotin-EDA-GTP.

Ten microliter reaction volumes containing 1×VCE buffer, $P^{32}$ uniformly labeled in vitro 300mer transcript RNA, 10 units of VCE and either 0.5 mM EDA-biotin-GTP, or 0.1 mM biotin-11-GTP were incubated at 37° C. for 60 minutes. The RNA from the reaction mixes were then purified on MEGAclear™ (Life Technologies, Grand Island, N.Y.) spin columns as directed by the manufacturer. 20 µl of each purified RNA (20% of the total volume) was mixed with 5 µl (5 µg) of φX174 DNA cleaved by HaeIII (New England Biolabs, Ipswich, Mass.). This mix was mixed with 125 µl of hydrophilic streptavidin magnetic beads (New England Biolabs, Ipswich, Mass.) that had been prepared by washing with a wash buffer (0.4 ml of wash buffer: 20 mM Tris-HCL pH 7.5, 500 mM NaCl, 1 mM EDTA) and incubated for 10 minutes at room temperature. The beads were then washed to elute unbound material by washing consecutively with 100 µl wash buffer, 120 µl wash buffer, 120 µl wash buffer and 400 µl of wash buffer. The beads were resuspended in 200 µl of wash buffer and radioactivity retained by the beads was determined by Cherenkov counting.

The results in FIG. 1 show that when biotin-11-GTP was used in the capping reaction of a 5' tri-phosphorylated RNA, no significant binding of the RNA to streptavidin beads was observed. However, when biotin-EDA-GTP (a mixture of 2' and 3' adducts) was used, about 10 fold more binding was observed than for biotin-11-GTP.

Example 2: Synthesis of 3' DBT-TEG-GTP

This example describes the method of synthesis of a novel labeled nucleotide. DBT is characterized here by a linker (TEG) that is attached to the oxygen on the C3 of the ribose. The linker is in turn linked to a DBT label which in contrast to Biotin has the property of being capable of being eluted from streptavidin without additional enzymatic reactions but solely by the addition of Biotin.

Figure 3:
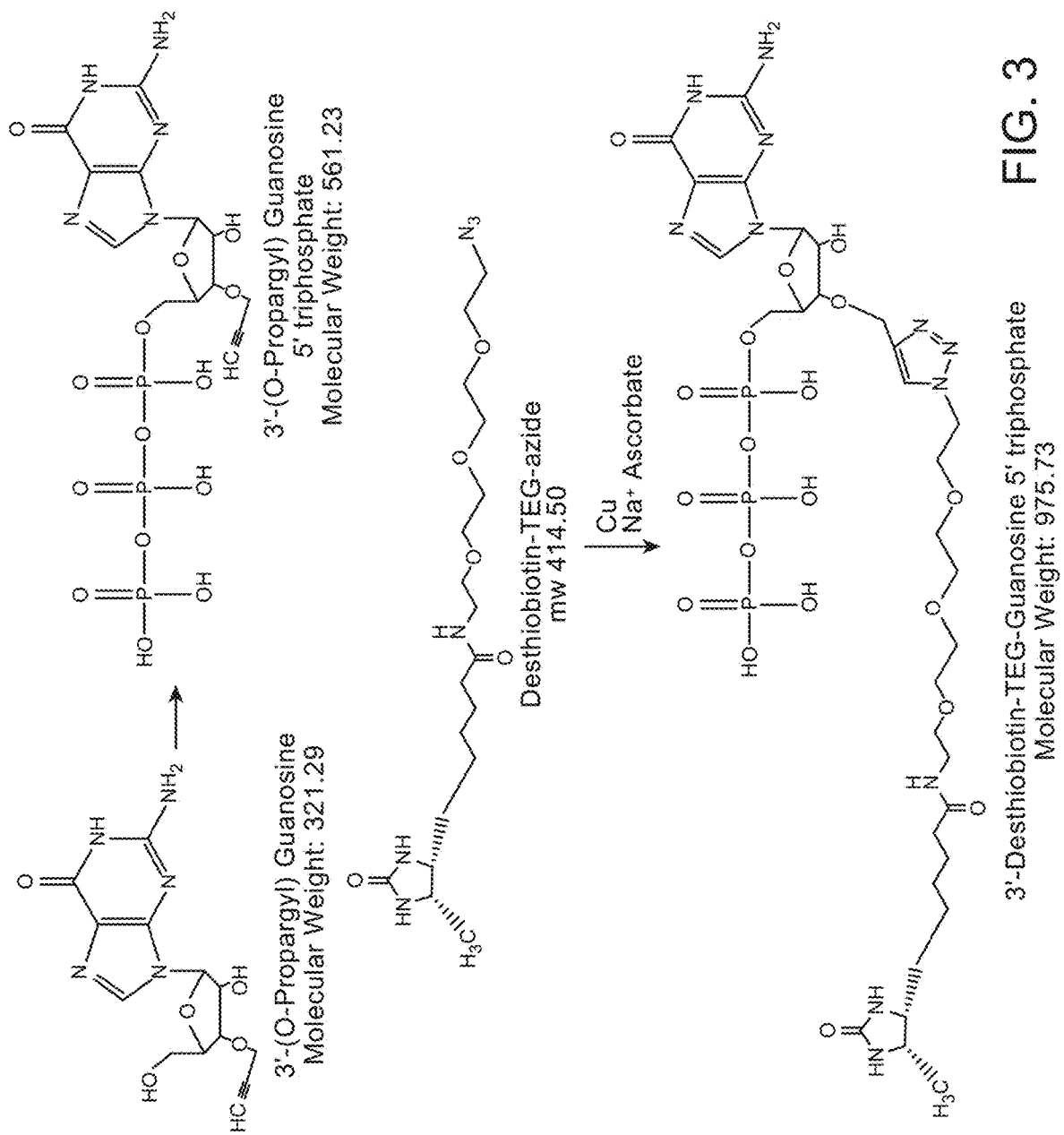
FIG. 3 shows a pathway for the chemical synthesis of 3' DBT-GTP.

Synthesis was initiated with 3'-(O-Propargyl) Guanosine (ChemGenes Corp. Wilmington, Mass.) followed by its conversion to 3'(O-Propargyl) Guanosine 5' Triphosphate via a one-pot, two step method (several published procedures). The 3'-(O-Propargyl) Guanosine 5' Triphosphate was then purified by both ion exchange chromatography and reverse phase HPLC. The isolated 3'(O-Propargyl) Guanosine 5' Triphosphate was converted to the DTB-GTP through the addition of DBT-TEG-azide (Berry and Associates, Inc., Dexter, Mich.) using copper-mediated azide-alkyne cycloaddition ("Click chemistry", Kolb and Sharpless, Scripps Res. Inst and BaseClick, Tutzing, GmbH). Final isolation of the target compound was performed using reverse phase HPLC. The pathway described here is shown in FIG. 3.

Example 3: Selective Specificity of the Label Position at 3' OH Position Versus the 2' OH in the Ribose Ring of the Nucleotide for RNA Capping Because biotin-EDA-GTP is a mixture of 2' and 3' adducts, it was decided to synthesize pure forms of the DBT-TEG-GTP with 2' adducts or 3' adducts and to test which of these were effective for binding RNA to streptavidin via the DBT. 2' DBT-TEG-GTP and 3' DBT-TEG-GTP (3' DBT-GTP) shown in FIGS. 2A and 2B were synthesized according to the protocol described in FIG. 3 and Example 2.

A 300mer uniformly $P^{32}$ labeled in vitro T7 transcript was incubated with VCE in VCE buffer and either 2' DBT-TEG-GTP or 3' DBT-TEG-GTP, or unlabeled control GTP.

The different modified labeled nucleotides were tested as follows: 10 µl reaction volumes containing 1×VCE buffer, $P^{32}$ uniformly labeled T7 in vitro 300mer transcript RNA, 10 units of VCE and either 0.5 mM 2' DBT-TEG-GTP (made according to the protocol in FIG. 3 and Example 2, where 2' 0-Propargyl Guanosine was substituted for 3' O-Propargyl Guanosine) or 3' DBT-TEG-GTP (made according to the protocol in FIG. 3 and Example 2), or GTP were incubated at 37° C. for 2 hours. 5 µl of MspI-digested pBR322 DNA (New England Biolabs, Ipswich, Mass.) was added to the RNA that was then purified on MEGAclear spin columns as directed by manufacturer. 50 µl (50% of the total volume) RNA was mixed with 50 µl of wash buffer 2 (10 mM Tris-HCl pH 7.5, 500 mM NaCl, 1 mM EDTA). This mix was added to the hydrophilic streptavidin magnetic beads that had been previously prepared by washing 3 times with 400 µl of 10 mM Tris-HCl pH 7.5, 50 mM NaCl. The beads were incubated for 10 minutes at room temperature. The beads were then washed with 100 µl of 10 mM Tris-HCl pH 7.5, 500 mM NaCl, 1 mM EDTA, and three times with 400 µl of 10 mM Tris-HCl pH 7.5, 500 mM NaCl, 1 mM EDTA, to elute unbound material. The beads were the resuspended in 50 µl of 10 mM Tris-HCl pH 7.5, 0.5M NaCl, 1 mM EDTA and an additional 50 µl of 10 mM Tris-HCl pH 7.5, 500 mM NaCl, 1 mM EDTA containing 20 mM biotin. The beads were kept resuspended for 20 minutes at room temperature by occasional quick mixing. To determine if the RNA had been selectively captured by the beads and eluted with the biotin, the beads were collected on the side of the tube with a magnet and the 100 µl supernatant was collected and radioactivity determined by scintillation counting.

Figure 4:
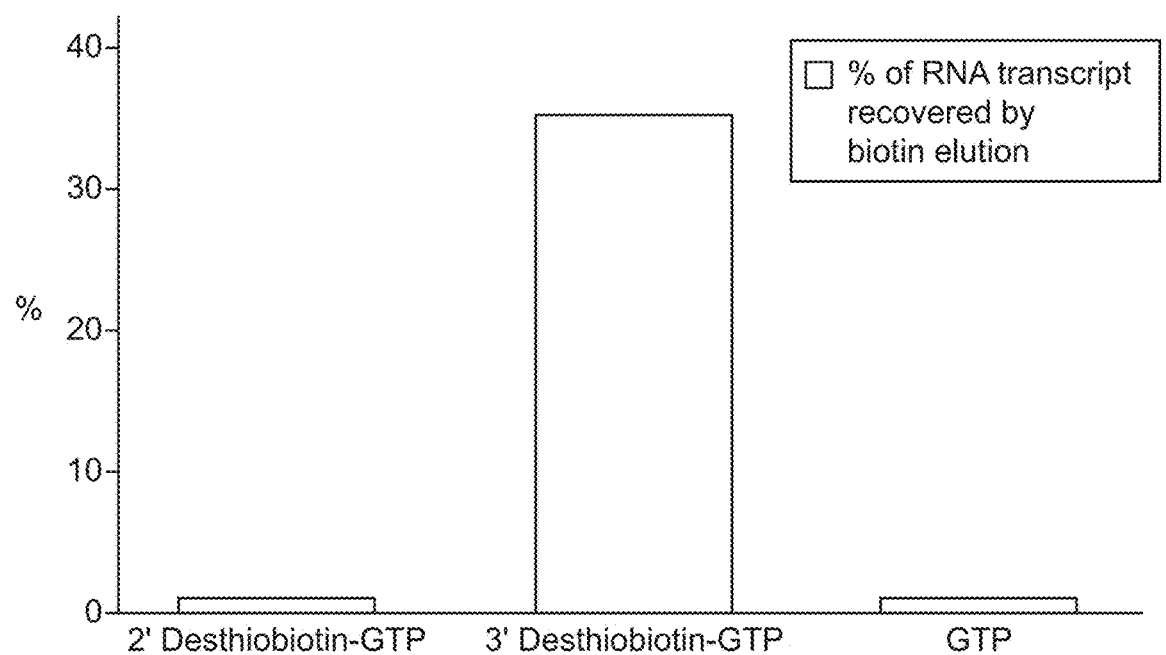
FIG. 4 shows results for capping of uncapped RNA with three different modified labeled nucleotides: 2' DBT-TEG-guanosine 5' triphosphate (2' DBT-GTP), 3' DBT-TEG-guanosine 5' triphosphate (3' DBT-GTP) and an unlabeled GTP control. The histogram shows that only RNA capped with 3' DBT-TEG-GTP (shown in FIG. 2A) was recovered after binding to streptavidin. In contrast, in the presence of a capping enzyme, RNA reacted with a mononucleotide, in which the DBT label was attached via a linker to the 2' hydroxyl group on the ribose moiety of GTP as described in Example 3, was surprisingly no better than control GTP for recovery.

The results showed that the transcript that was reacted with 3' DBT-TEG GTP was selectively bound to the streptavidin beads and eluted with 10 mM biotin whereas 10 mM biotin elution resulted in little to no $P^{32}$ when 2' DBT-TEG-GTP or GTP were used as substrates for the VCE reaction. The results are shown in FIG. 4.

In addition, 3' biotin-TEG-GTP was tested with VCE and a 27 nucleotide in vitro transcription RNA product. Polyacrylamide gel electrophoresis confirmed that the transcript was capped with 3'Biotin-TEG-GTP.

Example 4: Enriching 5' Triphosphorylated and 5' Diphosphorylated Prokaryotic RNA from a Mixture of Eukaryotic and Prokaryotic RNA 5' tri- and di phosphorylated RNA from *E. coli* could be enriched from a mixture of total human RNA and total *E. coli* RNA. 6 µg of Universal Human Reference (UHR) RNA (Agilent, Santa Clara, Calif.) was mixed with 6 µg of total *E. coli* RNA (prepared from an *E. coli* culture with FastRNA PROT™ Blue Kit, MP Biomedical, Santa Ana, Calif.) in a 70 µl volume containing 1×VCE buffer, 0.5 mM 3'DBT-TEG-GTP and 60 units of VCE and incubated at 37° C. for 2 hours. The resulting reaction was applied to a MEGAclear spin column and eluted with 100 µl of water. A ten microliter aliquot was saved as unenriched control. 50 µl of buffer 1 (20 mMTris-HCl pH 7.5 50 mM NaCl) was added to the remaining 90 µl and the total 140 µl solution was adsorbed to the hydrophilic streptavidin beads that had been previously washed with buffer 1. The beads were incubated at room temperature for 20 minutes and washed 4× with buffer 2 (20 mMTris-HCl, 500 mM NaCl, 1 mM EDTA). The beads were then suspended in 100 µl of buffer 1 containing 1 mM biotin and incubated at room temperature for 20 minutes with occasional mixing. The beads were collected on the side of the tube with a magnet and the 100 µl supernatant was collected. The resulting biotin eluted RNA product was isolated by use of MEGAclear Kit (Life Technologies, Grand Island, N.Y.). The biotin eluted RNA (enriched RNA) and the total RNA were then concentrated by use of "RNA Clean and Concentrator™" (Zymo Research, California) in 10 µl of water. Both RNA samples were prepared for sequencing by using the NEBNEXT Ultra Directional RNA Library Prep Kit for Illumina as described by the manufacturer and sequenced on the Illumina MISEQ.

Sequencing reads were quality filtered and the adaptors were trimmed. The reads were mapped to a composite genome made of the human (hg19) and *E. coli* (U00096.2) genomes using STAR [STAR: ultrafast universal RNA-seq aligner. Dobin].

The results showed that the proportion of sequenced RNAs that did not have tri- and di phosphorylated RNA (including prokaryotic and eukaryotic rRNA sequences and eukaryotic mRNA) was much reduced in the enriched fraction compared to the total RNA sample (before enrichment). More specifically, the number of prokaryotic non-rRNA increased more than 4-fold after enrichment, and the relative quantity of reads of prokaryotic non-rRNA in the sample increased from about 10% before enrichment to around 50% after enrichment.

TABLE 2

Analysis of Enrichment

| Reads mapping to: | Before Enrichment | After Enrichment |
|---|---|---|
| E. coli non-rRNA (RNA with 5' tri-and di phosphates) | 2211386 | 9129621 |
| E. coli ribosomes (Bacterial rRNA) | 4800190 | 2467861 |
| Human RNA (Eukaryotic RNA not 5' tri- and di phosphates) | 14888634 | 6532592 |

Example 5: Enriching 5' Triphosphorylated and 5' Diphosphorylated RNA from an E. coli Lysate Controls—in vitro synthesized Fluc RNA and Cluc RNA were prepared using T7 RNA polymerase (New England Biolabs, Ipswich, Mass.) to transcribe plasmid DNA containing either the Cluc gene (pCMV-Cluc 2 Control plasmid (New England Biolabs, Ipswich, Mass.)) or the Fluc gene (Fluc Control Template from T7 Quick high yield RNA synthesis kit (New England Biolabs, Ipswich, Mass.)). The Fluc transcript was further treated with VCE and GTP to convert it to m7G capped RNA.

6 μg of total E. coli RNA, 7 ng of Fluc (m7G capped) RNA and 12 ng of Cluc (5' triphosphate) RNA were incubated in a 70 μl reaction volume with 1×VCE buffer, 0.5 mM 3'DBT-GTP and 60 units of VCE for 2 hours at 37° C. The product of the reaction was applied to a MEGAclear spin column and eluted with 100 μl of water. A 33 μl aliquot was saved as unenriched sample.

125 μl hydrophilic streptavidin magnetic beads were prewashed with 3 times with a first wash buffer (0.4 ml of 10 mM Tris-HCl pH 7.5, 1 mM EDTA, 0.5 M NaCl) and then 1 time with a second wash buffer (0.4 ml of 10 mM Tris-HCl pH 7.5, 1 mM EDTA, 0.05 M NaCl). The beads were then suspended in 95 μl of the second wash buffer containing 2 μl of murine RNAase inhibitor (80 units) (New England Biolabs, Ipswich, Mass.). 33 μl of the 3' DBT GTP treated RNA was added to the streptavidin bead preparation. The beads were incubated at room temperature for 20 minutes with occasional mixing to keep the beads resuspended. The beads were then washed 2 times with the first buffer (0.4 ml 10 mM Tris-HCl pH 7.5, 1 mM EDTA, 0.5 M NaCl) containing 8 μl of the murine RNAase Inhibitor (320 units) and 2 times with 0.4 ml 10 mM Tris-HCl pH 7.5, 1 mM EDTA buffer, containing 8 μl of murine RNAase Inhibitor. The beads were then suspended in 100 μl of the second wash buffer (10 mM Tris-HCl pH 7.5, 1 mM EDTA, 0.05M NaCl) containing 1 mM biotin and incubated at room temperature for 20 minutes with occasional mixing. The beads were collected on the side of the tube with a magnet and the 100 μl supernatant was collected. The resulting biotin eluted RNA product and unenriched aliquot were then concentrated by use of "RNA Clean and Concentrator" in 10 μl of water. The two RNA samples were prepared for sequencing by using the NEBNEXT Ultra Directional RNA Library Prep Kit for Illumina as described by the manufacturer and sequenced on the Illumina MISEQ.

Enrichment of Cluc from a mixture of known amounts of Cluc (5' triphosphate RNA) and Fluc (m7G capped) in vitro synthesized transcripts was determined. Sequencing reads were quality filtered and the adaptors were trimmed. The reads were mapped to E. coli (U00096.2) genome and CLUC and FLUC transcript sequences using BWA [PMID: 19451168]. An enrichment of greater than about 10 fold enrichment of the tri-phosphorylated RNA (CLuc) compared with the G-capped RNA (Fluc) and unenriched CLuc was observed.

Enrichment of non-ribosomal prokaryotic RNA from an E. coli lysate was greater than 8 fold.

Example 6: Enriching 5' Tri-Phosphorylated polIII RNA from Total Human RNA

Ribo-Zero™ (Epicentre, Madison, Wis.) was used to remove human rRNA from the preparation of UHR RNA.

Approximately 100 ng of Ribo-Zero depleted UHR RNA was mixed with m7G capped Fluc transcript (0.07 ng) and 5' triphosphate Cluc transcript (0.12 ng). This was incubated in a 70 μl reaction volume with 1×VCE buffer, 0.5 mM 3'DBT-GTP and 60 units of VCE for 2 hours at 37° C.

The resulting reaction was applied to a MEGAclear spin column and eluted with 50 μl of water. A 20 μl aliquot was saved as unenriched sample. 30 μl of the DBT capped RNA was added to 95 μl of 10 mM Tris HCl pH 7.5, 50 mM NaCl buffer containing 2 μl of murine RNAse inhibitor and was adsorbed to 125 μl of hydrophilic streptavidin beads that had been previously washed with 3 times with 10 mM Tris HCl pH 7.5, 500 mM NaCl buffer followed by washing in 10 mM Tris HCl pH 7.5, 50 mM NaCl buffer. The beads were incubated at room temperature for 20 minutes with occasional mixing. The beads were then washed 2 times with 500 μl of 10 mM Tris-HCl pH 7.5, 1 mM EDTA, 500 mM NaCl and then 2 times with 500 μl of 10 mM Tris-HCl pH 7.5, 50 mM NaCl, 1 mM EDTA. All four washes contained 2 μl murine RNAase inhibitor. The beads were then suspended in 100 μl of 10 mM Tris-HCl pH 7.5, 1 mM EDTA, 50 mM NaCl containing 1 mM biotin, 2 μl murine RNAase inhibitor and incubated at room temperature for 20 minutes with occasional mixing. The beads were collected on the side of the tube with a magnet and the 100 μl supernatant was collected. The resulting biotin eluted RNA product and unenriched aliquot were then concentrated by use of "RNA Clean and Concentrator" in 10 μl of water. The three RNA samples were prepared for sequencing by using the NEB-NEXT Ultra Directional RNA Library Prep Kit for Illumina as described by the manufacturer and sequenced on the Illumina MISEQ.

Sequencing reads were quality filtered and the adaptors were trimmed. The reads were mapped to the human genome (hg19) using STAR [STAR: ultrafast universal RNA-seq aligner. Dobin]. The mapped reads were overlapped with annotated features from gencode v17 (PUBMED: 22955987) and the repeat features from UCSC (hg19). We defined human polymerase III (pol III) transcripts annotated as 7SK and 7SL where pol III has a 5' triphosphate, small nuclear RNA, Alu repeats and tRNAs. We defined polymerase II (pol II) transcripts as transcripts annotated with the term "protein coding" and these transcripts are characterized by being capped.

Figure 6:
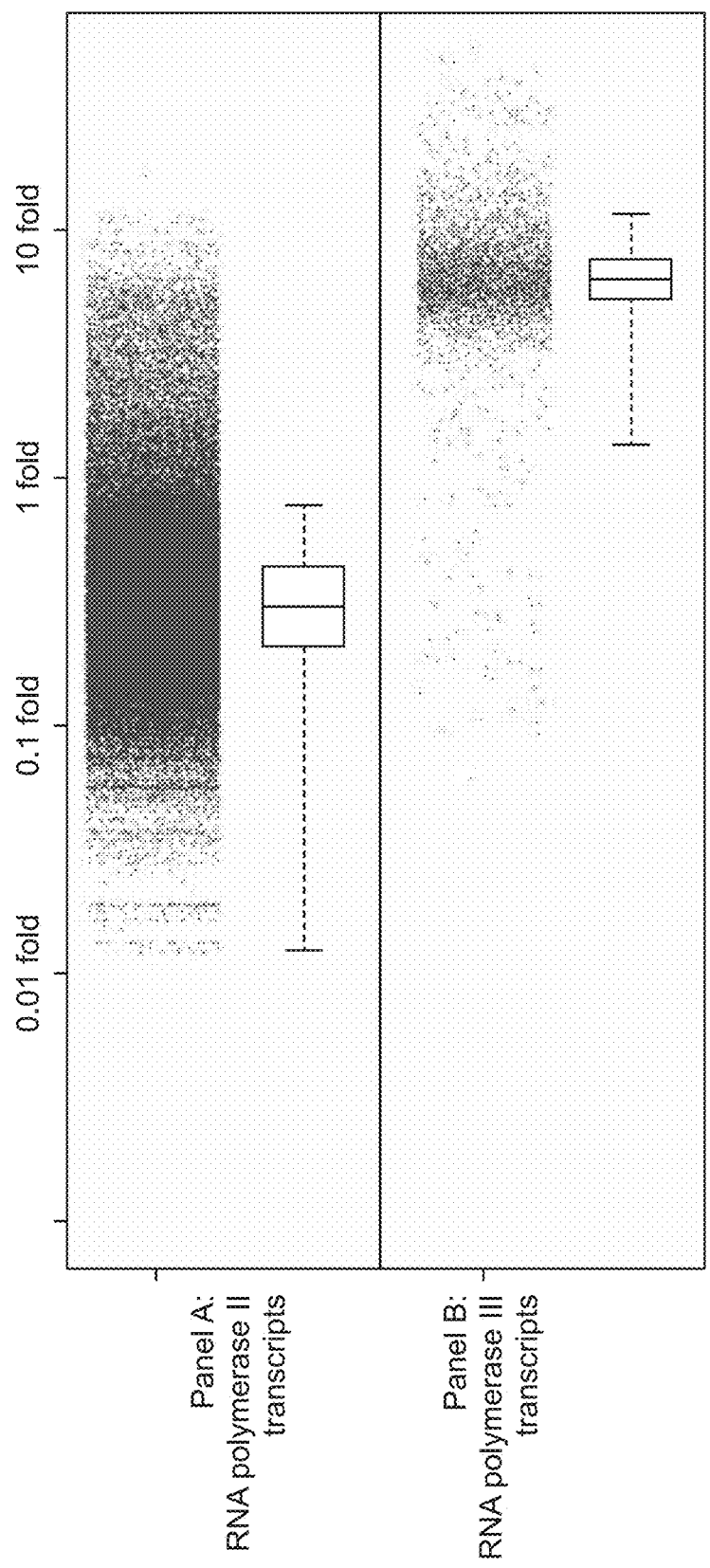
FIG. 6 shows a comparison of the distribution of points in a computer readout in which each point corresponds to the ratio between the relative amount of either an annotated pol II (panel A) or pol III RNA transcript (panel B) in the enriched versus total fraction. A majority of the pol III RNA transcripts were enriched at least 5 to 10 fold, whereas a majority of the pol II RNA transcripts were depleted demonstrating that Pol III transcripts were substrates for the modified labeled GTP, whereas the Pol II transcripts were not substrates.

As shown in FIG. 6, the human RNA polymerase III transcripts were enriched about 5-10 fold and the human RNA polymerase II transcripts were depleted.

Example 7: Comparison of Enzymatic Release of RNA with Competitive Elution Using Biotin of RNA Bound to Streptavidin Beads The RNA that had been prepared and bound to streptavidin beads as described in Example 1 and 3 was treated with (i) either Vaccinia decapping enzyme D9 or Vaccinia decapping enzyme D10 (Parrish, et al., J. Virol., 81(23): 12973-8 (2007)), or (ii) by addition of biotin to the immobilized RNA (as in Example 3). It was shown that both decapping enzymes successfully removed bound capped RNA from the beads. Thus, like elution of biotin-capped RNA using biotin, decapping enzymes are equally suitable for releasing captured capped RNA.

Example 8: Analysis of TSS by RNA-SEQ of Enriched RNA from a Prokaryote in a Method with Less than Single Base Resolution RNA was fragmented before the enrichment step following the protocol described below.

For the sample: 6 ug of total E. coli RNA and for controls: 7 ng of Fluc RNA and 24 ng of Cluc RNA; were incubated in a 70 µl reaction volume with 1×VCE buffer, 0.5 mM 3'DBT-GTP and 60 units of VCE for 2 hours at 37° C. The resulting reaction was applied to a MEGAclear spin column and eluted with 100 µl water.

The resulting RNA was reduced in size to about 200 nucleotides by incubation at 94° C. for ten minutes in the presence of 3.3×NEB First Strand Synthesis Buffer (New England Biolabs, Ipswich, Mass.).

A 30 µl aliquot was saved as unenriched sample. 35 µl of the DBT capped RNA was added to 70 µl of 10 mM Tris HCl pH 7.5, 50 mM NaCl buffer containing 2 µl of murine RNAse inhibitor. This mixture was adsorbed to 125 µl of hydrophilic streptavidin beads that had been previously washed with 3 times with 10 mM Tris HCl pH 7.5, 500 mM NaCl buffer followed by washing in 10 mM Tris HCl pH 7.5, 50 mM NaCl buffer. The beads were incubated at room temperature for 20 minutes with occasional mixing. The beads were then washed 2 times with 500 µl of 10 mM Tris-HCl pH 7.5, 1 mM EDTA, 500 mM NaCl for and then 2 times with 500 µl of 10 mM Tris-HCl pH 7.5, 50 mM NaCl, 1 mM EDTA all four washes contained 2 µl murine RNAase inhibitor. The beads were then suspended in 100 µl of 10 mM Tris-HCl pH 7.5, 1 mM EDTA, 50 mM NaCl containing 1 mM biotin, 2 µl murine RNAase inhibitor and incubated at room temperature for 20 minutes with occasional mixing. The beads were collected on the side of the tube with a magnet and the 100 µl supernatant was collected. The resulting biotin eluted RNA product and unenriched sample were then concentrated by use of "RNA Clean and Concentrator" in 10 µl of water. The three RNA samples were prepared for sequencing by using the NEBNEXT Ultra Directional RNA Library Prep Kit for Illumina as described by the manufacturer and sequenced on the Illumina MISEQ.

Sequencing reads were quality filtered and the adaptors were trimmed. The reads were mapped to E. coli (U00096.2) genome and CLUC and FLUC transcript sequences using BWA [PMID:19451168].

Figure 7:
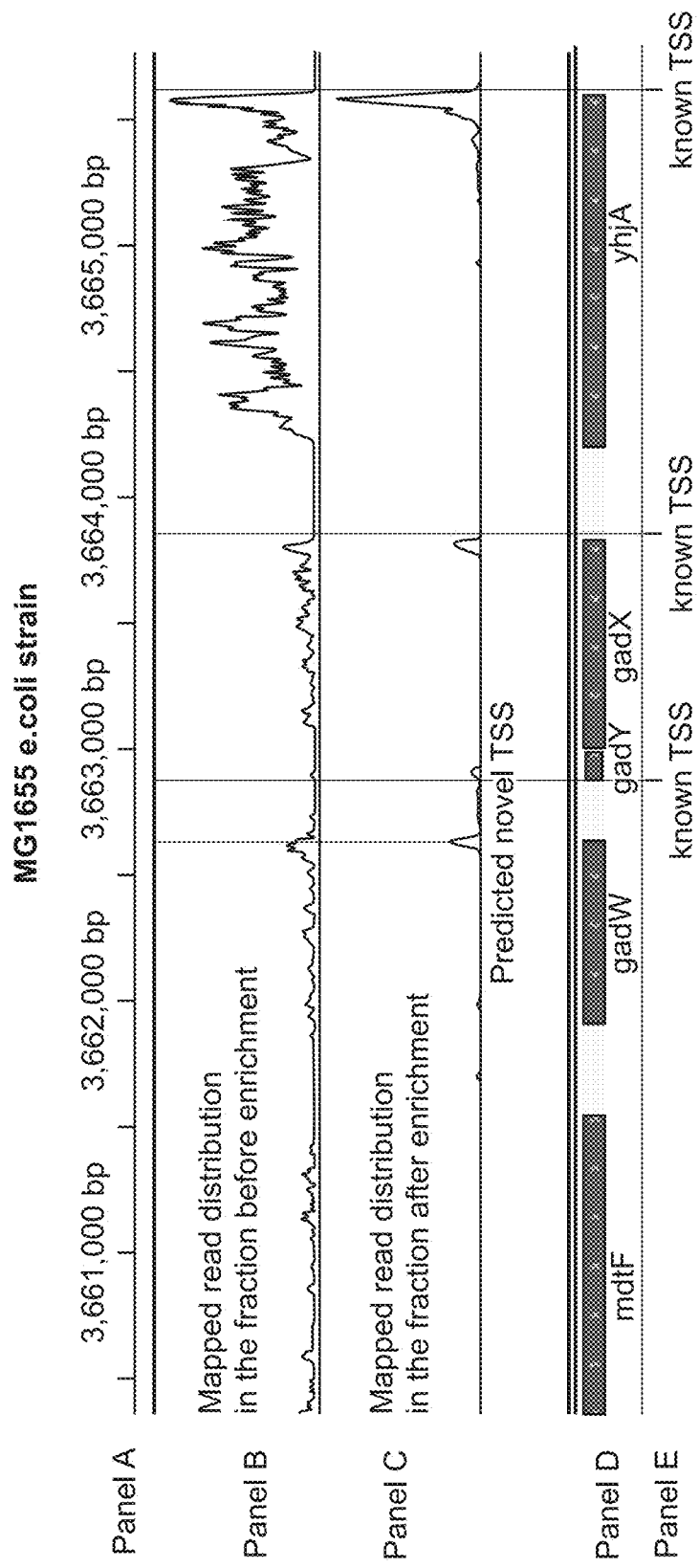
FIG. 7 provides a comparison of results for enriched and non-enriched 5' capped labeled prokaryotic RNA treated as described in Example 8. The total RNA was fragmented to about 200 nucleotide lengths prior to enrichment and then sequenced to identify TSS. In this example, TSS are detected at 3,662,888 bp, 3,663,865 bp and also at about 3,665,632 bp (U00096.2 genome). Panel (A) shows genomic region. Panel (B) shows mapped read distribution before enrichment. Panel (C) shows mapped read distribution in the fraction after enrichment showing peaks corresponding to three predicted TSS and a novel TSS. Panel (D) shows the location of genes to which the reads match. Panel (E) shows annotated TSS for the genes shown in (d) and shows that the enriched RNA shows a novel TSS at approximately 3662660.

The results in FIG. 7 shows an example of 5 kb E. coli genomic region (panel A) with the annotated genes (Panel D) and annotated TSS (Panel E) (see Kim, et al., PLoS genetics, 8(8), e1002867 (2012)). The un-enriched sample when sequenced provided a large number of reads (Panel B). The reads distribute more or less uniformly across the full lengths of the annotated genes. In contrast, the sample in Panel C was enriched and the number of sequencing reads was reduced with discrete peaks (although not single base resolution) at TSS at the beginning of the annotated genes. The maximum signal of reads for each gene correlated precisely with the annotated TSS (Panel E) with an additional peak at the gadW gene indicative of a novel TSS. This demonstrates the power of this method to identify TSS that were previously unknown.

The data in Table 3 confirms efficient depletion of rRNA from more than 95% of the reads in the fraction before enrichment to only about 20% in the fraction after enrichment.

TABLE 3

| Demonstrated Enrichment | | |
| --- | --- | --- |
| Reads | Before Enrichment | After Enrichment |
| Non-rRNA | 508658 | 3404912 |
| RRNA | 13620039 | 863987 |

Example 9: Analysis of TSS by Small RNA Library Preparation of Enriched RNA from a Prokaryote in a Method with Single Base Resolution Total RNA was obtained from lysed E. coli and enriched by capping with VCE and desthiobiotinylated nucleotide and binding to streptavidin beads. The beads were washed before elution with biotin.

7.5 µg of total E. coli RNA was incubated at 70° C. for 2 minutes in a 1 mM Tris-HCl pH 8.0, 0.1 mM NaCl the buffer was then adjusted to contain 50 mM Tris-HCl pH 8.0, 5 mM KCl, 1 mM MgCl2, 1 mM DTT, 0.1 mM SAM, 0.5 mM 3'DBT-GTP and 50 units of VCE for 30 minutes at 37° C. The RNA was then isolated by use of "RNA Clean and Concentrator" and eluted by 100 µl of 1 mM Tris-HCl pH 8.0, 0.1 mM EDTA.

The RNA was fragmented by adding 2.5 µl of 10×T4 Polynucleotide Kinase Buffer (absent of any ATP) to the 100 µl solution and was heated at 94° C. for 5 minutes. The RNA was collected by exposure to 1.8 volumes of AMPURE XP beads with an additional 1.5 volumes of 100% ethanol. The beads were washed with 80% ethanol two times and then dried for five minutes and eluted with 100 µl of 1 mM Tris-HCl ph 7.5, 0.1 mM EDTA. The 3' ends of RNA were dephosphorylated by incubating 75 µl of the RNA solution in 1×T4 polynucleotide kinase buffer with 40 units of T4 Polynucleotide Kinase (previously dialyzed in ATP-free kinase storage buffer) in a total volume of 82 µl for 15 minutes at 37° C.

The 75 µl of kinase treated RNA was divided into a 25 µl and 50 µl volume.

The 25 µl volume of the kinase treated RNA was purified by AMPURE XP beads as described above and eluted in 30 µl of 1 mM Tris-HCl ph 7.5, 0.1 mM EDTA. To the 50 volume of kinase treated RNA was added 30 µl of prewashed streptavidin beads. The beads were then washed 2 times with 500 µl of 10 mM Tris-HCl pH 7.5, 1 mM EDTA, 500 mM NaCl for and then 2 times with 500 µl of 10 mM Tris-HCl pH 7.5, 1 mM EDTA. The beads were collected on the side of the tube with a magnet and 30 µl supernatant was collected. This 30 µl was subjected to AMPURE XP bead/ethanol cleanup as above and eluted in 60 µl of 1 mM Tris-HCl, 0.1 mM EDTA. The 60 µl solution was split into two 30 µl samples. One of the two 30 µl samples was subjected to another round of streptavidin binding, washing and elution and AMPURE XP bead cleanup as described above. The three samples (a) no streptavidin enrichment, (b) 1 round of streptavidin enrichment and (c) 2 rounds of streptavidin enrichment were all subjected to RppH decapping as described here: to the 30 µl of solution was added 3.3 µl of 10× ThermoPol Buffer and 15 units of RppH and incubated for 60 minutes at 37° C. 0.5 µl of 0.5 M EDTA was added to each sample and then heated to 94° C. for 2 minutes. The samples were then collected on AMPURE XP beads as previously and eluted in 20 µl of 1 mM Tris-HCl, 0.1 mM EDTA.

The three RNA samples were prepared for sequencing by using the NEBNEXT Small RNA Library Prep Kit for Illumina as described by the manufacturer and sequenced on the Illumina MISEQ.

Figure 8:
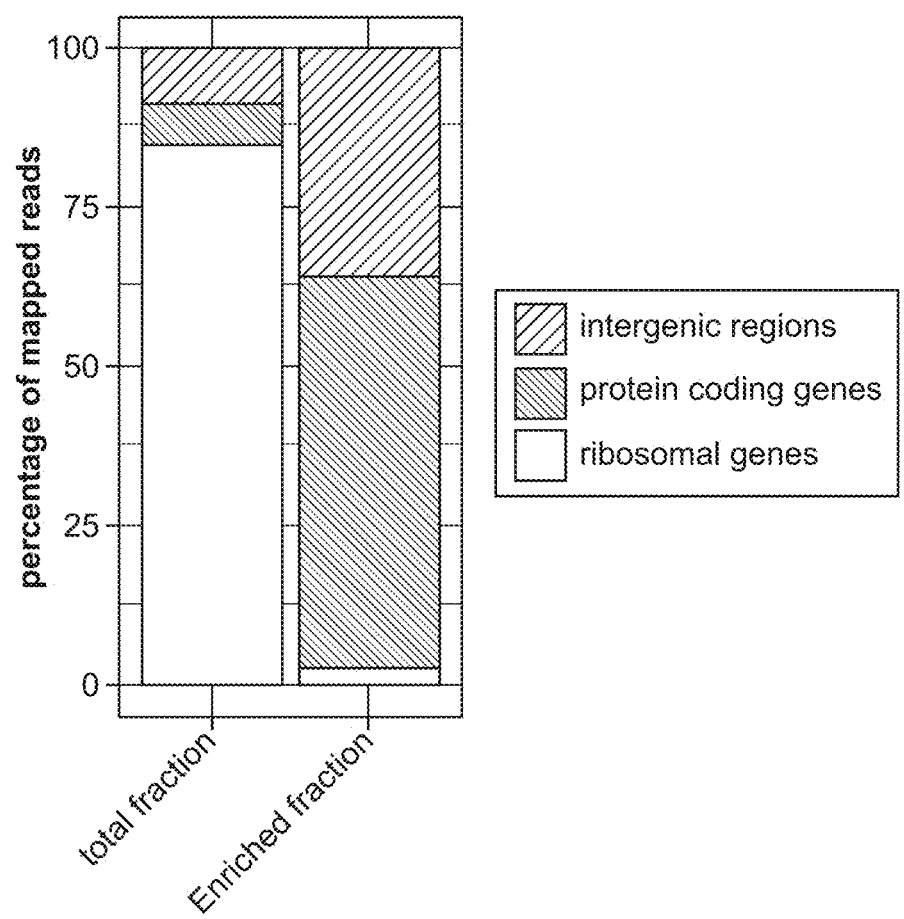
FIG. 8 shows the distribution of reads mapping to intergenic regions, protein coding regions and ribosomal genes for total RNA, and enriched RNA. Significantly, the mapped reads attributed to ribosomal genes is dramatically reduced in the enriched fraction from about 80% to about less than 5%. RNA mapping collectively in protein coding regions and intergenic regions increased from about 5% to greater than 95%. The y-axis is percentage of mapped reads. This data was obtained using NEBNEXT® Small RNA Library Prep, (New England Biolabs, Ipswich, Mass.) to make libraries from the total and enriched RNA which was then sequenced in the Illumina MISEQ. Reads were mapped to the *E. coli* genome (U00096.2). Ribosomal genes, intergenic regions and protein coding genes were also defined by the NCBI annotation U00096.2

The results shown in FIG. 8 depict the relative amount of RNA found from ribosomal and intergenic and protein coding regions in the unenriched fraction versus the enriched fraction (two streptavidin rounds).

The results are shown in FIG. 9 for single base resolution of the TSS. Single base resolution is obtained (panel—bound fraction) that exactly corresponds to the TSS of genes shown in panel (TSS). Panel—total RNA fraction shows the number of reads obtained at each position along the genome fragment from non-enriched (total), fragmented, 5' modified, capped RNA.

Here we define the TSS by requiring a minimum of 20 reads initiating at the same nucleotide position and compare this read distribution to that obtained from un-enriched total RNA requiring an enrichment of a base 2 logarithm greater than 1.

Example 10: Analysis of a Metatranscriptome (e.g. Microbiome)

With the recognition of the importance of the microbiome for human health, efforts have proceeded to obtain genome sequences for all the representative organisms in a microbiome to ascertain which organisms are present and how the population of microorganisms might vary in health and disease. A list of occurrences of microorganisms does not reveal the functional state of each organism. The level of transcription is not revealed with genomic DNA sequence. However transcriptional activity or gene expression level does reflect the active functional state of an organism. Another approach presented here is to analyze the entire RNA population of the microbiome after enrichment away from ribosomal and host RNA.

RNA from fecal matter is obtained by use of for example, PowerMicrobiome™ RNA Isolation Kit (Mo Bio, Carlsbad, Calif.). The obtained prokaryotic RNA is capped with a capping enzyme and a labeled modified nucleotide and the labeled RNA is reacted with coated beads that are capable of binding to the label on the capped RNA. All unbound RNA is washed away and the bound RNA is collected. This RNA is then sequenced using high throughput sequencing. The conditions optimized for a feces derived microbiome and a metatranscriptome may be optimized by first testing a synthetic microbiome which may contain a plurality of known organisms in a synthetic mixture (for example, 4 microorganism lysates). After high throughput sequencing, the sequences are mapped and quantified with respect to a database of genomes. These results characterize the relative expression of RNA transcripts in the microbiome of the host animal (for example, a mouse).

Example 11: Sequencing of the 5' End of Nascent Eukaryotic RNA

Total RNA is isolated from eukaryotic cells using TRIZOL and precipitated with ethanol. The lower molecular weight fraction of total RNA (below 100 nucleotides) is obtained by AMPURE XP bead differential size selection. Small RNA is enriched by first capping with 3' DBT GTP according to the methods described in Example 9. Half of the RNA is used as control, the remaining is adsorbed to hydrophilic Streptavidin beads and washed and then eluted with biotin. The RNA is decapped with RppH. The RNA is prepared for sequencing using NEBNEXT Small RNA Library Prep Kit or subjected to template switching library preparation (SMART® Ultralow RNA Kit, Clontech, Mountain View, Calif.) and sequenced using MISEQ. Prior to library preparation, the RNA can be released from streptavidin beads either in the presence of biotin or by decapping. Decapping or denaturation of the streptavidin would be preferred if the modified nucleotide used had a label for binding coated beads that was not readily elutable without decapping or denaturation of the streptavidin.

The resulting sequences will represent the position of the TSS of nascent RNA on the eukaryotic genome and the relative abundance of each nascent transcript.

Example 12: Template Switching to Reveal 5' End of Nascent Eukaryotic RNA

Figure 12:
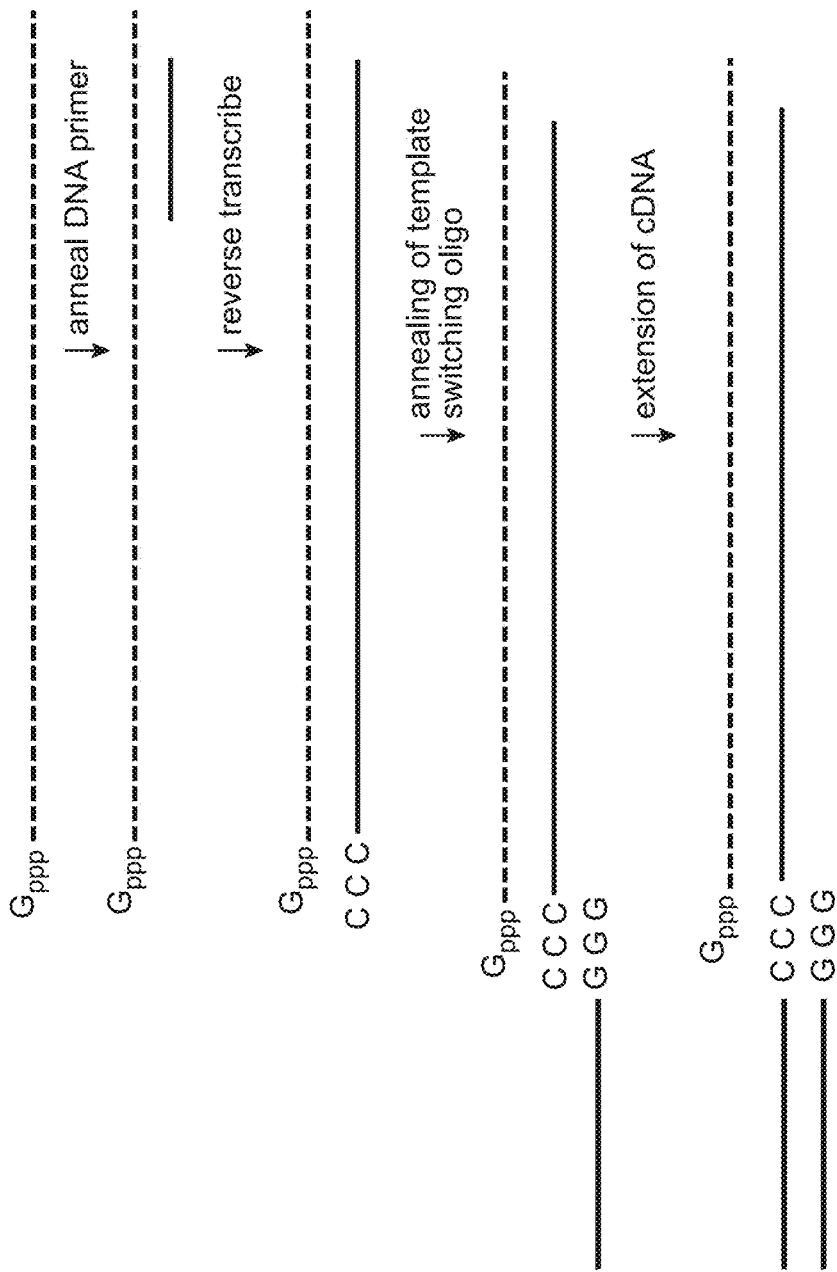
FIG. 12 shows template switching.

Total RNA is isolated from eukaryotic cells using TRIZOL and precipitated with ethanol. The lower molecular weight fraction of total RNA (below 100 nucleotides) is obtained by AMPURE XP bead differential size selection. In one embodiment, small RNA is enriched by first capping with DBT GTP according to the methods described in Example 9. The RNA is adsorbed to hydrophilic Streptavidin beads and washed and then eluted with biotin. This labeled capped RNAs can be reverse transcribed using a template switching oligonucleotide (New England Biolabs, Ipswich, Mass.) which enables introduction of a necessary priming sequence for the generation of DNA libraries for NextGen sequencing (see FIG. 12) with the expectation of single nucleotide resolution.

Example 13: Cap Jumping to Identify Di- and Tri-Phosphorylated Transcripts

Figure 2C:
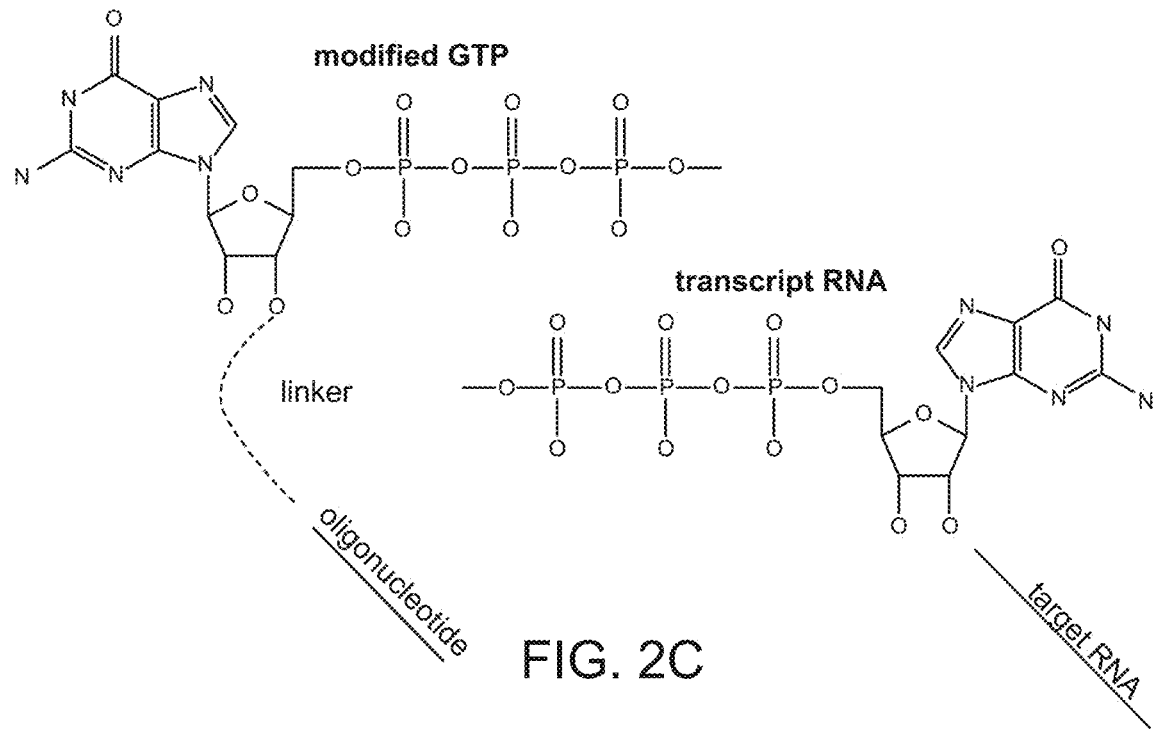
FIGS. 2C-2D shows an oligonucleotide modified nucleotide for capping and capped enzyme product.
Figure 2D:
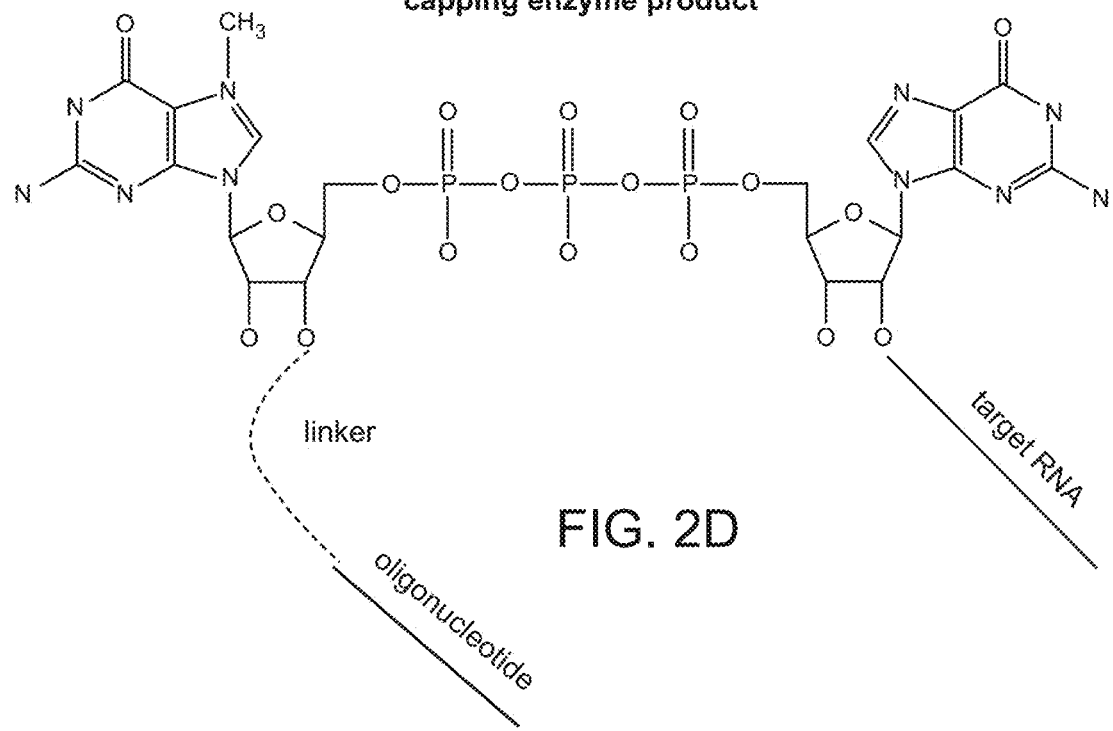
Figure 11:
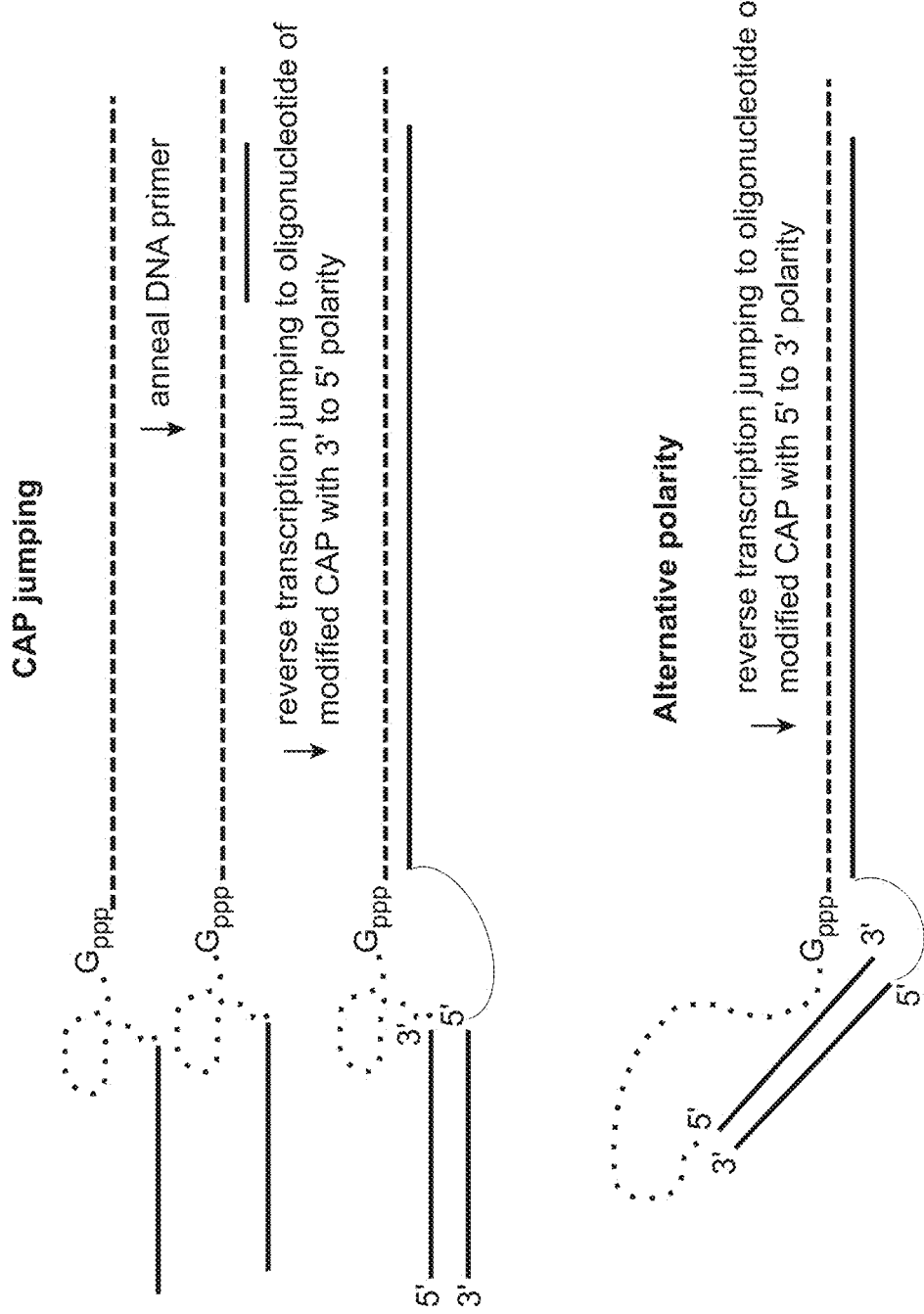
FIG. 11 shows cap jumping for selective amplification of a target RNA.

In this example total RNA is obtained from a bacterial culture and enriched by capping with VCE and a nucleotide modified at its 3' position with a linker attached to an oligonucleotide (see FIG. 2C and FIG. 2D). When the label of the capping nucleotide is composed of an oligonucleotide (FIG. 11), cap jumping (see for example, Efimov, et al., *Nucleic Acids Res.*, 29(22):4751-4759 (2001)) can be used to introduce the necessary priming sequence for the generation of DNA libraries for NextGen sequencing. In place of enrichment by affinity binding to a solid support, an oligonucleotide is attached through a capping reaction for direct use in amplification. Only artificially capped RNA is successfully reverse transcribed resulting in an adapter sequence for amplification. As shown in FIG. 11, it may be possible to attach an oligonucleotide label by the 5' end or the 3' end to the linker on the modified nucleotide. In one case, reverse transcription can jump to oligonucleotides of modified CAP with 3' to 5' polarity or vice versa. Using this approach, enrichment might be achieved by selection of amplicons as only those RNAs with tri- or di-phosphorylated 5' ends will be amenable to amplification.

Example 14: Association of SSM with a Phenotype

In this example, two cohorts of several hundred to several thousand humans are selected. One cohort is composed of patients with a disease condition, the other cohort is composed of healthy individuals or patients with another disease condition. Disease conditions can be for example, Crohn's disease, celiac disease, infections with or without resistance to a given antibiotics, diabetes, or pneumonia. For each individual, samples from the relevant body part can be taken for example an intestinal mucosal biopsy can be obtain using the intestinal mucosal brush methodology. From the biological sample, total RNA can be extracted using for example the PowerMicrobiome RNA Isolation Kit and 5' triphosphate RNA fragments can be isolated using for example the procedure described in Examples 9. For each initial sample, sequencing reads are adaptor trimmed and shortened to the desired length of the SSM (for example 30 bp) and processed into a data structure composed of a hash table with the key being the reads and the value being the incrementation of a particular key.

Figure 10:
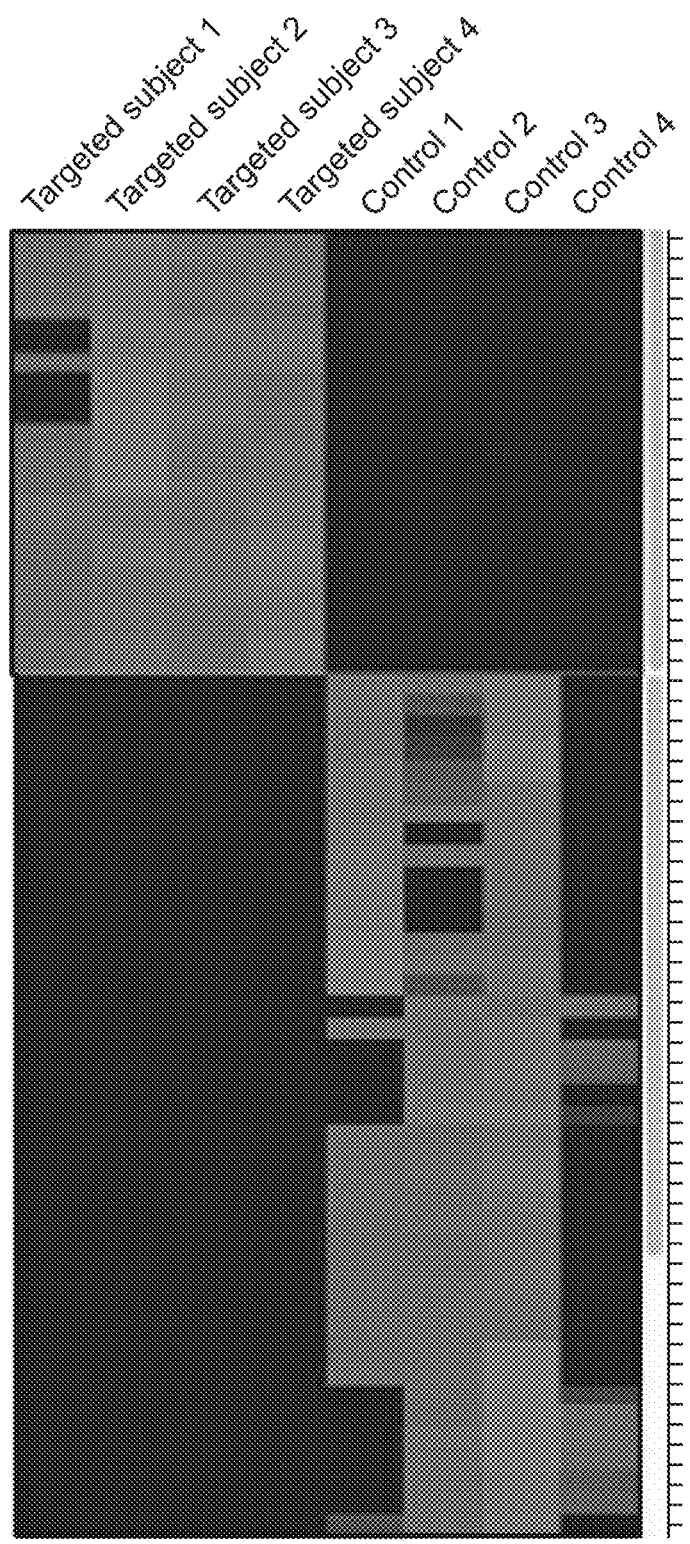
FIG. 10 shows a heat map from a subset of the microbiome signatures in 8 different samples, 4 controls and 4 treated subjects. Black corresponds to substantially no read representation whereas degrees of grey show a high degree of representation. The sequence signatures differentiate the control from the treated state. The horizontal bars along the right side vertical axis correspond to individual SSM.

For each cohort, a matrix can be derived where rows correspond to SSMs and columns correspond to individual sample. Using established linkage statistical methods, a set of significant SSMs associated to a given disease can be derived from comparing the two matrices. See for example FIG. 10 as a prophetic example where associated SSMs are depicted by a heat map of a cohort of 4 treated subjects and a cohort of 4 controls subjects. Those associated SSMs can be used for diagnostic purpose or can be used to find the causative genes or microbial species for, for example, drug development.

Example 15: Alternative Method for Obtaining a Signature

An alternative method for generating a signature may be obtained after NEBNEXT Ultra Directional RNA Library Preparation and sequencing. The RNA can be directly used for library preparation without decapping. Sequencing reads are assembled using existing algorithm for example trinity [Trinity: reconstructing a full-length transcriptome without a genome from RNA-Seq data] to assembled transcripts. Each assembled transcript would correspond to a SSMs and the collection of transcripts represent the signature. The quantitative value of a given SSM is the number of reads mapping to the SSM.

Example 16: Transcriptome Analysis of a Prokaryote by Obtaining and Characterizing Non-Ribosomal Prokaryotic RNA Prokaryotic non rRNA was enriched from prokaryotic total RNA and characterized by Nextgen sequencing.

15 µg of total E. coli RNA was incubated at 65° C. for 5 minutes in water. The RNA solution was adjusted to contain 50 mM Tris-HCl pH 8.0, 5 mM KCl, 1 mM MgCl2, 1 mM DTT, 0.1 mM SAM, 200 units RNAase inhibitor, 0.5 mM 3'DBT-GTP and 250 units of VCE for 35 minutes at 37° C. The RNA solution was aliquoted into two equal volumes and isolated by use of "RNA Clean and Concentrator" and each column was eluted by 50 µl water and then combined to 100 µl. The NaCl concentration was brought to 0.25 M by adding 100 µl of 0.5 M NaCl.

133 µl of the RNA solution was added to prewashed streptavidin beads representing 100 µl original bead volume. These beads were washed and eluted as described in Example 6 (Enriched fraction 1). Likewise the remaining 66 µl of RNA solution was added to 50 µl of beads. These beads were washed and eluted as described in example 6 except that the 10 mM Tris-HCL, 1 mM EDTA, 50 mM NaCl wash solution was substituted with 10 mM Tris-HCL, 1 mM EDTA and the 0.5 M NaCl solution was substituted with 10 mM Tris-HCL, 1 mM EDTA, 2 M NaCl (Enriched fraction 2).

The samples were then individually collected with 1.8 volume of AMPURE XP beads and eluted in 50 µl of 10 mM Tris-HCl, 1 mM EDTA. The two samples were then subjected to another round of streptavidin bead enrichment as described above. The samples were then collected with 1.8 volume of AMPURE XP beads and eluted in 50 µl of 10 mM Tris-HCl, 1 mM EDTA. These two samples (Enriched fraction 1 and Enriched fraction 2) as well as the starting total RNA were used to make NEBNEXT Ultra Directional RNA libraries and sequenced on an Illumina MISEQ.

Figure 5:
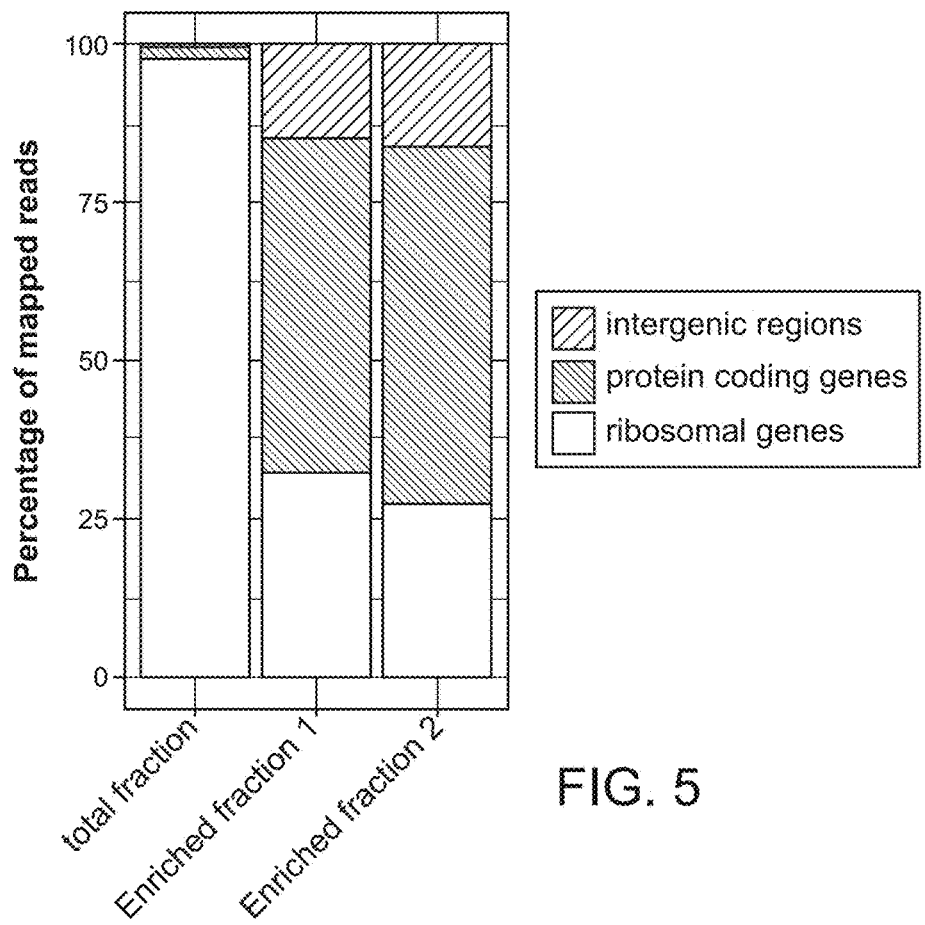
FIG. 5 shows the distribution of reads mapping to intergenic regions, protein coding regions and ribosomal genes for total RNA, and two enriched fractions. Significantly, the mapped reads corresponding to rRNA is dramatically reduced in the enriched samples. Whereas 70% to 75% of the mapped reads from the enriched fractions corresponds to non-rRNA increased from about 5% in the total RNA sample. The y-axis is percentage of mapped reads. This data was obtained from libraries made from the total and enriched RNA using RNA SEQ (NEBNEXT® Ultra™ Directional RNA Library Prep Kit for Illumina®, New England Biolabs, Ipswich, Mass.) which was then sequenced in the Illumina MISEQ® (Illumina, San Diego, Calif.) as described in Example 16. Reads were mapped to the *E. coli* genome (U00096.2). Ribosomal genes, intergenic regions and protein coding genes were also defined by the NCBI annotation U00096.2

FIG. 5 depicts the percentage of reads mapping to ribosomal genes, protein coding genes or intergenic regions of the E. coli (U00096.2) genome for total RNA and enriched RNA fractions. Reads were mapped to the E. coli genome (U00096.2). As can be seen in FIG. 5 the enriched RNA fraction is depleted of rRNA in both bead washing procedures (Enriched fraction 1 and 2). The E. coli non-rRNA was enriched to similar extents with both bead washing procedures.

Example 17: Novel Enrichment Strategy Reveals Unprecedented Number of Novel TSS at Single Base Resolution in a Model Prokaryote and the Gut Microbiome Presented here is believed to be a significant advance in transcriptomics to directly and universally target the first nucleotide that has been incorporated by the RNA polymerase upon initiation of transcription. This nucleotide marks the TSS on the genomic sequence. The strategy involves enzymatically labeling, with a biotin derivative, transcripts that have retained their original initiating 5' nucleotide. Only transcripts that have an intact 5' triphosphorylated (or 5' diphosphate) end are biotinylated and isolated from the in-vivo processed RNA. Enzymatic labeling of the 5' triphosphorylated end of RNA and subsequent enrichment and high-throughput sequencing is referred to as Cappable-seq.

Cappable-seq has a broad range of applications, offering the ability to investigate the triphosphorylated population of RNA molecules that would otherwise be masked by the overwhelming majority of their processed counterparts. By accurately anchoring the origin of the transcript to single base specific position on the genome, Cappable-seq reduces sequence complexity to a unique tag per transcript. The identification of the TSS to single base resolution enables the association between the regulatory state of a genome and its transcriptome. Thus, changes in transcription factor binding profiles and/or epigenetic states, notably at promoters, can be associated with changes in transcription by quantifying TSS usage.

Another method for determining prokaryotic TSS is called TEX, which relies on eliminating the processed transcripts by treating RNA samples with Xrn1 exonuclease (New England Biolabs, Ipswich, Mass.). This exonuclease preferentially degrades RNAs containing a 5' monophosphate, therefore resulting in an apparent enrichment of primary transcripts containing 5'-triphosphates. To increase the specificity of the TEX method, a control non-Xrn1 treated library is subtracted from the TEX library. This method is referred to as differential RNA-seq (dRNA-seq).

As a proof of concept, Cappable-seq was applied for the precise determination of TSS genome-wide in E. coli. Cappable-seq was performed on total RNA and a remarkable number of 16359 TSS at single base resolution were found. Cappable-seq is highly specific to triphosphorylated RNA characteristic of TSS. Compared to RNA-seq, Cappable-seq reduces the complexity of the transcriptome, enabling digital profiling of gene expression. Processed rRNA are also reduced from an overwhelming majority of total RNA to only 3%, allowing a deeper sequencing of the informative transcriptome at lower cost. By applying Cappable-seq to a mouse cecum sample, identification of TSS from a microbiome was demonstrated. TSS was identified in species from different bacterial phyla and found novel promoter consensus regions in all phyla analyzed. Leaderless transcripts account for 10 to 15% of identified TSS in some species of the microbiome such as Akkermansia muciniphila and *Bifidobacterium pseudolongum*. After Cappable-seq rRNA represents less than 5% of RNA for the majority of species analyzed suggesting that most of the sequences represent TSS of protein coding transcripts. Thus, this methodology provides a unique solution for TSS determination and digital profiling of gene expression of microbiomes while universally removing the contaminating rRNA that constitute the major cost burden of transcriptomes and meta-transcriptomes.

Materials and Methods

Materials:

3' DTB-GTP synthesis was initiated with 3'-(O-Propargyl) guanosine followed by its conversion to 3'(O-Propargyl) guanosine 5' triphosphate via a one-pot, two-step method (Kore et al, *Nucleosides Nucleotides Nucleic Acids* (2012) 31:423-431). The 3'-(O-Propargyl) Guanosine 5' triphosphate was then purified by both ion exchange chromatography and reverse phase HPLC. The isolated 3'(O-Propargyl) Guanosine 5' triphosphate was converted to the DTB-GTP through the addition of DBT-TEG-azide using copper-mediated azide-alkyne cycloaddition ("Click chemistry", Kolb and Sharpless, Scripps Res. Inst and BaseClick, Tutzing, GmbH) (Rostovtsev, et al, Angew Chem Int Ed (2002) 41:2596-2599; Hong et al, Angew Chem Int Ed (2009) 48:9879-9883). Final isolation of the target compound was performed using reverse phase HPLC. 2'DTB-GTP was synthesized as 3' DTB-GTP except 2'-(O-Propargyl) Guanosine was used and 3' biotin-GTP was synthesized as 3' DTB-GTP except that biotin-TEG-azide was substituted for DBT-TEG-azide. ATP free T4 polynucleotide kinase was prepared from T4 polynucleotide kinase by dialysis against 10 mM Tris-HCl, 50 mM KCl, 1 mM DTT, 0.1 mM EDTA, 50% Glycerol, pH 7.4.

Growth of E. coli and Isolation of Total RNA:

E. coli MG1655 cells were grown at 37° C. in M9 minimal media with 0.2% glucose. The culture was grown to mid-log phase and 2 volumes of RNAlater® (Life Technologies, Grand Island, N.Y.) were added. The culture was incubated at 4° C. overnight. The cells were collected by centrifugation and the RNA was extracted with FastRNA® Pro™ Blue Kit (MP Biomedicals, Santa Ana, Calif.). The RNA was then treated with DNAse I (New England Biolabs, Ipswich, Mass.) and further purified with MEGAclear kit. The resulting RNA had a RIN score of 9.0 as determined by Bioanalyzer (Agilent, Santa Clara, Calif.).

DBT-GTP Capping of E. coli RNA:

Three micrograms of *E. coli* RNA was incubated in 50 µl 1×VCE buffer supplemented with 0.1 mM S-adenosyl methionine, and 0.5 mM DTB-GTP and 50 units of VCE, for 30 minutes at 37° C. The RNA was purified on an RNA Clean & Concentrator-5 column for 200 nucleotide and greater RNA per manufacturer's instructions with a total of 4 washes with RNA wash buffer. The RNA was eluted in 100 µl of 1 mM Tris pH 7.5, 0.1 mM EDTA (low TE).

Capture of Capped T7 RNA Transcript with Streptavidin:

10 µl reaction volumes containing 1×VCE buffer, $^{32}$P uniformly labeled T7 in vitro 300mer transcript RNA, 10 units of VCE and either 0.5 mM 2' DBT-TEG-GTP or 3' DBT-TEG-GTP, or GTP were incubated at 37° C. for 2 hours. As carrier, 5 µl of MspI-digested pBR322 DNA (New England Biolabs, Ipswich, Mass.) was added to the RNA and purified on MEGAclear spin columns as directed by manufacturer and eluted in 100 µl low TE. 50 µl of the eluted RNA was mixed with 50 µl of 10 mM Tris-HCl pH 7.5, 500 mM NaCl, 1 mM EDTA (wash buffer A). This mix was added to the hydrophilic streptavidin magnetic beads that had been previously prepared by washing 3 times with 400 µl of 10 mM Tris-HCl pH 7.5, 1 mM EDTA, 50 mM NaCl (wash buffer B). The beads were incubated for 10 minutes at room temperature. The beads were then washed with 100 µl of wash buffer B, and three times with 400 µl of wash buffer A, to elute unbound material. The beads were then resuspended in 50 µl of wash buffer A and an additional 50 µl of wash buffer A containing 20 mM biotin. The beads were kept resuspended for 20 minutes at room temperature by occasional quick mixing. To determine if the RNA had been selectively captured by the beads and eluted with biotin, the beads were collected on the side of the tube with a magnet and the 100 µl supernatant was collected and radioactivity determined by scintillation counting.

Enrichment of RNA:

The DBT-GTP labeled RNA was fragmented by adding 2.5 µl of NEB 10×T4 polynucleotide kinase buffer to a 100 µl volume of capped RNA and incubated for 5 minutes at 94° C. The RNA was then collected by addition of 180 µl of AMPURE XP beads plus 420 µl of 100% ethanol. The beads were washed 2× with 80% ethanol. The RNA was eluted from the beads in 100 µl of low TE. 3' phosphates were removed from the RNA by addition 8.2 µl of 10×T4 polynucleotide buffer to 75 µl of the RNA solution and 4 µl of ATP-free T4 polynucleotide kinase was added and incubated for 15 minutes.

Hydrophilic streptavidin magnetic beads were prepared by washing 2 times with 400 µl of 10 mM Tris-HCl pH 7.5, 50 mM NaCl, 1 mM EDTA and 2 times with 400 µl of 10 mM Tris-HCl pH 7.5, 500 mM NaCl, 1 mM EDTA and suspended in their original suspension concentration of 4 mg/ml in wash buffer A. 50 µl of the kinase treated RNA was added to 30 µl of the prewashed streptavidin beads at room temperature with occasional resuspension for 20 minutes. The beads were then washed two times with 200 µl of wash buffer A, and two times with 200 µl of wash buffer B. The beads were then resuspended in 30 µl of wash buffer B and 1 mM biotin. The beads were incubated for 20 minutes at room temperature with occasional resuspension. The biotin eluted RNA was collected and bound to AMPURE XP beads by adding 1.8 volumes of AMPURE beads to the eluted RNA volume and adding 1.5 volumes of 100% ethanol to the resulting volume of the AMPURE/RNA mix. The beads were washed with 80% ethanol two times and the RNA eluted with 60 µl low TE. 30 µl of the RNA eluate was added to 30 µl of prewashed streptavidin beads for a second round of enrichment. The streptavidin beads were washed and eluted as above. The biotin eluted RNA was collected and bound to AMPURE beads as above and eluted with 30 µl low TE. The DBT cap was then removed to leave a 5' monophosphate terminus by adding 3.3 µl of 10× Thermopol buffer and µl (15 units) of RppH and incubating for 60 minutes at 37° C. The reaction was terminated by addition of 0.5 µl of 0.5 M EDTA and heating to 94° C. for 2 minutes. The RNA was then bound to AMPURE beads as described above, washed and eluted in 20 µl low TE.

Mouse Microbiome:

Two cecum samples were obtained from two C57 female mice from which two RNA preparations were isolated. The samples were incubated in RNAlater at 4° C. and then frozen. The RNA from the samples was prepared using RNeasy® kit (Qiagen, Valencia, Calif.) using manufacturer's protocol. 2.4 ug of total RNA were capped with 3'DTB-GTP, enriched on streptavidin beads as described above. All mouse protocols were approved by the New York University School of Medicine Institutional Animal Care and Use Committee.

RNA Sequencing Library Prep:

The NEBNEXT Small RNA Library Prep kit was used to generate Illumina sequencing libraries. The libraries were amplified through 15 cycles of PCR. For the *E. coli* libraries sequencing was performed on an Illumina MISEQ Instrument with single reads of 100 bases using V3 reagent kit. For the mouse microbiome, the libraries were sequenced on an Illumina GAII platform. All the raw reads have been deposited in the European Nucleotide Archive (ENA) website under the accession number PRJEB9717.

Data Analysis

*E. coli* Annotation:

The genome used is the K-12 MG1655 *E. coli* genome (U00096.2). Gene annotations are derived from the NCBI KU MG1665 annotation (GenBank: U00096.2). Processed sites from tRNA and rRNA are derived from the 000096.2 annotation selecting entries with feature tRNA or rRNA. The set of known TSS are derived from RegulonDB [16](RegulonDB 8.6, Apr. 11, 2014) combining the following files from the experimentally derived datasets: PromoterSigma24Set, PromoterSigma32Set, PromoterSigma54Set, PromoterSigma19Set, PromoterSigma28Set, PromoterSigma38Set, PromoterSigma70Set and PromoterUnknownSet. TEX comparison was done using the TSS described in supplemental file 1 (M63_0.4 condition) and table S1 (*E. coli*) from Thomason (Thomason et al, *J Bacteriol* (2015) 197:18-28) and Kim (Kim, et al, *PLoS Genet* (2012) 8:e1002867) respectively. The composite dataset of known TSS contains all the above datasets (known TSS from RegulonDB, Thomason (Thomason et al, *J Bacteriol* (2015) 197:18-28) and Kim (Kim, et al, *PLoS Genet* (2012) 8:e1002867) merged into one single file).

Mapping:

For the *E. coli* analysis, single end reads were trimmed for adaptors using cutadapt (version 1.3) with default parameters and -a AGATCGGAAGAGCACACGTCTGAACTCCAGTCAC (SEQ ID NO:14). The reads were mapped to the *E. coli* genome using Bowtie2 local (–L 16). To determine the 5' end, the resulting mapped reads were trimmed to the coordinates of the most 5' mappable end of the read (trimmed read). For the mouse microbiome analysis, NCBI genomes from the eubacteria taxonomic group (uid 2) were downloaded. If multiple versions of the genome are available for the same species, the representative genome or reference genome was used. If no representative/reference genome were found, one version of the genome was chosen at random. Reads were trimmed for adaptors (as describe above) and mapped to each genome separately using bowtie2 with the following parameters: --local --no-1mm-upfront -L 28 --score-min G,36,17.

Microbiome Analysis:

Present in the microbiome is defined as bacterial species with at least 300 clustered putative TSS genome-wide. Clustered putative TSS are positions on the genome of the strongest putative TSS within 100 bp (cluster_tss.pl --cutoff 50). A putative TSS is defined as the 5' end position of at least one uniquely mapped read (grep -v \'XS:\' on the mapped read sam file) using the following program: bam2firstbasegtf.pl --cutoff 0. The species with the highest number of TSS per phylum was selected as the representative species for this phylum. Next, for the representative species of each phylum, the positions of the high confident TSS were selected using the following parameters: bam2firstbasegtf.pl --cutoff 10 --absolute 1 and clustered using cluster_tss.pl --cutoff 50. This filtering resulted with 221 positions for *Lactobacillus johnsonii*, 886 positions for Akkermansia muciniphila, 894 positions for Lachnospiraceae bacterium and 174 positions for *Bifidobacterium pseudolongum* from replicate 1. For leaderless transcript annotation, the positions of the high-confident clustered TSS were compared to the annotation file for the respective species and TSS that locate at the start and in the same orientation of the annotated gene were considered as leaderless. For sequence bias analysis, the sequence context from −45 to +5 bp around the positions of the high-confident clustered TSS was compared to the overall sequence composition ([ATCG]) of the genome and a sequence logo was derived using weblogo with the following parameters: weblogo --format eps -s large -n 100 --composition [ATCG] --yaxis 1 --errorbars NO --color-scheme classic. For read composition analysis, reads were mapped to the four representative species (*Lactobacillus johnsonii*, Akkermansia muciniphila, Lachnospiraceae bacterium *Bifidobacterium pseudolongum*) using Bowtie2 with the following parameters: --end-to-end --score-min 'C,0,−1'-L 32. The number of reads overlapping with the annotated rRNA, tRNA, coding genes and intergenic regions were computed and plotted. For the replicate analysis, high-confident clustered TSS found in either replicate 1 or replicate 2 were retained. The RRS (see below) for each retained TSS was computed in both replicate 1 and 2 for all four representative species and plotted.

*E. coli* TSS Determination:

The number of trimmed reads mapping to each position on the genome is normalized to the total number of mapped reads using the following formula: RRS=(Rns/Rt)*1000000 with RRS being the RRS, Rns being the number of trimmed reads mapping to position n in the *E. coli* genome on strand s (− or +) and Rt being the total number of reads mapping to the *E. coli* genome. Positions and strands with a RRS of less than 1.5 in the Cappable-seq experiment were discarded. For each of the retained positions, the RRS is compared to the RRS obtained in the control experiment using the following formula: enrichment score=log 2(RRScap/RRScontrol) with RRScap being the RRS obtained in Cappable-seq experiment and RRScontrol being the RRS obtained in the control experiment. Positions with an enrichment score of 0 or above were considered as TSS. TSS were clustered using the cluster_tss.pl program with --cutoff 5. Clustered TSS corresponds to the Cappable-seq TSS dataset. The suite of programs to identify, filter and cluster TSS are freely available on github. The Cappable-seq TSS common to composite dataset of known TSS are TSS located within 25 bp from one or several TSS from the composite dataset of known TSS. The remaining Cappable-seq TSS are the Cappable-seq specific TSS.

Sequence Conservation for *E. coli*:

Pre-computed whole genome alignments in maf format between *Escherichia coli* KU, *Escherichia coli* APEC 01, *Enterobacter* 638, *Shigella flexneri* 2a, *Salmonella typhi*, *Salmonella enterica* Paratypi ATCC 9150, *Yersinia pestis* CO92, *Blochmannia floridanus*, *Buchnera* sp. were downloaded from the UCSC microbial genome browser (Chan et al, *Nucleic Acids Res* (2012) 40:D646-52). Conservation scores were computed using phastcon (Siepel et al, *J Comput Biol* (2004) 11:413-428). Combining phylogenetic and hidden Markov models in biosequence analysis running phyloFit with -tree "(((((eschColi_K12,eschColi_O157H7), eschColi_APEC_O1),ente638),shigFlex_2A),(salmTyph, salmEnte_PARATYPI_ATC)yersPest_CO92)" and phastcon with the following parameters: --target-coverage 0.25 --expected-length 1. PhyloP scores were computed using the above whole genome alignment and the output of phyloFit using the following parameters: --wig-scores --method SCORE --msa-format MAF.

Comparison with TEX:

Raw fastq files from the most recent d-RNA-seq experiment (Thomason et al, *J Bacteriol* (2015) 197:18-28) were downloaded from ENA website accession number SRP038698. Reads were trimmed to remove the poly(A) tail using Trimgalor and the trimmed reads were mapped to the *E. coli* genome using bowtie local as describe above. To be in comparable conditions, the mapped reads were downsampled to 8 millions for both TEX−,TEX+,Cappable-seq and control data.

Motif Search:

Over-represented motifs were searched using MEME version 4.8.0 (Bailey and Elkan, *Proc Int Conf Intell Syst Mol Biol ISMB* (1994) 2:28-36) with the -mod zoops -dna -minsites 120 -maxsize 1000000 options. Motifs logo were done using the weblogo3 program (Crooks et al, *Genome Res* (2004) 14:1188-1190).

Data Access:

The data sets supporting the results of this article are available in European Nucleotide Archive (ENA) accession number PRJEB9717, ("http" followed by "://www.ebi." followed by "ac.uk/ena/data/view/PRJEB9717").

Abbreviations bp: base pair; DTB-GTP: 3'-DBT-TEG-guanosine 5' triphosphate; R: purine; TSS: transcription start site; Y: pyrimidine; VCE: Vaccinia capping enzyme.

Figure 13:
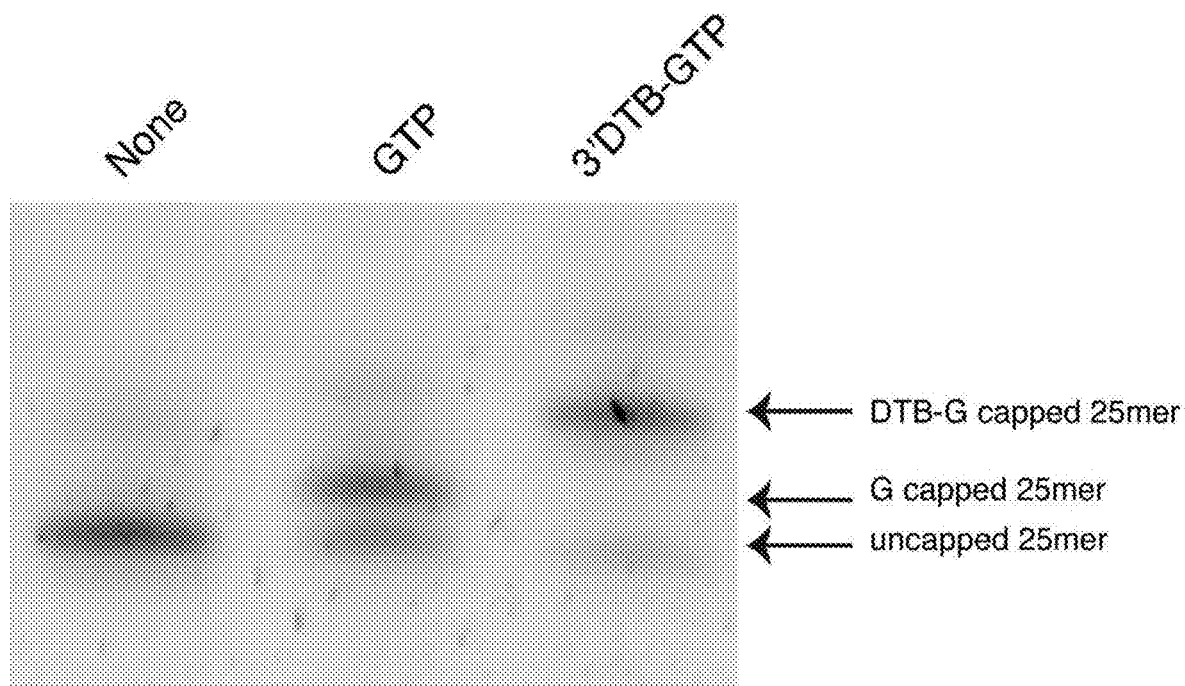
FIG. 13 shows capping RNA with 3'DTB-GTP.
Figure 14:
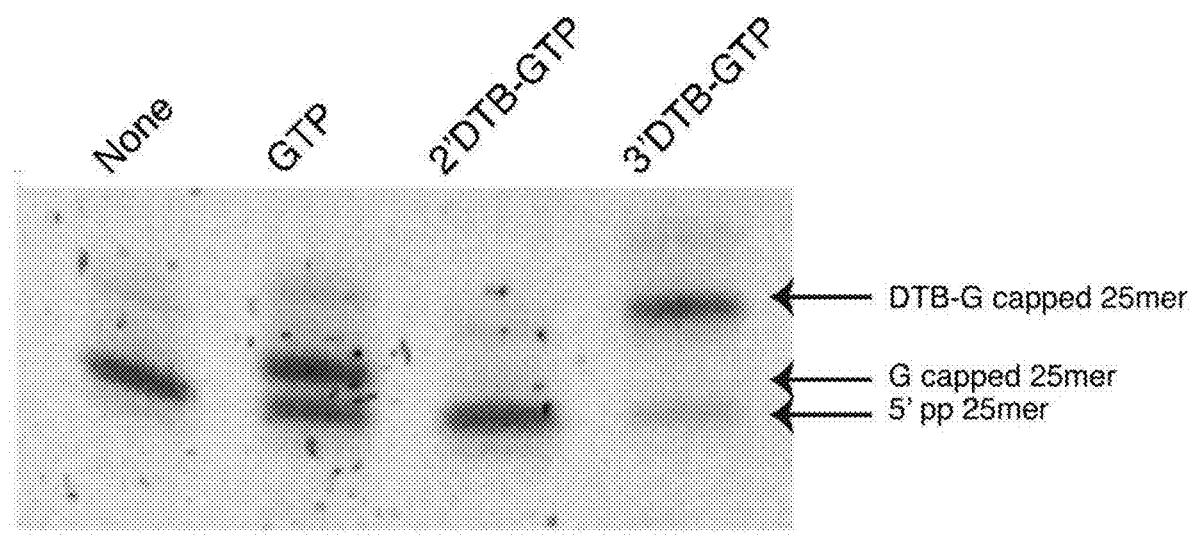
FIG. 14 shows 5' diphosphate RNA is a substrate for capping with 3'DTB-GTP.
Figure 15:
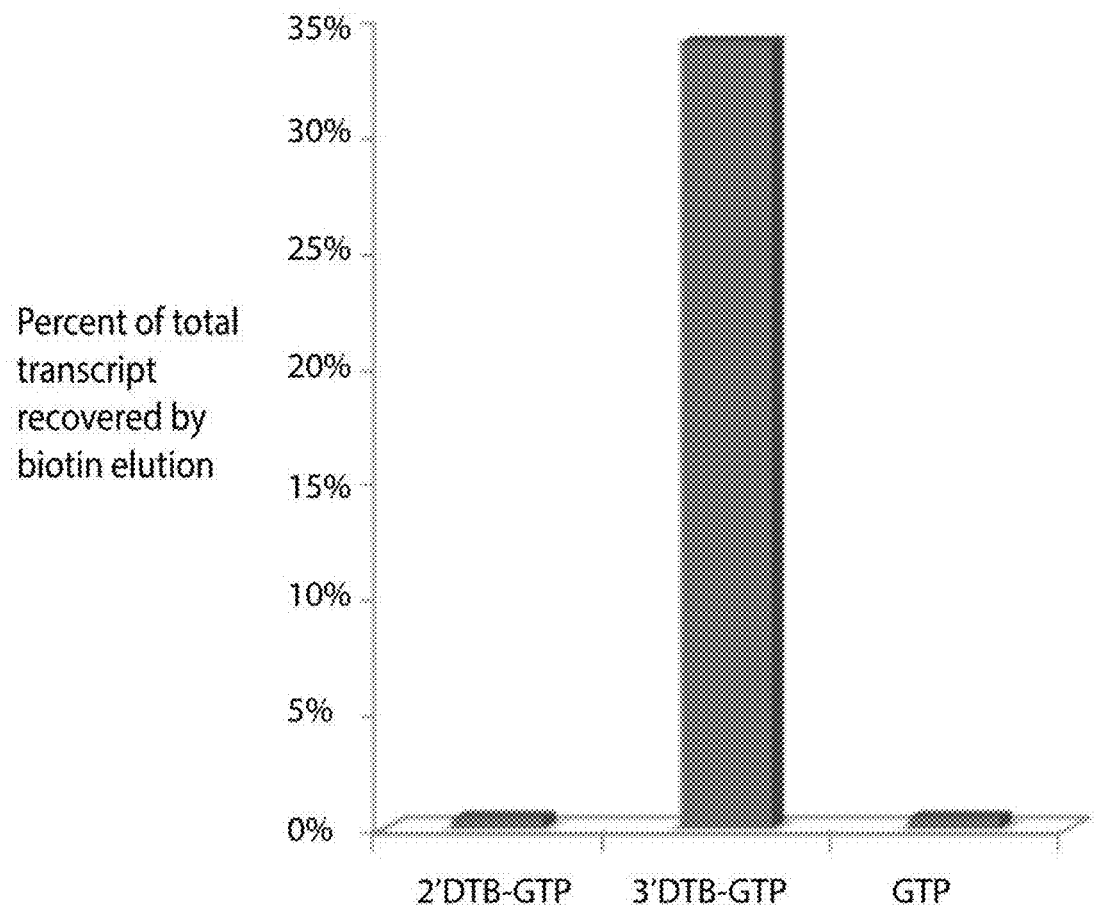
FIG. 15 shows capture of 3'DTB-GTP capped T7 RNA transcript with streptavidin.
Figure 16:
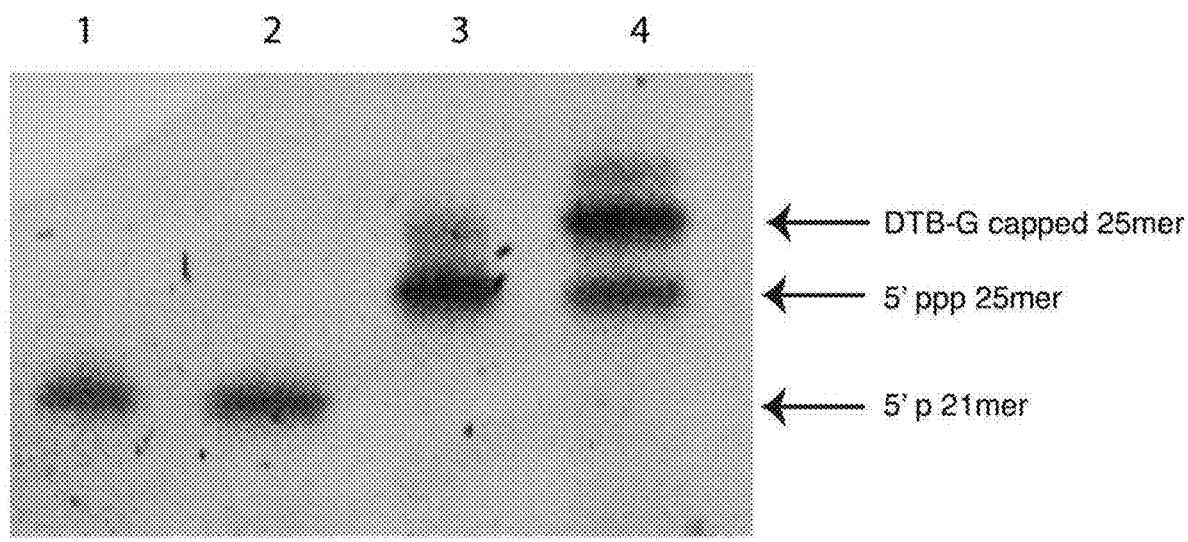
FIG. 16 shows that VCE discriminates between 5' monophosphate and 5' triphosphate RNA.

Results:

Cappable-Seq Captures the Triphosphorylated RNA and Enriches for Primary Transcripts Cappable-seq isolates the primary transcripts by enzymatically capping of the 5' triphosphorylated RNA with a biotinylated GTP using VCE. For this purpose, a number of biotinylated derivatives of GTP were screened and it was found that 3' OH modifications of ribose of GTP are acceptable substrates for VCE. The biochemistry of capping and decapping are presented below and in FIGS. 13-15. The reaction results in the specific labeling of 5'-di or triphosphorylated RNA ends while the 5'-monophosphorylated RNA ends characteristic of processed transcripts are not labeled (FIGS. 14 and 16). The biotinylated RNA can then be captured on streptavidin beads and isolated (FIG. 15).

Decapping DTB-GTP Capped RNA

Figure 17:
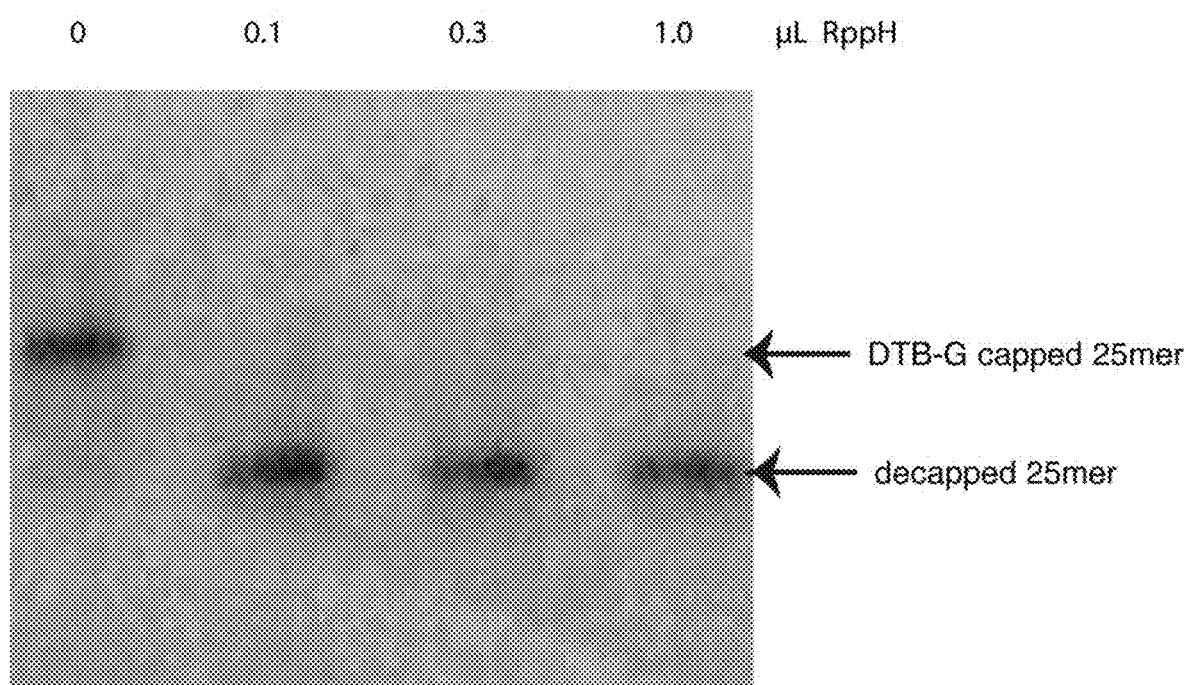
FIG. 17 shows decapping DTB-G capped RNA with 5' RppH.
Figure 18:
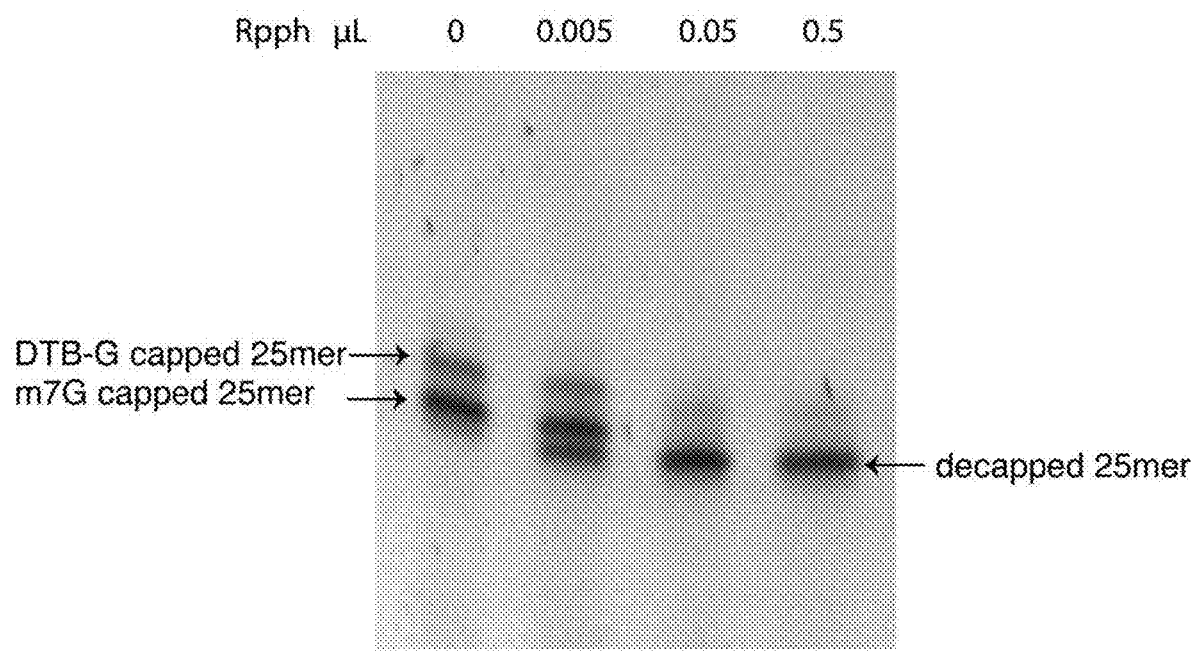
FIG. 18 shows decapping DTB-G and $^7$mG capped RNA with RppH.

The strategy for the preparation of sequencing libraries is based on ligation of the 5' end of transcripts. Analysis on Urea-PAGE demonstrates that RppH is capable of removing a $^7$mG cap, as well as a 3' DBT-G cap from RNA (FIGS. 17-18). In summary, VCE effectively caps a triphosphorylated 5' RNA end with 3' DTB-GTP and RppH effectively decaps DTB-GTP-capped RNA.

Application of Cappable-Seq to *E. coli* Reveals an Unprecedented Number of TSS

Cappable-seq was first applied for the genome-wide identification of TSS in the model organism *E. coli* MG1655. For this, total *E. coli* RNA was capped with DTB-GTP for reversible binding to streptavidin, fragmented to an approximate size of 200 bases, captured on streptavidin beads and eluted to obtain the 5' fragment of the primary transcripts (see method section and FIG. 19, panel A). To achieve single base resolution, a Cappable-seq library was generated by ligating 5' and 3' adaptors to the RNA. It was found that RppH efficiently removes the desthiobiotinylated cap structure to leave a ligatable 5'-monophosphate RNA (FIGS. 17-18).

A non-enriched control library was prepared using identical conditions as Cappable-seq except that the streptavidin capture step was omitted. Both libraries were sequenced using Illumina MISEQ yielding approximately 20 million single end reads. Reads were mapped to the *E. coli* genome using Bowtie2 (Langmead and Salzberg, *Nat Methods* (2012) 9:357-359). The orientation and mapped location of the first mapped base of the sequencing read determines the genomic position of the 5' end of the transcript at single base resolution. The number of reads at a specific position defines the relative expression level of the 5' end of the primary transcript. This number was normalized with the total number of mapped reads to obtain a RRS reflecting the strength of each TSS, thus defining a single quantifiable tag per transcript that can be used for digital gene expression profiling. A technical replicate generated using the same total *E. coli* RNA preparation resulted in a correlation coefficient of 0.983 demonstrating the high reproducibility of Cappable-seq (FIG. 19, panel B).

Figure 19:
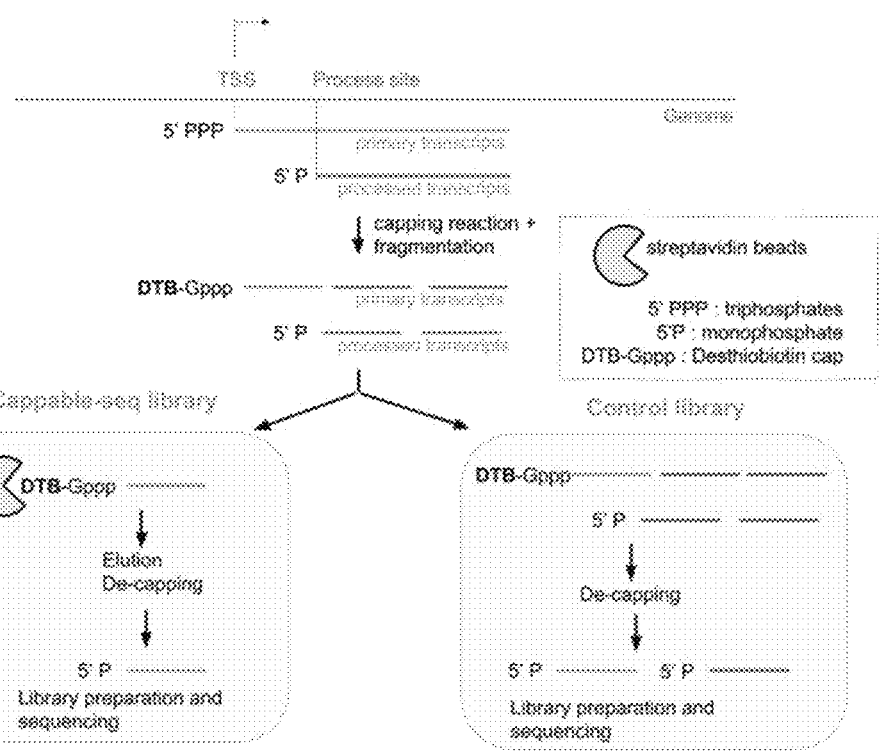
FIG. 19 shows the Cappable-seq pipeline for TSS identification.
Figure 19:
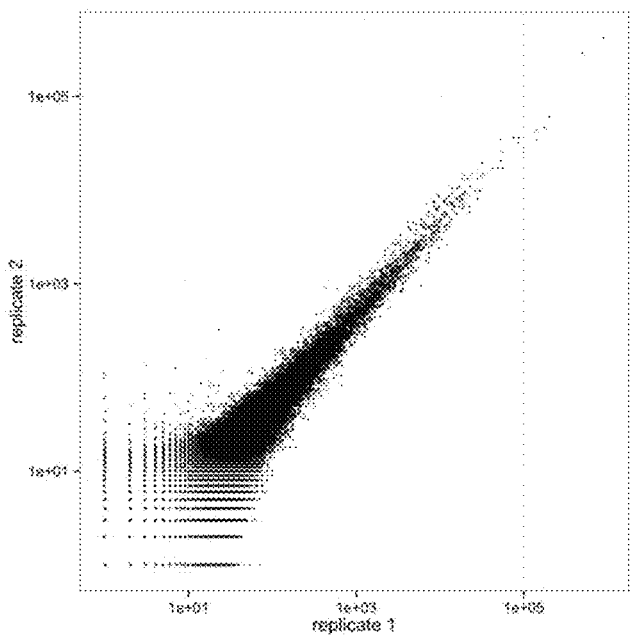
Figure 19:
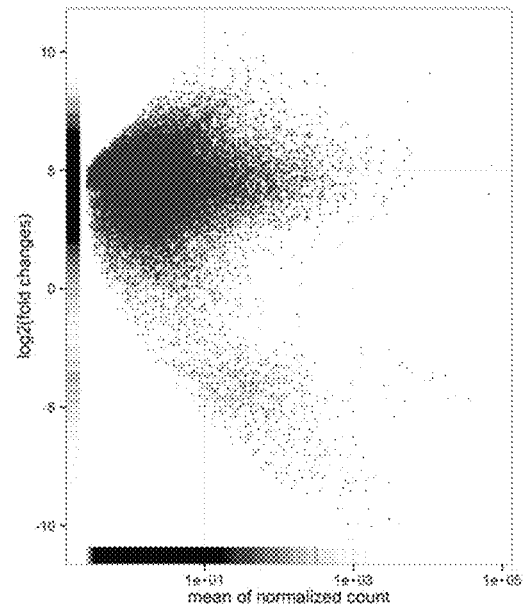

The ratio between the RRS from Cappable-seq and the non-enriched control libraries defines the enrichment scores with enriched positions corresponding to 5'-triphosphorylated ends characteristic of TSS and depleted positions corresponding to processed/degraded 5' ends (FIG. 19, panel C). To define TSS, positions on the genome were selected with a RRS of 1.5 and higher (equivalent to 20 reads or more) and found 36,078 positions satisfying this criteria. Next, the 1354 positions that are depleted in the Cappable-seq library were subtracted when compared to the non-enriched control library (method and FIG. 19, panel C). This resulted in 34724 unique positions that were defined as TSS. This step reduces the number of positions by only 3.7%. As most of the false positive positions are located in ribosomal genes, the exclusion of positions located within those genes drops the false positive rate to only 1.4%. Therefore the need to sequence a non-enriched RNA library in order to calculate an enrichment score is not critical with Cappable-seq whereas a non-enriched library is required to perform dRNA-seq.

The accurate description of TSS in prokaryotes relies on the differentiation of the 5'-triphosphorylated end which characterizes primary transcripts from the 5'-monophosphorylated end which characterizes processed sites. Comparing the results of Cappable-seq with the results Kim, et al (*PLoS Genet* (2012) 8:e1002867) and Thomason, et al (J Bacteriol (2015) 197:18-28) demonstrates the higher specificity of Cappable-seq for 5' triphosphate RNA (see below, and FIG. 20). Indeed while Cappable-seq correctly calls 110 out of 111 processed sites, dRNA-seq mis-annotated 40 of the processed sites as TSS (FIG. 20).

Figure 20:
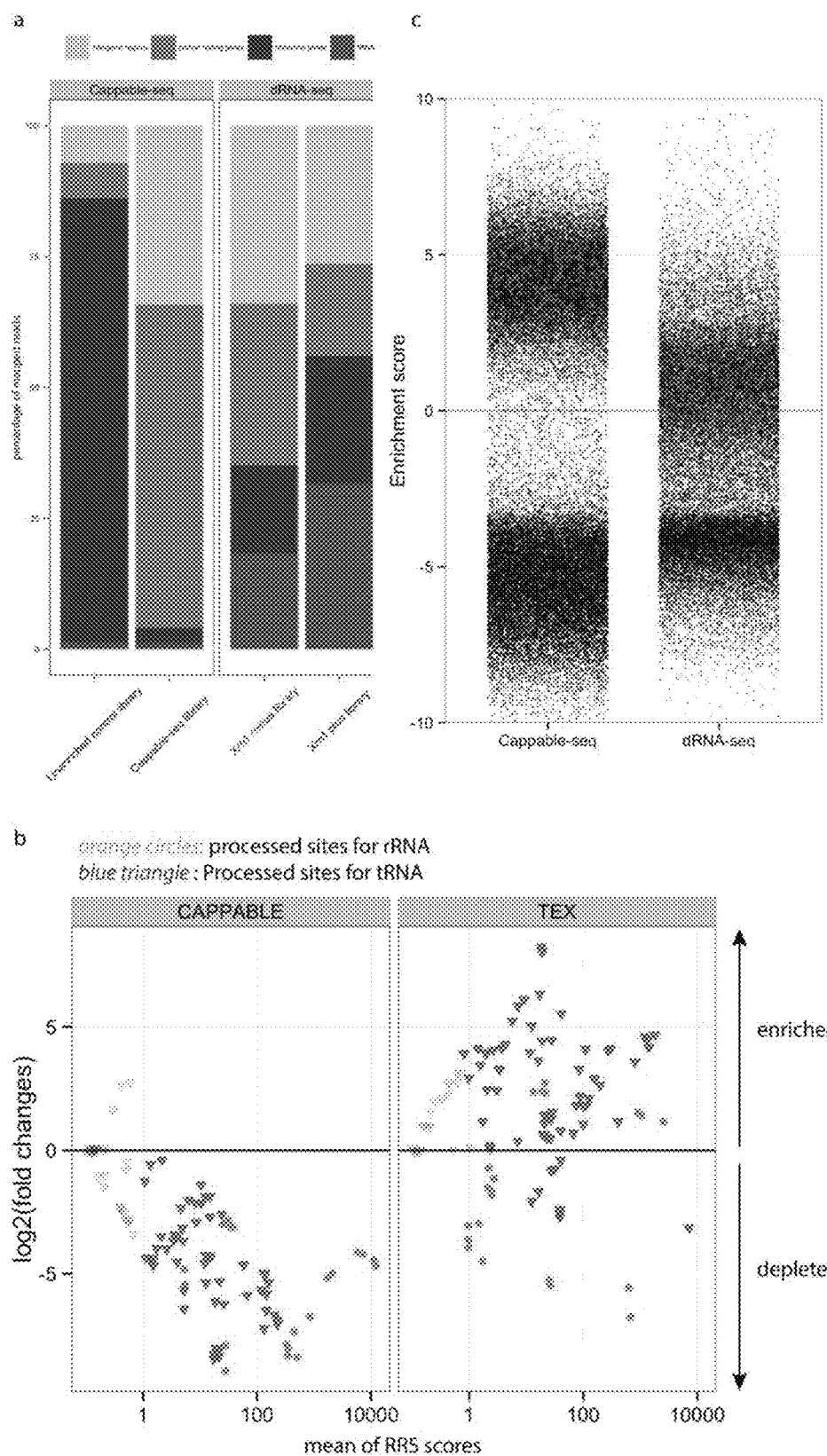
FIG. 20 shows the comparison between Cappable-seq and dRNA-seq.
Figure 21:
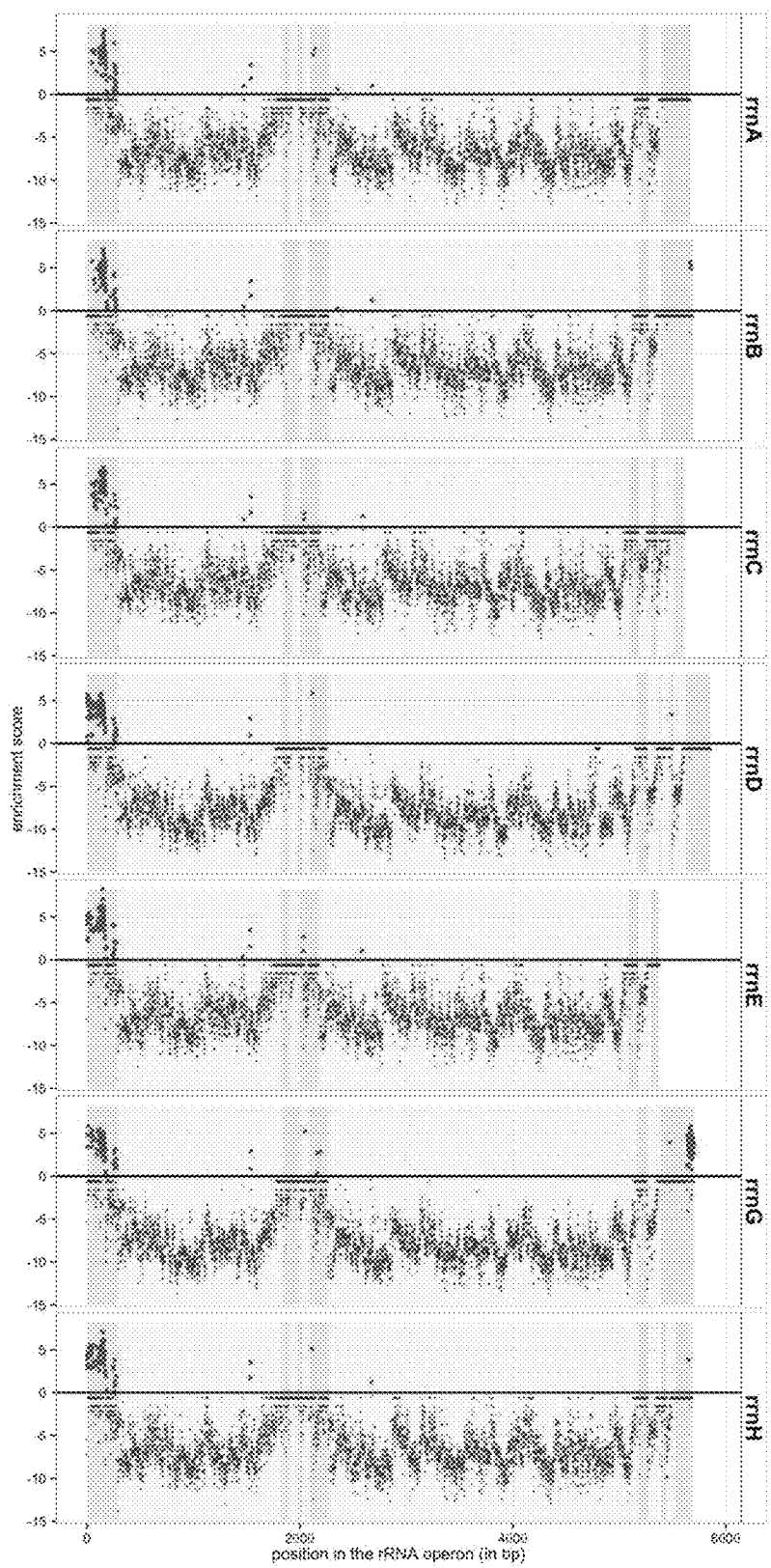
FIG. 21 shows the enrichment scores across seven ribosomal operons in *E. coli*. For each position in the seven ribosomal operons the enrichment score is calculated as described in methods. Only enriched positions with a RRS of greater than 1.5 in Cappable-seq library are candidate TSS (red). Grey boxes correspond to intragenic regions and light-blue boxes correspond to rRNA or tRNA. 26 bona-fide TSS are found within the rRNA genes.

The higher specificity of Cappable-seq for the 5' end of primary transcripts also has the desirable property of reducing reads mapping to rRNA from 85% of total reads to only 3% (FIG. 20, panel A). While some remaining reads may be background noise, 26 enriched positions within rRNA genes were identified suggesting bona-fide TSS falling within the rRNA genes (FIG. 21).

Ribosomal TSS can be Classified into 3 Categories

As Cappable-seq eliminates the vast majority of the processed rRNA, a detailed analysis of the triphosphorylated landscape of transcripts around and overlapping the ribosomal genes was performed. In E. coli rrn operons are known to be regulated by two promoters, P1 and P2, which are arranged in tandem and separated by 120 bp. In all 7 rrn operons, we found TSS corresponding to P1 and P2. Interestingly the ribosomal operons can be classified into 3 groups according to the P1/P2 usage: The first group includes the rrnA, rrnB and rrnC operons and is characterized by a relatively low number of transcripts that initiate at the P1 promoter and a moderate number at the P2 promoter. The second group comprised of the rrnD, rrnE and rrnH operons is characterized by a highly expressed TSS at both the P1 and P2 promoters. The last group corresponds to the rrnG operon and is characterized by an equal number at both P1 and P2 promoters (Table 4). Interestingly, additional positions were also observed within the ribosomal operons that are likely TSS. For example a candidate sense TSS was found within the small ribosomal subunit of all operons with a −10 box-like sequence (TACAAT) upstream of the TSS. For most of the ribosomal operons a TSS is detected upstream of the large subunit and a TSS within the large subunit (FIG. 21).

TABLE 4

Ribosomal TSS

| Ribosomal operon | rrsP1 | rrsP2 | Groups |
|---|---|---|---|
| rrnA | 255 (4033262) | 5061 (4033379) | 1 |
| rrnB | 289 (4164390) | 5189 (4164507) | 1 |
| rrnC | 284 (3939539) | 6444 (3939656) | 1 |
| rrnD | 22268 (3427069) | 9972 (3426962) | 2 |
| rrnE | 27737 (4205886) | 10714 (4205994) | 2 |
| rrnG | 6734 (2729470) | 6154 (2729354) | 3 |
| rrnH | 28075 (223485) | 9626 (223593) | 2 |

Table 4 shows the strength of the rrsP1 and rrsP2 promoter (in number of reads) for all 7 ribosomal operons. In parentheses are the chromosomal positions of the TSS (E. coli K12 assembly U00096.2). The TSS are classified into three groups: the highly expressed TSS (red) the medium expressed TSS (orange) and the low expressed TSS (green). The ribosomal operons can be classified into 3 groups based on the combination of strength of the P1/P2 promoters.

Cappable-Seq Demonstrates Specificity for TSS

The accurate description of TSS in prokaryotes relies on the differentiation of the 5'-triphosphorylated end characteristic of primary transcripts from the 5' monophosphorylated end characteristic of processed sites. The majority of published bacterial TSS are determined by treating RNA samples with a 5' to 3' exonuclease from S. cerevisiae, Xrn1 also known as Terminator™ 5'-Phosphate-Dependent Exonuclease (Epicentre, Madison, Wis.). This exonuclease preferentially degrades RNAs containing a 5' monophosphate, therefore resulting in an apparent enrichment of primary transcripts containing 5'-triphosphates. This method is generally referred to as TEX. An Xrn1 treated library is often compared with a non-enriched control library consisting of non-Xrn1 treated RNA to remove false positives. The resulting method is referred to as differential RNA-seq or dRNA-seq. Cappable-seq was compared to published dRNA seq dataset of E. coli MG1655 grown in minimal media (Thomason, et al, J Bacteriol (2015) 197:18-28) to evaluate the performance of both methods in defining TSS.

To this end, the levels of the rRNA and tRNA were analyzed as a proxy to evaluate the fate of processed transcripts in Cappable-seq and dRNA-seq libraries. rRNA and tRNA are well characterized representatives of processed RNA generated from a precise endoribonuclease cleavage of the primary transcripts and consequently, the 5' ends of mature tRNAs and rRNAs are monophosphates. It was found that the relative amount of tRNA and rRNA dropped from an overwhelming majority of 86% in the non-enriched control library to only 4% in the Cappable-seq library (FIG. 20, panel A). The remaining 4% of tRNA and rRNA in Cappable-seq may be a combination of contaminating tRNA and rRNA or bona fide TSS within ribosomal genes. These results shows Cappable-seq does not capture processed RNA. The same analysis performed using published dRNA-seq data reveals ribosomal and tRNA content in fact increased from 35% in the control library to 56% after Xrn1 treatment (FIG. 20, panel A). These results show that Xrn1 treatment does not remove the majority of reads mapping to tRNA and rRNA and thus, does not appear to completely degrade the processed rRNA.

To confirm this result, the annotated processed 5' ends were analyzed at single base resolution for both the rRNAs and tRNAs and only a small subset of tRNA and rRNA processed sites were found to be depleted after Xrn1 treatment (FIG. 20, panel B). More specifically, rRNA processed sites that are enriched in dRNA-seq correspond to the 5S rRNAs. Most of the tRNAs are enriched in dRNA-seq except for the methionyl-tRNAs (MetU, MetT, MetZ, MetW, MetV and MetY) that are significantly depleted.

In contrast all of the rRNAs and all but one of the 82 tRNAs' processed sites are strongly depleted with Cappable-seq (FIG. 20, panel B). Taken together, these results demonstrate that Xrn1 has a differential activity amongst 5' monophosphorylated RNA substrates leaving intact a number of 5' monophosphate processed ends. In the case of the known processed sites that we have looked at, the distinction between TSS and processed sites cannot be made when using Xrn1.

It was hypothesized that the inability of Xrn1 to degrade certain processed transcripts can be generalized beyond the well-characterized processed sites. To this end, the enrichment score was calculated for all positions in the genome for both Cappable-seq and dRNA-seq data. Cappable-seq separates the RNA into two distinct enriched and depleted populations. A collection of TSS from regulonDB were mapped to this data and it was found that the enriched population contains most of the known TSS (FIG. 20, panel C). This result suggests that the enriched population represents TSS and the depleted population represent processed sites. While dRNA-seq also separates into two distinct populations, both distributions are overlapping to a greater extent than Cappable-seq. As the difference of the enrichment score between enriched and depleted is greater for Cappable-seq than dRNA-seq, Cappable-seq more clearly distinguishes between the two populations, demonstrating that Cappable-seq has a higher specificity than dRNA-seq for triphosphorylated ends.

TSS from dRNA-seq that are depleted in Cappable-seq were individually analyzed. In addition to the known processed 5' ends of tRNA and rRNA annotated as TSS with dRNA-seq, intragenic sites were found within rRNA genes, the processed site of the transfer-messenger RNA (tmRNA) and a position in the intragenic region of the SerA gene. These results suggest that the Xrn1 reaction does not go to completion. In fact, others have reported inefficient digestions with Xrn1 on *Streptomyces coelicolor* RNA (Romero et al, *Mol Microbiol* (2014) 94:963-987). It was speculated that the high prevalence of stable secondary structures may account for the lack of degradation of the processed transcripts. Secondary structure and double-stranded recessed 5' ends of processed transcripts may account for the enzyme's performance and lead to the identification of spurious TSS. Cappable-seq on the other hand is based on directly targeting TSS and is not confounded by processed ends. Thus, Cappable-seq shows superior performance over dRNA-seq and consequently any TEX based technology.

Genomewide Position of TSS Suggests Both Precise and Imprecise Initiation of Transcription Many promoters have been observed to initiate a low level of transcription from multiple positions closely surrounding the major initiation site for a given TSS. It was hypothesized that those sites may have been generated from a single promoter and thus are considered dependent. TSS generated from a unique promoter event was clustered to one single position with the highest RRS resulting in 16359 unique positions that was defined as clustered TSS (see below, see FIG. 22, panel A; and data not shown).

While the RNA polymerase initiates transcription at imprecise positions for about 60% of the promoters, 40% have precise positions. The degree of precision in the initiation site is dependent on the sequence context at TSS where the −1 and +1 positions of the TSS correspond to pyrimidine (Y) and purine (R) respectively. The −1+1 YR motif correlates with precise initiation events (see below and FIG. 22, panel B).

Clustering of *E. coli* TSS

Figure 22:
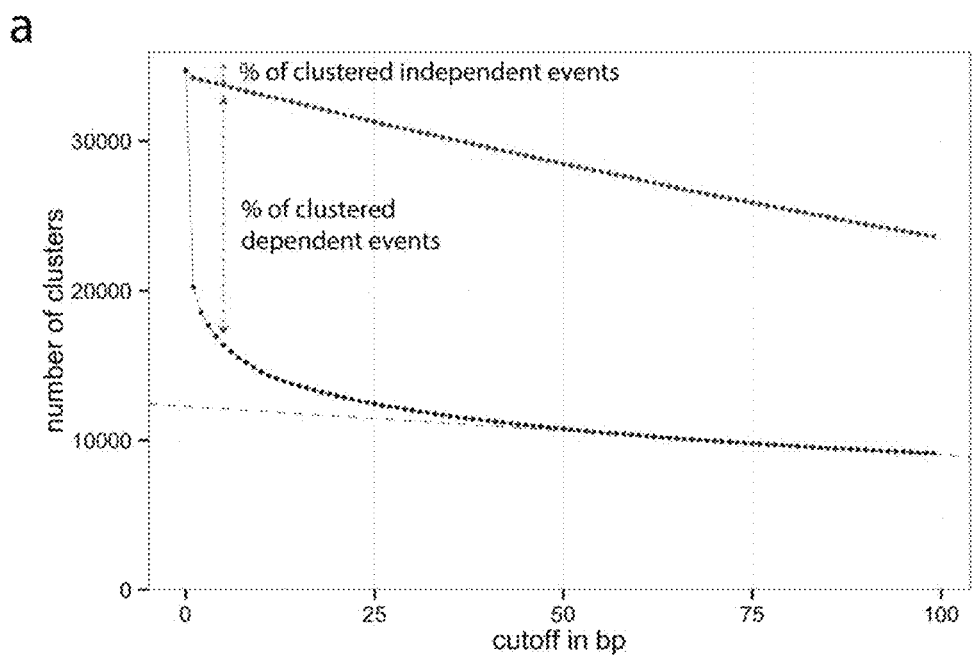
FIG. 22 shows the clustering of TSS.
Figure 22:
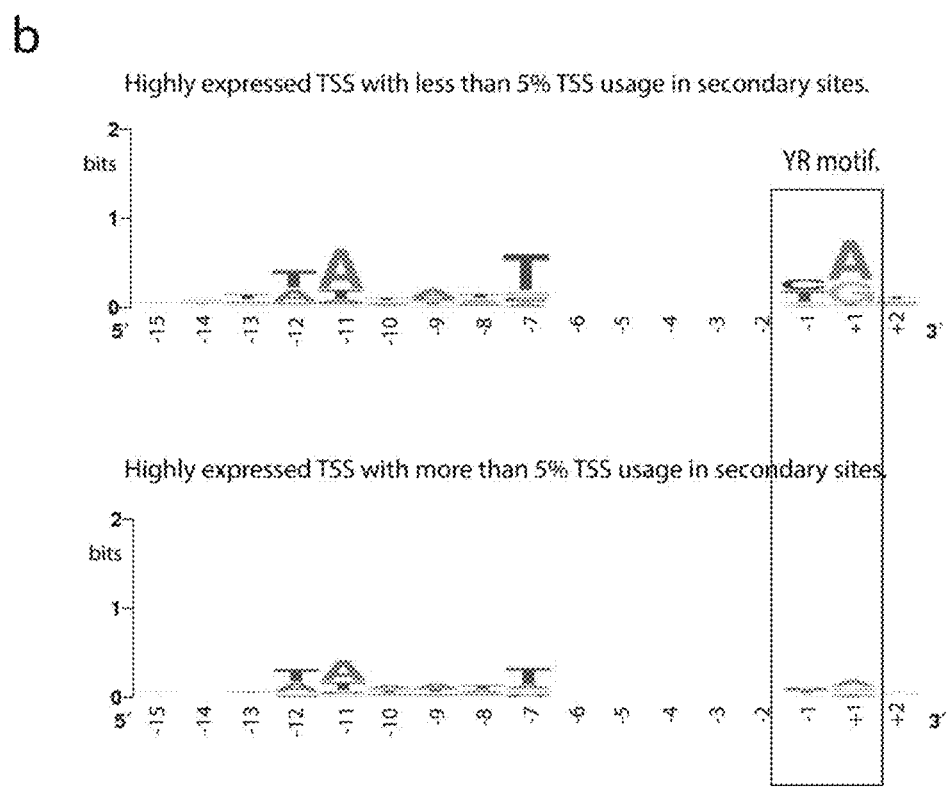

A closer look at the data at one base resolution identifies secondary starting sites in the immediate surrounding of what appear to be the major primary TSS. Those secondary sites tend to have lower expression relative to the primary sites and are likely to have been initiated from the same promoter. Thus, TSS sites were clustered and the position with the highest read score was retained as the TSS. The procedure should cluster most of the sites originating from the same promoter while minimizing the clustering of TSS generated from different promoters. To this end, the number of clusters obtained at distances ranging from 0 to 100 bp were calculated. The same analysis was performed with randomly generated positions and estimated that a 5 base cutoff, less than 3% of the independent events and more than 80% of the dependent events are clustered (FIG. 22, panel A). All TSS were clustered within a distance of 5 bases into single positions and retained the position with the highest read score and discard secondary positions. It was noticed that some TSS do not appear to have secondary starting sites despite being highly expressed. To further examine why some promoters appear to generate multiple TSS positions while others generate a single TSS position, highly expressed TSS (TSS with RRS>20) were divided into multiple and singlet clustered TSS and the sequence specificity was examined. Singlet clustered TSS were defined as TSS where less than 5% of the RRS belong to secondary start sites. Conversely multiple clustered TSS were defined as TSS where more than 5% of the RRS belong to secondary start sites. It was found that while the promoter specificity (−10) is similar in both groups, about 80% of the singlet clustered TSS have a −1 +1 YR motif characteristic of canonical TSS while less than 50% of the multiple clustered TSS have the YR configuration. Conversely, the promoter specificity (−10) is similar in both groups (FIG. 22, panel B).

41% of Cappable-Seq TSS in *E. coli* are Novel

Figure 23:
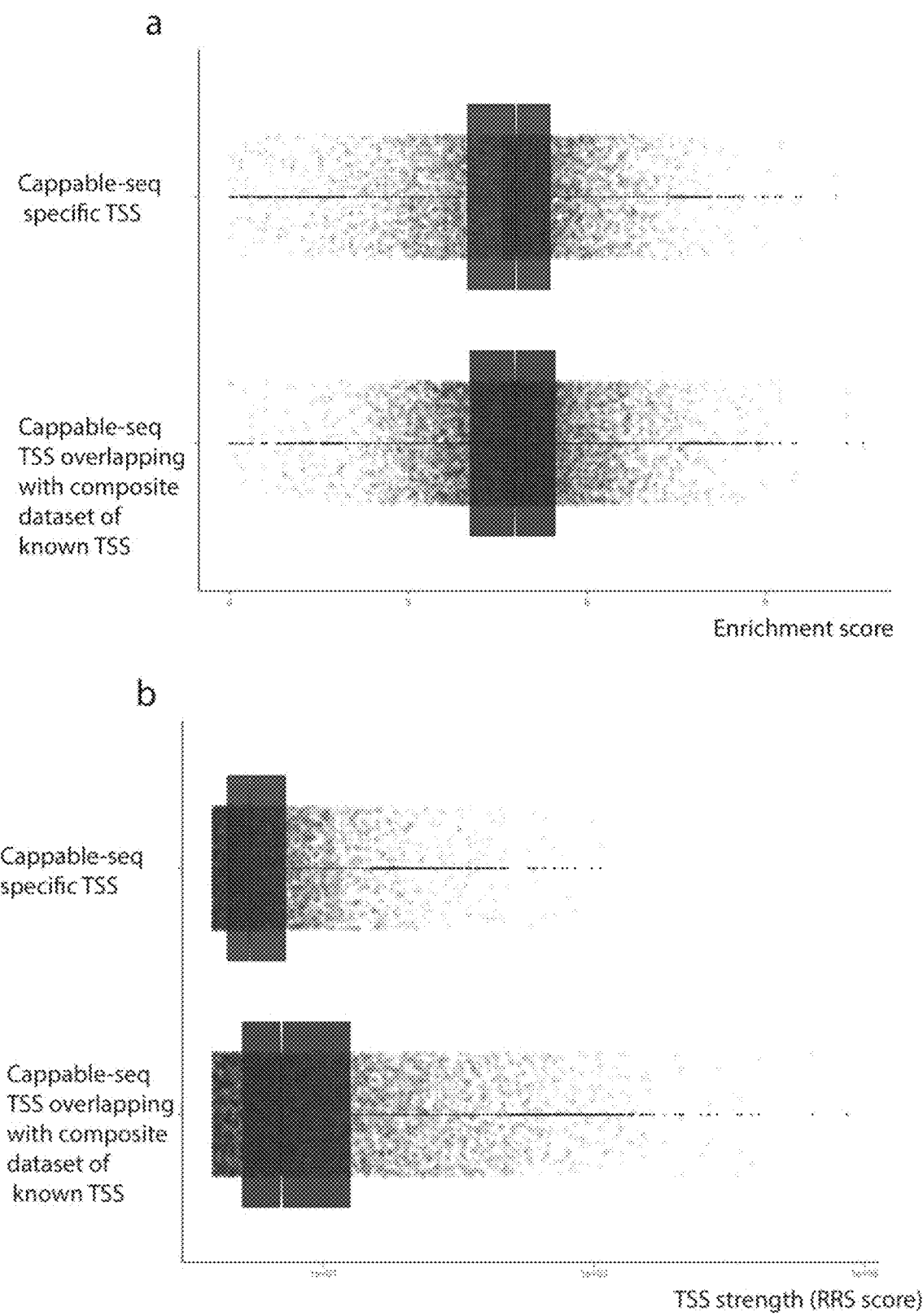
FIG. 23 shows the characterization of the Cappable-seq specific TSS and Cappable-seq TSS common to the composite dataset of known TSS.

To estimate how many of the TSS found by Cappable-seq are novel, a composite dataset of known TSS consisting of the annotated RegulonDB TSS plus TSS derived from high throughput methodologies that have been done on *E. coli* grown in similar conditions was compiled (Kim, et al, *PLoS Genet* (2012) 8:e1002867; Thomason, et al, *J Bacteriol* (2015) 197:18-28). The resulting 16855 TSS present in the composite dataset of known TSS were compared to the Cappable-seq TSS with 9600 TSS found common to both datasets and 6759 TSS found to be Cappable-seq specific TSS (41.3% of Cappable-seq TSS) (FIG. 19, panel C). The number of novel TSS that Cappable-seq identifies that have not been identified in previous studies under equivalent growth conditions is remarkable. The profile of enrichment scores is similar for both the common and Cappable-seq specific sets suggesting that those novel positions are bona fide TSS (FIG. 23, panel A).

One explanation for the high number of Cappable-seq specific TSS is the increased sensitivity due to the higher sequencing depth, revealing novel TSS that are weakly expressed. This question was addressed by looking at the distribution of expression level for both the previously annotated and novel TSS and found a higher number of weak TSS in the Cappable-seq specific set (mean of 2.8) compared to the common set (mean of 4.9) (FIG. 23, panel B). Taken together, these results suggest that some novel TSS are explained by the gain of sensitivity from a high sequencing depth.

Upstream Regions of TSS Display Characteristics of Known *E. coli* Promoters

Figure 24:
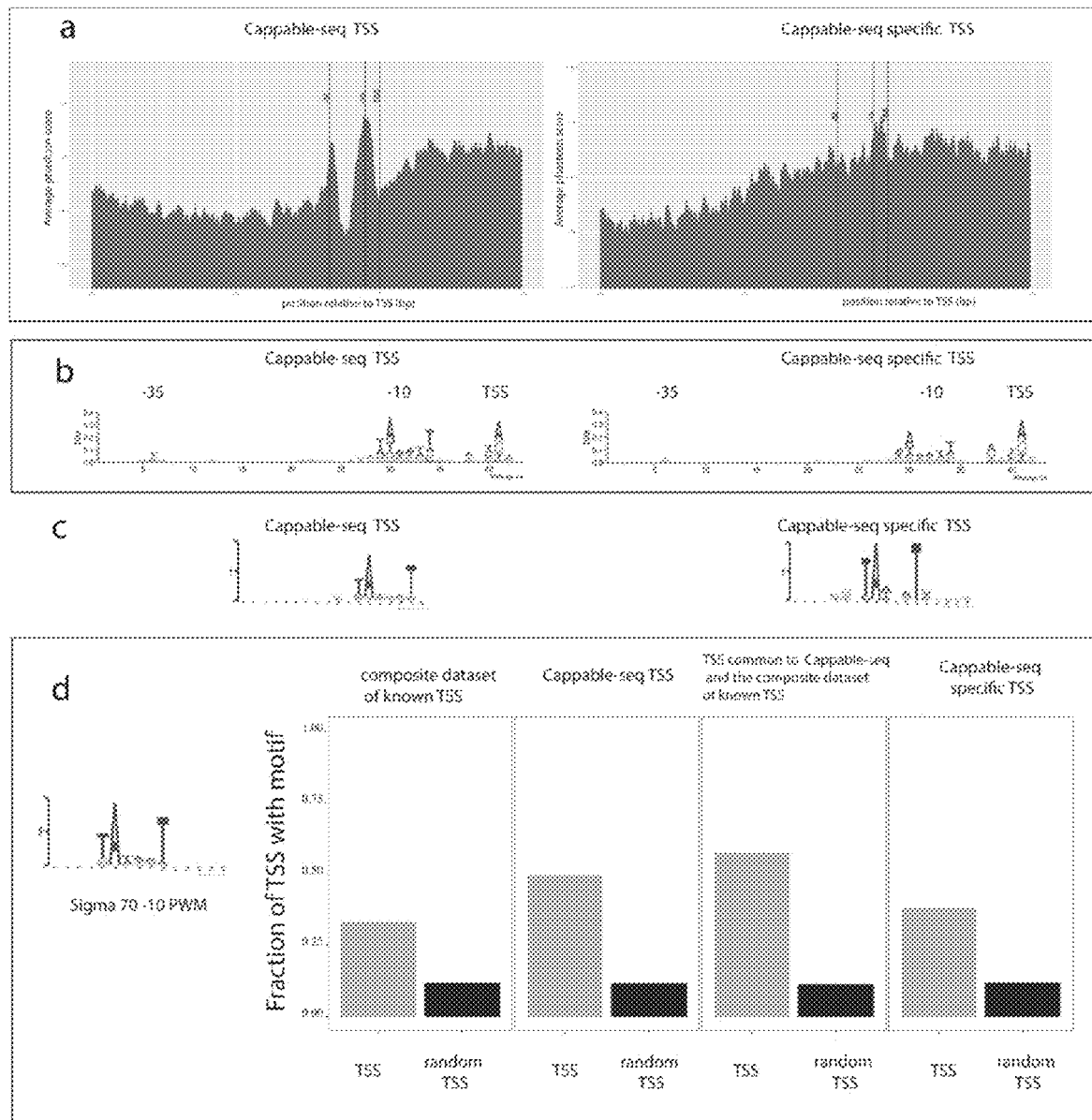
FIG. 24 shows promoter regions.

Next, the sequence conservation across related species and nucleotide bias upstream of the 16359 Cappable-seq TSS was analyzed. To calculate the overall conservation of the flanking regions of TSS, the phastcon scores derived from the genome-wide alignment of 10 related bacterial species including *E. coli* from UCSC were used (Material and Methods). The overall conservation score increased at around 10 and 35 bp upstream of TSS and gradually increased downstream of the TSS (FIG. 24, panel A). The upstream conservation is indicative of the presence of the −10 and −35 promoter elements suggesting that a significant fraction of promoters upstream of the Cappable-seq TSS are under positive selection. The downstream conservation across the ten listed species is indicative of open reading frames likely present downstream of TSS. Nucleotide bias in the region upstream of the TSS is in accordance with sequence conservation; there is a strong bias at −10 for a motif resembling the TATAAT box (FIG. 24, panel B) and a weaker bias at −35 resembling the sigma factor 70 binding site (FIG. 24, panels B and C). Taken together, these results are consistent with the structure of *E. coli* promoters, particularly the sigma 70 promoters upstream of a majority of TSS. The same analysis was performed with the 6759 Cappable-seq specific TSS and found that the regions show similar sequence bias at around −35 (FIG. 24, panel B) and −10 as that found for the entire set (FIG. 24, panels B and C). Despite similar sequence bias in both Cappable-seq specific TSS and annotated TSS, the Cappable-seq specific TSS show no increase of sequence conservation at −10 and −35 (FIG. 24, panel A).

To better estimate the fraction of promoters that contains a canonical −10 region, a position weight matrix (PWM) corresponding to the canonical sigma 70-10 motif from the known sigma 70 promoters TSS dataset (Salgado et al, *Nucleic Acids Res* (2013) 41:D203-13) was generated. Promoter regions of Cappable-seq TSS and composite dataset of known TSS were scanned for the presence of the −10 motif and compared to randomly selected regions. About 50% of Cappable-seq TSS was found to have a −10 motif in their promoter, while this fraction is about 40% for Cappable-seq specific TSS. For comparison this fraction drops to 33% in the composite dataset of known TSS. This result suggests that a significant fraction of TSS in Cappable-seq are bona fide TSS (FIG. 24, panel D). All Cappable-seq datasets (total, specific and common) have a higher fraction of promoters with a canonical −10 motif compared to the composite dataset of known TSS (FIG. 24, panel D).

Furthermore Cappable-seq TSS demonstrated an 80% nucleotide preference for either A or G (FIG. 3A). While this finding is in agreement with previous studies, the preference for A or G in Cappable-seq TSS is stronger than the preference found in annotated TSS from RegulonDB (60%). Despite motif preferences at the TSS, the sequence conservation across species is not elevated suggesting there is not a strong selective pressure to conserve a specific nucleotide.

Figure 25:
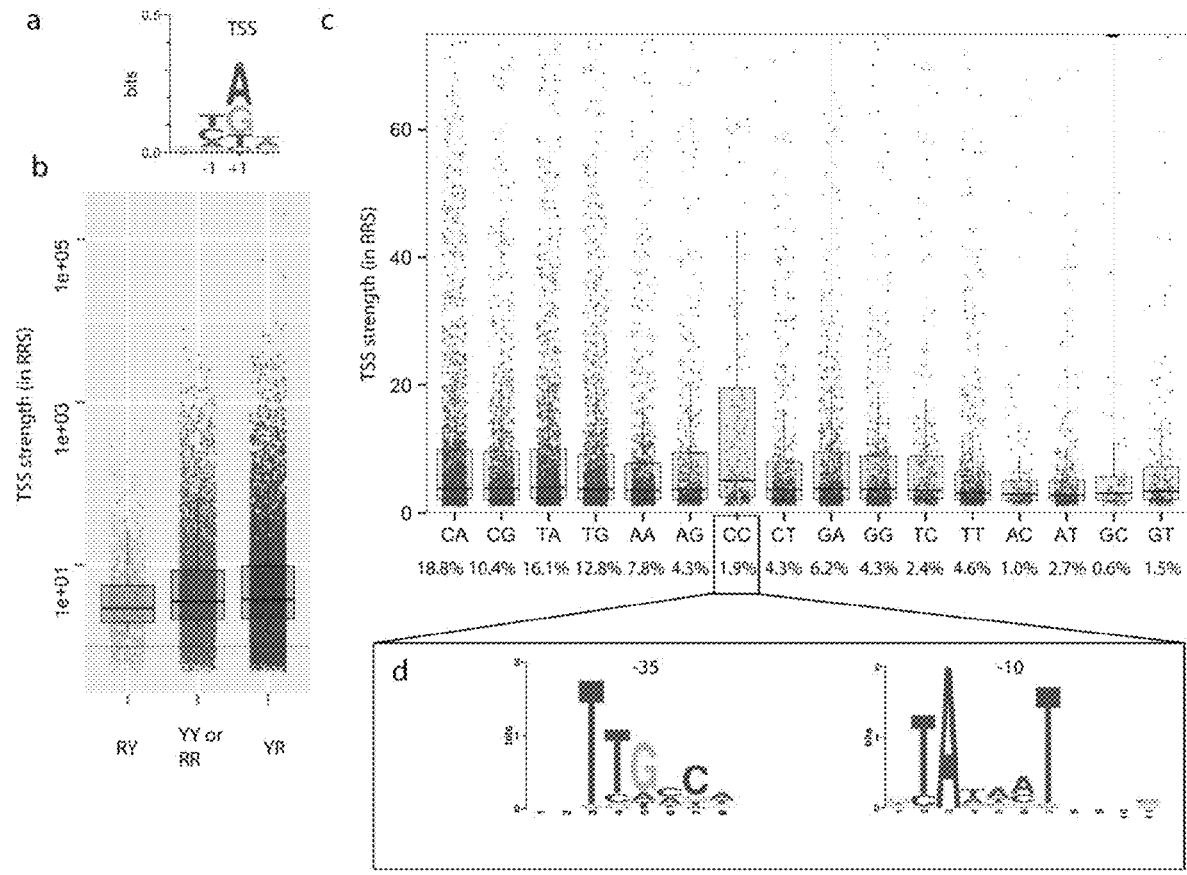
FIG. 25 shows the nucleotide preference at TSS.

Additionally, a nucleotide preference at minus 1 position with 76% of the nucleotides being pyrimidine (C or T) was observed. In summary, more than half of the TSS (57%) have a −1[CT]+1[AG] configuration with 18% of the TSS having a −1C+1A configuration and only 0.6% having the −1G+1C configuration (FIG. 25, panel C). Interestingly this pyrimidine (Y) purine (R) or "YR" configuration has been previously reported to be the preferred configuration at TSS in various prokaryotes and eukaryotes ranging from *C. elegans*, plant and human suggesting that the YR rule is conserved across kingdoms.

There is no correlation between the −1/+1 nucleotide and the enrichment score (data not shown) suggesting that the least favored configurations (−1[AG]+1[CT]) are genuine TSS. The strength of the TSS, as defined by the RRS, has a weak correlation with the −1/+1 nucleotide configuration. Indeed, YR configuration includes the most highly expressed TSS while the RY configuration is the weakest TSS (FIG. 25, panel B). Contrasting with this notion, the −1C+1C (YY configuration) has the highest fraction of highly expressed TSS (FIG. 25, panel C) including the five most highly expressed −1C+1C TSS upstream of ribosomal genes. This observation could be the result of an alternative promoter upstream of the −1C+1C TSS. To address this question, overrepresented motifs were searched for in the 40 bases upstream of −1C+1C TSS class using MEME (Bailey et al, *Nucleic Acids Res* (2009) 37:W202-8) and the canonical TATAAT box at −10 and sigma 70 motif at −35 was found suggesting that the majority of the −1C+1C TSS class is a subset of TSS from the sigma 70 promoter (FIG. 25, panel D).

Intragenic Sense TSS in *E. coli* have a Marked Preference for the First Nucleotide of Codons.

Figure 26:
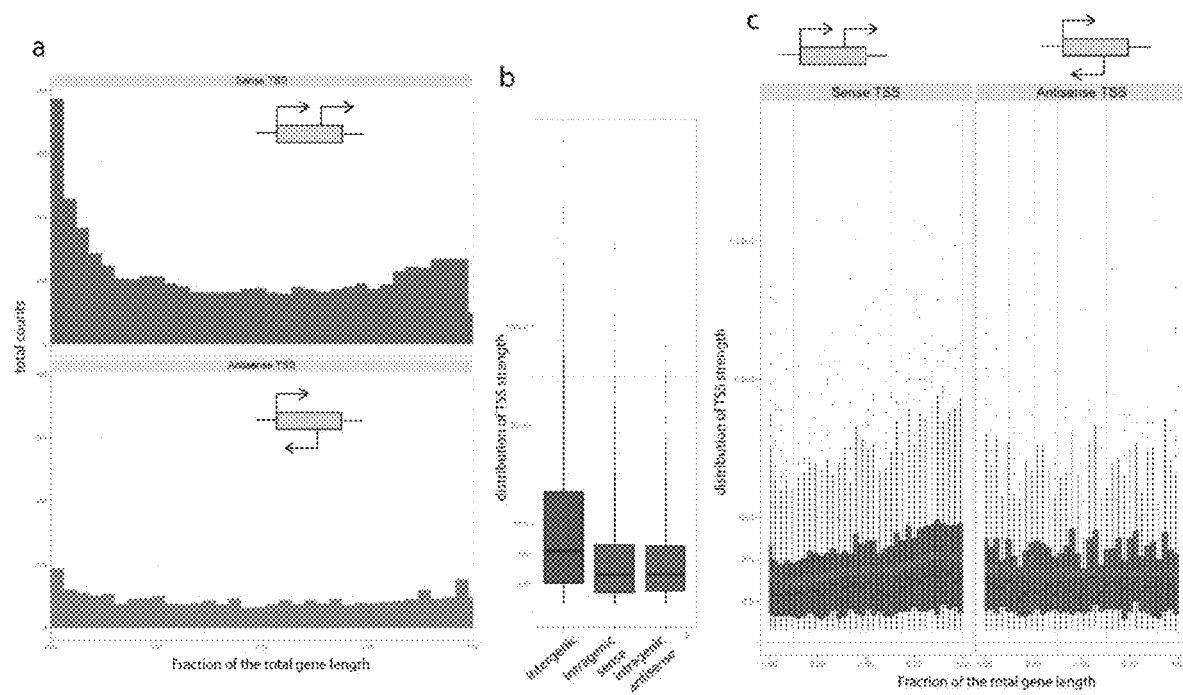
FIG. 26 shows intragenic TSS.

TSS identified by Cappable-seq that are within protein coding genes account for 63% (10741) of the total TSS with two-thirds of the intragenic TSS in the sense orientation in relation to the gene. Sense TSS tend to be located at the start of the protein coding regions. A slight tendency for locating sense TSS at 3' end of protein coding genes was identified. Antisense tend to be evenly distributed within the protein coding regions (FIG. 26, panel A). Intergenic TSS tend to have higher RRS than both sense and antisense intragenic TSS, suggesting that intergenic TSS tend to be stronger (FIG. 26, panel B). There is a correlation between the strength of sense intragenic TSS and their position relative to the coding gene with stronger TSS occurring towards the 3' end of genes (FIG. 26, panel C). Leaderless transcripts account for 0.4% (82) of TSS.

Figure 27:
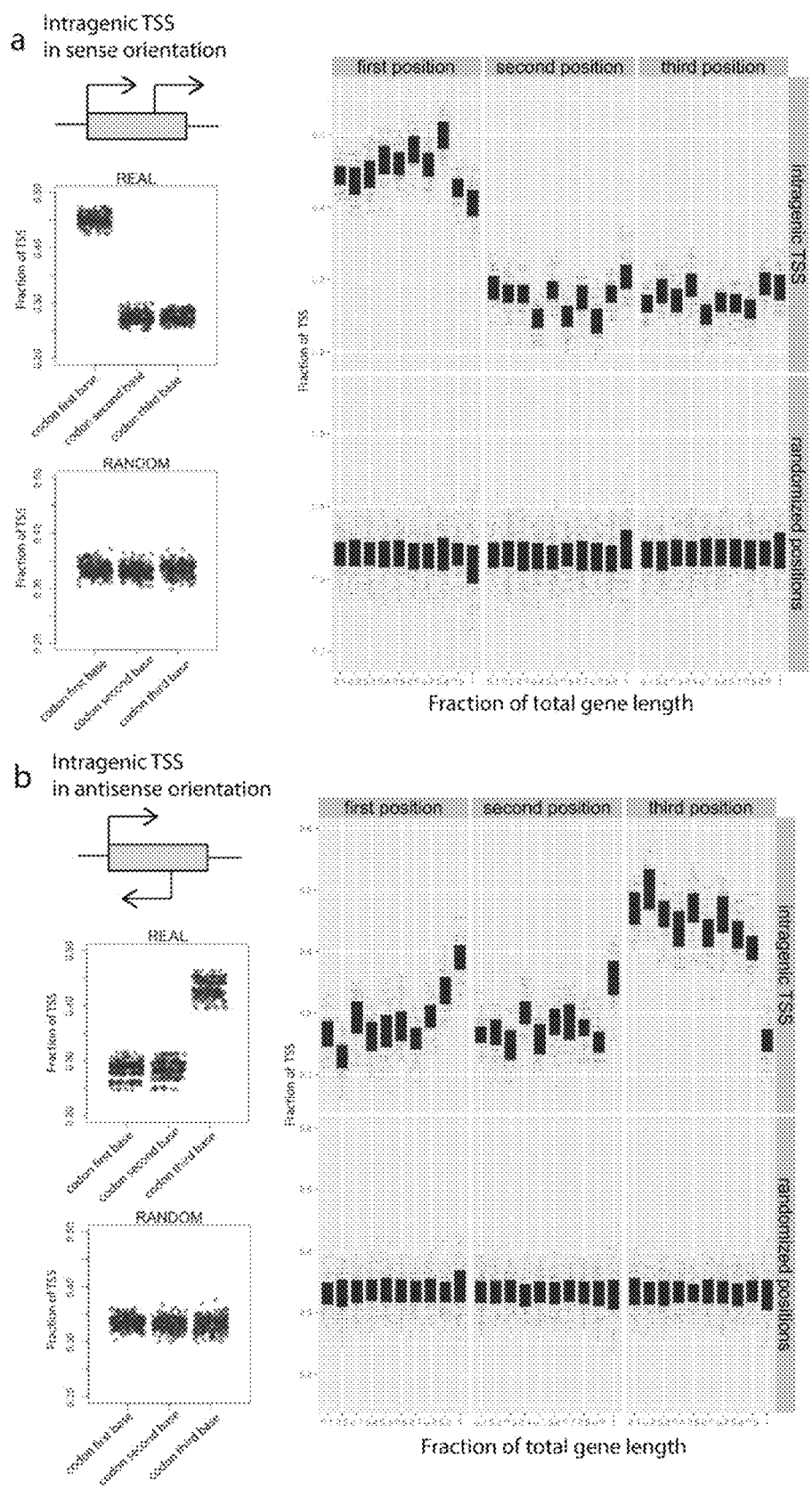
FIG. 27 shows the positional preference of TSS relative to codon.

Interestingly, intragenic TSS were found to have striking positional preference relative to the nucleotide triplet that defines the reading frame. 45% of the intragenic sense TSS were found located in the first position of codons while only 27% of TSS are located in the second and 27% in the third position (FIG. 27, panel A). The antisense TSS show a weaker but noticeable preference for the third position rather than the first, with 43% of TSS on the third position (FIG. 27, panel B). Sense and antisense preference is distributed throughout the protein coding gene (FIG. 27, panels A and B). This positional preference of the TSS relative to the codon may be influenced by the nucleotide frequency at codons with a higher A and G frequency at the first base of the codon. While other datasets derived from dRNA-seq experiments show similar preferences, this observation has not been previously reported. Interestingly, 168 TSS were found at the first nucleotide of an internal in-frame AUG codon. Those transcripts are putative leaderless transcripts leading possibly to a truncated form of the annotated protein.

TSS from a Microbiome.

Figure 28:
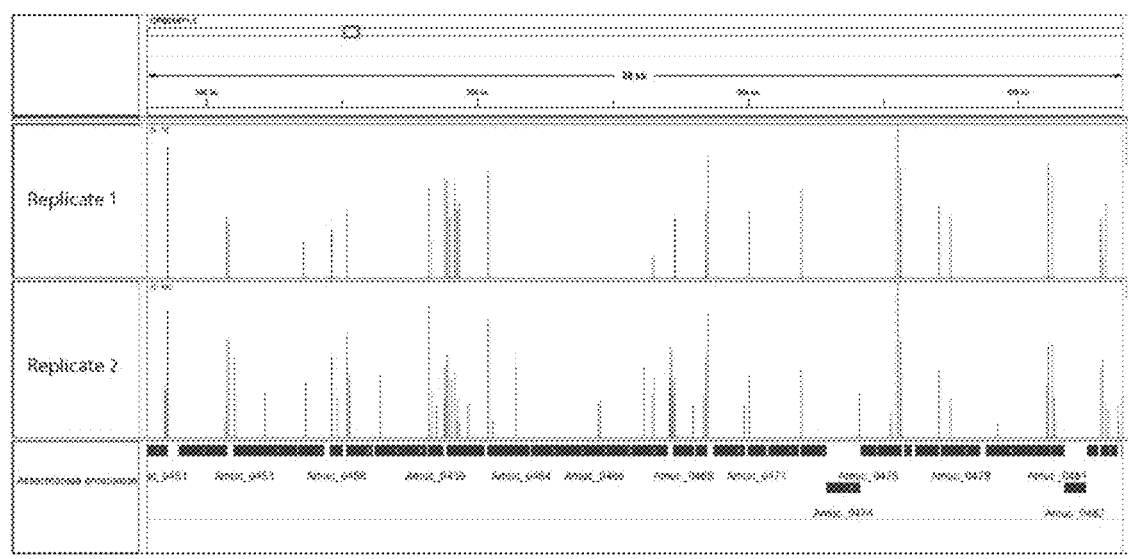
FIG. 28 shows the TSS of mouse get microbiome.
Figure 28:
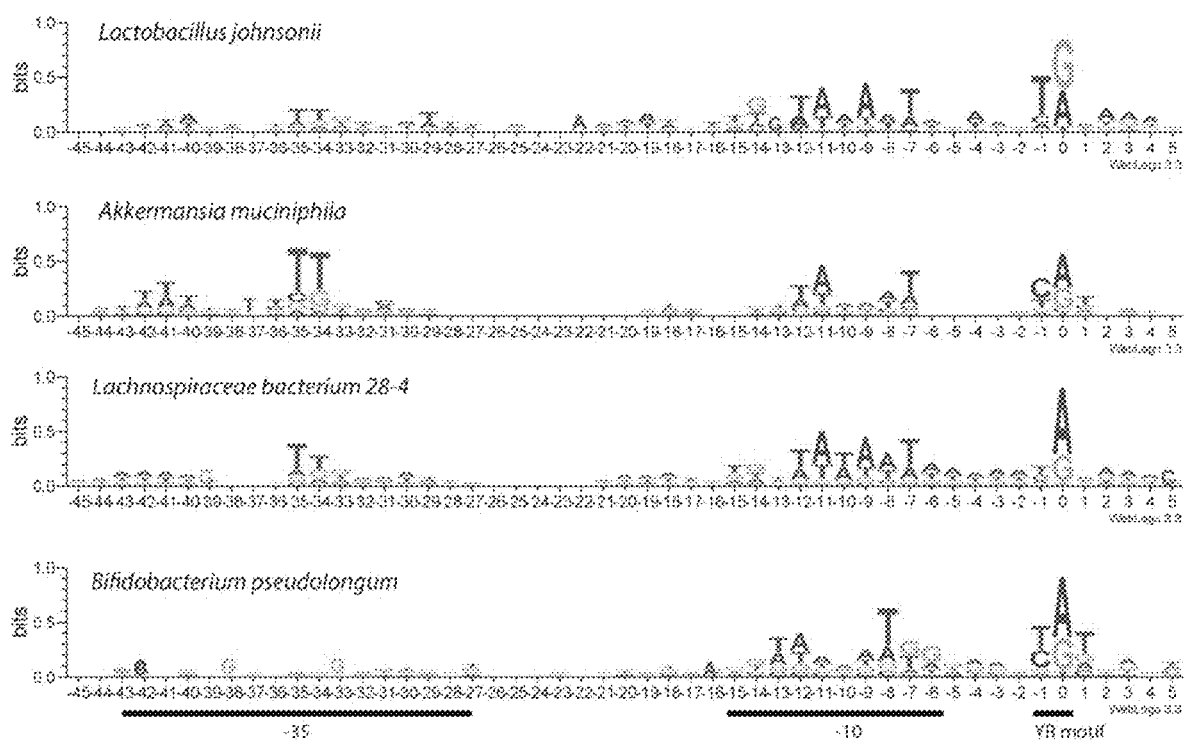
Figure 28:
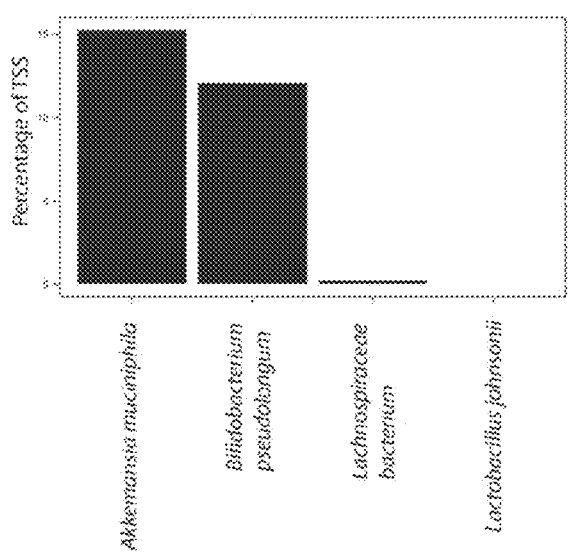
Figure 28:
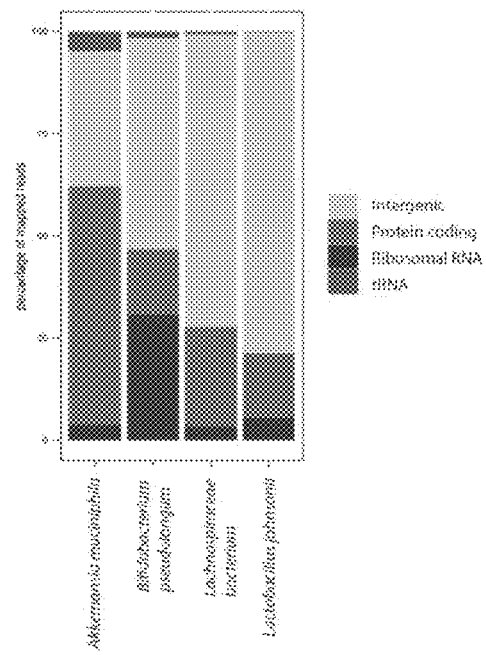
Figure 28:
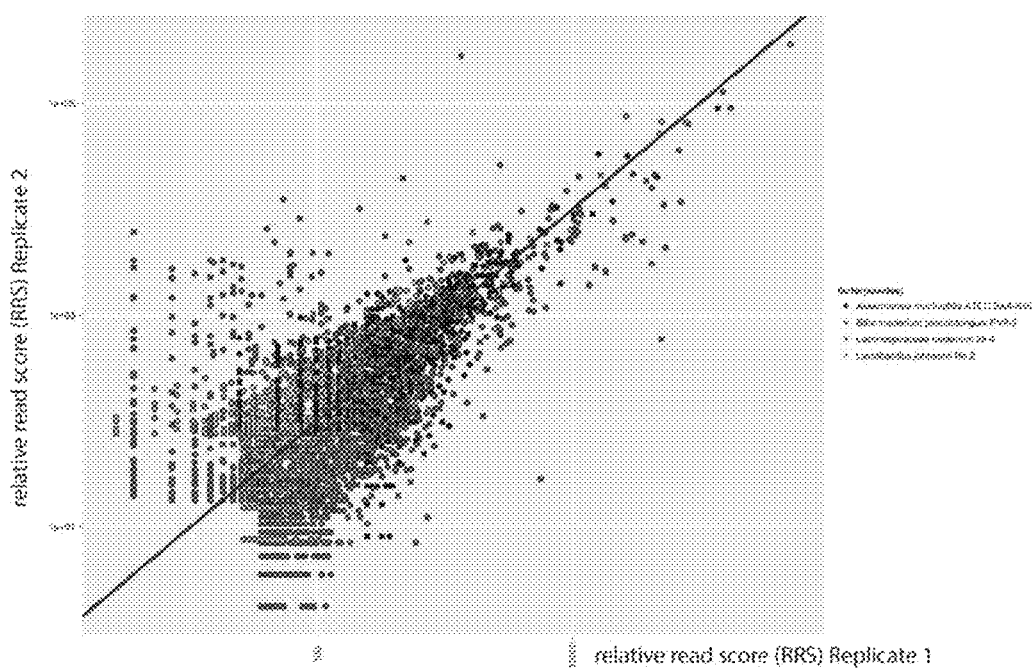

To demonstrate the applicability of the methodology on a complex mixture of bacteria, Cappable-seq was applied to two C57 female mice cecum microbiomes (Material and Methods). Reads were mapped to the bacterial genomes from NCBI and species with more than 300 identified clustered TSS were considered candidates and the species with the highest number of clustered TSS in each phylum were further analyzed. For all species, the majority of the reads mapped in either intergenic regions or in protein coding genes in accordance with the biology of TSS (FIG. 28, panel D). Accordingly, reads mapping to rRNA and tRNA less than 10% of mappable reads in *Lactobacillus johnsonii*, Akkermansia muciniphila and Lachnospiraceae bacterium. It was hypothesized that the higher fraction of rRNA reads in *Bifidobacterium pseudolongum* (around 30%) is due to the high level of rRNA sequence conservation leading to the spurious mapping of rRNA sequence originating from other species of *Bifidobacterium*. Taken together these data suggest that Cappable-seq depletes processed transcripts such as rRNA and tRNA from microbiomes total RNA with the same efficiency as observed in *E. coli*. Next a set of highly confident TSS per species was derived and sequence bias in regions flanking those TSS were identified. In agreement with promoter organization/structure in bacteria, a strong sequence bias at 35 bases and 10 bases upstream of the TSS was found for all analyzed species (FIG. 28, panel B) indicative of the −35 element and the TATAAT box respectively. Furthermore, the YR motif at position −1+1 can be identified in all cases, reinforcing the universality of the YR motif for TSS. Beyond the biological significance of these finding, these results shows that the specificity of Cappable-seq for TSS in a microbiome is similar to the specificity for TSS in *E. coli*. Interestingly, two of the four species analyzed (Akkermansia muciniphila and *Bifidobacterium pseudolongum*) show 10% and 15% of the TSS located at the start of the annotated protein coding genes signature of leaderless transcripts (FIG. 28, panel C). For comparison, *E. coli* shows only 0.4% leaderless TSS.

This result is in agreement with a previous computational predictions suggesting that leaderless transcripts are widespread in a variety of bacteria. Finally, the reproducibility of Cappable-seq in a microbiome was challenged by analyzing the TSS positions and strength (RRS) in two biological replicates from two different mice and good reproducibility in both qualitative and quantitative (correlation coefficient=0.81) measurements of TSS was found (FIG. 28, panels A-E) (Thorvaldsdottir et al, *Brief Bioinform* (2013) 14:178-192; Robinson et al, *Nat Biotech* (2011) 29:24-26).

Example 18: Use of *S. pombe* HNT3 as a Decapping Enzyme

The HNT3 gene of *S. pombe* is approximately 50% identical to the HNT3 gene of *S. cerevisiae* also known as the 5' deadenylase. Here it is shown that the *S. pombe* HNT3 protein can decap RNA.

Figure 29:
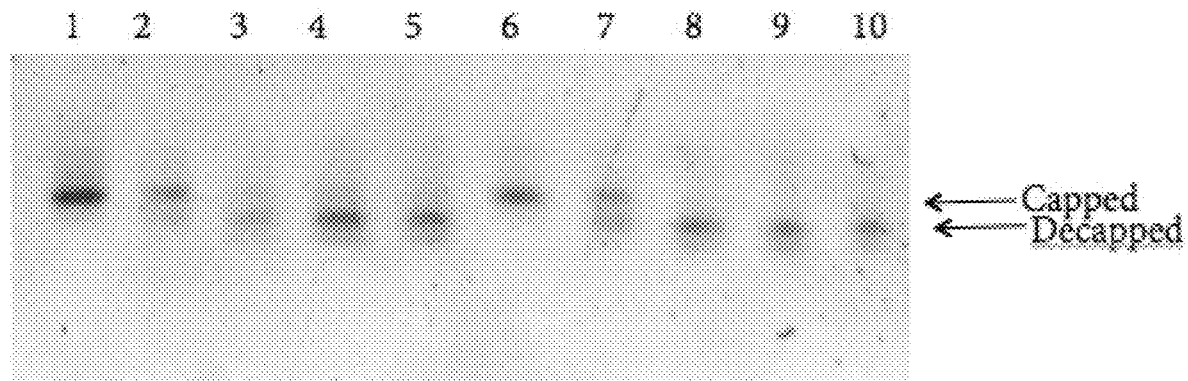
FIG. 29 shows that *S. pombe* HNT3 can decap capped RNA.

A 10 µl reaction mixture containing 10 mM succinate pH 6.0, 200 mM NaCl, and 2 mM MgCl2 and either a Cap0 or Cap1 25 mer transcript at 1.6 ng/µl was incubated 10 minutes at 30° C. with a dilution series of *S. pombe* HNT3 protein. Lane 1-5 is Cap1 RNA. Lane 1 no enzyme control, lane 2 contains 5 ng of protein; lane 3, 15 ng; lane 4, 45 ng; and lane 5, 135 ng of protein. Lane 6-10 is Cap0 RNA. Lane 6 no enzyme control, lane 7 contains 5 ng of protein; lane 8, 15 ng; lane 9, 45 ng; and lane 10, 135 ng of protein. The *S. pombe* HNT3 protein was prepared by expressing the HNT3 gene in *E. coli*. The protein was purified by DEAE and heparin chromatography. The reactions were stopped with an equal volume of 2×NEB RNA loading dye (New England Biolabs, Ipswich, Mass.) and analyzed by 15% TBE Urea polyacrylamide gel electrophoresis. Results are shown in FIG. 29.

The amino acid sequence of the *S. pombe* HNT3 protein is set forth below:

```
                                       (SEQ ID NO: 15)
MSVHKTNDAFKVLMNSAKEPIVEDIPKKYRKQSFRDNLKVYIESPESYKN

VIYYDDDVVLVRDMFPKSKMHLLLMTRDPHLTHVHPLEIMMKHRSLVEKL

VSYVQGDLSGLIFDEARNCLSQQLTNEALCNYIKVGFHAGPSMNNLHLHI

MTLDHVSPSLKNSAHYISFTSPFFVKIDTPTSNLPTRGTLTSLFQEDLKC

WRCGETFGRHFTKLKAHLQE
```

Example 19: Addition of a Propargyl Cap by a Capping Enzyme

Click chemical ligation is enabled by introducing a propargyl chemical group at the 5' end of RNA. It has been shown that 3' propargyl-GTP can be efficiently incorporated as a modified cap at the 5' end of a triphosphorylated RNA.

Figure 30:
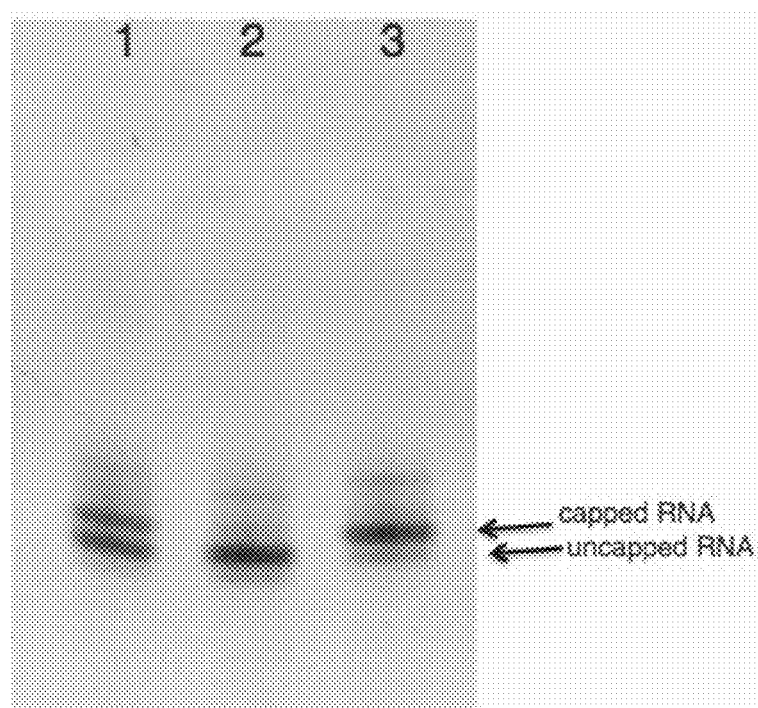
FIG. 30 shows that RNA can be enzymatically capped with a propargyl cap, thereby allowing the capped RNA to be linked to other moieties by click chemistry.

A 25 mer 5' triphosphorylated RNA was capped by a 3' propargyl-GTP as follows: A 200 µl reaction containing 1×VCE buffer, 10 ug of 25 mer 5' triphosphate RNA transcript, 0.1 mM SAM, 100 units of VCE and 0.5 mM 3' propargyl-GTP was incubated for 60 minutes at 37° C. The reaction product, lane 3, was analyzed by 15% TBE Urea polyacrylamide gel electrophoresis. Lane 1 is a control of a mixture of G-capped and uncapped 25mer RNA. Lane 2 is an uncapped 25mer RNA. The product of the reaction was run on a 15% TBE urea gel. These results are shown in FIG. 30. This data shows that RNA can be capped with a propargyl group by a capping enzyme.

Example 20: Decapping 7 Methyl G Capped Transcript and Recapping with DBT GTP A 15% TBE Urea polyacrylamide gel of a 25mer T7 $^7$mG capped transcript was first incubated with 5' deadenylase (decapping by removal of GMP leaving a 5' diphosphate mRNA terminus) and subsequently incubated with VCE and DTB-GTP (capping mRNA with 5' diphosphates with a DTB-GTP) where DTB=desthiobiotin. The results are shown in FIG. 3. This results shows that a 7 methyl G capped transcript can be decapped using a 5' deadenylase and then re-capped with a with a capture tag using a capping enzyme.

Example 21: Decapping 7 Methyl G Capped Transcript and Recapping with DBT GTP in the Presence of Total *E. coli* RNA A 15% TBE Urea polyacrylamide gel of a 25mer T7 $^7$mG capped transcript was first incubated with 5' deadenylase (decapping by removal of GMP leaving a 5' diphosphate mRNA terminus) and subsequently incubated with VCE and DTB-GTP (capping mRNA with 5' diphosphates with a DTB-GTP) where DTB=desthiobiotin, in the presence of total *E. coli* RNA. The results are shown in FIG. 4. The signal from the recapped RNA can be enhanced by increasing the concentration of 5' deadenylase.

The multiple bands in the upper portion of the gel are low molar concentrations of high MW RNAs. In contrast, the bands in the lower portion of the gel are high molar concentrations of lower molecular weight RNAs. These results show that the capping and decapping reaction can work if the sample is mixed, e.g., contains prokaryotic and eukaryotic RNA.

Example 22: Synthesis of a Cleavable 3'-Biotin-Labeled GTP Nucleotide

This example describes the method of synthesis of a novel chemically cleavable labeled nucleotide. Biotin is characterized here by a linker that comprises an allylic moiety that is attached to the oxygen on the C3 of the ribose. The linker is in turn linked to a biotin label, in this particular example by combination of polyethyleneoxy and 1,2,3-traizole moieties. In contrast to DBT, biotin is not easily eluted from streptavidin. Elution of guanosine nucleotide requires cleavage of the allylic linker mediated by palladium catalysis as described by Kim T.-S. et al., ChemBioChem 2010, 11:75-78; Kim, D.-R. et al., Bioorg. Med. Chem. Lett. 2014, 24:209-213.

Figure 36:
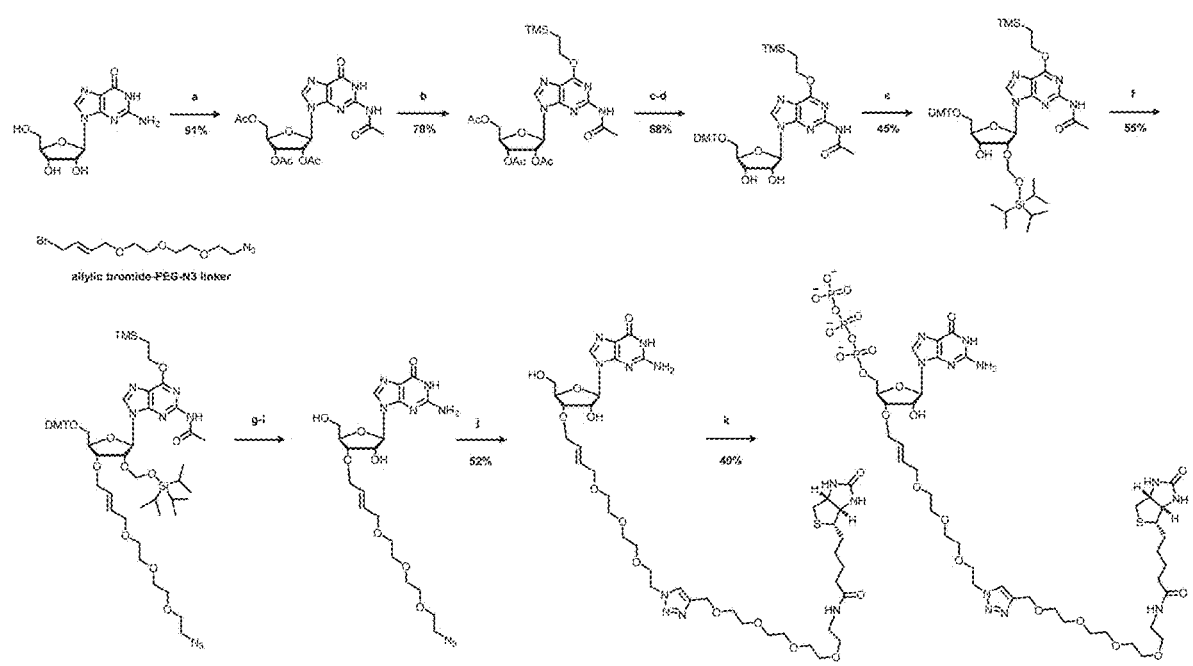
FIG. 36 shows a pathway for the chemical synthesis of a cleavable 3'-biotin labeled guanosine 5'-triphosphate, wherein the cleavable linker comprises a 3'-O-allyl linkage. Reaction conditions in this example: (a) Ac2O, pyridine, reflux, 2.5 hours; (b) trimethylsilyl ethanol, PPh3, diisopropyl azodicarboxylate, dioxane, 0° C. to RT, 20 hours; (c) NH$_4$OH, MeOH, overnight; (d) 4,4'-dimethoxytrityl chloride, pyridine, 0° C. to RT, 4 hours; (e) n-dibutyltin dichloride, N-ethyl-N,N-diisopropylamine, 1,2-dichloroethane, 1 hour, then (triisopropylsiloxy)methyl chloride, 80° C., 15 minutes; (f) allylic bromide-PEG-N3 linker, tetrabutylammonium bromide, NaOH, 6 hours; (g) tetrabutylammonium fluoride, THF, 30 minutes; (h) trichloroacetic acid, dichloromethane, 30 minutes; (i) NH$_4$OH, MeOH, 55° C., overnight; (j) Biotin-PEG4-acetylene (Click Chemistry Tools), CuSO4, sodium ascorbate, tris(3-hydroxypropyltriazolylmethyl)amine, DMSO, water, overnight; (k) trimethylphosphate, phosphorous oxychloride, −5° C., then tributylammonium pyrophosphate, tributylamine, acetonitrile, 10 minutes.
Figure 37:
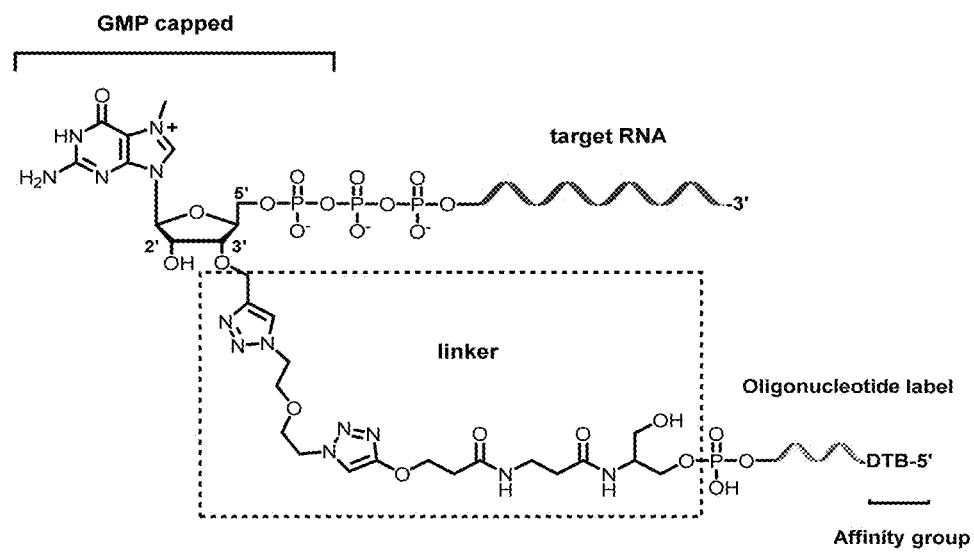
FIG. 37 shows an example of a 5'-GMP-capped target RNA, wherein the GMP cap is connected to an oligonucleotide label. The oligonucleotide label comprises a 5'-DTB modification and was coupled to the target RNA using copper-mediated azide-alkyne cycloaddition ("click chemistry"). The linker region between the oligonucleotide label and the GMP cap is shown.
Figure 38:
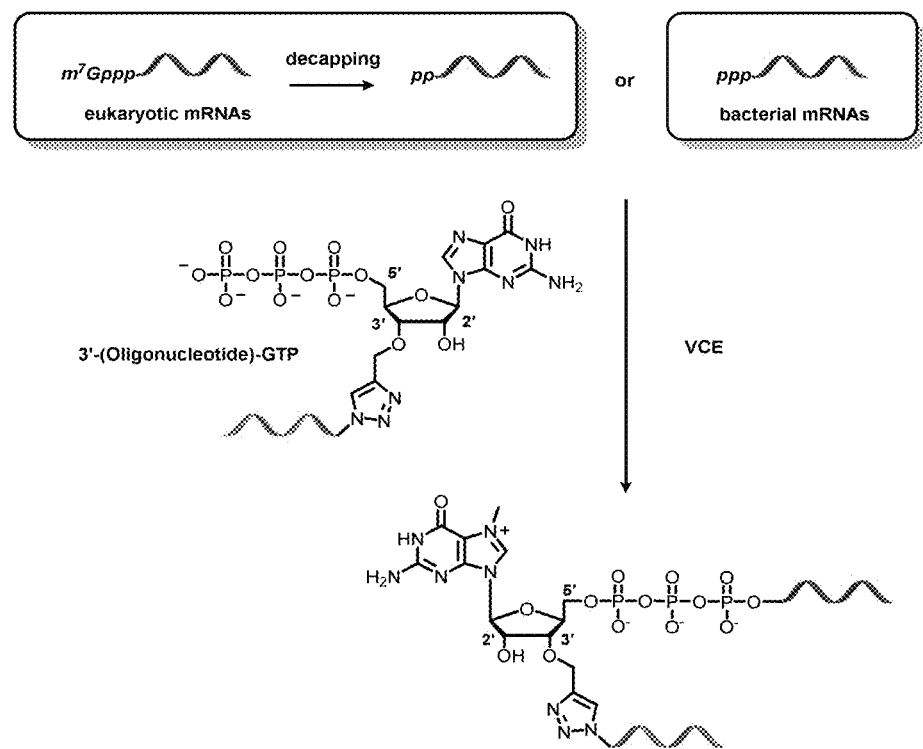
FIG. 38 shows a schematic diagram of a one-step approach to add an oligonucleotide reagent to a target RNA of interest comprising adding a preassembled oligonucleotide-labeled GTP to the target RNA using a capping enzyme to form an oligonucleotide-labeled GMP modified target RNA. The target RNA may be a capped eukaryotic mRNA which is decapped prior to the labeling reaction or the target RNA may be a prokaryotic triphosphate mRNA; and the capping enzyme is the VCE.
Figure 39:
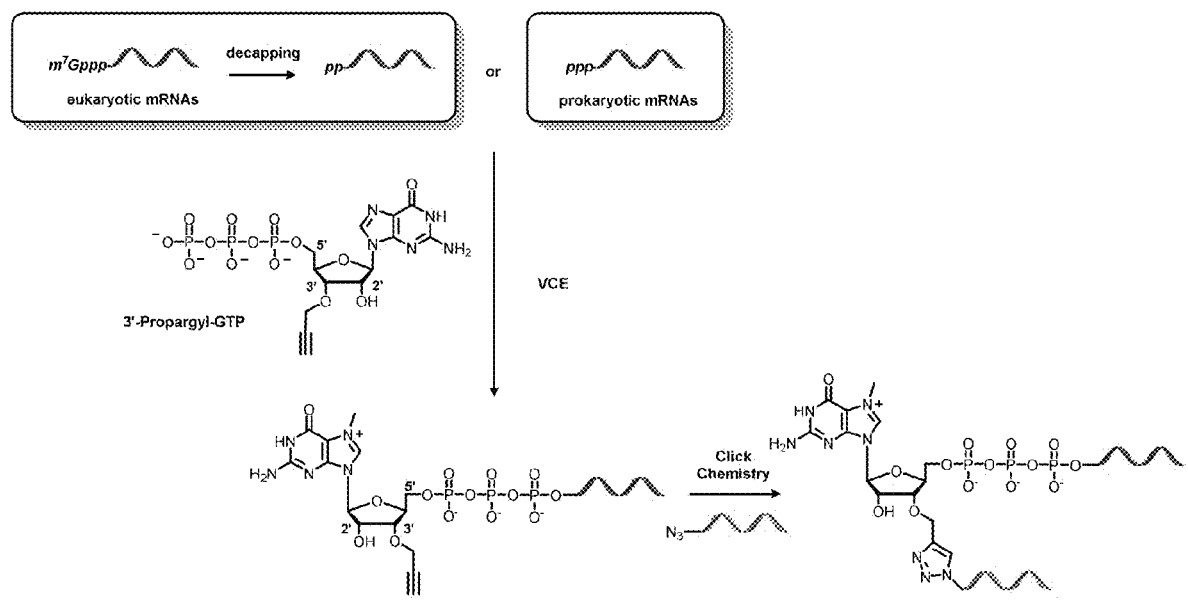
FIG. 39 shows a schematic diagram of a two-step approach to add an oligonucleotide reagent to a target RNA of interest comprising: (1) adding a reactive group-labeled GTP to the target RNA using a capping enzyme to form a reactive group-labeled GMP modified target RNA; and (2) reacting the reactive group-labeled target RNA with an oligonucleotide having a chemoselective reactive group so as to form an oligonucleotide-labeled target RNA. In this example, the reactive group-labeled GTP is a 3'-propargyl-GTP (alkyne GTP); the target RNA may be a capped eukaryotic mRNA which is decapped prior to the labeling reaction or the target RNA may be a prokaryotic triphosphate mRNA; the capping enzyme is the VCE; the reactive oligonucleotide is an azide ($N_3$) oligonucleotide; and the chemoselective reaction is a azide-alkyne cycloaddition reaction.

Synthesis was initiated with guanosine (Sigma-Aldrich Corp., St. Loius, Mo.) peracetylation, followed by protection of 06-oxygen with trimethylsilyl ethanol (Sigma-Aldrich Corp., St. Loius, Mo.), selective deacetylation and subsequent protection of the ribose 5'-O-position with 4,4'-dimethoxytrityl chloride (Sigma-Aldrich Corp., St. Loius, Mo.). Deacetylation of the ribose 2'- and 3'-O-positions followed by selective protection of 2'-O-position with (triisopropylsiloxy)methyl chloride and reaction of free 3'-OH with allylic bromide-PEG-N3 linker (synthesized based on methods published by Kim, D.-R. et al., Bioorg. Med. Chem. Lett. 2014, 24:209-213) resulted in key guanosine 3'-O-allylic intermediary. Removal of remaining protective groups, followed by attachment of biotin label through copper-mediated azide-alkyne cycloaddition ("Click Chemistry", Kolb and Sharpless, Scripps Res. Inst. and BaseClick, Tutzing, GmbH) with Biotin-PEG4-acetylene (Click Chemistry Tools, Scottsdale, Ariz.) and its conversion to 5'-triphosphate via a one pot, two-step phosphorylation method (several published procedures). Intermediary compounds were isolated and purified by silica-gel chromatography or reverse-phase HPLC. Final isolation of the target 3'-biotin-labeled guanosine 5'-triphosphate compound was performed by ion exchange chromatography and reverse-phase HPLC. The pathway described here is shown in FIG. 36.

Example 23: Addition of a Pre-Assembled Oligonucleotide-Labeled GTP to a 5'-Triphosphate Target RNA 1) Synthesis of an Oligonucleotide-Labeled GTP (3'-(5'-DTB-33mer-Triazole)-GTP):

An 3'-azido-oligonucleotide further modified with a 5'-DTB group (10 µL, final concentration 8 µM; sequence: 5'-DTB-ACACUCUUUCCCUACACGACGCUC-UUCCGAUCU-N$_3$-3') (SEQ ID NO:16) was dissolved in 2M TEAA buffer (10×, 12.5 µL, 200 µM final concentration, pH 7) and DMSO (25% of total reaction volume, 31.25 µL). 3'-O-Propargyl-GTP (final concentration 132 µM) was then added followed by ascorbic acid (12.7 µL, final concentration 500 µM). The reaction vial was then degassed with nitrogen, and the Cu(II)-TBTA solution was added (6.3 µL, final concentration 500 µM; Lumiprobes, 21050) and degassed again. The reaction (125 µL total volume) was incubated overnight at room temperature in the absence of light. The reaction was purified by Oligo Clean & Concentrator™ kit (Zymo, Irvine, Calif.) to yield 3'-(5'-DTB-33mer-Triazole)-GTP. When necessary, the oligonucleotide-labeled GTP was further purified by PAGE purification (see below). Reaction can be scaled up or down as necessary.

2) Enzymatic Capping Using Pre-Assembled Oligonucleotide-Labeled GTP:

The capping of a target 5'-triphosphate 25mer RNA (5 nmol) was performed at a 500 µL reaction volume using the Vaccinia Capping System (New England Biolabs, M2080): 100 µM 5'-triphosphate 25mer RNA (50 µL, final concentration 10 µM), water (100 µL), 10× Capping Buffer (50 µL; 50 mM Tris-HCl, 5 mM KCl, 1 mM MgCl$_2$, 1 mM DTT, pH 8 at 25° C.), 2.5 mM oligonucleotide-labeled GTP (100 µL, final concentration 500 µM, 3'-(5'-DTB-33mer-Triazole)-GTP), 1 mM SAM (100 µL, final concentration 200 µM), Pyrophosphatase (50 µL; NEB M2403S, 0.1 unit/µL), and VCE (50 µL; 1 unit/µL). The 25 mer target RNA and water were first combined, and the solution was heated to 65° C. for 5 minutes and placed on ice for an additional 5 minutes. The remaining reaction components were added, and the reaction was allowed to proceed at 37° C. overnight. The enzyme and small molecules were removed from the reaction using phenol/chloroform extraction with Phase Lock Gel tubes (5Prime, 2302810). Briefly, the reaction was vortexed with an equivalent amount (500 µL) of phenol:chloroform, 5:1, pH 4.7 (Ambion, 9720). Up to 500 µL of this mixture was added to a Phase Lock Gel tube and centrifuged for 5 minutes at 13,000 rpm. To ensure the separation of the phases, 250 µL of chloroform (99%, Sigma-Aldrich, 372978) was added, and the tube was centrifuged for 5 minutes at 13,000 rpm. The aqueous phase containing the oligonucleotide-capped target RNA was then transferred to a fresh tube and concentrated on a Savant™ SpeedVac™ (ThermoFisher Scientific, Waltham, Mass.). Reaction can be scaled down as needed.

This crude material was then purified using polyacrylamide gel electrophoresis (PAGE purification). The Sequa-Gel™ UreaGel System kit (National Diagnostics, Atlanta, Ga.) was used to make a 20% acrylamide gel: for 50 mL of acrylamide gel, a solution of UreaGel Concentrate (40 mL), UreaGel Diluent (5 mL) and UreaGel Buffer (5 mL) were mixed followed by APS 10% (400 µL) and tetramethylethylene diamine (20 µL, TEM ED, National Diagnostics, Atlanta, Ga.). The mixture was immediately poured into a gel cassette (height: 28 cm, width: 16.5 cm, thickness: 1.5 mm) with the appropriate comb and allowed to polymerize at room temperature. TBE 1× Buffer was prepared from a 5× stock (AccuGene™ 5×TBE Buffer, Lonza, Basel, Switzerland). The gel was equilibrated overnight at 600 V (constant voltage). The gel was then warmed prior to sample addition by increasing the maximum voltage to 800 V. The dried samples were resuspended in 50 µL of 7 M urea (prepared from powder: Qiagen, Germany 1000774) and heat-denatured at 70° C. for 5 minutes. The gel was run at 800 V (constant voltage) for up to 6 hours.

The oligonucleotide-capped target RNA was revealed by UV shadowing on a white background. The band of interest were cut out and crushed in 2 mL Eppendorf tubes with disposable plastic pestles and resuspended and vortexed in 500 mM Tris pH 7.5 (500 µL). The gel particles were heated at 60° C. for 15 minutes, immediately frozen at −80° C. for 30 minutes, and then left overnight at room temperature. The gel solution was centrifuged at 15,000 rpm for 30 minutes, and the supernatant was removed and filtered with Ultrafree®-MC 0.45 µm tubes (MilliporeSigma, Burlington, Mass.). An additional 500 µL of 500 mM Tris pH 7.5 was added to the particles, vortexed, and centrifuged again. The recovered supernatant fractions were pooled and precipitated with ethanol (100 µL of 3 M sodium acetate (Ambion, AM9740) and 2 mL of 100% absolute ethanol). The mixture was vortexed and frozen for at least 30 minutes at −80° C. The tube was centrifuged for 30 minutes at 15,000 rpm, and the solution was discarded. The pellet was washed with 500 µL of 70% ethanol and centrifuged again. The sample was vacuum-dried using a SpeedVac Concentrator. The pellet of purified oligonucleotide was resuspended in 50 µL of water, and the final oligonucleotide-capped target RNA concentration was estimated with a spectrophotometer (NanoDrop, ND-1000).

Figure 42:
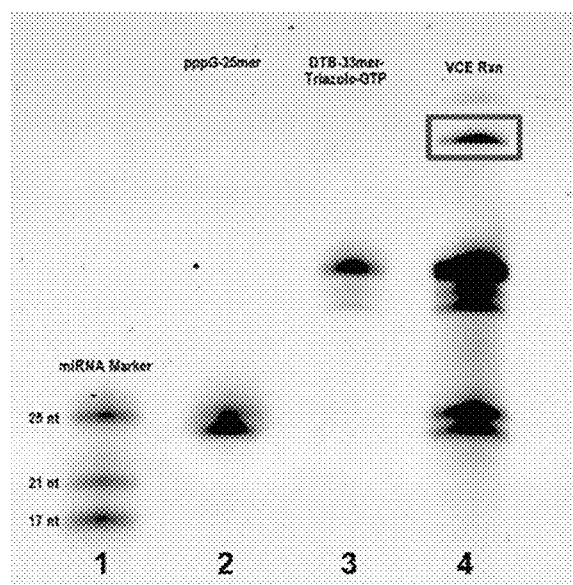
FIG. 42 shows that a target 5'-triphosphate RNA can be capped with a preassembled oligonucleotide-labeled GTP by a capping enzyme (one-step coupling approach). Lane 1: Marker. Lane 2: Target 25mer 5'-ppp-RNA. Lane 3: Preassembled oligonucleotide-labeled GTP (5'-DTB-33mer-Triazole-GTP). Lane 4: Enzymatically capping of the target 25mer 5'-ppp-RNA with 5'-DTB-33mer-Triazole-GTP mediated by VCE. The product oligonucleotide-capped target RNA can be visualized as the boxed band in Lane 4. DTB: Affinity group DBT attached to the 5'-position of the oligonucleotide.

These results are shown in FIG. 42. This data shows that a target 5'-triphosphate RNA can be capped with a preassembled oligonucleotide-labeled GTP by a capping enzyme.

Example 24: Addition of an Azide Oligonucleotide to an Alkyne-Labeled GMP Capped Target RNA 1) Synthesis of a 3'-Azido-Oligonucleotide from a 3'-Amino-Oligonucleotide Precursor:

An 3'-NH$_2$-modified oligonucleotide (50 nmol, final concentration 125 µM; example sequence: 5'-P rUrArGrCrAr-CrCrArUrUrUrGrArArArUrCrArGrUrGrU-rUTCGTATGCCGTCTTCTGCTTG-Am-MO-3' obtained from IDT) (SEQ ID NO:17) was dissolved in borate buffer (300 µL, 50 mM final concentration, pH 8.3). To this solution was added an appropriate azido-NHS ester (i.e. azidoacetic acid NHS ester, Click Chemistry Tools, 1070; 100 µL of 50 mM solution) in DMF (20% of the final volume, 10 mM final concentration). The reaction was stirred in the absence of light for 2 hours at room temperature, after which time the reaction was purified using the Oligo Clean & Concentrator kit (large capacity spin column). When necessary, the 3'-azido-oligonucleotide product was further purified by PAGE purification (see below). Reaction can be scaled up or down as necessary.

2) Addition of a 3'-Azido-Oligonucleotide to a 5'-(3'-Propargyl-GMP)-Capped Target RNA:

A 5'-(3'-propargyl-GMP)-capped target RNA synthesized according to Example 19 (final concentration 0.5 µM; and sequence: 5'-$^{m7}$G(3'-O-propargyl)pppCUAGAACUUCGU-CGAGUACGCUCAA-3') (SEQ ID NO:18) was dissolved in 2M triethylammonium acetate buffer (TEAA—10×, 1 µL, 200 µM final concentration, pH 7) and DMSO (25% of total reaction volume, 2.5 µL). The azido-oligonucleotide (final concentration 4 µM) was then added followed by ascorbic acid (1 µL, final concentration 500 µM). The reaction vial was then degassed with nitrogen, and the Cu(II)-TBTA solution (0.5 µL, final concentration 500 µM; Lumiprobes, 21050) was added and degassed again. The reaction (10 µL total volume) was incubated overnight at room temperature in the absence of light. The reaction was purified by Oligo Clean & Concentrator kit. When necessary, the oligonucleotide-labeled GMP-capped target RNA was further purified by PAGE purification. Reaction can be scaled up or down as necessary.

Figure 43:
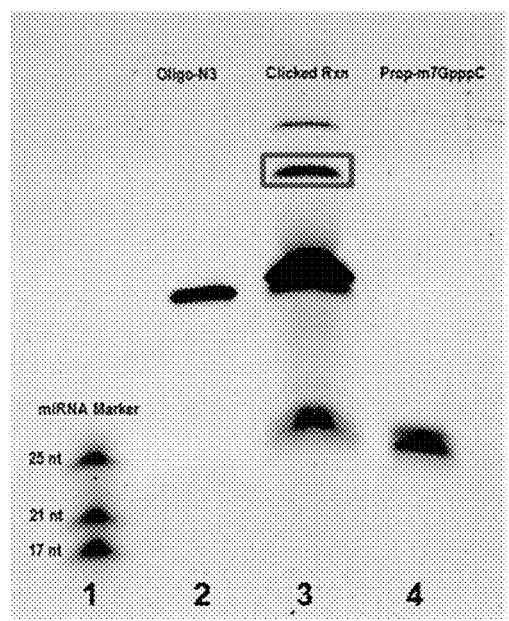
FIG. 43 shows that an azide-oligonucleotide can be chemically coupled to an alkyne-labeled GMP capped target RNA (two-step coupling approach). An alkyne-labeled target RNA is first synthesized by coupling a 5'-triphosphate target RNA with an alkyne-labeled GTP (3'-propargyl-GTP) in the presence of a capping enzyme (VCE); then the alkyne-labeled target RNA is coupled to an azide-modified oligonucleotide to form an oligonucleotide-labeled target RNA. Lane 1: Marker. Lane 2: Azide-modified oligonucleotide 5'-DTB-33mer-N3. Lane 3: Coupling of the azide-modified oligonucleotide 5'-DTB-33mer-N3 with a propargyl-capped target RNA via azide-alkyne cycloaddition (click chemistry reaction). Lane 4: Propargyl-capped target RNA, which was obtained from enzymatic capping of the target 25mer 5'-ppp-RNA with 3'-propargyl-GTP mediated by VCE and then purified by PAGE. The product oligonucleotide-capped target RNA can be visualized as the boxed band in Lane 3.

These results are shown in FIG. 43. This data shows that an azide-oligonucleotide can be chemically coupled to an alkyne-labeled GMP capped target RNA.

Figure 44:
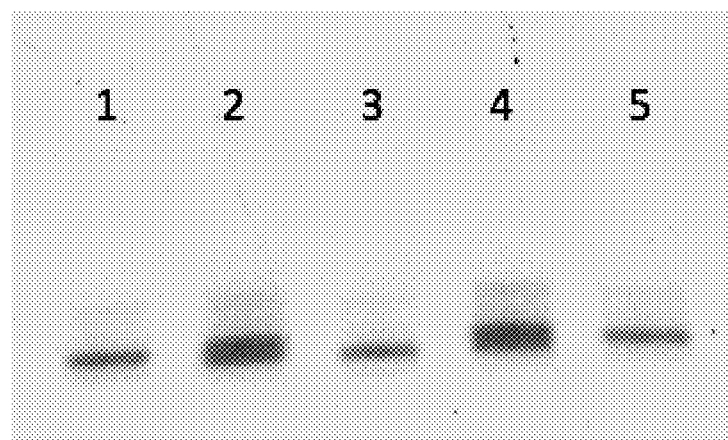
FIG. 44 shows that a target 5'-phosphate RNA can be capped with a 3'-azido-GTP nucleotide by a capping enzyme. Lane 1. 2.5 ul of the capping reaction of 5'-triphosphate 25mer RNA with VCE, 3'-Azido-2',3' ddGTP and E. coli inorganic pyrophosphatase (reaction A). Lane 2 is a mixture of 2.5 ul of reaction A plus 2.5 ul of 100 ng of unreacted RNA (control). Lane 3 is 2.5 ul of unreacted RNA (control). Lane 4 is a mixture of 2.5 ul of the capping reaction of 5'-triphosphate 25mer RNA with VCE, 3'-Azido-2',3' ddGTP and S-adenosylmethionine (SAM) (New England Biolabs, Ipswich, Mass.) (reaction B) plus 2.5 ul of 100 ng of unreacted RNA (control). Lane 5 is 2.5 ul of reaction B.

Example 25: Addition of an Alkyne Oligonucleotide to an Azide-Labeled GMP Capped Target RNA 1) Enzymatic Capping of a Target 5'-Triphosphate RNA with a 3'-Azido-GTP Nucleotide:

A 5'-triphosphate 25mer RNA (from T7 RNA polymerase transcription) was capped with a 3'-azido-GTP as follows: 10 µl reaction mixes of 100 ng of 5'-triphosphate 25mer RNA in 1×VCE buffer, 10 units of VCE 0.5 mM 3'-Azido-2',3' ddGTP (Tri Link Technologies), and either 0.05 units of E. coli inorganic pyrophosphatase (New England Biolabs, Ipswich, Mass.) (reaction A) or 0.1 mM SAM (reaction B) were incubated for 30 minutes at 37° C. The reaction was purified by Oligo Clean & Concentrator kit. The capping reaction can be scaled up or down as necessary. FIG. 44 shows that a target 5'-phosphate RNA can be capped with a 3'-azido-GTP nucleotide by a capping enzyme.

Figure 40:
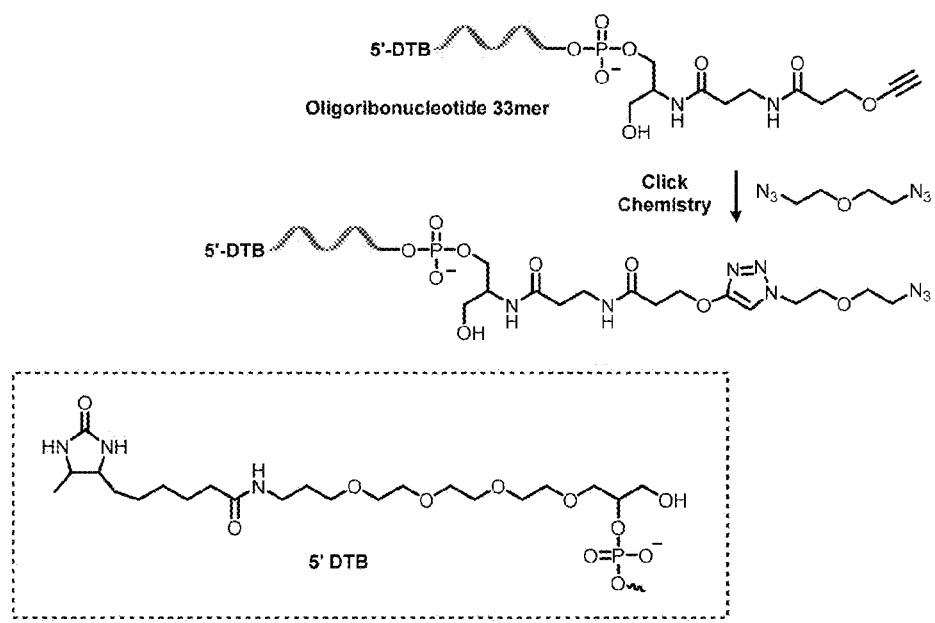
FIG. 40 shows a schematic diagram of the formation of a 33mer 5'-DTB-oligoribonucleotide with a 3'-azide modification (5'-DTB-33mer-N3) from a 33mer 5'-DTB-oligoribonucleotide precursor having an alkyne group. The sequence of 5'-DTB-ACACUCUUUCCUACACGACG-CUCUUCCGAUCU-$N_3$-3' (SEQ ID NO:16) is based on the R1 Illumina adaptor. The affinity group DTB which is attached through a linker to the 5'-position of the oligonucleotide is intended for affinity tag-based purification and enrichment of labeled target RNAs.

2) Addition of 3'-Alkyne-Oligonucleotide to a 5'-(3'-Azide-GMP)-Capped Target RNA:

A 5'-(3'-azide-GMP)-capped target RNA can be chemically labeled with the 5'-DTB-33mer-3'-alkyne oligoribonucleotide of FIG. 40 (sequence 5'-DTB-ACACUC-UUUCCCUACACGACGCUCUUCCGAUCU-3'-alkyne) (SEQ ID NO:16) as follows: A 5'-(3'-azide-GMP)-capped target RNA is dissolved in 2M triethylammonium acetate buffer (TEAA—10×, 1 µL, 200 µM final concentration, pH 7) and DMSO (25% of total reaction volume, 2.5 µL). The 3'-alkyne-oligonucleotide (final concentration 4 µM) is then added followed by ascorbic acid (1 µL, final concentration 500 µM). The reaction vial is optionally degassed with nitrogen, and then a Cu(II)-TBTA solution (0.5 µL, final concentration 500 µM; Lumiprobes, 21050) is added. The reaction (10 µL total volume) is incubated overnight at room temperature in the absence of light. The reaction is purified by Oligo Clean & Concentrator kit. When necessary, the oligonucleotide-labeled GMP-capped target RNA can be further purified by PAGE purification. Reaction can be scaled up or down as necessary.

Example 26: Generating a Target RNA Transcript with a 5' Affinity Tagged 33-Nucleotide Extension at the 5' End of the Transcript 1) Capping Target RNA Transcripts with 3'-(Propargyl)-GTP Nucleotide:

A 809 nucleotide long transcript of *Gaussia* luciferase gene was generated by in vitro transcription from the corresponding DNA template which was generated by PCR from the plasmid pCMV-GLuc-2 (New England Biolabs Ipswich, Mass.). The sense primer contained the T7 promoter and the antisense PCR primer was used to add a 3' terminal tail of 125 A residues. The RNA was purified with a spin column purification kit (MEGAclear). The target triphosphate-RNA Gluc transcript was concentrated with AMPURE beads to 1 ug/ul.

25 ul of Gluc transcript (22 ug) plus NEB Capping buffer 6 ul, 11 ul water, 6 ul 3'-(propargyl)-GTP (5 mM), 6 ul *E. coli* inorganic pyrophosphatase, and 6 ul of VCE was incubated for 30 minutes at 37° C. The propargyl-GMP capped Gluc RNA was purified by an adding an equal volume of AMPURE beads washing 2× with 80% ETOH and eluting in 26 ul of 1 mM Tris pH 7.5, 0.1 mM EDtA.

Gluc transcript sequence:
(SEQ ID NO: 19)
GGGAGACCCAAGCUUGGUACCGAGCUCGGAUCCAGCCACCAUGGGAGUCA

AAGUUCUGUUUGCCCUGAUCUGCAUCGCUGUGGCCGAGGCCAAGCCCACC

GAGAACAACGAAGACUUCAACAUCGUGGCCGUGGCCAGCAACUUCGCGAC

CACGGAUCUCGAUGCUGACCGCGGGAAGUUGCCCGGCAAGAAGCUGCCGC

UGGAGGUGCUCAAAGAGAUGGAAGCCAAUGCCCGGAAAGCUGGCUGCACC

AGGGGCUGUCUGAUCUGCCUGUCCCACAUCAAGUGCACGCCCAAGAUGAA

GAAGUUCAUCCCAGGACGCUGCCACACCUACGAAGGCGACAAAGAGUCCG

CACAGGGCGGCAUAGGCGAGGCGAUCGUCGACAUUCCUGAGAUUCCUGGG

UUCAAGGACUUGGAGCCCAUGGAGCAGUUCAUCGCACAGGUCGAUCUGUG

UGUGGACUGCACAACUGGCUGCCUCAAAGGGCUUGCCAACGUGCAGUGUU

CUGACCUGCUCAAGAAGUGGCUGCCGCAACGCUGUGCGACCUUUGCCAGC

AAGAUCCAGGGCCAGGUGGACAAGAUCAAGGGGGCCGGUGGUGACUAAGC

GGCCGCAAUAAAAUAUCUUUAUUUUCAUUACAUCUGUGUGUUGGUUUUUU

GUGUGUCUAGAAAUAAUUCUUACUGUAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

Figure 41:
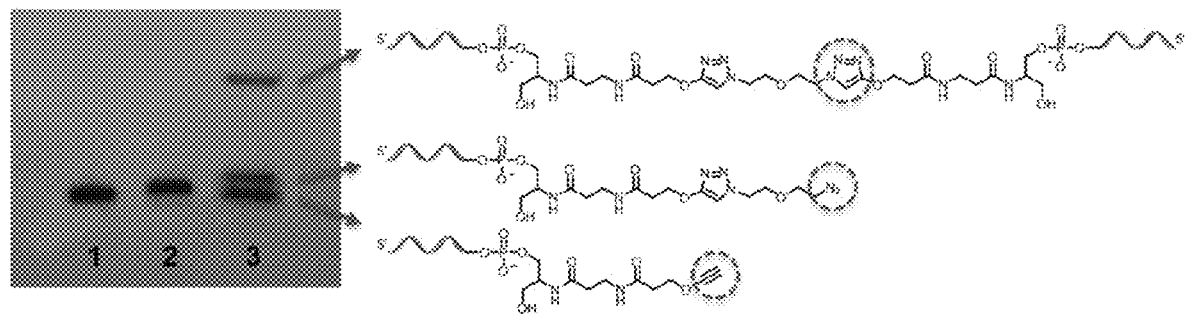
FIG. 41 shows that a 3'-azido oligonucleotide 33mer is functional in an azide-alkyne cycloaddition reaction. Lane 1: 3'-alkyne oligonucleotide 33mer. Lane 2: 3'-azido oligonucleotide 33mer (product of adding azide linker N3-PEG-N3 to the 3'-alkyne oligonucleotide 33mer shown in Lane 1). Lane 3: azide-alkyne cycloaddition (click chemistry reaction) between oligonucleotides shown in Lanes 1 and 2. The product is approximately twice as large as the parent oligonucleotides, indicating successful coupling.

2) Synthesis of a 33mer 5'-DTB-Oligoribonucleotide with a 3'-Azide Modification (5'-DTB-33mer-N3):

A 5'-DTB-33mer-3'-alkyne oligoribonucleotide was synthesized by standard solid-phase synthesis using a 3'-alkyne modifier serinol-cpg (BaseClick BCA-02) and 5'-DTB modifier (Glen Research #10-1952) and then PAGE purified. The sequence 5'-DTB-ACACUCUUUCCCUACACGACG-CUCUUCCGAUCU-3'-alkyne (SEQ ID NO:16) is based on the R1 Illumina adaptor. The 5'-DTB-33mer-3'-alkyne oligoribonucleotide (99.9 nmol) was dissolved in water (499.5 µL) and 2M TEAA buffer (99.9 µL, 10×, 200 µM final concentration, pH 7). $N_3$—PEG1-$N_3$ (9.99 µmol; Broad-Pharm, BP 20908) was dissolved in DMSO (25% of the total volume, 249.75 µL), and the DTB-Illumina R1 33mer-3'-alkyne oligoribonucleotide was added to this vial. Ascorbic acid was added (5 mM solution, 99.9 µL), and the vial was degassed with nitrogen via needle. Cu(II)-TBTA (10 mM solution, 49.95 µL, Lumiprobes, 21050) was added, and the vial was degassed again. The reaction was stirred at room temperature for 18 hours after which the reaction was dissolved in 0.1 M triethylammonium bicarbonate buffer (TEAB—15 mL) and purified by C18 HPLC. FIG. 40 shows a schematic of the formation of a 33mer 5'-DTB-oligoribonucleotide with a 3'-azide modification (5'-DTB-33mer-N3) from the precursor alkyne-oligoribonucleotide. The affinity group DTB which is attached through a linker to the 5'-position of the oligonucleotide is intended for affinity tag-based purification and enrichment of labeled target RNAs. FIG. 41 shows that an 3'-azido oligonucleotide 33mer is functional in an azide-alkyne cycloaddition reaction.

3) Adding a 33mer 5'-DBT-Oligoribonucleotide to 5' End of Gluc RNA:

Dilute the 5'-(3'-propargyl-GMP)-capped Gluc RNA to 50% of the total reaction volume (15 µL; RNA concentration from 60-100 ng/µL). Add 2M TEAA buffer (3 µL; 10×, 200 µM final concentration, pH 7) and stir to combine. 5'-DTB-33mer-3'-N3 was dissolved in DMSO/H2O so the final volume of DMSO is 25% of the total reaction volume (7.5 µL). The buffered 5'-(3'-propargyl-GMP)-capped Gluc RNA was then added to 5'-DTB-33mer-3'-N3 and mixed. Ascorbic acid (5 mM solution, 3 µL) was added, and the vial was degassed with nitrogen using a needle. Cu(II)-TBTA (10 mM solution, 1.5 µL, Lumiprobes, 21050) was added, and the vial was degassed again. The reaction was allowed to stir at room temperature for 16 hours. The reaction was purified by Oligo Clean & Concentrator kit, then enriched by binding to streptavidin beads, washed and eluted with biotin (see step 4 for details). This reaction can be scaled up as necessary.

4) Enrichment of a 5'-DBT-Oligoribonucleotide Attached to 5' End of Gluc RNA:

The 5'-DTB-33mer-labeled Gluc RNA was purified from the click chemistry reaction mix by using "RNA Clean and Concentrator"-5 kit using the greater than 200-nucleotide protocol. The 5'-DTB-33mer-labeled Gluc RNA was eluted in 20 ul 1 mM Tris pH 7.5, 0.1 mM EDTA. This step removed the unreacted 33mer oligonucleotide. 4.5 ul of 5M NaCl was added to 18 ul of the RNA. 200 ul of hydrophilic streptavidin magnetic beads (NEB) were washed with 1× with 400 ul of 2 M NaCl, 10 mM Tris pH 7.5, 1 mM EDtA. And 1× with 400 ul of of 250 mM NaCl, 10 mM Tris pH 7.5, 1 mM EDTA. And finally resuspended in 67 ul of 2 M NaCl, 10 mM Tris pH 7.5, 1 mM EDTA. 18 ul of the bead suspension was mixed with 18 ul of the RNA solution. The beads were mixed well by pipetting and then placed on a inverting mixer/rotator for 30 minutes at room temperature. The beads were then washed 1× by resuspension in 400 ul 2 M NaCl, 10 mM Tris pH 7.5, 1 mM EDTA and 1× with 400 ul 250 m M NaCl, 10 mM Tris pH 7.5, 1 mM EDTA. the beads were then suspended in 15 ul of 10 mM Tris pH 7.5, 1 mM EDTA, 500 mM NaCl and 1 mM biotin and incubated at 37° C. for 25 minutes with occasional (5×) resuspension. 7 ul of 2 M NaCl, 10 mM Tris pH 7.5, 1 mM EDTA was added and incubated and additional 5 minutes at 37 37° C. 20 ul of supernatant containing the enriched 5'-DTB-oligoribonucleotide labeled Gluc RNA was then recovered. 20 ul of 1 mM Tris pH 7.5, 0.1 mM EDTA was then added to the 20 ul solution of RNA and 72 ul of AMPURE beads (1.8× volume) were added. The suspension incubated for 15 minutes at room temperature, beads collected by magnet and then washed 2× with 80% ETOH. The beads were then eluted with 20 ul of 1 mM Tris pH 7.5, 0.1 mM EDTA. The enriched 5'-DTB-oligoribonucleotide-labeled Gluc RNA was then collected in 20 ul. By gel analysis it was estimated that 20% of the 5'-DTB-oligoribonucleotide labeled Gluc RNA was recovered after enrichment.

Figure 45:
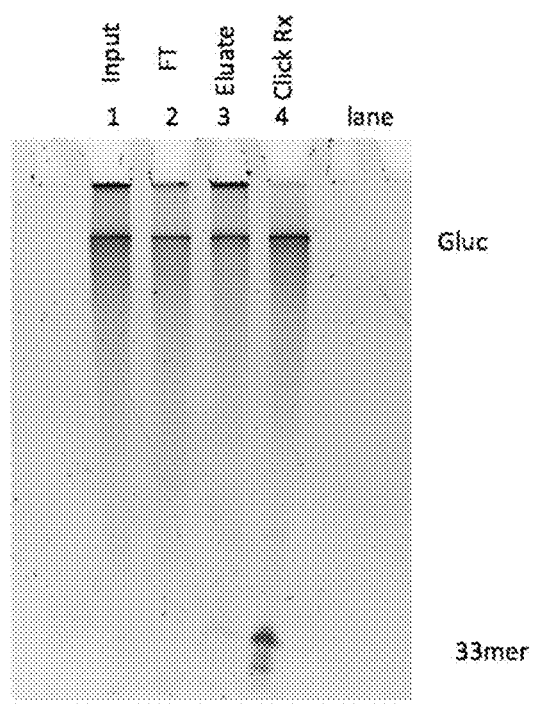
FIG. 45 shows the enrichment of a 5'-DBT-oligoribonucleotide attached to 5' end of Gluc RNA. Tris Borate Urea 6% acrylamide gel of propargyl-capped Gluc RNA transcript which has undergone coupling with azide-modified oligonucleotide 5'-DTB-33mer-N3 via a click chemistry reaction. The gel was stained with SYBR gold. Lane 1: One equivalent of the reacted propargyl-capped Gluc RNA transcript that was used as input for the streptavidin beads. Lane 2: One equivalent of the flow-through of the streptavidin beads. Lane 3: 5 equivalents of the product 5'-DTB-33mer-labeled Gluc RNA eluted from the streptavidin beads using excess of free biotin. Lane 4—One equivalent of the crude click chemistry reaction between 5'-DTB-33mer-N3 and propargyl-capped Gluc RNA before Zymo cleanup.

FIG. 45 shows that a 5'-DBT-oligoribonucleotide attached to the 5' end of Gluc RNA can be enriched using magnetic Strepavidin beads.

Example 27: Addition of a 5' Affinity Tagged 33-Nucleotide Extension to the 5' End of Target Eukaryotic mRNA Total eukaryotic RNA or polyA tailed enriched mRNA can be optionally dephosphorylated with phosphatase. The RNA is then decapped with a decapping enzyme, such as DcpS or 5' deadenylase, to leave a 5' diphosphate. The RNA is then recapped with a 5' affinity tagged nucleotide linked to 3' position of GTP, or alternatively recapped with 3' propargyl-GTP and subsequently incubated with 3'-azido, 5'-tagged nucleotide where the 3'-azido group reacts with the propargyl-GMP capped mRNA to form a 5' extended eukaryotic mRNA.

Example 28: 5' Affinity Tagged Nucleotide Extension to the 5' End of Target Yeast Poly A Plus RNA 5 ug of polyA enriched RNA from *Saccharomyces cerevisiae* was incubated in a 50 ul reaction mix, containing 10 mM BisTris-HCl pH 6.5, 1 mM EDTA, and 19 ug of DcpS (*S. cerevisiae*) for 60 minutes at 37° C. The RNA was the cleaned by Clean and Concentrator column following the >17 nucleotide protocol. The RNA was eluted in 35 ul of 1 mM Tris pH 7.5, 0.1 mM EDTA. To the 35 ul solution of RNA 6 ul of 10×VCE 10× buffer was added, as well as, 6 ul of 5 mM 3'-propargyl-GTP, 6 ul of *E. coli* inorganic pyrophosphatase and 0.6 ul of 32 mM SAM and 6 ul VCE. The reaction was incubated for 30 minutes at 37 degrees. The propargyl-GMP capped yeast RNA was again put through the Zymo column, eluting in 30 ul 1 mM Tris pH 7.5, 0.1 mM EDTA.

Example 29: Enzymatic Capping of Target RNAs with Modified GTP Analogues with a 2'-Substitution (Z=H, F, and NH2, and Ribose Sugar Replaced with an Arabinose Sugar)

The capping of 5'-triphosphate 25mer RNA (5 nmol) was performed at a 500 µL reaction volume using the Vaccinia Capping System: 100 µM 5'-triphosphate RNA (50 µL, final concentration 10 µM), water (100 µL), 10× Capping Buffer (50 µL; 50 mM Tris-HCl, 5 mM KCl, 1 mM $MgCl_2$, 1 mM DTT, pH 8 at 25° C.), 300 µM of a modified GTP (100 µl, final concentration 30 µM), 1 mM SAM (100 µL, final concentration 200 µM), Pyrophosphatase (50 µL; NEB M2403S, 0.1 unit/µL), and VCE (50 µL; 1 unit/µL). For modified GTP analogs, a 1 mM stock solution was used to provide a final concentration of 100 µM. The following modified GTP analogs were used: 2'-deoxyguanosine-5'-triphosphate (New England Biolabs, Ipswich, Mass.), 2'-fluoro-2'-deoxyguanosine-5'-triphosphate (TriLink Biotechnologies, San Diego, Calif.), 2'-amino-2'-deoxyguanosine-5'-triphosphate (TriLink Biotechnologies, San Diego, Calif.), and Araguanosine-5'-triphosphate (TriLink Biotechnologies, San Diego, Calif.). The target RNA and water were first combined, and the solution was heated to 65° C. for 5 minutes and placed on ice for an additional 5 minutes. The remaining reaction components were added, and the reaction was allowed to proceed at 37° C. overnight. The enzyme and small molecules were removed from the reaction using phenol/chloroform extraction with Phase Lock Gel tubes (5Prime, 2302810). Briefly, the reaction was vortexed with an equivalent amount (500 µL) of phenol:chloroform, 5:1, pH 4.7 (AM9720 Thermo Fisher Scientific, Waltham, Mass.). Up to 500 µL of this mixture was added to a Phase Lock Gel tube and centrifuged for 5 minutes at 13,000 rpm. To ensure the separation of the phases, 250 µL of chloroform (99%, Sigma-Aldrich, 372978) was added, and the tube was centrifuged for 5 minutes at 13,000 rpm. The aqueous phase containing the capped RNA was then transferred to a fresh tube and concentrated on a Savant SpeedVac.

This crude material was then purified using polyacrylamide gel electrophoresis. The SequaGel UreaGel System kit was used to make a 20% acrylamide gel: for 50 mL of acrylamide gel, a solution of UreaGel Concentrate (40 mL), UreaGel Diluent (5 mL) and UreaGel Buffer (5 mL) were mixed followed by APS 10% (400 µL) and tetramethylethylene diamine (20 µL, TEMED). The mixture was immediately poured into a gel cassette (height: 28 cm, width: 16.5 cm, thickness: 1.5 mm) with the appropriate comb and allowed to polymerize at room temperature. TBE 1× Buffer was prepared from a 5× stock (AccuGene 5×TBE Buffer, Lonza, 50836). The gel was equilibrated overnight at 600 V (constant voltage). The gel was then warmed prior to sample addition by increasing the maximum voltage to 800 V. The dried samples were resuspended in 50 µL of 7 M urea (prepared from powder: Qiagen, 1000774) and heat-denatured at 70° C. for 5 minutes. The gel was run at 800 V (constant voltage) for up to 6 hours.

The capped RNAs were revealed by UV shadowing on a white background. The band of interest were cut out and crushed in 2 mL Eppendorf tubes with disposable plastic pestles and resuspended and vortexed in 500 mM Tris pH 7.5 (500 µL). The gel particles were heated at 60° C. for 15 minutes, immediately frozen at −80° C. for 30 minutes, and then left overnight at room temperature. The gel solution was centrifuged at 15,000 rpm for 30 minutes, and the supernatant was removed and filtered with Ultrafree-MC 0.45 µm tubes. An additional 500 µL of 500 mM Tris pH 7.5 was added to the particles, vortexed, and centrifuged again. The recovered supernatant fractions were pooled and precipitated with ethanol (100 µL of 3 M sodium acetate (Ambion, AM9740) and 2 mL of 100% absolute ethanol). The mixture was vortexed and frozen for at least 30 minutes at −80° C. The tube was centrifuged for 30 minutes at 15,000 rpm, and the solution was discarded. The pellet was washed with 500 µL of 70% ethanol and centrifuged again. The sample was vacuum-dried using a SpeedVac Concentrator. The pellet of purified capped RNA was resuspended in 50 µL of water, and the final capped RNA concentration was estimated with a spectrophotometer (NanoDrop, ND-1000).

This example shows that VCE can tolerate modified GTP analogues with small substituents at the 2'-position (such as Z=H, F, and NH2) or ribose modifications such as the substitution of the ribose sugar with an arabinose sugar. Attempts to use larger substitutents at position 2' of ribose in the capping reaction mediated by VCE, such as in Example 3, failed give a capped product.

All references described herein are incorporated by reference

What is claimed is:

1. An RNA-oligonucleotide conjugate, comprising:
a eukaryotic, prokaryotic, archaeal, or viral target RNA comprising a 5' guanosine triphosphate cap; and
an oligonucleotide that is joined by its 3' or 5' end to the 3' position of the sugar of the guanosine via a linker, wherein the oligonucleotide comprises an affinity tag.

2. The RNA-oligonucleotide conjugate of claim 1, wherein the linker contains a substituted or unsubstituted triazole.

3. The RNA-oligonucleotide conjugate of claim 1, wherein the oligonucleotide is selected from an oligoribonucleotide, a oligodeoxyribonucleotide, a peptide nucleic acid (PNA), a lock nucleic acid (LNA), an unlock nucleic acid (UNA), a triazole nucleic acid, phosphorothioate oligonucleotide, or a combination thereof.

4. The RNA-oligonucleotide conjugate of claim 1, wherein the oligonucleotide comprises one or more modified nucleotides.

5. The RNA-oligonucleotide conjugate of claim 1, wherein the oligonucleotide is joined to the linker by a reactive group selected from an azide, an alkyne, an amine, an active ester, a thiol, and a maleimide.

6. The RNA-oligonucleotide conjugate of claim 1, wherein the affinity tag is attached to the oligonucleotide through an internal nucleotide or a branched spacer arm.

7. The RNA-oligonucleotide conjugate of claim 1, wherein the affinity tag is attached to the oligonucleotide at the 5' end if the 3' end is joined to the linker or the 3' position if the 5' end is joined to the linker.

8. The RNA-oligonucleotide conjugate of claim 1, wherein the affinity tag is selected from the group consisting of a biotin, desthiobiotin, avidin, streptavidin, protein A, maltose-binding protein, poly-histidine, HA-tag, c-myc tag, an epitope binding molecule, a self-labeling protein tag, S-tag and glutathione-S-transferase (GST).

9. The RNA-oligonucleotide conjugate of claim 1, wherein the RNA-oligonucleotide conjugate has the structure:

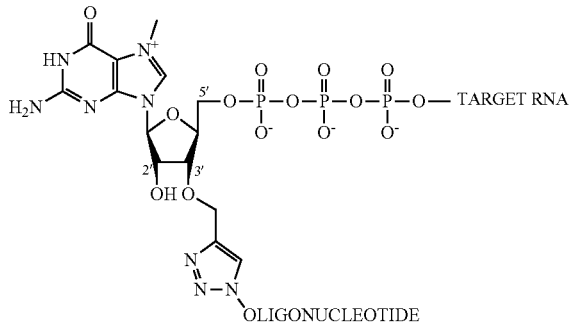

wherein the oligonucleotide comprises an affinity tag.

10. A method comprising sequencing the oligonucleotide-labeled target RNA of the RNA-oligonucleotide conjugate of claim 1 to produce a sequence.

11. An RNA-oligonucleotide conjugate, comprising:
a target RNA comprising a 5' guanosine triphosphate cap; and
an oligonucleotide that is attached to a linker through an internal nucleotide or a branched spacer arm, wherein the linker is joined to the 3' position of the sugar of the guanosine.

12. An RNA-oligonucleotide conjugate, comprising:
a eukaryotic, prokaryotic, archaeal or viral target RNA comprising a modified 5' cap,
wherein the modified 5' cap comprises (a) a guanosine or a deoxyguanosine, and (b) an oligonucleotide that is joined by its 3' or 5' end to the 3' position of the sugar of the guanosine or deoxyguanosine via a linker, wherein the oligonucleotide comprises an affinity tag.

13. The RNA-oligonucleotide conjugate of claim 12, wherein the guanosine comprises at its 2' position H, OH, SH, NH$_2$, methyl, methoxy, acetoxy, methylamine, acetamide, or a halogenyl.

14. The RNA-oligonucleotide conjugate of claim 13, wherein the linker contains a substituted or unsubstituted triazole.

15. An RNA-oligonucleotide conjugate according to the formula:

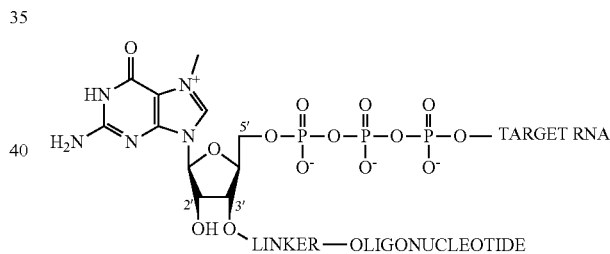

wherein the oligonucleotide comprises an affinity tag, wherein the affinity tag is optionally attached to the oligonucleotide through an internal nucleotide or a branched spacer area.

16. A method of linking an oligonucleotide to a target RNA, comprising adding a labeled GMP to a 5'-diphosphorylated or 5'-triphosphorylated 5' end of the target RNA molecules in a sample by incubating the sample with a capping enzyme and GTP linked to a label, wherein the label is an oligonucleotide that (a) is joined by its 3' or 5' end to the 3' position of the sugar of the guanosine via a linker or (b) is joined by an internal nucleotide or a branched spacer arm to the 3' position of the sugar of the guanosine via a linker, wherein the oligonucleotide comprises an affinity tag.

17. The method according to claim 16, wherein the oligonucleotide is selected from an oligoribonucleotide, a oligodeoxyribonucleotide, a peptide nucleic acid (PNA), a lock nucleic acid (LNA), an unlock nucleic acid (UNA), a triazole nucleic acid, or a combination thereof.

18. The method according to claim 16, wherein the oligonucleotide comprises one or more modified nucleotides.

19. The method according to claim 16, wherein the oligonucleotide is attached to the linker through an internal nucleotide or a branched spacer arm.

20. The method according to claim 16, wherein the oligonucleotide is attached to the linker by the oligonucleotide's 3' end or the 5' end.

21. The method according to claim 16, wherein the affinity tag is attached to the oligonucleotide through an internal nucleotide or a branched spacer arm.

22. The method according to claim 16, wherein the affinity tag is attached to the oligonucleotide at the 5' or 3' end.

23. The method according to claim 16, wherein the affinity tag is selected from the group consisting of a biotin, desthiobiotin, avidin, streptavidin, protein A, maltose-binding protein, poly-histidine, HA-tag, c-myc tag, an epitope binding molecule, a self-labeling protein tag, S-tag and glutathione-S-transferase (GST).

24. The method according to claim 16, wherein the method further comprises: purifying the oligonucleotide-labeled target RNA.

25. The method according to claim 24, wherein the oligonucleotide-labeled RNA is purified by one or more of the following methods: size-selection, gel electrophoresis, ion exchange, size-exclusion, phenol-chloroform extraction, alcohol precipitation, adsorption beads, isopycnic gradient, affinity beads, liquid chromatography, and hybridization.

26. The method of claim 16, wherein the sample comprises a target RNA from a eukaryote that is naturally 5'-m7Gppp capped and the method further comprises, prior to the incubating step, enzymatically decapping the 5'-m7Gppp capped RNA in the sample to produce the 5'-diphosphorylated or 5'-triphosphorylated target RNA molecules.

27. The method of claim 26, wherein enzymatically decapping the 5'-m7Gppp capped RNA further comprises deadenylating the RNA with a deadenylase having at least 90% identity to *Schizosaccharomyces pombe* HNT3 comprising the sequence of SEQ ID NO: 15.

28. The method of claim 26, wherein enzymatically decapping the 5'-m7Gppp capped RNA further comprises decapping the target RNA with an apyrase, a 5' RNA polyphosphatase (RppH), a RNA phosphohydrolase, a tobacco acid pyrophosphatase (TAP), a member of the histidine triad (HIT) superfamily of pyrophosphatases, DcpS, or an aprataxin (APTX).

29. The method of claim 16, wherein the method further comprises sequencing the oligonucleotide-labeled target RNA.

30. The method of claim 16, wherein the method further comprises enriching for the oligonucleotide-labeled target RNA and sequencing the enriched RNA.

31. The method of claim 16, wherein the method further comprises:
   (i) binding the oligonucleotide-labeled target RNA to an affinity matrix;
   (ii) eluting the enriched RNA from the affinity matrix;
   (iii) optionally removing the affinity tag from oligonucleotide-labeled target RNA; and
   (iv) obtaining a sequence for the target RNA.

32. The method according to claim 31, wherein the removing further comprises chemically cleaving the affinity tag to release the enriched RNA from the affinity matrix.

33. A method for making cDNA comprising: (a) treating a sample comprising a capped, eukaryotic or viral RNA with a decapping enzyme; (b) adding an oligonucleotide-labeled guanosine monophosphate (GMP) to the 5' end of the decapped RNA by incubating the decapped RNA with an oligonucleotide-labeled guanosine triphosphate (GTP), or a salt thereof, and a capping enzyme; (c) optionally including a purification step to purify the oligonucleotide-labeled RNA; (d) optionally adding a poly(A) tail or adaptor sequence in (a), (b), or (c); and (e) reverse transcribing the RNA to produce cDNA, wherein the oligonucleotide (i) is joined by its 3' or 5' end to the 3' position of the sugar of the guanosine via a linker or (ii) is joined by an internal nucleotide or a branched spacer arm to the 3' position of the sugar of the guanosine via a linker, wherein the oligonucleotide comprises an affinity tag.

34. The method according to claim 33, wherein complementary sequence of the covalently linked oligonucleotide is incorporated in the cDNA sequence.

35. A method comprising enriching for the RNA-oligonucleotide conjugate of claim 8 and sequencing the enriched RNA to produce a sequence.

36. The method of claim 35, wherein the enriching further comprises enriching for full length target RNA.

37. The method of claim 35, wherein the enriched RNA comprises a poly(A) tail.

38. The method of claim 35 further comprising identifying transcriptional start sites (TSS) using the sequence of the RNA.

39. The method of claim 35, wherein the sequencing comprises nanopore sequencing.

40. A method for making cDNA comprising: (a) adding an oligonucleotide-labeled guanosine monophosphate (GMP) to the 5' end of a eukaryotic, prokaryotic, or viral RNA having a 5' diphosphate or a 5' triphosphate by incubating the RNA with an oligonucleotide-labeled guanosine triphosphate (GTP), or a salt thereof, and a capping enzyme; (b) optionally including a purification step to purify the oligonucleotide-labeled RNA; (c) optionally adding a poly(A) tail or adaptor sequence in (a) or (b); and (d) reverse transcribing the RNA to produce cDNA, wherein the oligonucleotide (i) is joined by its 3' or 5' end to the 3' position of the sugar of the guanosine via a linker or (ii) is joined by an internal nucleotide or a branched spacer arm to the 3' position of the sugar of the guanosine via a linker, wherein the oligonucleotide comprises an affinity tag.

* * * * *